US011781125B2

(12) United States Patent
Frisch et al.

(10) Patent No.: US 11,781,125 B2
(45) Date of Patent: Oct. 10, 2023

(54) CAS9 VARIANTS AND METHODS OF USE

(71) Applicant: DANISCO USA INC, Palo Alto, CA (US)

(72) Inventors: Ryan L. Frisch, Newark, DE (US); Hongxian He, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 370 days.

(21) Appl. No.: 16/772,910

(22) PCT Filed: Dec. 11, 2018

(86) PCT No.: PCT/US2018/064955

§ 371 (c)(1),
(2) Date: Jun. 15, 2020

(87) PCT Pub. No.: WO2019/118463

PCT Pub. Date: Jun. 20, 2019

(65) Prior Publication Data

US 2020/0308561 A1 Oct. 1, 2020

Related U.S. Application Data

(60) Provisional application No. 62/599,176, filed on Dec. 15, 2017.

(51) Int. Cl.

| | |
|---|---|
| ***C12N 9/22*** | (2006.01) |
| ***C12N 15/113*** | (2010.01) |
| ***C12N 15/70*** | (2006.01) |
| ***C12N 15/75*** | (2006.01) |
| ***C12N 15/80*** | (2006.01) |

(52) U.S. Cl.
CPC .............. *C12N 9/22* (2013.01); *C12N 15/113* (2013.01); *C12N 15/70* (2013.01); *C12N 15/75* (2013.01); *C12N 15/80* (2013.01); *C12N 2310/20* (2017.05); *C12N 2800/101* (2013.01); *C12N 2800/80* (2013.01)

(58) Field of Classification Search
CPC ........ C12N 9/22; C12N 15/113; C12N 15/70; C12N 15/75; C12N 15/80; C12N 2310/20; C12N 2800/101; C12N 2800/80; C12N 15/102; C12N 15/8213
See application file for complete search history.

(56) References Cited

FOREIGN PATENT DOCUMENTS

| | | | |
|---|---|---|---|
| WO | 20170154714 | A1 | 9/2017 |
| WO | 2018183808 | A1 | 10/2018 |

OTHER PUBLICATIONS

Spencer et al. Deep mutational scanning of *S. pyogenes* Cas9 reveals important functional domains. Scientific Reports (2017), 7(1), pp. 1-14.*
Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Jeffrey M. Spencer et al., Deep mutational scanning of *S. pyogenes* Cas9 reveals important functional domains, Scientific Reports, Dec. 1, 2017, pp. 1-13, vol. 7, No. 1.
Hiroshi Nishimasu et al., Crystal Structure of Cas9 in Complex with Guide RNA and Target DNA, Cell, Feb. 1, 2014, pp. 935-949, vol. 156, No. 5.
Martin Jinek et al., A Programmable Dual-RNA-Guided DNA Endonuclease in Adaptive Bacterial Immunity, Science, Aug. 17, 2012, pp. 816-821, vol. 337, No. 6096.
Rimantas Sapranauskas et al., The *Streptococcus thermophilus* CRISPR/Cas system provides immunity in *Escherichia coli*, Nucleic Acids Research, Aug. 3, 2011, pp. 9275-9282, vol. 39, No. 21.
International Search Report—PCT/US2018/064955—dated Feb. 27, 2019.

* cited by examiner

*Primary Examiner* — Iqbal H Chowdhury

(57) ABSTRACT

Compositions and methods are provided for variant Cas systems and elements comprising such systems, including, but not limiting to, Cas endonuclease variants, guide polynucleotide/Cas endonuclease complexes comprising Cas endonuclease variants, as well as guide polynucleotides and guide RNA elements that can interact with Cas endonuclease variants. Compositions and methods are provided for genome modification of a target sequence in the genome of a cell. The methods and compositions employ a guide polynucleotide/Cas endonuclease system comprising a Cas9 endonuclease variant to provide an effective system for modifying or altering target sequences within the genome of a cell or organism.

8 Claims, 3 Drawing Sheets

Specification includes a Sequence Listing.

CAS9 VARIANTS AND METHODS OF USE

This application claims the benefit of U.S. Provisional Application No. 62/599,176 filed Dec. 15, 2017, incorporated herein in its entirety by reference.

FIELD

The present disclosure relates to the field of molecular biology, in particular, to compositions of guide polynucleotide/Cas endonuclease systems and compositions and methods thereof for modifying the genome of a cell.

REFERENCE TO SEQUENCE LISTING SUBMITTED ELECTRONICALLY

The official copy of the sequence listing is submitted electronically via EFS-Web as an ASCII formatted sequence listing with a file named 20181129_NB41317PCT_ST25.txt created on Nov. 29, 2018 and having a size of 476 kilobytes and is filed concurrently with the specification. The sequence listing contained in this ASCII formatted document is part of the specification and is herein incorporated by reference in its entirety.

BACKGROUND

Recombinant DNA technology has made it possible to insert DNA sequences at targeted genomic locations and/or modify specific endogenous chromosomal sequences. Site-specific integration techniques, which employ site-specific recombination systems, as well as other types of recombination technologies, have been used to generate targeted insertions of genes of interest in a variety of organism. Given the site-specific nature of Cas systems, genome modification/engineering techniques based on these systems have been described, including in mammalian cells (see, e.g., Hsu et al., 2014). Cas-based genome engineering, when functioning as intended, confers the ability to target virtually any specific location within a complex genome, by designing a recombinant crRNA (or equivalently functional guide polynucleotide) in which the DNA-targeting region (i.e., the variable targeting domain) of the crRNA is homologous to a desired target site in the genome, and combining the crRNA with a Cas endonuclease (through any convenient and conventional means) into a functional complex in a host cell.

Although Cas-based genome engineering techniques have been applied to a number of different host cell types, these techniques have known limitations. For example, the efficiency of transforming certain host cells, such as but not limiting to *Bacillus* species, remains low and costly.

Therefore, there remains a need for developing more effective, efficient or otherwise more robust or flexible Cas-based genome modification methods and compositions thereof for modifying/altering a genomic target site in a prokaryotic or eukaryotic cell.

BRIEF SUMMARY

Compositions and methods are provided for variant Cas systems and elements comprising such systems, including, but not limiting to, Cas endonuclease variants, guide polynucleotides, guide polynucleotide/Cas endonuclease complexes, guide RNA/Cas endonuclease systems, in particular, to Cas9 endonuclease variants comprising at least one amino acid modification located outside of its HNH and RuvC domain, and optionally wherein the Cas9 endonuclease variant has at least one improved property, when compared to its parent Cas9 endonuclease that does not have the at least one amino acid modification.

Compositions and methods are also provided for direct delivery of Cas9 endonuclease variants, guide polynucleotides and guide polynucleotide/Cas endonuclease systems comprising at least one Cas9 endonuclease variant and at least one guide RNA, as well as for genome modification of a target sequence in the genome of a prokaryotic or eukaryotic cell, for gene editing and for inserting or deleting a polynucleotide of interest into or from the genome of an organism.

In one embodiment of the disclosure, the Cas9 endonuclease variant is a Cas9 endonuclease variant, or an active fragment thereof, having at least 80% amino acid identity to a parent Cas9 polypeptide set forth in SEQ ID NO: 2 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity. Said Cas9 endonuclease variant can have at least one amino acid substitution selected from the group consisting of Y155H, Y155N, Y155E, Y155F (at position 155), F86A (at position 86) and F98A (at position 98). The Cas9 endonuclease variant can have at least one improved property selected from the group consisting of improved transformation efficiency and improved editing efficiency, when compared to its parent Cas9 endonuclease. The Cas9 endonuclease variant, or active fragment thereof, can have at least 1, 2, 3, 4, 5, 6, 7, 8, 9, 10 amino acid substitutions when compared to its parent Cas9 endonuclease.

In one embodiment of the disclosure, the Cas9 endonuclease variant is a Cas9 endonuclease variant, or active fragment thereof, wherein said variant comprises an amino acid sequence having 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 2.

In one embodiment of the disclosure, the Cas9 endonuclease variant is a Cas9 endonuclease variant, wherein the improved property is improved transformation efficiency and wherein said variant, or active fragment thereof, also has an improved editing efficiency.

In one embodiment of the disclosure, the composition is a composition comprising a Cas9 endonuclease variant disclosed herein, or a functional fragment thereof. The composition can be selected from the group consisting of a guide polynucleotide/Cas9 endonuclease complex, a guide RNA/Cas9 endonuclease complex, and a fusion protein comprising said Cas9 endonuclease variant.

In one embodiment of the disclosure, the polynucleotide is a polynucleotide comprising a nucleic acid sequence encoding any one Cas9 endonuclease variant disclosed herein.

In one embodiment of the disclosure, the guide polynucleotide/Cas endonuclease complex (PGEN) is a PGEN comprising at least one guide polynucleotide and at least one Cas9 endonuclease variant described herein, wherein said guide polynucleotide is a chimeric non-naturally occurring guide polynucleotide, wherein said guide polynucleotide/

Cas endonuclease complex is capable of recognizing, binding to, and optionally nicking, unwinding, or cleaving all or part of a target sequence In one embodiment of the disclosure, the method comprises a method for modifying a target site in the genome of a cell, the method comprising introducing into a cell at least one PGEN comprising at least one guide polynucleotide and at least one Cas9 endonuclease variant described herein, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

In one embodiment of the disclosure, the method comprises a method for editing a nucleotide sequence in the genome of a cell, the method comprising introducing into at least one PGEN comprising at least one guide polynucleotide and at least one Cas9 endonuclease variant described herein and a polynucleotide modification template, wherein said polynucleotide modification template comprises at least one nucleotide modification of said nucleotide sequence In one embodiment of the disclosure, the method comprises a method for modifying a target site in the genome of a cell, the method comprising introducing into a cell at least one PGEN comprising at least one guide polynucleotide and at least one Cas9 endonuclease variant described herein and at least one donor DNA, wherein said donor DNA comprises a polynucleotide of interest.

In one embodiment of the disclosure, the method comprises a method for improving at least one property of a Cas9 endonuclease variant, said method comprising introducing at least one amino acid modification in a parent Cas9 endonuclease, wherein said at least one amino acid modification is located outside the RuvC and HNH domain of the parent Cas9 endonuclease, thereby creating said Cas9 endonuclease variant, wherein said Cas9 endonuclease variant shows an improvement in at least one property when compared to said parent Cas9 endonuclease. The at least one amino acid modification can be an amino acid substitution at a position selected from the group consisting of position 86, position 98, position 155 and a combination thereof, wherein the amino acid positions of the variant are numbered by correspondence with the amino acid sequence of said parent Cas9 endonuclease. The at least one amino acid substitution can be selected from the group consisting of Y155H, Y155N, Y155E, Y155F (at position 155), F86A (at position 86) and F98A (at position 98).

Also provided are expression cassettes, recombinant DNAs, nucleic acid constructs, prokaryotic and eukaryotic cells having a modified target sequence or having a modification at a nucleotide sequence in the genome of the prokaryotic and eukaryotic cells produced by the methods described herein. Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1 depicts a schematic representation of a Cas9 polypeptide and its Cas9 protein domains. Shown in black fill is the RuvC nuclease domain, cross hatch indicates the bridge helix, diagonal dash fill indicates the REC I domain, medium gray fill indicates the REC II domain, light gray fill indicates the HNH nuclease domain, ball fill indicates the PAM recognition domain. (Adapted from Jinek M., Jiang F., Taylor D. W. et al. 2014, Science 343, 1247997). The Y155 modification of the Cas9 endonuclease variant described herein is located in the REC1 domain.

Figure 1:
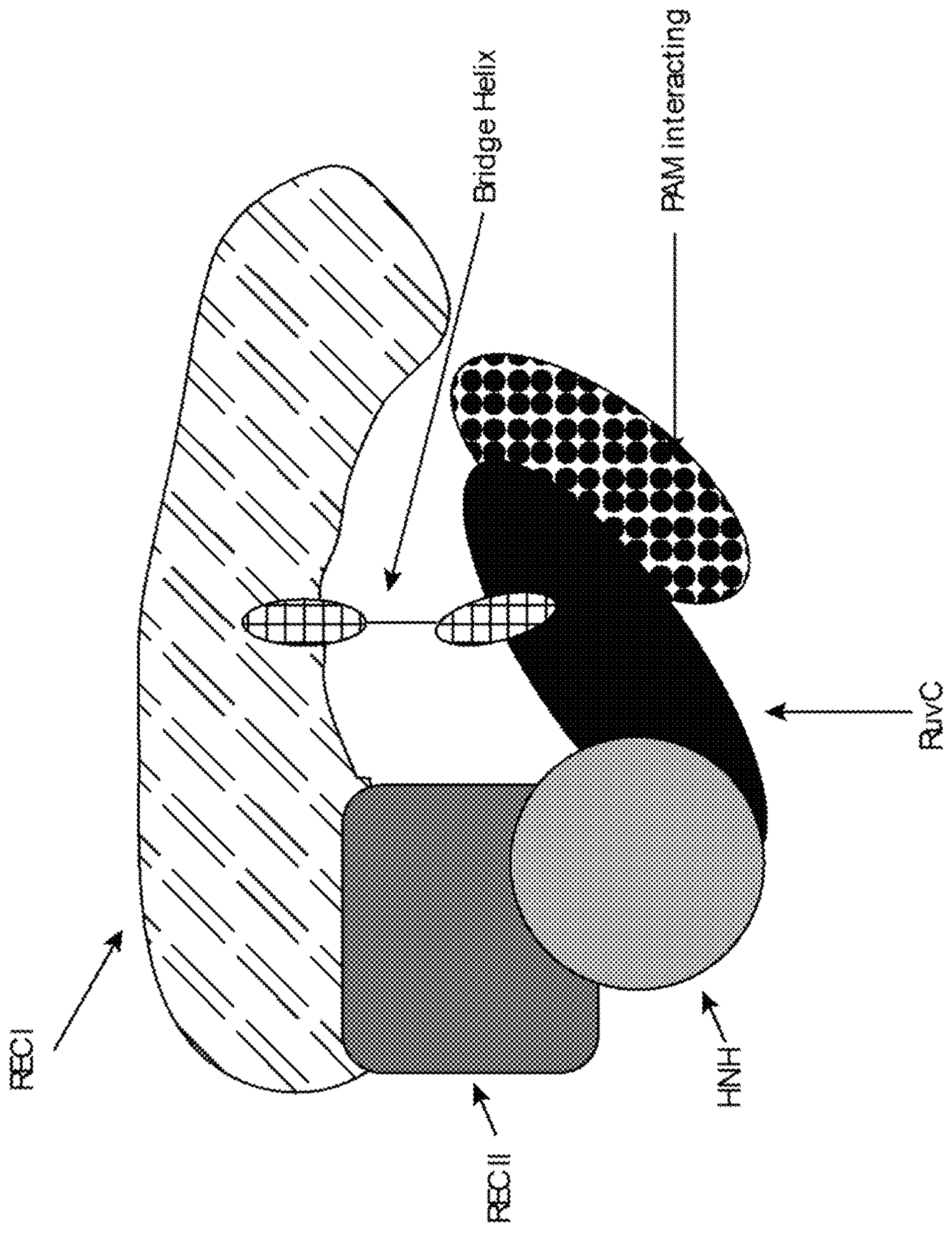
Figure 2:
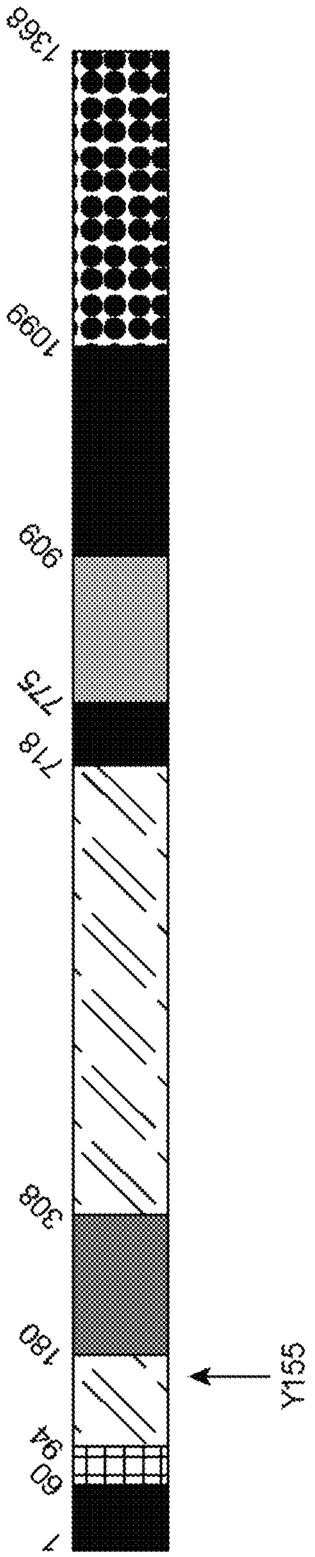
FIG. 2 depicts the domain architecture mapped onto the primary amino acid structure of a Cas9 endonuclease. The location of the Y155 modification of the Cas9 Y155 endonuclease variant (in the REC1 domain) described herein is indicated by an arrow.
Figure 3:
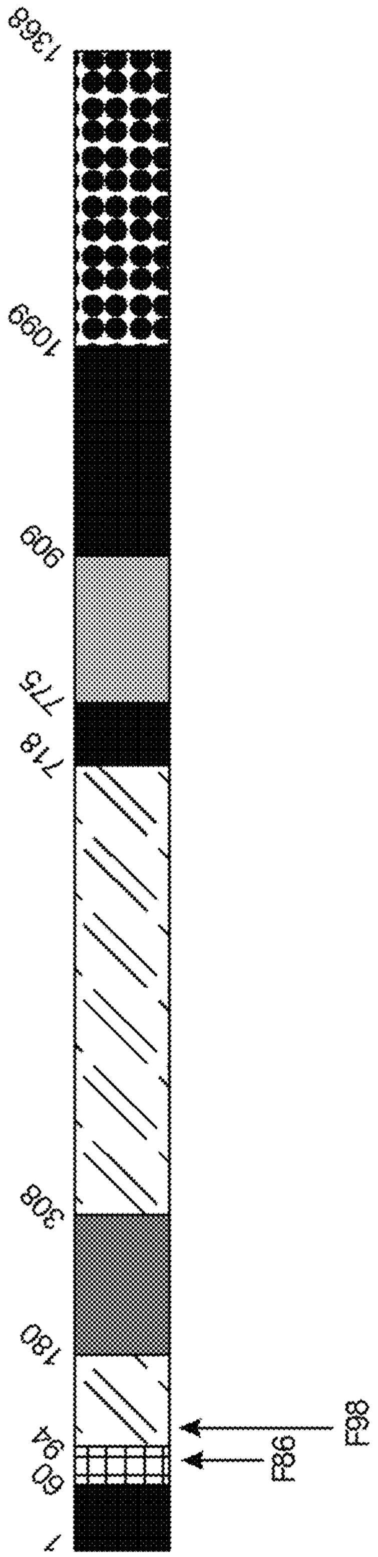
FIG. 3 depicts the domain architecture mapped onto the primary amino acid structure of a Cas9 endonuclease. The location of the F86 and F98 modifications of the Cas9 endonuclease F86-F98 variant described herein are indicated by an arrow.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5 (a-bis), and Section 208 and Annex C of the Administrative Instructions. The symbols and format used for nucleotide and amino acid sequence data comply with the rules set forth in 37 C.F.R. § 1.822.

SEQ ID NO:1 sets forth the amino acid sequence of *Streptococcus pyogenes Cas*9.

SEQ ID NO:2 sets forth the nucleotide sequence of *Bacillus* codon optimized Cas9 gene, encoding the wild type Cas9 protein of *Streptococcus pyogenes* Cas9.

SEQ ID NO:3 sets forth the amino acid sequence of N-terminal NLS.

SEQ ID NO:4 sets forth the amino acid sequence of C-terminal NLS.

SEQ ID NO:5 sets forth the amino acid sequence of deca-Histidine tag.

SEQ ID NO:6 sets forth the nucleotide sequence of 6 aprE promoter.

SEQ ID NO:7 sets forth the nucleotide sequence of terminator.

SEQ ID NOs: 8-9, 12-13, 38-39, 41-42, 50-51, 54-55, 59-60, 67-68, 71-72, 79-80, 88-89, 91-92, 111-112, 119-120, 138-139, 145-146, 151-152, 156-157 set forth the nucleotide sequence of a primer.

SEQ ID NO: 10 sets forth the nucleotide sequence of the pKB320 backbone.

SEQ ID NO: 11 sets forth the nucleotide sequence of pKB320.

SEQ ID NO: 14 sets forth the nucleotide sequence of plasmid RSP1.

SEQ ID NO: 15 sets forth the nucleotide sequence of plasmid RSP2.

SEQ ID NOs: 16-27 sets forth the nucleotide sequence of plasmids FSP1, FSP2, FSP3, FSP4, FSP5, FSP6, FSP7, RSP3, FSP8, pRF694, pRF801 and pRF806, respectively.

SEQ ID NO: 28 sets forth the nucleotide sequence of target site 1 of *Bacillus licheniformis.*

SEQ ID NO: 29 sets forth the nucleotide sequence of target site 1 of *Bacillus licheniformis.*

SEQ ID NO: 30 sets forth the nucleotide sequence of serA1 open reading frame.

SEQ ID NO: 31 sets forth the nucleotide sequence of of target site 1+PAM of *Bacillus licheniformis.*

SEQ ID NO: 32 sets forth the nucleotide sequence of DNA encoding variable targeting domain 1

SEQ ID NO: 33 sets forth the nucleotide sequence of DNA encoding CER domain.

SEQ ID NO: 34 sets forth the nucleotide sequence of gRNA targeting target site 1.

SEQ ID NO: 35 sets forth the nucleotide sequence of spac promoter.

SEQ ID NO: 36 sets forth the nucleotide sequence of t0 terminator

SEQ ID NO: 37 sets forth the nucleotide sequence of serA1 homology arm 1 of *Bacillus licheniformis.*

SEQ ID NO: 40 sets forth the nucleotide sequence of serA1 homology arm 2 of *Bacillus licheniformis.*

SEQ ID NO: 43 sets forth the nucleotide sequence of DNA encoding ts1 gRNA expression cassette.

SEQ ID NO: 44 sets forth the nucleotide sequence of serA1 deletion editing template.

SEQ ID NO: 45 sets forth the nucleotide sequence of rghR1 open reading frame of *Bacillus licheniformis.*

SEQ ID NO: 46 sets forth the nucleotide sequence of target site 2 of *Bacillus licheniformis.*

SEQ ID NO: 47 sets forth the nucleotide sequence of target site 2+PAM of *Bacillus licheniformis.*

SEQ ID NO: 48 sets forth the nucleotide sequence of DNA encoding variable targeting domain 2.

SEQ ID NO: 49 sets forth the nucleotide sequence of the guide RNA (gRNA) targeting target site 2.

SEQ ID NO: 50 sets forth the nucleotide sequence of homology arm 1 of rghR1 from *Bacillus licheniformis.*

SEQ ID NO: 53 sets forth the nucleotide sequence of homology arm 2 of rghR1 from *Bacillus licheniformis.*

SEQ ID NO: 56 sets forth the nucleotide sequence of DNA encoding ts2 expression cassette.

SEQ ID NO: 57 sets forth the nucleotide sequence of rghR1 deletion editing template.

SEQ ID NO: 58 sets forth the amino acid sequence of Cas9 Y155H variant.

SEQ ID NO: 61 sets forth the nucleotide sequence of pRF827.

SEQ ID NO: 62 sets forth the nucleotide sequence of Cas9 Y155H variant expression cassette.

SEQ ID NO: 63 sets forth the nucleotide sequence of pRF856,

SEQ ID NO: 64 sets forth the nucleotide sequence of pBL.comK-syn.

SEQ ID NO: 65 sets forth the nucleotide sequence of the target site 1 locus from *Bacillus licheniformis.*

SEQ ID NO: 66 sets forth the nucleotide sequence of the target site 1 edited locus.

SEQ ID NO: 69 sets forth the nucleotide sequence of the target site 2 locus from *Bacillus licheniformis.*

SEQ ID NO: 70 sets forth the nucleotide sequence of the target site 2 edited locus.

SEQ ID NO: 73 sets forth the nucleotide sequence of *Yarrowia* codon optimized Cas9.

SEQ ID NO: 74 sets forth the nucleotide sequence of SV40 NLS.

SEQ ID NO: 75 sets forth the nucleotide sequence of *Yarrowia* FBA1 promoter.

SEQ ID NO: 76 sets forth the nucleotide sequence of *Yarrowia* Cas9 expression cassette.

SEQ ID NO: 77 sets forth the nucleotide sequence of pZufCas9.

SEQ ID NO: 78 sets forth the nucleotide sequence of Cas9-SV40 fusion.

SEQ ID NO: 81 sets forth the nucleotide sequence of Cas9-SV40 PCR product.

SEQ ID NOs: 82-83 sets forth the nucleotide sequence of pBAD/HisB and pRF48, respectively.

SEQ ID NO: 84 sets forth the nucleotide sequence of the *E. coli* optimized Cas9 expression cassette;

SEQ ID NO: 85-86 sets forth the nucleotide sequence of pKO3 and pRF97, respectively.

SEQ ID NO: 87 sets forth the nucleotide sequence of the Cas9 Y155H encoding synthetic fragment;

SEQ ID NO: 90 sets forth the nucleotide sequence of pRF97-Y155H fragment.

SEQ ID NO: 93 sets forth the nucleotide sequence of pRF861 SEQ ID NO: 94 sets forth the nucleotide sequence of the nac gene from *E. coli.*

SEQ ID NO: 95 sets forth the nucleotide sequence of nac target site 1.

SEQ ID NO: 96 sets forth the nucleotide sequence of nac target site 1+PAM *E. coli.*

SEQ ID NO: 97 sets forth the nucleotide sequence of nac target site 1.

SEQ ID NO: 98 sets forth the nucleotide sequence of nac target site 1+PAM.

SEQ ID NO: 99 sets forth the nucleotide sequence of N25 phage promoter

SEQ ID NO: 100 sets forth the nucleotide sequence of nac target site 1 gRNA expression cassette.

SEQ ID NO: 101 sets forth the nucleotide sequence of nac target site 2 gRNA expression cassette.

SEQ ID NO: 102 sets forth the nucleotide sequence of nac upstream deletion arm.

SEQ ID NO: 103 sets forth the nucleotide sequence of nac downstream deletion arm.

SEQ ID NO: 104 sets forth the nucleotide sequence of nac deletion editing template.

SEQ ID NO: 105 sets forth the nucleotide sequence of 5' pRF97 or pRF861 identity.

SEQ ID NO: 106 sets forth the nucleotide sequence of 3' pRF97 or pRF861 identity.

SEQ ID NO: 107 sets forth the nucleotide sequence of nacETsite1.

SEQ ID NO: 108 sets forth the nucleotide sequence of nacETsite2.

SEQ ID NO: 109 sets forth the nucleotide sequence of pRF97-cassette.

SEQ ID NO: 110 sets forth the nucleotide sequence of pRF861-cassette.

SEQ ID NO: 113 sets forth the nucleotide sequence of pRF97-nacETsite1.

SEQ ID NO: 114 sets forth the nucleotide sequence of pRF97-nacETsite2.

SEQ ID NO: 115 sets forth the nucleotide sequence of pRF861-nacETsite1.

SEQ ID NO: 116 sets forth the nucleotide sequence of pRF861-nacETsite2.

SEQ ID NO: 117 sets forth the nucleotide sequence of the wild type (WT) nac locus from *E. coli.*

SEQ ID NO: 118 sets forth the nucleotide sequence of the edited nac locus.

SEQ ID NO: 121 sets forth the nucleotide sequence of *Streptococcus pyogenes* Cas9.

SEQ ID NO: 122 sets forth the nucleotide sequence encoding the Cas9 Y155H variant.

SEQ ID NO: 123 sets forth the amino acid sequence of the Cas9 Y155N variant.

SEQ ID NO: 124 sets forth the nucleotide sequence encoding the Cas9 Y155N variant.

SEQ ID NO: 125 sets forth the amino acid sequence of the Cas9 Y155E variant.

SEQ ID NO: 126 sets forth the nucleotide sequence encoding the Cas9 Y155E variant.

SEQ ID NO: 127 sets forth the amino acid sequence of the Cas9 Y155F variant.

SEQ ID NO: 128 sets forth the nucleotide sequence encoding the Cas9 Y155F variant.

SEQ ID NO: 129 sets forth the amino acid sequence of the Cas9 F86A-F98A variant.

SEQ ID NO: 130 sets forth the nucleotide sequence of the F86A-F98A synthetic fragment.

SEQ ID NO: 131 sets forth the nucleotide sequence of pRF801 backbone for F86A F98A.

SEQ ID NO: 132 sets forth the nucleotide sequence of pRF801 backbone forward.

SEQ ID NO: 133 sets forth the nucleotide sequence of pRF801 backbone reverse SEQ ID NO: 134 sets forth the nucleotide sequence of F86A-F98A synthetic forward.

SEQ ID NO: 135 sets forth the nucleotide sequence of F86A-F98A synthetic reverse.

SEQ ID NO: 136 sets forth the nucleotide sequence of *Bacillus* F86A F98A expression cassette.

SEQ ID NO: 137 sets forth the nucleotide sequence of pRF866.

SEQ ID NO: 140 sets forth the nucleotide sequence of RNR2p promoter.

SEQ ID NO: 141 sets forth the nucleotide sequence of 2-micron replication origin 1.

SEQ ID NO: 142 sets forth the nucleotide sequence of KanMX expression cassette.

SEQ ID NO: 143 sets forth the nucleotide sequence of SNR52p promoter.

SEQ ID NO: 144 sets forth the nucleotide sequence of pSE087 plasmid.

SEQ ID NO: 147 sets forth the nucleotide sequence of targeting sgRNA+T(6) terminator.

SEQ ID NO: 148 sets forth the nucleotide sequence of 50 bp upstream homology arm.

SEQ ID NO: 149 sets forth the nucleotide sequence of URA3 targeting sgRNA+T(6) terminator.

SEQ ID NO: 150 sets forth the nucleotide sequence of 50 bp downstream homology arm.

SEQ ID NO: 153 sets forth the nucleotide sequence of 2-micron replication origin 2.

SEQ ID NO: 154 sets forth the nucleotide sequence of 154 ampicillin resistant gene.

SEQ ID NO: 155 sets forth the nucleotide sequence of RNR2 terminator.

DETAILED DESCRIPTION

Compositions and methods are provided for variant Cas systems and elements comprising such systems, including, but not limiting to, Cas endonuclease variants, guide polynucleotide/Cas endonuclease complexes comprising Cas endonuclease variants, as well as guide polynucleotides and guide RNA elements that can interact with Cas endonuclease variants. Compositions and methods are also provided for direct delivery of Cas endonucleases variants, guide RNAs and guide RNA/Cas endonucleases complexes. The present disclosure further includes compositions and methods for genome modification of a target sequence in the genome of a cell, for gene editing, and for inserting a polynucleotide of interest into the genome of a cell.

The present document is organized into a number of sections for ease of reading; however, the reader will appreciate that statements made in one section may apply to other sections. In this manner, the headings used for different sections of the disclosure should not be construed as limiting.

The headings provided herein are not limitations of the various aspects or embodiments of the present compositions and methods which can be had by reference to the specification as a whole. Accordingly, the terms defined immediately below are more fully defined by reference to the specification as a whole.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Cas Genes and Proteins

CRISPR (clustered regularly interspaced short palindromic repeats) loci refers to certain genetic loci encoding components of DNA cleavage systems, for example, used by bacterial and archaeal cells to destroy foreign DNA (Horvath and Barrangou, 2010, Science 327:167-170; WO2007/025097, published Mar. 1, 2007). A CRISPR locus can consist of a CRISPR array, comprising short direct repeats (CRISPR repeats) separated by short variable DNA sequences (called 'spacers'), which can be flanked by diverse Cas (CRISPR-associated) genes. The number of CRISPR-associated genes at a given CRISPR locus can vary between species. Multiple CRISPR/Cas systems have been described including Class 1 systems, with multisubunit effector complexes (comprising type I, type III and type IV subtypes), and Class 2 systems, with single protein effectors (comprising type II and type V subtypes, such as but not limiting to Cas9, Cpf1, C2c1, C2c2, C2c3). Class 1 systems (Makarova et al. 2015, Nature Reviews; Microbiology Vol. 13:1-15; Zetsche et al., 2015, Cell 163, 1-13; Shmakov et al., 2015, Molecular_Cell 60, 1-13; Haft et al., 2005, Computational Biology, PLoS Comput Biol 1(6): e60. doi:10.1371/journal.pcbi. 0010060 and WO 2013/176772 A1 published on Nov. 23, 2013 incorporated by reference herein). The type II CRISPR/Cas system from bacteria employs a crRNA (CRISPR RNA) and tracrRNA (trans-activating CRISPR RNA) to guide the Cas endonuclease to its DNA target. The crRNA contains a spacer region complementary to one strand of the double strand DNA target and a region that base pairs with the tracrRNA (trans-activating CRISPR RNA) forming a RNA duplex that directs the Cas endonuclease to cleave the DNA target. Spacers are acquired through a not fully understood process involving Cas1 and Cas2 proteins. All type II CRISPR/Cas loci contain cas1 and cas2 genes in addition to the cas9 gene (Chylinski et al., 2013, RNA Biology 10:726-737; Makarova et al. 2015, Nature Reviews Microbiology Vol. 13:1-15). Type II CRISPR-Cas loci can encode a tracrRNA, which is partially complementary to the repeats within the respective CRISPR array, and can comprise other proteins such as Csn1 and Csn2. The presence of cas9 in the vicinity of Cas 1 and cas2 genes is the hallmark of type II loci (Makarova et al. 2015, Nature Reviews Microbiology Vol. 13:1-15). Type I CRISPR-Cas (CRISPR-associated) systems consist of a complex of proteins, termed Cascade (CRISPR-associated complex for antiviral defense), which function together with a single CRISPR RNA (crRNA) and Cas3 to defend against invading viral DNA (Brouns, S. J. J. et al. *Science* 321:960-964; Makarova et al. 2015, Nature Reviews; Microbiology Vol. 13:1-15, which are incorporated in their entirety herein).

The term "Cas gene" herein refers to a gene that is generally coupled, associated or close to, or in the vicinity of flanking CRISPR loci. The terms "Cas gene", "cas gene", "CRISPR-associated (Cas) gene" and "Clustered Regularly Interspaced Short Palindromic Repeats-associated gene" are used interchangeably herein.

The term "Cas protein" or "Cas polypeptide" refers to a polypeptide encoded by a Cas (CRISPR-associated) gene. A Cas protein includes a Cas endonuclease.

A Cas protein may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other aspects, Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. A Cas protein includes a Cas9 protein, a Cpf1 protein, a C2c1 protein, a C2c2 protein, a C2c3 protein, Cas3, Cas3-HD, Cas 5, Cas7, Cas8, Cas10, or combinations or complexes of these.

The term "Cas endonuclease" refers to a Cas polypeptide (Cas protein) that, when in complex with a suitable polynucleotide component, is capable of recognizing, binding to, and optionally nicking or cleaving all or part of a specific DNA target sequence. A Cas endonuclease is guided by the guide polynucleotide to recognize, bind to, and optionally nick or cleave all or part of a specific target site in double stranded DNA (e.g., at a target site in the genome of a cell). A Cas endonuclease described herein comprises one or more nuclease domains. The Cas endonucleases employed in donor DNA insertion methods described herein are endonucleases that introduce single or double-strand breaks into the DNA at the target site. Alternatively, a Cas endonuclease may lack DNA cleavage or nicking activity, but can still specifically bind to a DNA target sequence when complexed with a suitable RNA component.

As used herein, a polypeptide referred to as a "Cas9" (formerly referred to as Cas5, Csn1, or Csx12) or a "Cas9 endonuclease" or having "Cas9 endonuclease activity" refers to a Cas endonuclease that forms a complex with a crNucleotide and a tracrNucleotide, or with a single guide polynucleotide, for specifically binding to, and optionally nicking or cleaving all or part of a DNA target sequence. A Cas9 endonuclease comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Makarova et al. 2015, Nature Reviews Microbiology Vol. 13:1-15, Hsu et al, 2013, Cell 157:1262-1278). Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA (Makarova et al. 2015, Nature Reviews Microbiology Vol. 13:1-15).

A "functional fragment", "fragment that is functionally equivalent" and "functionally equivalent fragment" of a Cas endonuclease are used interchangeably herein, and refer to a portion or subsequence of the Cas endonuclease in which the ability to recognize, bind to, and optionally unwind, nick or cleave (introduce a single or double-strand break in) the target site is retained.

The terms "functional variant", "variant that is functionally equivalent" and "functionally equivalent variant" of a Cas endonuclease of the present disclosure, are used interchangeably herein, and refer to a variant of the Cas endonuclease of the present disclosure in which the ability to recognize, bind to, and optionally unwind, nick or cleave all or part of a target sequence is retained.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in host cell/organism, and then examining the predicted DNA target site for the presence of an indel (a Cas protein in this particular assay would have endonucleolytic activity [single or double-strand cleaving activity]). Examining for the presence of an indel at the predicted target site could be done via a DNA sequencing method or by inferring indel formation by assaying for loss of function of the target sequence, for example. In another example, Cas protein activity can be determined by expressing a Cas protein and suitable RNA component in a host cell/organism that has been provided a donor DNA comprising a sequence homologous to a sequence in at or near the target site. The presence of donor DNA sequence at the target site (such as would be predicted by successful HR between the donor and target sequences) would indicate that targeting occurred.

A variant of a Cas endonuclease, also referred to as "Cas endonuclease variant", refers to a variant of a parent Cas endonuclease wherein the Cas endonuclease variant retains the ability to recognize, bind to, and optionally unwind, nick or cleave all or part of a DNA target sequence, when associated with a crNucleotide and a tracrNucleotide, or with a single guide polynucleotide, (such as a guide polynucleotide described herein). A Cas endonuclease variant includes a Cas endonuclease variant described herein, where the Cas endonuclease variant differs from the parent Cas endonuclease, in such a manner that the Cas endonuclease variant (when in complex with a guide polynucleotide to form a polynucleotide-guided endonuclease complex capable of modifying a target site) has at least one improved property such as, but not limited to, increased transformation efficiency increased DNA editing efficiency, reduced off target cleavage, or any combination thereof, when compared to the parent Cas endonuclease (in complex with the same guide polynucleotide to form a polynucleotide-guided endonuclease complex capable of modifying the same target site).

As used herein, the term "transformation efficiency" is defined by diving the number of transformed cells obtained when a Cas9 variant is used in combination with a guide polynucleotide to form a polynucleotide-guided endonuclease PGEN complex capable of modifying a target site, with the number of transformed cells obtained when the parent (wild type) Cas9 is used in combination with the same guide polynucleotide to form a PGEN complex as the Cas endonuclease component of a PGEN capable of modifying the same target site. This number can be multiplied by 100 to express it as a %.

$$\text{Transformation efficiency} = \frac{\left(\begin{array}{c}\text{number of transformed cells}\\ \text{with } Cas9 \text{ variant}\end{array}\right)}{\left(\begin{array}{c}\text{number of transformed cells}\\ \text{with parent } WT\ Cas9\end{array}\right)}$$

A transformation efficiency of 1 (or 100%) indicates that the number of transformed cells obtained when a Cas9 variant is used is about the same or identical to the number of number of transformed cells obtained when a WT Cas9 variant. In this case the Cas9 variant would not have an improved property when compared to its parent Cas9 endonuclease. In contrast, a transformation efficiency of greater than 1 indicates that the number of transformed cells obtained when a Cas9 variant is used is greater than the number of transformed cells obtained when a WT Cas9 variant. In this case the Cas9 variant does have an improved property, e.g. an improved transformation efficiency, when compared to the parent Cas9 endonuclease.

As used herein, the term "editing efficiency" or "DNA editing efficiency" is used interchangeably herein and is defined by diving the number of cells comprising a DNA edit (edited cell) obtained when a Cas9 variant is used in combination with a guide polynucleotide to form a polynucleotide-guided endonuclease PGEN complex capable of modifying a target site, with the number of edited cells obtained when the parent (wild type) Cas9 is used in combination with the same guide polynucleotide to form a PGEN complex as the Cas endonuclease component of a PGEN capable of modifying the same target site. This number can be multiplied by 100 to express it as a %.

$$\text{Editing efficiency} = \frac{\left(\begin{array}{c}\text{number of cells comprising a } DNA \text{ edit}\\ \text{made by } Cas9 \text{ variant}\end{array}\right)}{\left(\begin{array}{c}\text{number of cells comprising a } DNA \text{ edit}\\ \text{made by parent } Cas9\end{array}\right)}$$

A DNA editing efficiency of 1 (or 100%) indicates that the number of edited cells obtained when a Cas9 variant is used is about the same or identical to the number of number of edited cells obtained when a WT Cas9 variant is used. In this case the Cas9 variant would not have an improved property when compared to its parent cas9 endonuclease. In contrast, a DNA editing efficiency of greater than 1 indicates that the number of transformed cells obtained when a Cas9 variant is used is greater than the number of transformed cells obtained when a parent (WT) Cas9 variant is used. In this case the Cas9 variant does have an improved property, e.g. an improved editing efficiency, when compared to the parent Cas9 endonuclease.

A Cas endonuclease variant may comprise an amino acid sequence that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the parent Cas endonuclease.

A variant Cas endonuclease gene (variant cas gene) may comprise a nucleotide sequence that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the parent Cas endonuclease nucleotide sequence.

Non limiting examples of parent Cas endonucleases herein can be Cas endonucleases from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella*, or *Thermotoga*. Furthermore, a parent Cas endonuclease herein can be encoded, for example, by any of SEQ ID NOs: 462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

Furthermore, a parent Cas9 endonuclease herein may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), *Peptostreptococcaceae, Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), *Coriobacteriaceae* (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus* (e.g., *L. plantarum*), *Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium, F. soli*) species, for example. In one aspect a *S. pyogenes* parent Cas9 endonuclease is described herein. As another example, a parent Cas9 endonuclease can be any of the Cas9 proteins disclosed in Chylinski et al. (*RNA Biology* 10:726-737), which is incorporated herein by reference.

The sequence of a parent Cas9 endonuclease herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJO19166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. Alternatively, a Cas9 protein herein can be encoded by any of SEQ ID NOs: 462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example.

Given that certain amino acids share similar structural and/or charge features with each other (i.e., conserved), the amino acid at each position in a Cas9 can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Fragments and variants can be obtained via methods such as site-directed mutagenesis and synthetic construction. Methods for measuring endonuclease activity are well known in the art such as, but not limiting to, PCT/US13/39011, filed May 1, 2013, PCT/US16/32073 filed May 12, 2016, PCT/US16/32028 filed May 12, 2016, incorporated by reference herein).

In one embodiment, the Cas endonuclease variant is a Cas9 endonuclease variant described herein. As used herein, a "Cas9 endonuclease variant" or "Cas9 variant" refers to a variant of a parent Cas9 endonuclease wherein the Cas9 endonuclease variant retains the ability to recognize, bind to, and optionally unwind, nick or cleave all or part of a DNA target sequence, when associated with a crNucleotide and a tracrNucleotide, or with a single guide polynucleotide (such as a guide polynucleotide described herein. A Cas9 endonuclease variant includes a Cas9 endonuclease variant described herein, where the Cas endonuclease variant differs from the parent Cas9 endonuclease, in such a manner that the Cas9 endonuclease variant (when in complex with a guide polynucleotide to form a polynucleotide-guided endonuclease complex capable of modifying a target site) has at least one improved property such as, but not limited to, increased transformation efficiency increased DNA editing efficiency, reduced off target cleavage, or any combination thereof, when compared to the parent Cas9 endonuclease (in complex with the same guide polynucleotide to form a polynucleotide-guided endonuclease complex capable of modifying the same target site).

A Cas9 endonuclease variant described herein includes a variant that can bind to and nick a double strand DNA target site when associated with a crNucleotide and a tracrNucleotide, or with a single guide polynucleotide, whereas the parent Cas endonuclease can bind to and make a double strand break (cleave) at the target site, when associated with a crNucleotide and a tracrNucleotide, or with a single guide polynucleotide.

As described herein, it has been found surprisingly and unexpectedly that a Cas9 endonuclease variant having at least one an amino acid modification outside its HNH and RuvC domain (when in complex with a guide polynucleotide to form a polynucleotide-guided endonuclease complex capable of modifying a target site) can have at least one improved property such as, but not limited to, an increased transformation efficiency, an increased DNA editing efficiency, or a combination thereof, when compared to its parent Cas9 endonuclease (in complex with the same guide polynucleotide to form a polynucleotide-guided endonuclease complex capable of modifying the same target site).

In one aspect the Cas9 endonuclease variant described herein comprises a RuvC nuclease domain and an HNH (H—N—H) nuclease domain, and at least one amino acid modification (deletion, substitution or insertion of at least one amino acid) located outside the HNH and RuvC domain.

In one aspect the Cas9 endonuclease variant described herein, or an active fragment thereof, comprises at least 1, 2, 3, 4, 5, 6, 7, 8, 9, 10 amino acid substitutions when compared to the parent Cas9 endonuclease.

In one aspect the Cas9 endonuclease variant described herein has an amino acid modification outside its HNH and RuvC domain, wherein said Cas9 endonuclease has increased transformation efficiency and/or DNA editing efficiency when compared to a parent Cas9 endonuclease that does not comprises said amino acid modification, wherein said guide polynucleotide and Cas9 endonuclease variant can form a complex capable of recognizing, binding to, and optionally nicking, unwinding, or cleaving all or part of said target sequence.

In one aspect, the Cas9 endonuclease variant described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to a parent Cas9 polypeptide set forth in SEQ ID NO: 1 and has at least one amino acid substitution at position 155, wherein the amino acid positions of the variant are numbered by correspondence with the amino acid sequence of the parent Cas9 polypeptide, wherein said Cas9 endonuclease variant has endonuclease activity.

The Cas9 endonuclease variant substitution at position 155 can be selected from the group consisting of Y155H, Y155 N, Y 155 E, Y155 F resulting in a Cas9 Y155H variant (SEQ ID NO: 58), Cas9 Y155N variant (SEQ ID NO: 123), Cas9 Y155E variant (SEQ ID NO: 125 and Cas9 Y155F variant (SEQ ID NO: 127), respectively. DNA sequences encoding the Cas9 Y155 variants can be optimized for expression in a particular host organism as is well known in the art. Examples of DNA sequences encoding Cas9Y155 variant proteins are set forth in SEQ ID NOs: 122, 124, 126 and 128.

In one aspect, the Cas9 endonuclease variant described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to a parent Cas9 polypeptide set forth in SEQ ID NO: 1 and has at least two amino acid substitutions, one at position 86 and another one at position 98, wherein the amino acid positions of the variant are numbered by correspondence with the amino acid sequence of the parent Cas9 polypeptide, wherein said Cas9 endonuclease variant has endonuclease activity.

The Cas9 endonuclease variant substitution at position 86 can be an F86A substitution resulting in a Cas9 F86A variant.

The Cas9 endonuclease variant substitution at position 89 can be an F98A substitution resulting in a Cas9 F98A variant.

The Cas9 endonuclease variant can comprise at least two substitutions, a first substitution at position 86, such as a F86A substitution and a second substitution at position 98 such as a F98A substitution, resulting in a Cas9 F86A-F98A variant set forth in SEQ ID NO: 129

The Cas9 endonuclease variant can comprise at least three substitutions wherein the at least three substitutions comprise a first substitution at position 86, such as a F86A substitution, a second substitution at position 98 such as a F98A substitution, and a third substitution a selected from the group consisting of a Y155H, Y155 N, Y 155 E, Y155 F.

DNA sequences encoding the Cas9 Y155 variants can be optimized for expression in a particular host organism as is well known in the art. Examples of DNA sequences encoding Cas9Y155 variant proteins are set forth in SEQ ID NOs: 122, 124, 126 and 128. Examples of a DNA sequence encoding the Cas9F86A-F98A variant protein is set forth in SEQ ID NO: 130.

The Cas9 endonuclease variant comprising at least one, at least two, or at least three substitutions selected form the group consisting of positions 86, 98 and 155, or any combination thereof, when in complex with a guide polynucleotide to form a polynucleotide-guided endonuclease complex capable of modifying a target site) can have at least one improved property such as, but not limited to, an increased transformation efficiency, an increased DNA editing efficiency, or a combination thereof, when compared to its parent Cas9 endonuclease (in complex with the same guide polynucleotide to form a polynucleotide-guided endonuclease complex capable of modifying the same target site).

The at least one, at least two, or at least three substitutions selected form the group consisting of positions 86, 98 and 155 (or any combination) thereof can be combined with any other amino acid modification known to one skilled in the art. In one aspect, any one of the substitutions (or any one combination thereof) selected form the group consisting of positions 86, 98 and 155 described herein can be combined with any amino acid substitution located in the HNH and RuvC domain known to one skilled in the art to cause a Cas9 endonuclease to act as a nickase (Trevino A. E. and Feng Zhang, 2014, Methods in Enzymology, volume 546 pg 161-174). A "nickase" Cas9 (Cas9n) can be generated by alanine substitution at key catalytic residues within the HNH or RuvC domains—SpCas9 D10A inactivates RuvC (Jinek, M, et al, 2012, Science, 337(6096), 816-821), while N863A has been found to inactivate HNH (Nishimasu et al., 2014; Shen et al 2014 Nature Methods 11, 399-402). A H840A mutation (Shen et al 2014 Nature Methods 11, 399-402) was also reported to convert Cas9 into a nicking enzyme, however, this mutant had reduced levels of activity in mammalian cells compared with N863A (Nishimasu et al. 2014, Cell, 156(5), 935-949.)

In one aspect, Cas9(N863A), Cas9(D10A) and/or Cas9 (H840A) can be further modified to include the at least one substitution selected form the group consisting of positions 86, 98 and 155 (or any combination) described herein, optionally resulting in an improved property of the modified Cas9(N863A), Cas9(D10A) and/or Cas9(H840A), respectively.

In one aspect, any one of the substitutions selected form the group consisting of positions 86, 98 and 155 (or any combination thereof) described herein can be combined with the amino acid substitutions selected from the group consisting of D10A, H840A or N863A and H840A.

In one aspect, a Cas9 endonuclease variant having at least one amino acid substitution at position 155, wherein the amino acid positions of the variant are numbered by correspondence with the amino acid sequence of the parent Cas9 polypeptide, has at least one improved property selected from an increased transformation efficiency, an increased DNA editing efficiency, or a combination thereof when compared to said parent Cas9 endonuclease.

In one aspect, a Cas9 endonuclease variant having a Y155H substitution at position 155, wherein the amino acid positions of the variant are numbered by correspondence with the amino acid sequence of the parent Cas9 polypeptide, has an increased transformation efficiency, when compared to said parent Cas9 endonuclease. In one aspect this increased transformation efficiency is observed in a prokaryotic host cell, such as but not limiting to a *Bacillus* species or *Escherichia coli* (*E. coli*) host cell.

In one aspect, a Cas9 endonuclease variant having a Y155H substitution at position 155, wherein the amino acid positions of the variant are numbered by correspondence with the amino acid sequence of the parent Cas9 polypeptide, has an increased transformation efficiency and an increased DNA editing efficiency, when compared to said parent Cas9 endonuclease. In one aspect this increased transformation efficiency and increased DNA editing efficiency is observed in a prokaryotic host cell, such as but not limiting to a *Bacillus* species or *Escherichia coli* (*E. coli*) host cell.

The improved property of a Cas9 variant described herein includes increased transformation efficiency, wherein the transformation efficiency, when compared to the parent Cas endonuclease is increased by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 440, 450, 460, 470, 480, 490, or up to 500 fold, when compared to the parent Cas endonuclease.

The improved property of a Cas9 variant described herein includes increased DNA editing efficiency, wherein the DNA editing efficiency, when compared to the parent Cas endonuclease is increased by at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 110%, 120%, 130%, 140%, 150%, 160%, 170%, 180%, 190%, 200%, 210%, 220%, 230%, or 250%, or at least about 2, 3, 4, 5, 6, 7, 8, 9, up to 10 fold, when compared to the parent Cas endonuclease.

Cas endonuclease variants described herein, can be used for genome modification of prokaryotic and eukaryotic cells and organisms as further described herein.

The Cas endonuclease, or functional fragment or variant thereof, for use in the disclosed methods, can be isolated from a recombinant source where the genetically modified host cell (e.g. a bacterial cell, an insect cell, a fungal cell, a yeast cell or human-derived cell line) is modified to express the nucleic acid sequence encoding the Cas protein. Alternatively, the Cas protein can be produced using cell free protein expression systems or be synthetically produced.

The Cas endonuclease, including the Cas9 Y155 endonuclease variant described herein, can comprise a modified form of the Cas polypeptide. The modified form of the Cas polypeptide can include an amino acid change (e.g., deletion, insertion, or substitution) that reduces the naturally-occurring nuclease activity of the Cas protein. For example, in some instances, the modified form of the Cas protein, including the Cas9 Y155 endonuclease variant described herein, has less than 50%, less than 40%, less than 30%, less than 20%, less than 10%, less than 5%, or less than 1% of the nuclease activity of the corresponding wild-type Cas polypeptide (US patent application US20140068797 A1, published on Mar. 6, 2014). In some cases, the modified form of the Cas polypeptide has no substantial nuclease activity and is referred to as catalytically "inactivated Cas" or "deactivated Cas (dCas)." An inactivated Cas/deactivated Cas includes a deactivated Cas endonuclease (dCas). A catalytically inactive Cas, including one originating from the Cas9 Y155 endonuclease variant described herein can be fused to a heterologous sequence as described herein.

Recombinant DNA constructs expressing the Cas endonuclease and guide polynucleotides described herein (including functional fragments thereof, bacterial-, fungal-, plant-, microbe-, or mammalian-codon optimized Cas proteins) can be stably integrated into the genome of an organism. For example, microorganisms can be produced that comprise a Cas gene stably integrated in the microbe's genome.

The Cas endonuclease described herein (such as but not limited to the Cas9 endonuclease Y155 variant described herein) can be expressed and purified by methods known in the art (such as those described in Example 2 of WO2016/186946, published Nov. 24, 2016 and incorporated herein by reference).

Cas Protein Fusions

A Cas endonuclease, or Cas endonuclease variant described herein, can be part of a fusion protein comprising one or more heterologous protein domains (e.g., 1, 2, 3, or more domains in addition to the Cas polypeptide). Such a fusion protein may comprise any additional protein sequence, and optionally a linker sequence between any two domains, such as between Cas polypeptide and a first heterologous domain. Examples of protein domains that may be fused to a Cas polypeptide include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas endonuclease can also be in fusion with a protein that binds DNA molecules or other molecules, such as maltose binding protein (MBP), S-tag, Lex A DNA binding domain (DBD), GAL4A DNA binding domain, and herpes simplex virus (HSV) VP16.

A Cas endonuclease can comprise a heterologous regulatory element such as a nuclear localization sequence (NLS). A heterologous NLS amino acid sequence may be of sufficient strength to drive accumulation of a Cas endonuclease in a detectable amount in the nucleus of a cell herein. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. The Cas gene can be operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region. Non-limiting examples of suitable NLS sequences herein include those disclosed in U.S. Pat. Nos. 6,660,830 and 7,309,576, which are both incorporated by reference herein. A heterologous NLS amino acid sequence include plant, viral and mammalian nuclear localization signals.

A catalytically active and/or inactive Cas endonuclease, can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 endonuclease can also be fused to a FokI nuclease to generate double-strand breaks (Guilinger et al. Nature biotechnology, volume 32, number 6, June 2014).

Guide Polynucleotides

As used herein, the term "guide polynucleotide", relates to a polynucleotide sequence that can form a complex with a Cas endonuclease, and enables the Cas endonuclease to recognize, bind to, and optionally nick or cleave a DNA target site. The guide polynucleotide can be a single molecule or a double molecule. The guide polynucleotide sequence can be a RNA sequence, a DNA sequence, or a combination thereof (a RNA-DNA combination sequence).

Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA".

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. (U.S. Patent Application US20150082478, published on Mar. 19, 2015 and US20150059010, published on Feb. 26, 2015, both are herein incorporated by reference). In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In certain embodiments, the RNA that guides the RNA/Cas9 endonuclease complex is a duplexed RNA comprising a duplex crRNA-tracrRNA.

In one aspect, the guide polynucleotide is a guide polynucleotide capable of forming a PGEN comprising at least one guide polynucleotide and at least one Cas9 endonuclease variant described herein, wherein said guide polynucleotide comprises a first nucleotide sequence domain (VT domain) that is complementary to a nucleotide sequence in a target DNA, and a second nucleotide sequence domain that interacts with said Cas endonuclease polypeptide.

In one aspect, the guide polynucleotide is a guide polynucleotide described herein, wherein the first nucleotide sequence domain (VT domain) and the second nucleotide sequence domain is selected from the group consisting of a DNA sequence, a RNA sequence, and a combination thereof.

In one aspect, the guide polynucleotide is a guide polynucleotide described herein, wherein the first nucleotide sequence and the second nucleotide sequence domain is selected from the group consisting of RNA backbone modifications that enhance stability, DNA backbone modifications that enhance stability, and a combination thereof (see Kanasty et al., 2013, Common RNA-backbone modifications, Nature Materials 12:976-977)

The guide polynucleotide includes a dual RNA molecule comprising a chimeric non-naturally occurring crRNA (non-covalently) linked to at least one tracrRNA. A chimeric non-naturally occurring crRNA includes a crRNA that comprises regions that are not found together in nature (i.e., they are heterologous with each other). For example, a non-naturally occurring crRNA is a crRNA wherein the naturally occurring spacer sequence is exchanged for a heterologous Variable Targeting domain. A non-naturally occurring crRNA comprises a first nucleotide sequence domain (referred to as Variable Targeting domain or VT domain) that can hybridize to a nucleotide sequence in a target DNA, linked to a second nucleotide sequence (also referred to as a tracr mate sequence) such that the first and second sequence are not found linked together in nature.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) the target site.

The term "variable targeting domain" or "VT domain" is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length.

The variable targeting domain can comprises a contiguous stretch of 12 to 30, 12 to 29, 12 to 28, 12 to 27, 12 to 26, 12 to 25, 12 to 26, 12 to 25, 12 to 24, 12 to 23, 12 to 22, 12 to 21, 12 to 20, 12 to 19, 12 to 18, 12 to 17, 12 to 16, 12 to 15, 12 to 14, 12 to 13, 13 to 30, 13 to 29, 13 to 28, 13 to 27, 13 to 26, 13 to 25, 13 to 26, 13 to 25, 13 to 24, 13 to 23, 13 to 22, 13 to 21, 13 to 20, 13 to 19, 13 to 18, 13 to 17, 13 to 16, 13 to 15, 13 to 14, 14 to 30, 14 to 29, 14 to 28, 14 to 27, 14 to 26, 14 to 25, 14 to 26, 14 to 25, 14 to 24, 14 to 23, 14 to 22, 14 to 21, 14 to 20, 14 to 19, 14 to 18, 14 to 17, 14 to 16, 14 to 15, 15 to 30, 15 to 29, 15 to 28, 15 to 27, 15 to 26, 15 to 25, 15 to 26, 15 to 25, 15 to 24, 15 to 23, 15 to 22, 15 to 21, 15 to 20, 15 to 19, 15 to 18, 15 to 17, 15 to 16, 16 to 30, 16 to 29, 16 to 28, 16 to 27, 16 to 26, 16 to 25, 16 to 24, 16 to 23, 16 to 22, 16 to 21, 16 to 20, 16 to 19, 16 to 18, 16 to 17, 17 to 30, 17 to 29, 17 to 28, 17 to 27, 17 to 26, 17 to 25, 17 to 24, 17 to 23, 17 to 22, 17 to 21, 17 to 20, 17 to 19, 17 to 18, 18 to 30, 18 to 29, 18 to 28, 18 to 27, 18 to 26, 18 to 25, 18 to 24, 18 to 23, 18 to 22, 18 to 21, 18 to 20, 18 to 19, 19 to 30, 19 to 29, 19 to 28, 19 to 27, 19 to 26, 19 to 25, 19 to 24, 19 to 23, 19 to 22, 19 to 21, 19 to 20, 20 to 30, 20 to 29, 20 to 28, 20 to 27, 20 to 26, 20 to 25, 20 to 24, 20 to 23, 20 to 22, 20 to 21, 21 to 30, 21 to 29, 21 to 28, 21 to 27, 21 to 26, 21 to 25, 21 to 24, 21 to 23, 21 to 22, 22 to 30, 22 to 29, 22 to 28, 22 to 27, 22 to 26, 22 to 25, 22 to 24, 22 to 23, 23 to 30, 23 to 29, 23 to 28, 23 to 27, 23 to 26, 23 to 25, 23 to 24, 24 to 30, 24 to 29, 24 to 28, 24 to 27, 24 to 26, 24 to 25, 25 to 30, 25 to 29, 25 to 28, 25 to 27, 25 to 26, 26 to 30, 26 to 29, 26 to 28, 26 to 27, 27 to 30, 27 to 29, 27 to 28, 28 to 30, 28 to 29, or 29 to 30 nucleotides.

The variable targeting domain can be composed of a DNA sequence, a RNA sequence, a modified DNA sequence, a modified RNA sequence, or any combination thereof. The VT domain can be complementary to target sequences derived from prokaryotic or eukaryotic DNA.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide (also referred to as "loop") can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. The loop can be 3-4, 3-5, 3-6, 3-7, 3-8, 3-9, 3-10, 3-11, 3-12, 3-13, 3-14, 3-15, 3-20, 3-30, 3-40, 3-50, 3-60, 3-70, 3-80, 3-90, 3-100, 4-5, 4-6, 4-7, 4-8, 4-9, 4-10, 4-11, 4-12, 4-13, 4-14, 4-15, 4-20, 4-30, 4-40, 4-50, 4-60, 4-70, 4-80, 4-90, 4-100, 5-6, 5-7, 5-8, 5-9, 5-10, 5-11, 5-12, 5-13, 5-14, 5-15, 5-20, 5-30, 5-40, 5-50, 5-60, 5-70, 5-80, 5-90, 5-100, 6-7, 6-8, 6-9, 6-10, 6-11, 6-12, 6-13, 6-14, 6-15, 6-20, 6-30, 6-40, 6-50, 6-60, 6-70, 6-80, 6-90, 6-100, 7-8, 7-9, 7-10, 7-11, 7-12, 7-13, 7-14, 7-15, 7-20, 7-30, 7-40, 7-50, 7-60, 7-70, 7-80, 7-90, 7-100, 8-9, 8-10, 8-11, 8-12, 8-13, 8-14, 8-15, 8-20, 8-30, 8-40, 8-50, 8-60, 8-70, 8-80, 8-90, 8-100, 9-10, 9-11, 9-12, 9-13, 9-14, 9-15, 9-20, 9-30, 9-40, 9-50, 9-60, 9-70, 9-80, 9-90, 9-100, 10-20, 20-30, 30-40, 40-50, 50-60, 70-80, 80-90 or 90-100 nucleotides in length.

In another aspect, the nucleotide sequence linking the crNucleotide and the tracrNucleotide of a single guide polynucleotide can comprise a tetraloop sequence, such as, but not limiting to a GAAA tetraloop sequence.

The single guide polynucleotide includes a chimeric non-naturally occurring single guide RNA. The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). A chimeric non-naturally occurring guide RNA comprising regions that are not found together in nature (i.e., they are heterologous with each other). For example, a chimeric non-naturally occurring guide RNA comprising a first nucleotide sequence domain (referred to as Variable Targeting domain or VT domain) that can hybridize to a nucleotide sequence in a target DNA, linked to a second nucleotide sequence that can recognize the Cas endonuclease, such that the first and second nucleotide sequence are not found linked together in nature.

The chimeric non-naturally occurring guide RNA can comprise a crRNA or and a tracrRNA of the type II CRISPR/Cas system that can form a complex with a type II Cas endonuclease, such as the Cas9 endonuclease variant described herein, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

Production and Stabilization of Guide Polynucleotides

The guide polynucleotide can be produced by any method known in the art, including chemically synthesizing guide polynucleotides (such as but not limiting to Hendel et al. 2015, Nature Biotechnology 33, 985-989), in vitro generated guide polynucleotides, and/or self-splicing guide RNAs (such as but not limiting to Xie et al. 2015, PNAS 112: 3570-3575).

A method of expressing RNA components such as guide RNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161). This strategy has been successfully applied in cells of several different species including maize and soybean (US20150082478, published on Mar. 19, 2015). Methods for expressing RNA components that do not have a 5' cap have been described (WO2016/025131, published on Feb. 18, 2016).

In some aspects, a subject nucleic acid (e.g., a guide polynucleotide, a nucleic acid comprising a nucleotide sequence encoding a guide polynucleotide; a nucleic acid encoding Cas protein; a crRNA or a nucleotide encoding a crRNA, a tracrRNA or a nucleotide encoding a tracrRNA, a nucleotide encoding a VT domain, a nucleotide encoding a CPR domain, etc.) comprises a modification or sequence that provides for an additional desirable feature (e.g., modified or regulated stability; subcellular targeting; tracking, e.g., a fluorescent label; a binding site for a protein or protein complex; etc.). Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The terms "5'-cap" and "7-methylguanylate ($m^7G$) cap" are used interchangeably herein. A 7-methylguanylate residue is located on the 5' terminus of messenger RNA (mRNA) in eukaryotes. RNA polymerase II (Pol 11) transcribes mRNA in eukaryotes. Messenger RNA capping occurs generally as follows: The most terminal 5' phosphate group of the mRNA transcript is removed by RNA terminal phosphatase, leaving two terminal phosphates. A guanosine monophosphate (GMP) is added to the terminal phosphate of the transcript by a guanylyl transferase, leaving a 5'-5' triphosphate-linked guanine at the transcript terminus. Finally, the 7-nitrogen of this terminal guanine is methylated by a methyl transferase.

Guided Cas Systems

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "Polynucleotide-guided endonuclease", "PGEN" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s), or fragments and variants thereof, and suitable polynucleotide component(s) of any of the known CRISPR systems (Horvath and Barrangou, 2010, Science 327:167-170; Makarova et al. 2015, Nature Reviews Microbiology Vol. 13:1-15; Zetsche et al., 2015, Cell 163, 1-13; Shmakov et al., 2015, Molecular_Cell 60, 1-13). A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component.

A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas protein disclosed herein), or a variant thereof retaining some or all activity in each endonuclease domain of the Cas protein, is a suitable example of a Cas endonuclease that can cleave both strands of a DNA target sequence.

A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (*Proc. Natl. Acad. Sci. U.S.A.* 109:E2579-E2586), Jinek et al. (*Science* 337: 816-821), Sapranauskas et al. (*Nucleic Acids Res.* 39:9275-9282) and U.S. Patent Appl. Publ. No. 2014/0189896, which is incorporated by reference herein.

For example, a Cas9 nickase herein can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains). Also for example, a Cas9 nickase herein can comprise an *S. pyogenes* Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., *Cell* 156:935-949).

A Cas9 nickase herein can be used for various purposes in host cells of the disclosed invention. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

A pair of Cas nickases can be used to increase the specificity of DNA targeting. In general, this can be done by providing two Cas nickases that, by virtue of being associated with RNA components with different guide sequences, target and nick nearby DNA sequences on opposite strands in the region for desired targeting. Such nearby cleavage of each DNA strand creates a double-strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas nickase proteins herein can be used in a Cas nickase pair. For example, a Cas9 nickase with a mutant RuvC domain, but functioning HNH domain (i.e., Cas9 HNH+/RuvC−), can be used (e.g., *Streptococcus pyogenes* Cas9 HNH+/RuvC−). Each Cas9 nickase (e.g., Cas9 HNH+/RuvC−) can be directed to specific DNA sites nearby each other (up to 100 base pairs apart) by using suitable RNA components herein with guide RNA sequences targeting each nickase to each specific DNA site.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. Non-limiting examples of such a Cas9 protein comprise any of the RuvC and HNH nuclease domain mutations disclosed above (e.g., an *S. pyogenes* Cas9 with an Asp-10 substitution such as Asp-10-Ala and a His-840 substitution such as His-840-Ala). A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain.

A guide polynucleotide/Cas endonuclease complex can comprise a Cas endonuclease variant, or active fragment thereof, described herein, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.

In one aspect the guide polynucleotide/Cas endonuclease complex is a complex of a guide polynucleotide and a Cas9 endonuclease variant described herein, wherein said guide polynucleotide is a chimeric non-naturally occurring guide polynucleotide, wherein said Cas9 endonuclease variant has at least one improved property such as, but not limited to, increased transformation efficiency increased DNA editing efficiency, reduced off target cleavage, or any combination thereof, when compared to a its parent Cas endonuclease (in complex with the same guide polynucleotide to form a polynucleotide-guided endonuclease complex capable of modifying the same target site).

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide described herein and having at least one amino acid substitution at a position outside its HNH and RuVC domain, wherein the amino acid positions of the variant are numbered by correspondence with the amino acid sequence of the parent Cas9 polypeptide, wherein said Cas9 endonuclease variant has endonuclease activity.

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide set forth in SEQ ID NO: 1 and having at least one amino acid substitution at position 155, wherein the amino acid positions of the variant are numbered by correspondence with the amino acid sequence of the parent Cas9 polypeptide, wherein said Cas9 endonuclease variant has endonuclease activity.

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide set forth in SEQ ID NO: 1 and having at least two amino acid substitution, a first one at position 86 and a second one at position 98 wherein the amino acid positions of the variant are numbered by correspondence with the amino acid sequence of the parent Cas9 polypeptide, wherein said Cas9 endonuclease variant has endonuclease activity.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease, that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site The guided Cas systems described herein can be expressed in a host cell from one or more expression constructs. In some aspects, the Cas endonuclease variant described herein can be expressed from an expression cassette directing the expression of the Cas protein in a prokaryotic or eukaryotic cell, and the guide polynucleotide can be expressed from a second expression cassette directing the expression of the guide polynucleotide in the prokaryotic or eukaryotic cell.

The present disclosure further provides expression constructs for expressing in a prokaryotic or eukaryotic cell/organism a guide RNA/Cas system that is capable of recognizing, binding to, and optionally nicking, unwinding, or cleaving all or part of a target sequence.

Expression Cassettes and Recombinant DNA Constructs

Polynucleotides disclosed herein can be provided in an expression cassette (also referred to as DNA construct) for expression in an organism of interest. The term "expression", as used herein, refers to the production of a functional end-product (e.g., a crRNA, a tracrRNA, a mRNA, a guide RNA, or a polypeptide (protein) in either precursor or mature form. The term "expression" includes any step involved in the production of a polypeptide including, but not limited to, transcription, post-transcriptional modification, translation, post-translational modification, and secretion.

The expression cassette can include 5' and 3' regulatory sequences operably linked to a polynucleotide as disclosed herein.

"Operably linked" is intended to mean a functional linkage between two or more elements. For example, an operable linkage between a polynucleotide of interest and a regulatory sequence (e.g., a promoter) is a functional link that allows for expression of the polynucleotide of interest (i.e., the polynucleotide of interest is under transcriptional control of the promoter). Operably linked elements may be contiguous or non-contiguous. When used to refer to the joining of two protein coding regions, by operably linked is intended that the coding regions are in the same reading frame.

The expression cassettes disclosed herein may include in the 5'-3' direction of transcription, a transcriptional and translational initiation region (i.e., a promoter), a polynucleotide of interest, and a transcriptional and translational termination region (i.e., termination region) functional in the host cell (e.g., a eukaryotic cell). Expression cassettes are also provided with a plurality of restriction sites and/or recombination sites for insertion of the polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, “heterologous” in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein or known in the art. The stacked polynucleotides may be operably linked to the same promoter as the initial polynucleotide, or may be operably linked to a separate promoter polynucleotide.

Expression cassettes may comprise a promoter operably linked to a polynucleotide of interest, along with a corresponding termination region. The termination region may be native to the transcriptional initiation region, may be native to the operably linked polynucleotide of interest or to the promoter sequences, may be native to the host organism, or may be derived from another source (i.e., foreign or heterologous). Convient termination regions are available from phage sequences, e.g. lambda phage t0 termination region or stong terminators from prokaryotic ribosomal RNA operons. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed or targeted organism. For example, the polynucleotides can be synthesized or altered to use organism-preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary m RNA structures.

The expression cassettes may additionally contain 5' leader sequences. Such leader sequences can act to enhance translation. 5' leader sequences used interchangeably with 5' untranslated regions could come from well known and well characterized bacterial UTRs such as those from the *Bacillus subtilis* aprE gene or the *Bacillus licheniformis* amyl gene or any bacterial ribosomal protein gene. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In some embodiments, a nucleotide sequence encoding a guide nucleotide and/or a Cas protein is operably linked to a control element, e.g., a transcriptional control element, such as a promoter. The transcriptional control element may be functional in either a eukaryotic cell, e.g., a plant, mammalian cell or fungal cell; or a prokaryotic cell (e.g., bacterial or archaeal cell). In some embodiments, a nucleotide sequence encoding a guide nucleotide and/or a Cas protein is operably linked to multiple control elements that allow expression of the nucleotide sequence encoding a guide nucleotide and/or a Cas protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. The expression cassette may also contain a ribosome binding site for translation initiation and a transcription terminator. The expression cassette may also contain one or more nuclear localization sequences (NLS sequences) to direct the guide nucleotide and/or a Cas protein to the nucleus in a eukaryotic cell. The expression cassette may also include appropriate sequences for amplifying expression. The expression cassette may also include nucleotide sequences encoding protein tags (e.g., 6×His tag, hemagglutinin tag, green fluorescent protein, etc.) that are fused to the Cas protein, thus resulting in a chimeric polypeptide.

For transcription in a fungal host, non-limiting examples of useful promoters include those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* glucoamylase, *Rhizomucor miehei* lipase, *Aspergillus oryzae* alkaline protease, *Aspergillus oryzae* triose phosphate isomerase, *Aspergillus nidulans* acetamidase and the like. When a gene encoding a Cas endonuclease is expressed in a bacterial species such as an *E. coli*, a suitable promoter can be selected, for example, from a bacteriophage promoter including a T7 promoter and a phage lambda promoter. Along these lines, examples of suitable promoters for the expression in a yeast species include, but are not limited to, the Gal 1 and Gal 10 promoters of *Saccharomyces cerevisiae* and the *Pichia pastoris* AOX1 or AOX2 promoters. Expression in filamentous fungal host cells often involves cbh1, which is an endogenous, inducible promoter from *T. reesei* or constitutive glycolytic promoters (e.g., pki). For example, see Liu et al. 2008.

Non-limiting examples of promoters for directing the transcription of a DNA sequence (such as but not limiting to DNA sequences encoding a Cas endonuclease variant described herein) in a bacterial host, include the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xylA and xylB genes, and the like.

Expression cassettes can be comprised in lineair DNA, in circular DNA, in recombinant DNA, in plasmid or in vectors.

As used herein, "recombinant" refers to an artificial combination of two otherwise separated segments of sequence, e.g., by chemical synthesis or by the manipulation of isolated segments of nucleic acids by genetic engineering techniques. The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompasses a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

As used herein, "recombinant DNA construct" or "recombinant DNA" refers to an expression cassette comprising an artificial combination of nucleic acid fragments. The recombinant DNA construct can include 5' and 3' regulatory sequences operably linked to a polynucleotide as disclosed herein.

For example, a recombinant DNA construct may comprise regulatory sequences and coding sequences that are derived from different sources. Such a construct may be used by itself or may be used in conjunction with a vector. If a vector is used, then the choice of vector is dependent upon the method that will be used to introduce the vector into the host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, N.Y. (1989).

In one aspect, the recombinant DNA construct includes heterologous 5' and 3' regulatory sequences operably linked to a Cas9 endonuclease variant as disclosed herein. These regulatory sequences include but are not limited to a transcriptional and translational initiation region (i.e., a promoter), a nuclear localization signal, and a transcriptional and translational termination region (i.e., termination region) functional in the host cell (such as bacterial or fungal cell).

In one aspect, the recombinant DNA construct comprises a DNA encoding a Cas9 endonuclease variant described herein, wherein said Cas9 endonuclease variant is operably linked to or comprises a heterologous regulatory element such as a nuclear localization sequence (NLS).

In one aspect, the expression cassette or the recombinant DNA herein comprises a promoter operably linked to a nucleotide sequence encoding a Cas9 endonuclease variant described herein and a promoter operably linked to a guide RNA of the present disclosure. The promoter is capable of driving expression of an operably linked nucleotide sequence in a prokaryotic or eukaryotic cell/organism.

The terms "plasmid" or "vector" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded polynucleotide, derived from any source, in which a number of nucleotide sequences have been joined or recombined into a unique construction which is capable of introducing a polynucleotide of interest into a cell.

Target Sites

The terms “target site”, “target sequence”, “target site sequence, “target DNA”, “target locus”, “genomic target site”, “genomic target sequence”, “genomic target locus” and “protospacer”, are used interchangeably herein and refer to a polynucleotide sequence such as, but not limited to, a nucleotide sequence on a chromosome, episome, a transgenic locus, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave.

The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms “endogenous target sequence” and “native target sequence” are used interchangeable herein to refer to a target sequence that is endogenous or native to the genome of a cell and is at the endogenous or native position of that target sequence in the genome of the cell. An “artificial target site” or “artificial target sequence” are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An “altered target site”, “altered target sequence”, “modified target site”, “modified target sequence” are used interchangeably herein and refer to a target sequence as disclosed herein that comprises at least one alteration when compared to non-altered target sequence. Such “alterations” include, for example: (i) replacement of at least one nucleotide, (ii) a deletion of at least one nucleotide, (iii) an insertion of at least one nucleotide, or (iv) any combination of (i)-(iii).

The target site for a Cas endonuclease can be very specific and can often be defined to the exact nucleotide position, whereas in some cases the target site for a desired genome modification can be defined more broadly than merely the site at which DNA cleavage occurs, e.g., a genomic locus or region that is to be deleted from the genome. Thus, in certain cases, the genome modification that occurs via the activity of Cas/guide RNA DNA cleavage is described as occurring “at or near” the target site.

Methods for “modifying a target site” and “altering a target site” are used interchangeably herein and refer to methods for producing an altered target site.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other cases, the incisions could be staggered to produce single-stranded overhangs, also called “sticky ends”, which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by a Cas endonuclease.

Assays to measure the single or double-strand break of a target site by an endonuclease are known in the art and generally measure the overall activity and specificity of the agent on DNA substrates containing recognition sites.

Protospacer Adjacent Motif (PAM)

A “protospacer adjacent motif” (PAM) herein refers to a short nucleotide sequence adjacent to a target sequence (protospacer) that is recognized (targeted) by a guide polynucleotide/Cas endonuclease (PGEN) system. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

A PAM herein is typically selected in view of the type of PGEN being employed. A PAM sequence herein may be one recognized by a PGEN comprising a Cas, such as the Cas9 variants described herein, derived from any of the species disclosed herein from which a Cas can be derived, for example. In certain embodiments, the PAM sequence may be one recognized by an RGEN comprising a Cas9 derived from *S. pyogenes, S. thermophilus, S. agalactiae, N. meningitidis, T. denticola*, or *F. novicida*. For example, a suitable Cas9 derived from *S. pyogenes*, Including the Cas9 Y155 variants described herein, could be used to target genomic sequences having a PAM sequence of NGG; N can be A, C, T, or G). As other examples, a suitable Cas9 could be derived from any of the following species when targeting DNA sequences having the following PAM sequences: *S. thermophilus* (NNAGAA), *S. agalactiae* (NGG), NNAGAAW [W is A or T], NGGNG), *N. meningitidis* (NNNNGATT), *T. denticola* (NAAAAC), or *F. novicida* (NG) (where N's in all these particular PAM sequences are A, C, T, or G). Other examples of Cas9/PAMs useful herein include those disclosed in Shah et al. (*RNA Biology* 10:891-899) and Esvelt et al. (*Nature Methods* 10:1116-1121), which are incorporated herein by reference.

Uses of Guided Cas Protein Systems

The compositions and methods provided herein find use in a wide variety of host cells. As used herein, a “host cell,” refers to any cell type (such as but not limiting to, an in vivo or in vitro cell, a eukaryotic cell, a prokaryotic cell, or a cell from a multicellular organism (e.g., a cell line) cultured as a unicellular entity), used as recipients for a nucleic acid or for a genome modification system (such as the guide polynucleotide/Cas endonuclease system described herein). The term "host cell" includes the progeny of the original cell which has been transformed, transfected or transduced by the nucleic acid or guide polynucleotide/Cas endonuclease complex described herein. A "recombinant host cell" (also referred to as a "genetically modified host cell") is a host cell into which has been introduced a heterologous nucleic acid, e.g., a recombinant DNA construct, or which has been introduced and comprises a genome modification system such as the guide polynucleotide/Cas endonuclease system described herein. For example, a subject bacterial host cell includes a genetically modified bacterial host cell by virtue of introduction into a suitable bacterial host cell of an exogenous nucleic acid (e.g., a plasmid or recombinant DNA construct) and a subject eukaryotic host cell includes a genetically modified eukaryotic host cell (e.g., a fungal, mammalian germ cell or plant cell), by virtue of introduction into a suitable eukaryotic host cell of an exogenous nucleic acid.

In some embodiments, the host cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The guide polynucleotide/Cas systems described herein can be used for gene targeting.

The terms "gene targeting", "targeting", and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with a Cas endonuclease associated with a suitable polynucleotide component. Once a single or double-strand break is induced in the DNA, the cell's DNA repair mechanism is activated to repair the break via nonhomologous end-joining (NHEJ) or Homology-Directed Repair (HDR) processes which can lead to modifications at the target site.

The terms "knock-out", "gene knock-out" and "genetic knock-out" are used interchangeably herein. A knock-out represents a DNA sequence of a cell that has been rendered partially or completely inoperative by targeting with a Cas endonuclease, such as a Cas9 endonuclease variant described herein; such a DNA sequence prior to knock-out could have encoded an amino acid sequence, or could have had a regulatory function (e.g., promoter), for example.

As described herein, a guided Cas endonuclease can recognize, bind to a DNA target sequence and introduce a single strand (nick) or double-strand break. Once a single or double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements (such as chromosomal translocations) are possible (Siebert and Puchta, 2002, Plant Cell 14:1121-31; Pacher et al., 2007, Genetics 175:21-9).

A knock-out may be produced by an indel (insertion or deletion of nucleotide bases in a target DNA sequence through NHEJ), or by specific removal of sequence that reduces or completely destroys the function of sequence at or near the targeting site. The term "indel" herein refers to an insertion or deletion of nucleotide bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70p, 80, 90, or 100 bases If an indel is introduced within an open reading frame (ORF) of a gene, oftentimes the indel disrupts wild type expression of protein encoded by the ORF by creating a frameshift mutation.

In one embodiment, the disclosure describes a method for modifying a target site in the genome of a cell, the method comprising introducing into a cell at least one guide polynucleotide and at least one Cas9 endonuclease variant described herein, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

The guide polynucleotide/Cas endonuclease system can be used in combination with at least one polynucleotide modification template to allow for editing (modification) of a genomic nucleotide sequence of interest.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure comprises a method for editing a nucleotide sequence in the genome of a cell, the method comprising introducing into a cell at least one guide polynucleotide, at least one Cas9 endonuclease variant described herein, and a polynucleotide modification template, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, wherein said polynucleotide modification template comprises at least one nucleotide modification of said nucleotide sequence, and optionally further comprising selecting at least one cell that comprises the edited nucleotide sequence.

The nucleotide to be edited can be located within or outside a target site recognized and cleaved by a Cas endonuclease. In one embodiment, the at least one nucleotide modification is not a modification at a target site recognized and cleaved by a Cas endonuclease, such as the Cas9 endonuclease variant described herein. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

The method for editing a nucleotide sequence in the genome of a cell can be a method without the use of an exogenous selectable marker by restoring function to a non-functional gene product as described in WO2017/070029, published Apr. 27, 2017 and WO2017/070032, published Apr. 27, 2017.

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination (HR) to provide integration of the polynucleotide of Interest at the target site. In one method described herein, a polynucleotide of interest is introduced into the organism cell via a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome.

The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, Nature Methods Vol. 10: 957-963).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., 2004, Plant Cell 16:342-52). Ectopic and/or epigenic DNA sequences may also serve as a DNA repair template for homologous recombination (Puchta, (1999) Genetics 152: 1173-81).

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932).

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some instances the regions of homology share significant sequence homology to the genomic sequence immediately flanking the target site, it is recognized that the regions of homology can be designed to have sufficient homology to regions that may be further 5' or 3' to the target site. The regions of homology can also have homology with a fragment of the target site along with downstream genomic regions In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Alteration of the genome of a prokaryotic and eukaryotic cell or organism cell, for example, through homologous recombination (HR), is a powerful tool for genetic engineering. Homologous recombination has been demonstrated in plants (Halfter et al., (1992) Mol Gen Genet 231:186-93) and insects (Dray and Gloor, 1997, Genetics 147:689-99). Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate *Tetrahymena thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo (Watson et al., 1992, Recombinant DNA, 2nd Ed., (Scientific American Books distributed by WH Freeman & Co.).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In one aspect, the disclosure comprises a method for modifying a target site in the genome of a cell, the method comprising introducing into a cell at least one guide polynucleotide, at least one Cas9 endonuclease variant described herein, and at least one donor DNA, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, wherein said donor DNA comprises a polynucleotide of interest, and optionally, further comprising identifying at least one cell that said polynucleotide of interest integrated in or near said target site.

In one aspect, the disclosure comprises a method for modifying the genome of a *Bacillus* host cell, said method comprising providing to a *Bacillus* host cell comprising at least one target sequence to be modified, at least one non-naturally occurring guide RNA and at least one Cas9 endonuclease variant described herein wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Bacillus* host cell, wherein the at least one genome target sequence has been modified. The modification at said target site can be selected from the group consisting of (i) a replacement of at least one nucleotide, (ii) a deletion of at least one nucleotide, (iii) an insertion of at least one nucleotide, and (iv) any combination of (i)-(iii).

In one aspect, the disclosure comprises a method for modifying the genome of an *E. coli* host cell, said method comprising providing to an *E. coli* host cell comprising at least one target sequence to be modified, at least one non-naturally occurring guide RNA and at least one Cas9 endonuclease variant described herein, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *E. coli* host cell, wherein the at least one genome target sequence has been modified.

In one aspect, the disclosure comprises a method for modifying the genome of a *Saccharomyces cerevisiae* host cell, said method comprising providing to a *Saccharomyces cerevisiae* host cell comprising at least one target sequence to be modified, at least one non-naturally occurring guide RNA and at least one Cas9 endonuclease variant described herein, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Saccharomyces cerevisiae* host cell, wherein the at least one genome target sequence has been modified.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Multiplexing

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide a guide polynucleotide/Cas endonuclease complex to a unique DNA target site.

The Cas9 endonuclease variants described herein can be used for targeted genome editing (via simplex and multiplex double-strand breaks and nicks) and targeted genome regulation (via tethering of epigenetic effector domains to either the Cas9 or sgRNA. Cas9 endonuclease variants described herein may also be engineered to function as an RNA-guided recombinase, and via RNA tethers could serve as a scaffold for the assembly of multiprotein and nucleic acid complexes (Mali et al. 2013 Nature Methods Vol. 10: 957-963.).

Complex Trait Loci

Polynucleotides of interest and/or traits can be stacked together in a complex trait locus as described in WO2012/129373, published Mar. 14, 2013 and in PCT/US13/22891, published Jan. 24, 2013, both hereby incorporated by reference. The guide polynucleotide/Cas endonuclease system, such as the system comprising a Cas9 endonuclease variant described herein, provides for an efficient system to generate single or double-strand breaks and allows for traits to be stacked in a complex trait locus.

Introduction of Polynucleotides, Polypeptides, Expression Cassettes, Recombinant DNA, or any One Component of a Guided Cas Protein System The polynucleotides, polypeptides, expression cassettes or recombinant DNA disclosed herein can be introduced into an organism using any method known in the art. Any one component of the guide polynucleotide/Cas system, the guide polynucleotide/Cas complex itself, as well as the polynucleotide modification template(s) and/or donor DNA(s), can be introduced into a cell by any method known in the art.

"Introducing" is intended to mean presenting to the organism, such as a cell or organism, the polynucleotide or polypeptide or polynucleotide-protein complex (such as a RGEN or PGEN), in such a manner that the component(s) gains access to the interior of a cell of the organism or to the cell itself. The methods and compositions do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a nucleic acid, protein or polynucleotide-protein complex (PGEN, RGEN) to the cell.

Methods for introducing polynucleotides, polypeptides, expression cassettes, recombinant DNA or a polynucleotide-protein complexes (PGEN, RGEN) into cells or organisms are known in the art including, but not limited to, natural competence (as described in WO2017/075195, WO2002/14490 and WO2008/7989), microinjection Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6), stable transformation methods, transient transformation methods, ballistic particle acceleration (particle bombardment) (U.S. Pat. Nos. 4,945,050; 5,879,918; 5,886,244; 5,932,782), whiskers mediated transformation (Ainley et al. 2013, Plant Biotechnology Journal 11:1126-1134; Shaheen A. and M. Arshad 2011 Properties and Applications of Silicon Carbide (2011), 345-358 Editor(s): Gerhardt, Rosario. Publisher: InTech, Rijeka, Croatia. CODEN: 69PQBP; ISBN: 978-953-307-201-2), *Agrobacterium*-mediated transformation (U.S. Pat. Nos. 5,563,055 and 5,981,840), direct gene transfer (Paszkowski et al., (1984) *EMBO J* 3:2717-22), viral-mediated introduction (U.S. Pat. Nos. 5,889,191, 5,889,190, 5,866,785, 5,589,367 and 5,316,931), transfection, transduction, cell-penetrating peptides, mesoporous silica nanoparticle (MSN)-mediated direct protein delivery, topical applications, sexual crossing, sexual breeding, and any combination thereof. Stable transformation is intended to mean that the nucleotide construct introduced into an organism integrates into a genome of the organism and is capable of being inherited by the progeny thereof. Transient transformation is intended to mean that a polynucleotide is introduced (directly or indirectly) into the organism and does not integrate into a genome of the organism or a polypeptide is introduced into an organism. Transient transformation indicates that the introduced composition is only temporarily expressed or present in the organism.

The guide polynucleotide (guide RNA, crNucleotide+tracrNucleotide, guide DNA and/or guide RNA-DNA molecule) can be introduced into a cell directly (transiently) as a single stranded or double stranded polynucleotide molecule. The guide RNA (or crRNA+tracrRNA) can also be introduced into a cell indirectly by introducing a recombinant DNA molecule comprising a heterologous nucleic acid fragment encoding the guide RNA (or crRNA+tracrRNA), operably linked to a specific promoter that is capable of transcribing the guide RNA (crRNA+tracrRNA molecules) in said cell. The specific promoter can be, but is not limited to, a RNA polymerase III promoter, which allow for transcription of RNA with precisely defined, unmodified, 5'- and 3'-ends (Ma et al., 2014, Mol. Ther. Nucleic Acids 3:e161; DiCarlo et al., 2013, Nucleic Acids Res. 41: 4336-4343; WO2015026887, published on Feb. 26, 2015). Any promoter capable of transcribing the guide RNA in a cell can be used and includes a heat shock/heat inducible promoter operably linked to a nucleotide sequence encoding the guide RNA.

A Cas endonuclease herein, can be introduced into a cell by directly introducing the Cas polypeptide itself (referred to as direct delivery of Cas endonuclease), the mRNA encoding the Cas protein, and/or the guide polynucleotide/Cas endonuclease complex itself, using any method known in the art. The Cas endonuclease can also be introduced into a cell indirectly by introducing a recombinant DNA molecule that encodes the Cas endonuclease. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in WO2016/073433, published May 12, 2016. Any promoter capable of expressing the Cas endonuclease variant herein in a cell can be used and includes a heat shock/heat inducible promoter operably linked to a nucleotide sequence encoding the Cas endonuclease.

Direct delivery of a polynucleotide modification template into cells can be achieved through particle mediated delivery, and any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in cells, such as eukaryotic cells.

The donor DNA can be introduced by any means known in the art. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed genome of the organism, such as a plant.

Direct delivery of any one of the guided Cas system components described herein can be accompanied by direct delivery (co-delivery) of other mRNAs that can promote the enrichment and/or visualization of cells receiving the guide polynucleotide/Cas endonuclease complex components. For example, direct co-delivery of the guide polynucleotide/Cas endonuclease components (and/or guide polynucleotide/Cas endonuclease complex itself) together with mRNA encoding phenotypic markers (such as but not limiting to transcriptional activators such as CRC (Bruce et al. 2000 The Plant Cell 12:65-79) can enable the selection and enrichment of cells without the use of an exogenous selectable marker by restoring function to a non-functional gene product as described in WO2017/070029, published Apr. 27, 2017 and WO 2017/070032, published Apr. 27, 2017.

Introducing a guide RNA/Cas endonuclease complex (RGEN) as described herein into a cell includes introducing the guide RNA/Cas endonuclease complex as a ribonucleotide-protein into the cell. The ribonucleotide-protein can be assembled prior to being introduced into the cell as described herein. The components comprising the guide RNA/Cas endonuclease ribonucleotide protein can be assembled in vitro or assembles by any means known in the art prior to being introduced into a cell (targeted for genome modification as described herein).

Plants, fungal and bacterial cells differ from human and animal cells in that plant, fungal and bacterial cells contain a cell wall which may act as a barrier to the direct delivery of the RGEN ribonucleoproteins and/or of the direct delivery of the RGEN components.

Direct delivery of the RGEN ribonucleoproteins into plant, fungal and bacterial cells can be achieved through particle mediated delivery (particle bombardment. Based on the experiments described herein, a skilled artesian can now envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RGEN ribonucleoproteins into fungal and bacterial cells.

Direct delivery of the RGEN ribonucleoprotein, allows for genome editing at a target site in the genome of a cell which can be followed by rapid degradation of the complex, and only a transient presence of the complex in the cell. This transient presence of the RGEN complex may lead to reduced off-target effects. In contrast, delivery of RGEN components (guide RNA, Cas9 endonuclease) via plasmid DNA sequences can result in constant expression of RGENs from these plasmids which can intensify off target effects (Cradick, T. J. et al (2013) Nucleic Acids Res 41:9584-9592; Fu, Y et al (2014) Nat. Biotechnol. 31:822-826.

Direct delivery can be achieved by combining any one component of the guide RNA/Cas endonuclease complex (RGEN), described herein, (such as at least one guide RNA, at least one Cas9 endonuclease variant), with a particle delivery matrix comprising a microparticle such as but not limited to of a gold particle, tungsten particle, and silicon carbide whisker particle)(see also WO2017/070029, published Apr. 27, 2017 and WO 2017/070032, published Apr. 27, 2017, which are incorporated herein in their entirety by reference).

In one aspect the guide polynucleotide/Cas endonuclease complex (RGEN), is a complex wherein the guide RNA and Cas9 endonuclease variant described herein forming the guide RNA/Cas endonuclease complex are introduced into the cell as RNA and protein, respectively.

In one aspect the guide polynucleotide/Cas endonuclease complex, is a complex wherein the guide RNA and Cas9 endonuclease variant described herein forming the guide RNA/Cas endonuclease complex are preassem bled in vitro and introduced into the cell as a ribonucleotide-protein complex.

Nucleic acids and proteins can be provided to a cell by any method including methods using molecules to facilitate the uptake of anyone or all components of a guided Cas system (protein and/or nucleic acids), such as cell-penetrating peptides and nanocariers (US20110035836, published Feb. 20, 2011), incorporated herein by reference.

Cells, Organisms

The presently disclosed Cas endonuclease variants, polynucleotides, peptides, guide polynucleotides, Cas endonucleases, polynucleotide modification templates, donor DNAs, guide polynucleotide/Cas endonuclease systems and any one combination thereof, can be introduced into a cell.

Cells include, but are not limited to, human, non-human, animal, bacterial, fungal, insect, yeast, non-conventional yeast, microbial, and plant cells as well as plants and seeds produced by the methods described herein.

Microbial cells employed in the methods and compositions disclosed herein may be any fungal host cells, filamentous fungal cells and bacterial cells. As used herein, the term "fungal cell", "fungi", "fungal host cell", and the like, as used herein includes the phyla Ascomycota, Basidiomycota, Chytridiomycota, and Zygomycota (as defined by Hawksworth et al., 1995), as well as the Oomycota (Hawksworth et al., 1995) and all mitosporic fungi (Hawksworth et al., 1995). In certain embodiments, the fungal host cell is a yeast cell, wherein the term "yeast" is meant ascosporogenous yeast (Endomycetales), basidiosporogenous yeast, and yeast belonging to the Fungi Imperfecti (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica*.

The term "non-conventional yeast" herein refers to any yeast that is not a *Saccharomyces* (e.g., *S. cerevisiae*) or *Schizosaccharomyces* yeast species. (see Non-Conventional Yeasts in Genetics, Biochemistry and Biotechnology: Practical Protocols" (K. Wolf, K. D. Breunig, G. Barth, Eds., Springer-Verlag, Berlin, Germany, 2003). Non-conventional yeast includes member of a genus selected from the group consisting of *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen*. Non-conventional yeast includes yeast that favor non-homologous end-joining (NHEJ) DNA repair processes over repair processes mediated by homologous recombination (HR). Definition of a non-conventional yeast along these lines—preference of NHEJ over HR—is further disclosed by Chen et al. (PLoS ONE 8:e57952), which is incorporated herein by reference. The term "yeast" herein refers to fungal species that predominantly exist in unicellular form. Yeast can alternative be referred to as "yeast cells" herein. A suitable example of a *Yarrowia* species is *Y. lipolytica*. Suitable examples of *Pichia* species include *P. pastoris, P. methanolica, P. stipitis, P. anomala* and *P. angusta*. Suitable examples of *Schwanniomyces* species include *S. castellii, S. alluvius, S. hominis, S. occidentalis, S. capriottii, S. etchellsii, S. polymorphus, S. pseudopolymorphus, S. vanrijiae* and *S. yamadae*. Suitable examples of *Kluyveromyces* species include *K. lactis, K. marxianus, K. fragilis, K. drosophilarum, K. thermotolerans, K. phaseolosporus, K. vanudenii, K. waltii, K. africanus* and *K. polysporus*. Suitable examples of Arxula species include *A. adeninivorans* and *A. terrestre*. Suitable examples of *Trichosporon* species include *T. cutaneum, T. capitatum, T. inkin* and *T. beemeri*. Suitable examples of *Candida* species include *C. albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis* and *C. zemplinina*. Suitable examples of *Ustilago* species include *U. avenae, U. esculenta, U. hordei, U. maydis, U. nuda* and *U. tritici*. Suitable examples of *Torulopsis* species include *T. geochares, T. azyma, T. glabrata* and *T. candida*. Suitable examples of *Zygosaccharomyces* species include *Z. bailii, Z. bisporus, Z. cidri, Z. fermentati, Z. florentinus, Z. kombuchaensis, Z. lentus, Z. mellis, Z. microellipsoides, Z. mrakii, Z. pseudorouxii* and *Z. rouxii*. Suitable examples of Trigonopsis species include *T. variabilis*. Suitable examples of *Cryptococcus* species include *C. laurentii, C. albidus, C. neoformans, C. gattii, C. uniguttulatus, C. adeliensis, C. aerius, C. albidosimilis, C. antarcticus, C. aquaticus, C. ater, C. bhutanensis, C. consortionis, C. curvatus, C. phenolicus, C. skinneri, C. terreus* and *C. vishniacci*. Suitable examples of *Rhodotorula* species include *R. acheniorum, R. tula, R. acuta, R. americana, R. araucariae, R. arctica, R. armeniaca, R. aurantiaca, R. auriculariae, R. bacarum, R. benthica, R. biourgei, R. bogoriensis, R. bronchialis, R. buffonii, R. calyptogenae, R. chungnamensis, R. cladiensis, R. coraffina, R. cresolica, R. crocea, R. cycloclastica, R. dairenensis, R. diffluens, R. evergladiensis, R. ferulica, R. foliorum, R. fragaria, R. fujisanensis, R. futronensis, R. gelatinosa, R. glacialis, R. glutinis, R. gracilis, R. graminis, R. grinbergsii, R. himalayensis, R. hinnulea, R. histolytica, R. hylophila, R. incarnata, R. ingeniosa, R. javanica, R. koishikawensis, R. lactosa, R. lamellibrachiae, R. laryngis, R. lignophila, R. lini, R. longissima, R. ludwigii, R. lysinophila, R. marina, R. martyniae-fragantis, R. matritensis, R. meli, R. minuta, R. mucilaginosa, R. nitens, R. nothofagi, R. oryzae, R. pacifica, R. paffida, R. peneaus, R. philyla, R. phylloplana, R. pilatii, R. pilimanae, R. pinicola, R. plicata, R. polymorpha, R. psychrophenolica, R. psychrophila, R. pustula, R. retinophila, R. rosacea, R. rosulata, R. rubefaciens, R. rubella, R. rubescens, R. rubra, R. rubrorugosa, R. rufula, R. rutila, R. sanguines, R. sanniei, R. sartoryi, R. silvestris, R. simplex, R. sinensis, R. slooffiae, R. sonckii, R. straminea, R. subericola, R. suganii, R. taiwanensis, R. taiwaniana, R. terpenoidalis, R. terrea, R. texensis, R. tokyoensis, R. ulzamae, R. vaniffica, R. vuilleminii, R. yarrowii, R. yunnanensis* and *R. zsoltii*. Suitable examples of Phaffia species include *P. rhodozyma*. Suitable examples of Sporobolomyces species include *S. alborubescens, S. bannaensis, S. beijingensis, S. bischofiae, S. clavatus, S. coprosmae, S. coprosmicola, S. coraffinus, S. dimmenae, S. dracophyffi, S. elongatus, S. gracilis, S. inositophilus, S. johnsonii, S. koalae, S. magnisporus, S. novozealandicus, S. odorus, S. patagonicus, S. productus, S. roseus, S. sasicola, S. shibatanus, S. singularis, S. subbrunneus, S. symmetricus, S.*

*syzygii, S. taupoensis, S. tsugae, S. xanthus* and *S. yunnanensis*. Suitable examples of *Pachysolen* species include *P. tannophilus*.

As used herein, the term "filamentous fungal cell" includes all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

In certain embodiments, the microbial host cells are bacterial cells, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* or a *Streptomyces* such as, e.g., a *Streptomyces lividans* or *Streptomyces murinus* or a gram negative bacterium, such as, e.g., an *E. coli* or a *Pseudomonas* sp.

For the aforementioned species, it is understood that the disclosure and source species would encompass both the perfect and imperfect states of such organisms, and other taxonomic equivalents thereof, e.g., anamorphs, regardless of the species name by which they are known. Those skilled in the art will readily recognize the identity of appropriate equivalents of such source species.

Strains of the above-mentioned species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The Cas9 endonuclease variants described herein can be used in methods for homologous recombination in a microbial cell and/or in methods for genome editing in a microbial cell. Methods employing a guide RNA/Cas endonuclease system for inserting a donor DNA with one or more short homology arms at a target site in the genome of a microbial cell (e.g., a filamentous fungal cell) have been disclosed (WO2017/019867, published Feb. 2, 2017). When modification of the genome of the microbial cell results in a phenotypic effect, a donor DNA is often employed that includes a polynucleotide of interest that is (or encodes) a phenotypic marker. Any convenient phenotypic marker can be used, including any selectable or screenable marker that allows one to identify, or select for or against a fungal cell that contains it, often under particular culture conditions. Thus, in some aspects of the present disclosure, the identification of microbial cells having a desired genome modification includes culturing the microbial population of cells that have received the Cas9 endonuclease variant and guide polynucleotide (and optionally a donor DNA) under conditions to select for cells having the modification at the target site. Any type selection system may be employed, including assessing for the gain or loss of an enzymatic activity in the fungal cell (also referred to as a selectable marker), e.g., the acquisition of antibiotic resistance or gain/loss of an auxotrophic marker.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by "grain" is intended the mature seed produced by commercial growers for purposes other than growing or reproducing the species. Progeny, variants, and mutants of the regenerated plants are also included within the scope of the disclosure, provided that these parts comprise genomic modifications of the regenerated plant such as those resulting from transformation or genome editing.

Any plant or plant part can be used, including monocot and dicot plants or plant parts.

Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum* species, *Triticum aestivum, Triticum monococcum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses.

The term "dicotyledonous" or "dicot" refers to the subclass of angiosperm plants also knows as "dicotyledoneae" and includes reference to whole plants, plant organs (e.g., leaves, stems, roots, etc.), seeds, plant cells, and progeny of the same. Examples of dicot plants that can be used include, but are not limited to, soybean (*Glycine max*), *Brassica* species (Canola) (*Brassica napus, B. campestris, Brassica rapa, Brassica. juncea*), alfalfa (*Medicago sativa*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum, Gossypium barbadense*), and peanut (*Arachis hypogaea*), tomato (*Solanum lycopersicum*), potato (*Solanum tuberosum*.

Plants that can be used include safflower (*Carthamus tinctorius*), *sweet potato* (*Ipomoea batatus*), cassava (*Manihot esculenta*), coffee (*Coffea* spp.), coconut (*Cocos nucifera*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum.*

Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*).

The term "plant" includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A fertile plant is a plant that produces viable male and female gametes and is self-fertile. Such a self-fertile plant can produce a progeny plant without the contribution from any other plant of a gamete and the genetic material contained therein.

Definitions

An "allele" or "allelic variant" is one of several alternative forms of a gene occupying a given locus on a chromosome. When all the alleles present at a given locus on a chromosome are the same, that organism is homozygous at that locus. If the alleles present at a given locus on a chromosome differ, that organism is heterozygous at that locus. An allelic variant of a polypeptide is a polypeptide encoded by an allelic variant of a gene.

"Coding sequence" refers to a polynucleotide sequence which codes for a specific amino acid sequence. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended. Methods are available in the art for synthesizing codon-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a host organism. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given host organism (such as a plant), as calculated by reference to known genes expressed in the host cell. When possible, the sequence is modified to avoid one or more predicted hairpin secondary mRNA structures.

The term “conserved domain” or “motif” means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or “signatures”, to determine if a protein with a newly determined sequence belongs to a previously identified protein family.

As used herein, “nucleic acid” means a polynucleotide and includes a single or a double-stranded polymer of deoxyribonucleotide or ribonucleotide bases. Nucleic acids may also include fragments and modified nucleotides. Thus, the terms “polynucleotide”, “nucleic acid sequence”, “nucleotide sequence” and “nucleic acid fragment” are used interchangeably to denote a polymer of RNA and/or DNA and/or RNA-DNA that is single- or double-stranded, optionally containing synthetic, non-natural, or altered nucleotide bases. Nucleotides (usually found in their 5'-monophosphate form) are referred to by their single letter designation as follows: “A” for adenosine or deoxyadenosine (for RNA or DNA, respectively), “C” for cytosine or deoxycytosine, “G” for guanosine or deoxyguanosine, “U” for uridine, “T” for deoxythymidine, “R” for purines (A or G), “Y” for pyrimidines (C or T), “K” for G or T, “H” for A or C or T, “I” for inosine, and “N” for any nucleotide (nucleotide (e.g., N can be A, C, T, or G, if referring to a DNA sequence; N can be A, C, U, or G, if referring to an RNA sequence).

The term “increased” as used herein may refer to a quantity or activity that is at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 440, 450, 460, 470, 480, 490, or 500 fold fold more than the quantity or activity for which the increased quantity or activity is being compared. The terms “increased”, “greater than”, and “improved” are used interchangeably herein. The term “increased” can be used to characterize the transformation or gene editing efficiency of a protein such as the Cas9 endonuclease variant described herein.

In one aspect the increase is an increase in transformation efficiency of a prokaryotic or eukaryotic cell when a Cas9 variant described herein, such as but not limiting to a Cas9 Y155 variant or a Cas9 F86A+F98A variant, is used as part of a PGEN when compared to the same PGEN but comprising its parent (wild type) Cas9 instead, wherein the increase in transformation efficiency is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 440, 450, 460, 470, 480, 490, or 500 fold In one aspect the increase is an increase in DNA editing efficiency of a prokaryotic or eukaryotic cell when a Cas9 variant described herein, such as but not limiting to a Cas9 Y155 variant or a Cas9 F86A+F98A variant, is used as part of a PGEN when compared to the same PGEN but comprising its parent (wild type) Cas9 instead, wherein the increase in gene editing efficiency is at least 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%.

“Open reading frame” is abbreviated ORF.

“Gene” includes a nucleic acid fragment that expresses a functional molecule such as, but not limited to, a specific protein, including regulatory sequences preceding (5' non-coding sequences) and following (3' non-coding sequences) the coding sequence. “Native gene” refers to a gene as found in nature with its own regulatory sequences.

A “mutated gene” is a gene that has been altered through human intervention. Such a “mutated gene” has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas protein system as disclosed herein. A mutated cell or organism is a cell or organism comprising a mutated gene.

The term “genome” as it applies to a prokaryotic and eukaryotic cell or organism cells encompasses not only chromosomal DNA found within the nucleus, but organelle DNA found within subcellular components (e.g., mitochondria, or plastid) of the cell.

Polynucleotides of interest are further described herein and include polynucleotides reflective of the commercial markets and interests of those involved in the production of enzymes (such as, but not limiting to, through fermentation of bacteria or fungi thereby producing the enzymes or by plants producing the enzymes) and development of the crops.

Crops and markets of interest change, and as developing nations open up world markets, new crops and technologies will emerge also. In addition, as our understanding of agronomic traits and characteristics such as yield and heterosis increase, the choice of genes for genetic engineering will change accordingly. Polynucleotides of interest include, but are not limited to, polynucleotides encoding important traits for agronomics, herbicide-resistance, insecticidal resistance, disease resistance, nematode resistance, herbicide resistance. microbial resistance, fungal resistance, viral resistance, fertility or sterility, grain characteristics, and commercial products.

General categories of polynucleotides of interest include, for example, genes of interest involved in information, such as zinc fingers, those involved in communication, such as kinases, and those involved in housekeeping, such as heat shock proteins. More specific polynucleotides of interest include, but are not limited to, genes involved in crop yield, grain quality, crop nutrient content, starch and carbohydrate quality and quantity as well as those affecting kernel size, sucrose loading, protein quality and quantity, nitrogen fixation and/or utilization, fatty acid and oil composition, genes encoding proteins conferring resistance to abiotic stress (such as drought, nitrogen, temperature, salinity, toxic metals or trace elements, or those conferring resistance to toxins such as pesticides and herbicides), genes encoding proteins conferring resistance to biotic stress (such as attacks by fungi, viruses, bacteria, insects, and nematodes, and development of diseases associated with these organisms).

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in organisms. Methods for suppressing gene expression in organisms using polynucleotides in the sense orientation are known in the art. The methods generally involve transforming an organism with a DNA construct comprising a promoter that drives expression in an organism operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such asp-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as sulphonylureas, glufosinate ammonium, bromoxynil, imidazolinones, and 2,4-dichlorophenoxyacetate (2,4-D). See for example, Acetolactase synthase (ALS) for resistance to sulfonylureas, imidazolinones, triazolopyrimidine sulfonamides, pyrimidinylsalicylates and sulphonylaminocarbonyl-triazolinones Shaner and Singh, 1997, Herbicide Activity: Toxicol Biochem Mol Biol 69-110); glyphosate resistant 5-enolpyruvylshikimate-3-phosphate (EPSPS) (Saroha et al. 1998, J. Plant Biochemistry & Biotechnology Vol 7:65-72);

Polynucleotides of interest includes genes that can be stacked or used in combination with other traits, such as but not limited to herbicide resistance or any other trait described herein. Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference.

A variety of methods are available for identifying those cells with insertion into the genome at or near to the target site. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering an organism from the cell comprising a polynucleotide of interest integrated into its genome.

A polypeptide of interest includes any protein or polypeptide that is encoded by a polynucleotide of interest described herein.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1 SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

As used herein, the term "promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

Examples of strong promoters useful herein include those disclosed in U.S. Patent Appl. Publ. Nos. 2012/0252079 (DGAT2), 2012/0252093 (EL1), 2013/0089910 (ALK2), 2013/0089911 (SPS19), 2006/0019297 (GPD and GPM), 2011/0059496 (GPD and GPM), 2005/0130280 (FBA, FBAIN, FBAINm), 2006/0057690 (GPAT) and 2010/0068789 (YAT1), which are incorporated herein by reference. Other examples of suitable strong promoters include those listed in Table 2 of WO2016/025131, published on Feb. 19, 2016, incorporated herein by reference.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *Cabios* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

As used herein, "RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

As used herein, a "targeted mutation" is a mutation in a gene (referred to as the target gene), including a native gene, that was made by altering a target sequence within the target gene using any method known to one skilled in the art, including a method involving a guided Cas protein system. Where the Cas protein is a cas endonuclease, a guide polynucleotide/Cas endonuclease induced targeted mutation can occur in a nucleotide sequence that is located within or outside a genomic target site that is recognized and cleaved by the Cas endonuclease.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (*MacMillan Publishing Company, New York*) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory or analysis. In some examples a recognition site and/or target site can be contained within an intron, coding sequence, 5' UTRs, 3' UTRs, and/or regulatory regions.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kb" means kilobase(s).

Non-limiting examples of compositions and methods disclosed herein are as follows:

1. A Cas9 endonuclease variant, or an active fragment thereof, having at least 80% amino acid identity to a parent Cas9 polypeptide set forth in SEQ ID NO: 1 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity.

2. The Cas9 endonuclease variant of embodiment 1, wherein the at least one amino acid substitution is selected from the group consisting of Y155H, Y155N, Y155E, Y155F (at position 155), F86A (at position 86) and F98A (at position 98).

3. The Cas9 endonuclease variant of embodiment 1, wherein the Cas9 endonuclease variant has at least one improved property selected from the group consisting of improved transformation efficiency and improved editing efficiency, when compared to said parent Cas9 endonuclease.

4. The Cas9 endonuclease variant, or active fragment thereof, of any preceding embodiments, wherein said variant comprises an amino acid sequence having 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 1.

5. The Cas9 endonuclease variant of embodiment 3, wherein the improved property is improved transformation efficiency and wherein said variant, or active fragment thereof, has also an improved editing efficiency.

6. The Cas9 endonuclease variant, or active fragment thereof, of any preceding claims, comprising at least 1, 2, 3, 4, 5, 6, 7, 8, 9, 10 amino acid substitutions when compared to the parent Cas9 endonuclease.

7. A composition comprising the Cas9 endonuclease, or a functional fragment thereof, of any of the preceding embodiments.

8. The composition of embodiment 7, wherein said composition is selected from the group consisting of a guide polynucleotide/Cas9 endonuclease complex, a guide RNA/Cas9 endonuclease complex, and a fusion protein comprising said Cas9 endonuclease variant.

9. A polynucleotide comprising a nucleic acid sequence encoding the Cas9 endonuclease variant of any of the preceding embodiments.

10. A guide polynucleotide/Cas endonuclease complex (PGEN) comprising at least one guide polynucleotide and at least one Cas9 endonuclease variant of any one of embodiments 1-6, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.

11. A recombinant DNA construct comprising the polynucleotide of embodiment 9.

12. A host cell comprising the Cas9 endonuclease, or functional fragment thereof, of any one of embodiments 1-6.

13. A host cell comprising the polynucleotide of embodiment 9.

14. The host cell of embodiment 13, wherein the cell is a prokaryotic cell or eukaryotic cell.

15. The host cell of embodiment 14, wherein the cell is selected from the group consisting of a human, non-human, animal, bacterial, fungal, insect, yeast, non-conventional yeast, and plant cell.

15b. A kit comprising the PGEN of embodiment 7.

15c. A delivery particle comprising the Cas9 endonuclease variant according to embodiments 1, 2, 3, 4, 5, or 6.

15d. The delivery particle of embodiment 15c, wherein the Cas9 endonuclease variant protein is complexed with a guide polynucleotide.

16. A method for modifying a target site in the genome of a cell, the method comprising introducing into a cell at least one PGEN of embodiment 10, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

17. A method for editing a nucleotide sequence in the genome of a cell, the method comprising introducing into at least one PGEN of embodiment 10 and a polynucleotide modification template, wherein said polynucleotide modification template comprises at least one nucleotide modification of said nucleotide sequence.

18. The method of embodiment 17, further comprising selecting at least one cell that comprises the edited nucleotide sequence.

19. A method for modifying a target site in the genome of a cell, the method comprising introducing into a cell at least one PGEN of embodiment 10 and at least one donor DNA, wherein said donor DNA comprises a polynucleotide of interest.

20. The method of embodiment 19, further comprising identifying at least one cell that said polynucleotide of interest integrated in or near said target site.

21. The method of any one of embodiments 16-21, wherein the cell is selected from the group consisting of a human, non-human, animal, bacterial, fungal, insect, yeast, non-conventional yeast, and plant cell.

22. The methods of embodiments 16-21, wherein in the PGEN is introduced into the cell as a pre-assembled polynucleotide-protein complex.

23. The method of any one of embodiments 16-21, wherein the guide polynucleotide/Cas endonuclease is a guide RNA/Cas endonuclease.

24. The method of embodiment 22 wherein the guide RNA/Cas endonuclease complex is assembled in-vitro prior to being introduced into the cell as a ribonucleotide-protein complex.

25. A method for improving at least one property of a Cas9 endonuclease variant, said method comprising introducing at least one amino acid modification in a parent Cas9 endonuclease, wherein said at least one amino acid modification is located outside the RuVC and HNH domain of the parent Cas9 endonuclease, thereby creating said Cas9 endonuclease variant, wherein said Cas9 endonuclease variant shows an improvement in at least one property when compared to said parent Cas9 endonuclease.

26. The method of embodiment 25, wherein said at least one amino acid modification is an amino acid substitution at a position selected from the group consisting of position 86, position 98, position 155 and a combination thereof, wherein the amino acid positions of the variant are numbered by correspondence with the amino acid sequence of said parent Cas9 endonuclease.

27. The method of embodiment 26, wherein the at least one amino acid substitution is selected from the group consisting of Y155H, Y155N, Y155E, Y155F (at position 155), F86A (at position 86) and F98A (at position 98).

28. The method of embodiment 25, wherein the Cas9 endonuclease variant has at least one improved property selected from the group consisting of improved transformation efficiency and improved editing efficiency, when compared to said parent Cas9 endonuclease.

29. A cas9 endonuclease variant produced by the method of any of embodiments 24-27.

30. A method for modifying the genome of a *Bacillus* host cell, said method comprising providing to a *Bacillus* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Bacillus* host cell, wherein the at least one genome target sequence has been modified.

31. The method of 30, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

32. The method of 29, wherein the *Bacillus* host cell is selected from the group of *Bacillus* species consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis.*

33. A method for modifying the genome of an *E. coli* host cell, said method comprising providing to an *E. coli* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *E. coli* host cell, wherein the at least one genome target sequence has been modified.

34. A method for modifying the genome of a *Saccharomyces cerevisiae* host cell, said method comprising providing to a *Saccharomyces cerevisiae* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Saccharomyces cerevisiae* host cell, wherein the at least one genome target sequence has been modified.

35. A method for modifying the genome of a fungal host cell, said method comprising providing to a fungal host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one fungal host cell, wherein the at least one genome target sequence has been modified.

36. A Cas9 endonuclease variant for the modification of a target site in a cell, said Cas9 endonuclease variant comprising an amino acid modification outside its HNH domain and RuVC domain, wherein said Cas9 endonuclease has at least one improved property, when compared to a parent Cas9 endonuclease that does not comprises said amino acid modification, wherein Cas9 endonuclease variant can form a complex with a said guide polynucleotide wherein said complex is capable of recognizing, binding to, and optionally nicking, unwinding, or cleaving all or part of said target sequence.

37. The Cas9 endonuclease variant of embodiment 34, wherein the Cas9 endonuclease variant has at least one improved property selected from the group consisting of improved transformation efficiency, improved fold transformation, improved editing efficiency and improved fold editing, when compared to said parent Cas9 endonuclease.

38. A method for modifying an organism or a non-human organism by increasing editing efficiency by using a Cas9 endonuclease variant for the modification of a target site in a genomic locus of interest in a cell, said method comprising providing a non-naturally occurring guide polynucleotide and a Cas9 endonuclease variant to said cell, wherein said Cas9 endonuclease variant comprises an amino acid modification outside its HNH and RuvC domain, wherein said Cas9 endonuclease has increased gene editing efficiency when compared to a parent Cas9 endonuclease that does not comprises said amino acid modification, wherein said guide polynucleotide and Cas9 endonuclease variant can form a complex capable of recognizing, binding to, and optionally nicking, unwinding, or cleaving all or part of said target sequence.

39. A method of expressing a Cas endonuclease variant in a prokaryotic or eukaryotic cell, the method comprising:

(a) introducing into a prokaryotic or eukaryotic cell a recombinant DNA construct of embodiment 11; and, (b) incubating the a prokaryotic or eukaryotic cell of step (a) under conditions permitting expression of said Cas endonuclease variant. 38. A Cas9 endonuclease variant selected from the group of consisting of SEQ ID NO: 58 (CasY155H variant), SEQ ID NO: 123 (CasY155N variant), SEQ ID NO: 125 (Cas9 Y155E variant), SEQ ID NO: 127 (Cas9 Y155F variant), SEQ ID NO: 129 (Cas9 F86A-F98A variant).

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Construction of Cas9 Expression Cassettes Targeting Target Site 1 and Target Site 2 in *Bacillus*

The Cas9 protein from *Streptococcus pyogenes* (SEQ ID NO: 1) was codon optimized for expression in *Bacillus* (SEQ ID NO: 2) and with the addition of an N-terminal nuclear localization sequence (NLS; "APKKKRKV"; SEQ ID NO: 3), a C-terminal NLS ("KKKKLK"; SEQ ID NO: 4), a deca-histidine tag ("HHHHHHHHHH"; SEQ ID NO: 5), the aprE promoter from *B. subtilis* (SEQ ID NO: 6) and a terminator sequence (SEQ ID NO: 7) and was amplified using Q5 DNA polymerase (NEB) per manufacturer's instructions with the forward/reverse primer pair set forth below in Table 1.

TABLE 1

| Forward and reverse primer pair | | |
|---|---|---|
| Forward | ATATATGAGTAAACTTGGTCTGACA GAATTCCTCCATTTTCTTCTGCTAT | SEQ ID NO: 8 |
| Reverse | TGCGGCCGCGAATTCGATTACGAAT GCCGTCTCCC | SEQ ID NO: 9 |

The backbone (SEQ ID NO: 10) of plasmid pKB320 (SEQ ID NO: 11) was amplified using Q5 DNA polymerase (NEB) per manufacturer's instructions with the forward/reverse primer pair set forth below in Table 2.

TABLE 2

| Forward and reverse primer pair | | |
|---|---|---|
| Forward | *GGGAGACGGCATTCGTAATCGAATT CGCGGCCGCA* | SEQ ID NO: 12 |
| Reverse | ATAGCAGAAGAAAATGGAGGAATTC TGTCAGACCAAGTTTACTCATATAT | SEQ ID NO: 13 |

The PCR products were purified using Zymo clean and concentrate 5 columns per manufacturer's instructions. Subsequently, the PCR products were assembled using prolonged overlap extension PCR (POE-PCR) with Q5 Polymerase (NEB) mixing the two fragments at equimolar ratio. The POE-PCR reactions were cycled: 98° C. for five (5) seconds, 64° C. for ten (10) seconds, 72° C. for four (4) minutes and fifteen (15) seconds for 30 cycles. Five (5) μl of the POE-PCR (DNA) was transformed into Top10 *E. coli* (Invitrogen) per manufacturer's instructions and selected on lysogeny (L) Broth (Miller recipe; 1% (w/v) Tryptone, 0.5% Yeast extract (w/v), 1% NaCl (w/v)), containing fifty (50) pg/ml kanamycin sulfate and solidified with 1.5% Agar. Colonies were allowed to grow for eighteen (18) hours at 37° C. Colonies were picked and plasmid DNA prepared using Qiaprep DNA miniprep kit per manufacturer's instructions and eluted in fifty-five (55) μl of $ddH_2O$. The plasmid DNA was Sanger sequenced to verify correct assembly, using the sequencing primers set forth below in Table 3.

TABLE 3

| Sequencing primers | | |
|---|---|---|
| Reverse | CCGACTGGAGCTCCTATATTACC | SEQ ID NO: 14 |
| Forward | GTCTTTTAAGTAAGTCTACTCT | SEQ ID NO: 16 |
| Forward | CCAAAGCGATTTTAAGCGCG | SEQ ID NO: 17 |
| Forward | CCTGGCACGTGGTAATTCTC | SEQ ID NO: 18 |
| Forward | GGATTTCCTCAAATCTGACG | SEQ ID NO: 19 |
| Forward | GTAGAAACGCGCCAAATTACG | SEQ ID NO: 20 |
| Forward | GCTGGTGGTTGCTAAAGTCG | SEQ ID NO: 21 |
| Forward | GGACGCAACCCTCATTCATC | SEQ ID NO: 22 |
| Reverse | CAGGCATCCGATTTGCAAGG | SEQ ID NO: 23 |
| Forward | GCAAGCAGCAGATTACGCG | SEQ ID NO: 24 |

The correctly assembled plasmid, pRF694 (SEQ ID NO: 25) was used to construct plasmids pRF801 (SEQ ID NO: 26) and pRF806 (SEQ ID NO: 27) for editing the *Bacillus licheniformis* genome at target site 1 (SEQ ID NO: 28) and target site 2 (SEQ ID NO: 29) as described below.

The serA1 open reading frame (SEQ ID NO: 30) of *B. licheniformis* contains a unique target site, target site 1 (SEQ ID NO: 28) in the reverse orientation. The target site lies adjacent to a protospacer adjacent motif (SEQ ID NO: 31) in the reverse orientation. The target site can be converted into the DNA encoding a variable targeting domain (SEQ ID NO: 32). The DNA sequence encoding the VT domain (SEQ ID NO: 32) is operably fused to the DNA sequence encoding the Cas9 endonuclease recognition domain (CER, SEQ ID NO: 33) such that when transcribed by RNA polymerase of the bacterial cell it produces a functional gRNA targeting target site 1 (SEQ ID NO: 34). The DNA encoding the gRNA was operably linked to a promoter operable in *Bacillus* sp. cells (e.g., the spac promoter; SEQ ID NO: 35) and a terminator operable in *Bacillus* sp. cells (e.g., the t0 terminator of phage lambda; SEQ ID NO: 36), such that the promoter was positioned 5' of the DNA encoding the gRNA (SEQ ID NO: 33) and the terminator is positioned 3' of the DNA encoding the gRNA (SEQ ID NO: 33).

A polynucleotide modification template (also referred to as an editing template) to delete the serA1 gene in response to Cas9/gRNA cleavage was created by amplification of two homology arms from *B. licheniformis* genomic DNA (gDNA). The first fragment corresponds to the 500 bp directly upstream of the serA1 open reading frame (SEQ ID NO: 37). This fragment was amplified using Q5 DNA polymerase per the manufacturer's instructions and the primers listed in Table 4 below. The primers incorporate 18 bp homologous to the 5' end of the second fragment on the 3' end of the first fragment and 20 bp homologous to pRF694 to the 5' end of first fragment.

TABLE 4

| Forward and reverse primer pair. | | |
|---|---|---|
| Forward | TGAGTAAACTTGGTCTGACAAA TGGTTCTTTCCCCTGTCC | SEQ ID NO: 38 |
| Reverse | AGGTTCCGCAGCTTCTGTGTAAG ATTTCCTCCTAAATAAGCGTCAT | SEQ ID NO: 39 |

The second fragment corresponds to the 500 bp directly downstream of the 3' end of the serA1 open reading frame (SEQ ID NO: 40). This fragment was amplified using Q5 DNA polymerase per manufacturer's instructions and the primers listed in Table 5 below. The primers incorporate 28 bp homologus to the 3' end of the first fragment on the 5' end of the second fragment and 21 bp homologous to pRF694 on the 3' end of the second fragment.

TABLE 5

| Forward and reverse primer pair. | | |
|---|---|---|
| Forward | ATGACGCTTATTTAGGAGGAAATC TTACACAGAAGCTGCGGAACCT | SEQ ID NO: 41 |
| Reverse | CAGAAGAAAATGGAGGAATTCGAA TATCGACCGGAACCCAC | SEQ ID NO: 42 |

The DNA encoding the target site 1 gRNA expression cassette (SEQ ID NO: 43), the first (SEQ ID NO: 37) and second homology arms (SEQ ID NO: 40) were assembled into pRF694 (SEQ ID NO: 25) using standard molecular biology techniques generating pRF801 (SEQ ID NO: 26), an *E. coli-B. licheniformis* shuttle plasmid containing a Cas9 expression cassette (SEQ ID NO: 2), a gRNA expression cassette (SEQ ID NO: 43) encoding a gRNA targeting target site 1 within the serA1 open-reading frame and an editing template (SEQ ID NO: 44) composed of the first (SEQ ID NO: 37) and second (SEQ ID NO: 40) homology arms. The plasmid was verified by Sanger sequencing with the oligos set forth in Table 3.

The rghR1 open reading frame of *B. licheniformis* (SEQ ID NO: 45) contains a unique target site on the reverse strand, target site 2 (SEQ ID NO: 46). The target site lies adjacent to a protospacer adjacent motif (last three basis of SEQ ID NO: 47) on the reverse strand. The target site can be converted into the DNA encoding a variable targeting (VT) domain (SEQ ID NO: 48) of a guide RNA. The DNA sequence encoding the VT domain (SEQ ID NO: 48) is operably fused to the DNA sequence encoding the Cas9 endonuclease recognition domain (CER, SEQ ID NO: 33) such that when transcribed by RNA polymerase of the bacterial cell it produces a functional guideRNA (gRNA) targeting target site 2 (SEQ ID NO: 49). The DNA encoding the gRNA was operably linked to a promoter operable in *Bacillus* sp. cells (e.g., the spac promoter from *B. cutilis*; SEQ ID NO: 35) and a terminator operable in *Bacillus* sp. cells (e.g., the t0 terminator of phage lambda; SEQ ID NO: 36), such that the promoter was positioned 5' of the DNA encoding the gRNA (SEQ ID NO: 43) and the terminator is positioned 3' of the DNA encoding the gRNA (SEQ ID NO: 43).

A polynucleotide modification template (also referred to as an editing template) to modify the rghR1 gene in response to Cas9/gRNA cleavage was created by amplification of two homology arms from *B. licheniformis* genomic DNA (gDNA). The first fragment corresponds to the 500 bp directly upstream of the rghR1 open reading frame (SEQ ID NO: 50). This fragment was amplified using Q5 DNA polymerase per the manufacturer's instructions and the primers listed in Table 6 below. The primers incorporate 23 bp homologous to the 5' end of the second fragment on the 3' end of the first fragment and 20 bp homologous to pRF694 to the 5' end of first fragment.

TABLE 6

| Forward and reverse primer pair. | | |
|---|---|---|
| Forward | TGAGTAAACTTGGTCTGACATT GATATTCAGCACCCTGCG | SEQ ID NO: 51 |
| Reverse | TGTGCCGCGGAGAAGTATGGCC AAAACCTCGCAATCTC | SEQ ID NO: 52 |

The second fragment corresponds to the 500 bp directly downstream of the 3' end of the rghR1 open reading frame (SEQ ID NO: 53). This fragment was amplified using Q5 DNA polymerase per manufacturer's instructions and the primers listed in Table 7 below. The primers incorporate 20 bp homologous to the 3' end of the first fragment on the 5' end of the second fragment and 21 bp homologous to pRF694 on the 3' end of the second fragment.

TABLE 7

| Forward and reverse primer pair. | | |
|---|---|---|
| Forward | GAGATTGCGAGGTTTTGGCCATACTTCTCCGCGGCACA | SEQ ID NO: 54 |
| Reverse | CAGAAGAAAATGGAGGAATTCATTTCTCGGGTTTAAACAGCCAC | SEQ ID NO: 55 |

The DNA encoding the target site 2 gRNA expression cassette (SEQ ID NO: 56), the first (SEQ ID NO: 50) and second homology arms (SEQ ID NO: 53) were assembled into pRF694 (SEQ ID NO: 25) using standard molecular biology techniques generating pRF806 (SEQ ID NO: 27), an *E. coli-B. licheniformis* shuttle plasmid containing a Cas9 expression cassette (SEQ ID NO: 2), a gRNA expression cassette (SEQ ID NO: 56) encoding a gRNA targeting target site 2 within the rghR1 open-reading frame and an editing template (SEQ ID NO: 57) composed of the first (SEQ ID NO: 50) and second (SEQ ID NO: 53) homology arms. The plasmid was verified by sanger sequence with the oligos set forth in Table 3.

Example 2

Creation of Cas9 Y155 Variants

In the present example, the Y155H variant of *S. pyogenes* Cas9 (referred to as Cas9 Y155H variant, herein, SEQ ID NO: 58) was created in the pRF801 (SEQ ID NO: 26) and pRF806 plasmids (SEQ ID NO: 27). To introduce the Cas9 Y155H variant in the pRF801 plasmid (SEQ ID NO: 26) or the pRF806 plasmid (SEQ ID NO: 27) site-directed mutagenesis was performed using Quikchange mutagenesis kit per the manufacturer's instructions and the oligos in Table 8 below using pRF801 (SEQ ID NO: 26) or pRF806 (SEQ ID NO: 27) as template DNA.

TABLE 8

| Forward and reverse primer pair. | | |
|---|---|---|
| Forward | GATCTGCGTTTAATCCATCTTGCGTTAGCGCAC | SEQ ID NO: 59 |
| Reverse | GTGCGCTAACGCAAGATGGATTAAACGCAGATC | SEQ ID NO: 60 |

The resultant products of the reaction, pRF827 (SEQ ID NO: 61) contained a Cas9 Y155H variant expression cassette (SEQ ID NO: 62), a gRNA expression cassette (SEQ ID NO: 43) encoding a gRNA targeting target site 1 within the serA1 open-reading frame and an editing template (SEQ ID NO: 44) composed of the first (SEQ ID NO: 37) and second (SEQ ID NO: 40) homology arms or pRF856 (SEQ ID NO: 63) which contained a Cas9 Y155H variant expression cassette (SEQ ID NO: 62), a gRNA expression cassette (SEQ ID NO: 56) targeting target site 2 within the rghR1 open reading frame and an editing template (SEQ ID NO: 57) composed of the first (SEQ ID NO: 50) and second (SEQ ID NO: 53) homology arms. The plasmid DNAs were Sanger sequenced to verify correct assembly, using the sequencing primers set forth in Table 3.

Other Cas9 Y155 variants were created in a similar matter as described above. A Cas9 Y155N variant was created and is set forth in SEQ ID NO: 123 (amino acid sequence encoded by SEQ ID NO: 124), a Cas9 Y155E variant was created and is set forth in SEQ ID NO: 125 (amino acid sequence encoded by SEQ ID NO: 126), a Cas9 Y155F variant was created and is set forth in SEQ ID NO: 127 (amino acid sequence encoded by SEQ ID NO: 128).

Example 3

Y155H Variant of *Streptococcus pyogenes* Cas9 (Cas9 Y155H Variant) has Increased Transformation Efficiency and Equal or Increased DNA Editing Efficiency in *Bacillus* Cells Compared to Wild Type *Streptococcus pyogenes* Cas9 (WT Cas9).

In the present example, the pRF694 (SEQ ID NO: 25), pRF801 (SEQ ID NO: 26), pRF806 (SEQ ID NO: 27), pRF827 (SEQ ID NO: 61), and pRF856 (SEQ ID NO: 63) plasmids described above were amplified using rolling circle amplification (Sygnis) for 18 hours according to manufacturer's instructions. The rolling circle amplified plasmids were transformed into competent (parental) *B. licheniformis* cells comprising (harboring) a pBL.comK plasmid (SEQ ID NO: 64) as generally described in International PCR publication Nos. WO2017/075195, WO2002/14490 and WO2008/7989. Cell/DNA transformation mixes were plated onto L-broth (Miller recipe) containing 20 pg/ml of kanamycin and solidified with 1.5% Agar. Colonies were allowed to form at 37° C. Colonies that grew on the L agar plates containing kanamycin were picked and streaked on L agar plates to recover. Colonies from transformations with pRF801 (SEQ ID NO: 26) and pRF827 (SEQ ID NO: 61) were screened for editing by Amplifying the target site 1 locus (SEQ ID NO: 65) using Q5 DNA polymerase according to the manufacturer's instructions and the forward/reverse primer pair set forth below in Table 9. The WT and edited target site 1 locus in *Bacillus* cells can be differentiated based on the size of the amplified locus with the WT amplicon (SEQ ID NO: 65) being larger in size than the edited amplicon (SEQ ID NO: 66).

TABLE 9

| Forward and reverse primer pair. | | |
|---|---|---|
| Forward | TAGAGACGAGACGTCTCACC | SEQ ID NO: 67 |
| Reverse | GTATCAATCCGACTCCTACGG | SEQ ID NO: 68 |

Colonies from the transformation with plasmids pRF806 (SEQ ID NO: 27) or pRF856 (SEQ ID NO: 63) were analyzed for editing efficiency by amplifying the target site 2 locus (SEQ ID NO: 69) using Q5 DNA polymerase according to the manufacturer's instructions and the forward/reverse primer pair set forth below in Table 10. The WT (SEQ ID NO: 69) and edited target site 2 locus (SEQ ID NO: 70) can be differentiated based on the size of the edited locus (SEQ ID NO: 70) with the WT amplicon (SEQ ID NO: 69) being larger in size.

TABLE 10

| Forward and reverse primer pair. | | |
|---|---|---|
| Forward | ATCAAACATGCCATGTTTGC | SEQ ID NO: 71 |
| Reverse | AGGTTGAGCAGGTCTTCG | SEQ ID NO: 72 |

The number of transformants obtained on medium selective for the plasmid (L agar containing 20 $\mu g \cdot ml^{-1}$ kanamycin sulfate) is displayed in Table 11. The transformation efficiency is the ratio of the number of transformants obtained from a given Cas9 variant with a specific gRNA and editing template by the number of transformants from the parent (WT) Cas9 with the same gRNA expression cassette and editing template. The results are displayed in Table 11 demonstrating that the Cas9 Y155H variant increased the transformation efficiency of Cas9 variants (delivered by plasmids) by at least 84 to-402 fold.

TABLE 11

Transformation efficiency and editing frequency at *B. licheniformis* targets.

| Cas9 | Target site | Trans-formants | Transformation Efficiency (Variant or WT/WT) | Editing Frequency | Editing Efficiency (Variant or WT/ WT) |
|---|---|---|---|---|---|
| WT | Site 1 | 1 | 1 | 1.00 | 1.0 |
| Y155H | Site 1 | 402 | 402 | 1.00 | 1.0 |
| WT | Site 2 | 3 | 1 | 0.33 | 1.0 |
| Y155H | Site 2 | 84 | 28 | 0.75 | 2.3 |

The results shown in Table 11 demonstrate that the Cas9 Y155H Variant had an editing efficiency that is at least equal to or at least 2.3 fold (or 230%) greater than the DNA editing efficiency of the WT Cas9.

Example 4

Construction of Cas9 F86A-F98A Variant

In the present example a Cas9 F86A-F98A variant (SEQ ID NO: 129) was constructed in the backbone of the pRF801 plasmid (SEQ ID NO: 26) in order to test the Cas9 F86A-F98A variant for transformation efficiency and editing frequency in *B. licheniformis.*

A synthetic fragment containing a portion of Cas9 including F86A and F98A (SEQ ID NO: 130) was ordered from an external vendor. The backbone of pRF801 (SEQ ID NO: 131) was amplified using the oligos set forth in Table 12 using standard PCR techniques.

TABLE 12

Forward and reverse primer pair.

| | | |
|---|---|---|
| Forward | AAAGAAAAATGGTCTGTTTG | SEQ ID NO: 132 |
| Reverse | AATACGATTTTTACGACGTG | SEQ ID NO: 133 |

The synthetic fragment (SEQ ID NO: 130) was amplified using oligos set forth in Table 13 below using standard PCR techniques.

TABLE 13

Forward and reverse primer pair.

| | | |
|---|---|---|
| Forward | AAAGAAAAATGGTCTGTTTG | SEQ ID NO: 134 |
| Reverse | AATACGATTTTTACGACGTG | SEQ ID NO: 135 |

The pRF801 backbone fragment (SEQ ID NO: 131) was assembled with the F86A-F98A synthetic fragment using standard molecular biology techniques to create plasmid pRF866 (SEQ ID NO: 137). pRF866 contains the F86A F98A Cas9 expression cassette for *Bacillus* (SEQ ID NO: 136), the DNA encoding the expression cassette for the gRNA targeting serA1 ts1 (SEQ ID NO: 43), and the serA1 deletion editing template (SEQ ID NO: 44).

The plasmid pRF866 was transformed into *B. licheniformis* cells.

Example 5

A Cas9 Variant of *Streptococcus pyogenes* Comprising a First Amino Acid Substitution at F86 and a Second Amino Acid Substitution at F98 has Increased Transformation Efficiency and Equal DNA Editing Efficiency in *Bacillus* Cells Compared to its Parent (Wild Type) *Streptococcus pygenes* Cas9 (WT Cas9).

A Cas9 variant (referred to as Cas9 F86-F98 variant) of *Streptococcus pyogenes* comprising a first amino acid substitution at F86 (such as F86A) and a second amino acid substitution at F98 (such as F98A), wherein the amino acid positions of the variant are numbered by correspondence with the amino acid sequence of the parent Cas9 polypeptide set forth in SEQ ID NO 1 (*Streptococcus pyogenes* WT Cas9) was created as described in Example 4. The transformation efficiency and editing efficiency were analyzed as described in Example 3 and shown in Table 14.

TABLE 14

Transformation efficiency and editing frequency at a *B. licheniformis* targets using a Cas9 F86-F98 variant.

| Cas9 | Target site | Trans-formants | Transformation Efficiency (ratio variant or WT/WT) | Editing Frequency | Editing efficiency (ratio variant or WT/WT) |
|---|---|---|---|---|---|
| WT | Site 1 | 1 | 1 | 1.0 | 1.0 |
| F86A F98A | Site 1 | 248 | 248 | 1.0 | 1.0 |

Table 14 clearly shows that the Cas9 F86-F98A variant increased the transformation efficiency 248 fold (or 24,800%) when compared to the WT Cas9. Colonies transformed with editing plasmids were screened as described in Example 3 for editing efficiency by determining the percentage of screened colonies containing the desired edit. The results shown in Table 14 demonstrate that the Cas9 F86A-F98A variant had an editing efficiency equal to that of the WT Cas9.

Example 6

Construction of an *Escherichia coli* Cas9 Vector

In the present example an inducible Cas9 expression vector for genome editing in *Escherichia coli* (*E. coli*) was constructed. Cas9 expression in response to an inducer was confirmed.

The Cas9 protein from *Streptococcus pyogenes* M1 GAS SF370 (SEQ ID NO: 1) was codon optimized per standard techniques known in the art (SEQ ID NO: 73). In order to localize the Cas9 protein to the nucleus of the cells, Simian virus 40 (SV40) monopartite (MAPKKKRKV, SEQ ID NO: 74) nuclear localization signal was incorporated at the carboxy terminus of the Cas9 open reading frame. The *Yarrowia* codon optimized Cas9 gene was fused to a *Yarrowia* constitutive promoter, FBA1 (SEQ ID NO: 75), by standard molecular biology techniques. An example of a *Yarrowia* codon optimized Cas9 expression cassette (SEQ ID NO: 76) containing the constitutive FBA promoter, *Yarrowia* codon optimized Cas9, and the SV40 nuclear localization signal. The Cas9 expression cassette was cloned into the plasmid pZuf and the new construct called pZufCas9 (SEQ ID NO: 77).

The *Yarrowia* codon optimized Cas9-SV40 fusion gene (SEQ ID NO: 78) was amplified from pZufCas9 using standard molecular biology techniques using the primers from Table 15 below.

TABLE 15

| Forward and reverse primer pair. | | |
|---|---|---|
| Forward | GGGGGAATTCGACAAGAAATACTCCATCGGCCTGG | SEQ ID NO: 79 |
| Reverse | CCCCAAGCTTAGCGGCCGCTTAGACCTTTCG | SEQ ID NO: 80 |

The primers in Table 12 added a 5' EcoRI site and a 3' HindIII site to the fusion. The PCR product (SEQ ID NO: 81) was purified using standard techniques. The purified fragment was cloned into the EcoRI and HindIII sites of pBAD/HisB from life technologies (SEQ ID NO: 82) to create pRF48 (SEQ ID NO: 83).

The *E. coli* Cas9 expression cassette (SEQ ID NO: 84) was inserted into a low copy plasmid pKO3 (SEQ ID NO: 85) to create pRF97 (SEQ ID NO: 86) a low copy *E. coli* plasmid containing a Cas9 expression cassette.

Example 7

Creating the Cas9 Y155H Variant in the *E. coli* Cas9 Plasmid

In the present example the Cas9 Y155H variant was introduced into the Cas9 protein encoded on pRF97 (SEQ ID NO: 86).

A synthetic DNA fragment encoding a portion of the Cas9 protein from pRF97 but containing substitutions encoding the Y155H variant (SEQ ID NO: 87) was produced. The synthetic fragment was amplified using standard PCR conditions and the primers listed in Table 16.

TABLE 16

| Forward and reverse primer pair. | | |
|---|---|---|
| Forward | CTCCAGTCGTCTGCTCTTCG | SEQ ID NO: 88 |
| Reverse | CCAACGAGATGGCCAAGGTG | SEQ ID NO: 89 |

The pRF97 plasmid (SEQ ID NO: 86) was amplified to accept insertion of the Y155H synthetic fragment (SEQ ID NO: 87) using standard PCR techniques and the primers listed below in Table 17 to produce the pRF97-Y155H fragment (SEQ ID NO: 90).

TABLE 17

| Forward and reverse primer pair. | | |
|---|---|---|
| Forward | CACCTTGGCCATCTCGTTGG | SEQ ID NO: 91 |
| Reverse | CGAAGAGCAGACGACTGGAG | SEQ ID NO: 92 |

The Y155H synthetic fragment (SEQ ID NO: 87) and the pRF97-Y155H fragment (SEQ ID NO: 90) were combined to create pRF861 (SEQ ID NO: 93) a low copy plasmid containing an *E. coli* expression cassette for the Cas9 Y155H variant.

Example 8

Deletion of the Nitrogen Assimilation Control Gene of *E. coli* Using a WT Cas9 and a Cas9 Y155H Variant In the present example, the nac gene encoding the nitrogen assimilation control gene of *E. coli* was deleted using either the WT Cas9 or the Cas9 Y155H variant.

The *E. coli* nac gene (SEQ ID NO: 94) contains two target sites; target site 1 (SEQ ID NO: 95) and PAM (last three bases of SEQ ID NO: 96), and target site 2 (SEQ ID NO: 97) and PAM (last three bases of SEQ ID NO: 98). As described in example 1 by adding the DNA encoding the CER domain (SEQ ID NO: 33) to the 3' end of the DNA encoding the target site operably fusing a promoter active in *E. coli* (e.g. The N25 phage promoter (SEQ ID NO: 99)) to the 5' end of the target site and a terminator active in *E. coli* (e.g. the lambda phage t0 terminator (SEQ ID NO: 36) to the 3' end of the CER domain an operable gRNA expression cassette can be made for nac site 1 (SEQ ID NO: 100) and nac site 2 (SEQ ID NO: 101). *E. coli* mainly repairs DNA via homology directed repair and for efficiency Cas9 mediated editing requires and editing template.

The 491 bp upstream of the nac start codon and the first three codons (SEQ ID NO: 102) was operably linked to the 491 bp downstream of the nac stop codon and the last three codons of the nac open reading frame (SEQ ID NO: 103) to create an editing template that deletes all but the first three and last three codons of the nac open reading frame (SEQ ID NO: 104).

The site 1 gRNA expression cassette (SEQ ID NO: 100) or the site 2 gRNA expression cassette (SEQ ID NO: 102) was operably linked to the nac deletion editing template (SEQ ID NO: 104) and with 20 bp of identity to pRF97 (SEQ ID NO: 86) and pRF861 (SEQ ID NO: 93) on the 5' end (SEQ ID NO: 105) and 21 bp of identity (SEQ ID NO: 106) to pRF97 (SEQ ID NO: 86) and pRF861 (SEQ ID NO: 93) on the 3' end and ordered as nacETsite1 (SEQ ID NO: 107) and nacETsite2 (SEQ ID NO: 108) synthetic DNA fragments.

pRF97 (SEQ ID NO: 86) or pRF861 (SEQ ID NO: 93) were amplified using standard molecular biology techniques and the primers listed in Table 18 below to create linear fragments pRF97-cassette (SEQ ID NO: 109) or pRF861-cassette (SEQ ID NO: 110).

TABLE 18

| Forward and reverse primer pair. | | |
|---|---|---|
| Forward | GGTTTATTGACTACCGGAAGC | SEQ ID NO: 111 |
| Reverse | GCCGTCAATTGTCTGATTCG | SEQ ID NO: 112 |

The pRF97-cassette (SEQ ID NO: 109) or the pRF861-cassette (SEQ ID NO: 110) was assembled with either the nacETsite1 (SEQ ID NO: 107) or nacETsite1 (SEQ ID NO: 108) using standard molecular biology techniques to create pRF97/nacETsite1 (SEQ ID NO:113), pRF97/nacETsite2 (SEQ ID NO: 114), pRF861/nacETsite1 (SEQ ID NO: 115), and pRF861/nacETsite2 (SEQ ID NO: 116).

MG1655 *E. coli* cells were made electrocompetent as described previously (Short protocols in molecular biology) and transformed with 1 μl of pRF97/nacETsite1 (SEQ ID NO:113), pRF97/nacETsite2 (SEQ ID NO: 114), pRF861/nacETsite1 (SEQ ID NO: 115), or pRF861/nacETsite2 (SEQ ID NO: 116). Cells were plated on L broth solidified with 1.5% w·v$^{-1}$ agar containing 25 μg·ml$^{-1}$ chloramphenicol and 0.1% w·v$^{-1}$ L-arabinose (to induce Cas9 expression). Colonies from the transformation were counted after 24 hours of growth at 30° C.

To determine if a colony contained an edited allele up to 8 colonies from each transformation were screened by PCR for the presence of the WT nac locus (SEQ ID NO: 117) or the edited nac locus (SEQ ID NO: 118) by PCR amplification using standard techniques and the primers in Table 19 below.

TABLE 19

| Forward and reverse primer pair. | | |
|---|---|---|
| Forward | GGTTTATTGACTACCGGAAGC | SEQ ID NO: 119 |
| Reverse | GCCGTCAATTGTCTGATTCG | SEQ ID NO: 120 |

Colonies which gave amplification products corresponding to the edited nac locus (SEQ ID NO: 118) which is smaller than the WT nac locus (SEQ ID NO: 117) were counted as edited for the calculation of editing frequency. The editing frequency is the percentage of screened cells that demonstrated the presence of the edited nac locus (SEQ ID NO 118) from PCR. The results in Table 20 show the editing frequency and the transformation efficiency (Transformants/transformants WT Cas9).

TABLE 20

Transformation efficiency and editing frequency of WT Cas9 and Y155H Cas9 in *E. coli*

| Cas9 | Target site | Transformants | Transformation Efficiency | Editing Frequency | Editing Efficiency |
|---|---|---|---|---|---|
| WT | Site 1 | 4 | 1.0 | 75 | 1.00 |
| Y155H | Site 1 | 13 | 3.3 | 86 | 1.15 |
| WT | Site 2 | 11 | 1.0 | 63 | 1.00 |
| Y155H | Site 2 | 8 | 0.7 | 100 | 1.59 |

Table 20 clearly demonstrates the Cas9 Y155H variant is operable in *E. coli* and does show an increase in editing efficiency of at least 15% to 59% when compared to the WTCas9 editing frequency.

Example 9

Construction of Cas9-gRNA Vectors for Editing the *Saccharomyces cerevisiae* Chromosomal URA3 Gene Deletion In order to test the transformation and editing efficiencies of Cas9 Y155H variant vs Cas9 wild type (wt) for editing *Saccharomyces cerevisiae* chromosomal URA3 gene deletion, Cas9 Y155H-gRNA and Cas9 wt-gRNA expressing plasmids with a G-418 resistance gene (KanMX) as a selection marker are made as described below.

Fragment A (Cas9 wt) containing a synthetic polynucleotide encoding the Cas9 wild type protein from *S. pyogenes* (SEQ ID NO: 1), comprising an N-terminal nuclear localization sequence (NLS; "APKKKRKV"; SEQ ID NO: 3), a C-terminal NLS ("KKKKLK"; SEQ ID NO: 4) and a deca-histidine tag ("HHHHHHHHHH"; SEQ ID NO: 5), is amplified from pRF694 plasmid (SEQ ID NO: 25) using Q5 DNA polymerase (NEB) per manufacturer's instructions with the forward/reverse primer pair set forth below in Table 21. Fragment A' (Cas9 Y115H) containing a synthetic polynucleotide encoding the Cas9 Y115H variant (SEQ ID NO: 58), comprising an N-terminal nuclear localization sequence, a C-terminal NLS and a deca-histidine tag, is amplified from pRF827 plasmid (SEQ ID NO: 61) using Q5 DNA polymerase (NEB) per manufacturer's instructions with the forward (SEQ ID NO: 138)/reverse (SEQ ID NO: 138) primer pair set forth below in Table 21.

TABLE 21

| Forward and reverse primer pair. | | |
|---|---|---|
| Forward | AAAAGAAATATATAGAGAGATACTCTTATCAATGATGGTGATGAT GATGGTGATG | SEQ ID NO: 138 |
| Reverse | ACACGTATTTATTTGTCCAATTACCATGGCCCCAAAAAAGAAACG CAAGGTTATGGAT | SEQ ID NO: 139 |

Fragment B containing the RNR2p promoter (SEQ ID NO: 140), 2-micron replication origin 1 (SEQ ID NO: 141), KanMX expression cassette (SEQ ID NO: 142), and SNR52p promoter (SEQ ID NO: 143), is amplified from pSE087 plasmid (SEQ ID NO: 144) using Q5 DNA polymerase (NEB) per manufacturer's instructions with the forward (SEQ ID NO: 145)/reverse (SEQ ID NO: 146) primer pair set forth below in Table 22.

TABLE 22

| Forward and reverse primer pair. | | |
|---|---|---|
| Forward | CTCCGCAGTGAAAGATAAATGATCGCCCAAAATTTGTTTACTAAAAAC ACATGTGGA | SEQ ID NO: 145 |
| Reverse | GAATTGGGTACCGGGCCCTTAGAGTAAAAAATTGTACTTGGCGGATAA TGCCTTTAGC | SEQ ID NO: 146 |

The pSE087 plasmid is a 2p shuttle vector with a heterologous KanMX expression cassette. The plasmid contains the cas9 gene from *S. pyogenes* under the control of the RNR2 promoter, the SNR52 promoter upstream of stuffer fragment containing the targeting sgRNA+T(6) terminator (SEQ ID NO: 147). The sgRNA is flanked by BsmBI binding sites that are oriented such that the linearization of the plasmid by BsmBI releases the sgRNA stuffer leaving incompatible overhangs on the digested plasmid.

Fragment C containing a synthetic polynucleotide of the 50 bp upstream homology arm (SEQ ID NO: 148), URA3 targeting sgRNA+T(6) terminator (SEQ ID NO: 149), and 50 bp downstream (SEQ ID NO: 150), is amplified using Q5 DNA polymerase (NEB) per manufacturer's instructions with the forward (SEQ ID NO: 151)/reverse (SEQ ID NO: 152) primer pair set forth below in Table 23.

TABLE 23

| Forward and reverse primer pair. | | |
|---|---|---|
| Forward | CCGCCAAGTACAATTTTTTACTCTAAGGGCCCGGTACCCAATTCGCC CTATAGTGAG | SEQ ID NO: 151 |
| Reverse | CATCATCACCATCATTGATAAGAGTATCTCTCTATATATTTCTTTTTACG CAGTCTC | SEQ ID NO: 152 |

Fragment D containing the 2-micron replication origin 2 (SEQ ID NO: 153), ampicillin resistant gene (SEQ ID NO: 154) and RNR2 terminator (SEQ ID NO: 155), is amplified from pSE087 plasmid using Q5 DNA polymerase (NEB) per manufacturer's instructions with the forward (SEQ ID NO: 156)/reverse (SEQ ID NO: 157) primer pair set forth below in Table 24.

TABLE 24

| Forward and reverse primer pair. | | |
|---|---|---|
| Forward | CCTTGCGTTTCTTTTTTGGGGCCATGGTAATTGGAcAAATAAATACG TGTATTAAG | SEQ ID NO: 156 |
| Reverse | TGTTTTTAGTAAACAAATTTTGGGCGATCATTTATCTTTCACTGCGGAG AAGTTTC | SEQ ID NO: 157 |

The PCR fragments are purified using the Qiagen PCR purification kit (QIAGEN, Inc) per manufacturer's instructions. Subsequently, the PCR fragments are assembled on the 2-micron plasmid backbone by gap repair in yeast according to below protocol.

*S. cerevisiae* ura3Δ competent cells are prepared by using Frozen-EZ Yeast Transformation II™ kit (Zymo Research, Inc) per manufacturer's instructions. The 50 μl of *S. cerevisiae* ura3Δ competent cells are mixed with 0.1-0.2 μg DNA of each PCR product of the fragment A, B, C, and D to create pWS572 (Cas9 wt). The 50 μl of *S. cerevisiae* ura3Δ competent cells are mixed with 0.1-0.2 μg DNA of each PCR product of the fragment A', B, C, and D to create pWS573 (Cas9 Y115H). The 500 μl EZ 3 solution that is provided from the kit is added and mixed thoroughly. After incubating the mixture at 30° C. for 45 minutes, 50-150 μl of the transformation mixture spreads on the YPD medium plate supplemented with 200 ug/ml Geneticin (G418) antibiotic. The plates incubated at 30° C. for 2-4 days to allow for growth of transformants.

The resulting plasmids of pWS572 (Cas9 wt) and pWS573 (Cas9 Y155H) are prepared from 1 ml of the transformants grown in the YPD medium supplemented with 200 ug/ml Geneticin (G418) antibiotic by using the ChargeSwitch® Plasmid Yeast Mini kit (Invitrogen, Inc).

Example 10

*Saccharomyces Cerevisiae* Chromosomal URA3 Gene Deletion by Using PWS572 (Cas9 Wt) and PWS573 (Cas9 Y155H)

In this example, the transformation and editing efficiencies of pWS573 (Cas9 Y155H) vs pWS572 (Cas9 wt) for *Saccharomyces cerevisiae* chromosomal URA3 gene deletion are compared. *S. cerevisiae* wild type competent cells are prepared by using Frozen-EZ Yeast Transformation II™ kit (Zymo Research, Inc) per manufacturer's instructions, and transformed with 100 ng plasmid DNA of pWS573 (Cas9 Y155H) and pWS572 (Cas9 wt), separately. 50-150 μl of the transformation mixture spreads on the YPD medium plate supplemented with 200 ug/ml Geneticin (G418) antibiotic. The plates incubated at 30° C. for 2-4 days to allow for growth of transformants. The correct ura3Δ, colonies are screened for uracil auxotroph by streaking transformants on the synthetic complete media (1× yeast nitrogen base without amino acids, 1× amino acid mix lacking uracil) supplemented with 2 g/L glucose and incubating cells at 30° C. for 2-4 days to allow for growth of transformants. The deletion of the URA3 gene is confirmed by PCR and sequencing with flanking primers of the URA3 target region. The editing frequency for each plasmid is determined by dividing the number of ura3Δ, colonies by the total number of tested colonies.

What is claimed is:

1. A CRISPR-associated endonuclease 9 (Cas9) endonuclease variant, or an active fragment thereof, having at least 80% amino acid identity to a parent Cas9 polypeptide set forth in SEQ ID NO: 1 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity.

2. The Cas9 endonuclease variant of claim 1, wherein the at least one amino acid substitution is selected from the group consisting of Y155H, Y155N, Y155E, Y155F (at position 155), F86A (at position 86) and F98A (at position 98).

3. The Cas9 endonuclease variant of claim 1, wherein the Cas9 endonuclease variant has at least one improved property selected from the group consisting of improved transformation efficiency and improved editing efficiency, when compared to said property of said parent Cas9 endonuclease.

4. The Cas9 endonuclease variant, or active fragment thereof, of claim 1, wherein said variant comprises an amino acid sequence having 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 1.

5. The Cas9 endonuclease variant of claim 3, wherein the improved property is improved transformation efficiency when compared to said property of said parent Cas9 endonuclease, and wherein said variant, or active fragment thereof, also has an improved editing efficiency.

6. The Cas9 endonuclease variant, or active fragment thereof, of claim 1, comprising at least 2 amino acid substitutions when compared to the parent Cas9 endonuclease.

7. A composition comprising the Cas9 endonuclease, or a functional fragment thereof, of claim 1.

8. The composition of claim 7, wherein said composition is selected from the group consisting of a guide polynucleotide/Cas9 endonuclease complex, a guide RNA/Cas9 endonuclease complex, and a fusion protein comprising said Cas9 endonuclease variant.

* * * * *

SEQUENCE LISTING

<160> NUMBER OF SEQ ID NOS: 157

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

```
Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
```

-continued

```
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170
```

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 2
<211> LENGTH: 5056
<212> TYPE: DNA
<213> ORGANISM: Artificial sequence
<220> FEATURE:
<223> OTHER INFORMATION: Bacillus codon optimized Cas9

<400> SEQUENCE: 2
aattcctcca ttttcttctg ctatcaaaat aacagactcg tgattttcca aacgagcttt 60
caaaaaagcc tctgcccctt gcaaatcgga tgcctgtcta taaaattccc gatattggtt 120
aaacagcggc gcaatggcgg ccgcatctga tgtctttgct tggcgaatgt tcatcttatt 180
tcttcctccc tctcaataat tttttcattc tatccctttt ctgtaaagtt tatttttcag 240
aatactttta tcatcatgct ttgaaaaaat atcacgataa tatccattgt tctcacggaa 300
gcacacgcag gtcatttgaa cgaatttttt cgacaggaat ttgccgggac tcaggagcat 360
ttaacctaaa aaagcatgac atttcagcat aatgaacatt tactcatgtc tattttcgtt 420
cttttctgta tgaaaatagt tatttcgagt ctctacggaa atagcgagag atgatatacc 480
taaatagaga taaaatcatc tcaaaaaaat gggtctacta aaatattatt ccatctatta 540
caataaattc acagaatagt cttttaagta agtctactct gaattttttt aaaaggagag 600
ggtaactagt ggccccaaaa aagaaacgca aggttatgga taaaaaatac agcattggtc 660
tggatatcgg aaccaacagc gttgggtggg cagtaataac agatgaatac aaagtgccgt 720
caaaaaaatt taaggttctg gggaatacag atcgccacag cataaaaaag aatctgattg 780
gggcattgct gtttgattcg ggtgagacag ctgaggccac gcgtctgaaa cgtacagcaa 840
gaagacgtta cacacgtcgt aaaaatcgta tttgctactt acaggaaatt ttttctaacg 900

```
aaatggccaa ggtagatgat agtttcttcc atcgtctcga agaatctttt ctggttgagg    960
aagataaaaa acacgaacgt caccctatct ttggcaatat cgtggatgaa gtggcctatc   1020
atgaaaaata ccctacgatt tatcatcttc gcaagaagtt ggttgatagt acggacaaag   1080
cggatctgcg tttaatctat cttgcgttag cgcacatgat caaatttcgt ggtcatttct   1140
taattgaagg tgatctgaat cctgataact ctgatgtgga caaattgttt atacaattag   1200
tgcaaaccta taatcagctg ttcgaggaaa accccattaa tgcctctgga gttgatgcca   1260
aagcgatttt aagcgcgaga ctttctaagt cccggcgtct ggagaatctg atcgcccagt   1320
taccagggga aaagaaaaat ggtctgtttg gtaatctgat tgccctcagt ctggggctta   1380
ccccgaactt caaatccaat tttgacctgg ctgaggacgc aaagctgcag ctgagcaaag   1440
atacttatga tgatgacctc gacaatctgc tcgcccagat tggtgaccaa tatgcggatc   1500
tgtttctggc agcgaagaat ctttcggatg ctatcttgct gtcggatatt ctgcgtgtta   1560
ataccgaaat caccaaagcg cctctgtctg caagtatgat caagagatac gacgagcacc   1620
accaggacct gactcttctt aaggcactgg tacgccaaca gcttccggag aaatacaaag   1680
aaatattctt cgaccagtcc aagaatggtt acgcgggcta catcgatggt ggtgcatcac   1740
aggaagagtt ctataaattt attaaaccaa tccttgagaa aatggatggc acggaagagt   1800
tacttgttaa acttaaccgc gaagacttgc ttagaaagca acgtacattc gacaacggct   1860
ccatcccaca ccagattcat ttaggtgaac ttcacgccat cttgcgcaga caagaagatt   1920
tctatccctt cttaaaagac aatcgggaga aaatcgagaa gatcctgacg ttccgcattc   1980
cctattatgt cggtcccctg gcacgtggta attctcggtt tgcctggatg acgcgcaaaa   2040
gtgaggaaac catcacccct tggaactttg aagaagtcgt ggataaaggt gctagcgcgc   2100
agtcttttat agaaagaatg acgaacttcg ataaaaactt gcccaacgaa aaagtcctgc   2160
ccaagcactc tcttttatat gagtacttta ctgtgtacaa cgaactgact aaagtgaaat   2220
acgttacgga aggtatgcgc aaacctgcct ttcttagtgg cgagcagaaa aaagcaattg   2280
tcgatcttct ctttaaaacg aatcgcaagg taactgtaaa acagctgaag gaagattatt   2340
tcaaaaagat cgaatgcttt gattctgtcg agatctcggg tgtcgaagat cgtttcaacg   2400
cttccttagg gacctatcat gatttgctga agataataaa agacaaagac tttctcgaca   2460
atgaagaaaa tgaagatatt ctggaggata ttgttttgac cttgacctta ttcgaagata   2520
gagagatgat cgaggagcgc ttaaaaacct atgcccacct gtttgatgac aaagtcatga   2580
agcaattaaa gcgccgcaga tatacggggt ggggccgctt gagccgcaag ttgattaacg   2640
gtattagaga caagcagagc ggaaaaacta tcctggattt cctcaaatct gacggatttg   2700
cgaaccgcaa ttttatgcag cttatacatg atgattcgct tacattcaaa gaggatattc   2760
agaaggctca ggtgtctggg caaggtgatt cactccacga acatatagca aatttggccg   2820
gctctcctgc gattaagaag gggatcctgc aaacagttaa agttgtggat gaacttgtaa   2880
aagtaatggg ccgccacaag ccggagaata tcgtgataga aatggcgcgc gagaatcaaa   2940
cgacacaaaa aggtcaaaag aactcaagag agagaatgaa gcgcattgag gaggggataa   3000
aggaacttgg atctcaaatt ctgaaagaac atccagttga aaacactcag ctgcaaaatg   3060
aaaaattgta cctgtactac ctgcagaatg gaagagacat gtacgtggat caggaattgg   3120
atatcaatag actctcggac tatgacgtag atcacattgt ccctcagagc ttcctcaagg   3180
atgattctat agataataaa gtacttacga gatcggacaa aaatcgcggt aaatcggata   3240
```

-continued

```
acgtcccatc ggaggaagtc gttaaaaaga tgaaaaacta ttggcgtcaa ctgctgaacg   3300

ccaagctgat cacacagcgt aagtttgata atctgactaa agccgaacgc ggtggtctta   3360

gtgaactcga taaagcagga tttataaaac ggcagttagt agaaacgcgc caaattacga   3420

aacacgtggc tcagatcctc gattctagaa tgaatacaaa gtacgatgaa aacgataaac   3480

tgatccgtga agtaaaagtc attaccttaa aatctaaact tgtgtccgat ttccgcaaag   3540

attttcagtt ttacaaggtc cgggaaatca ataactatca ccatgcacat gatgcatatt   3600

taaatgcggt tgtaggcacg gcccttatta agaaataccc taaactcgaa agtgagtttg   3660

tttatgggga ttataaagtg tatgacgttc gcaaaatgat cgcgaaatca gaacaggaaa   3720

tcggtaaggc taccgctaaa tacttttttt attccaacat tatgaatttt tttaagaccg   3780

aaataactct cgcgaatggt gaaatccgta aacggcctct tatagaaacc aatggtgaaa   3840

cgggagaaat cgtttgggat aaaggtcgtg actttgccac cgttcgtaaa gtcctctcaa   3900

tgccgcaagt taacattgtc aagaagacgg aagttcaaac aggggggattc tccaaagaat   3960

ctatcctgcc gaagcgtaac agtgataaac ttattgccag aaaaaaagat tgggatccaa   4020

aaaaatacgg aggctttgat tcccctaccg tcgcgtatag tgtgctggtg gttgctaaag   4080

tcgagaaagg gaaaagcaag aaattgaaat cagttaaaga actgctgggt attacaatta   4140

tggaaagatc gtcctttgag aaaaatccga tcgacttttt agaggccaag ggtataaggg   4200

aagtgaaaaa agatctcatc atcaaattac cgaagtatag tctttttgag ctggaaaacg   4260

gcagaaaaag aatgctggcc tccgcgggcg agttacagaa gggaaatgag ctggcgctgc   4320

cttccaaata tgttaatttt ctgtaccttg ccagtcatta tgagaaactg aagggcagcc   4380

ccgaagataa cgaacagaaa caattattcg tggaacagca taagcactat ttagatgaaa   4440

ttatagagca aattagtgaa ttttctaagc gcgttatcct cgcggatgct aatttagaca   4500

aagtactgtc agcttataat aaacatcggg ataagccgat tagagaacag gccgaaaata   4560

tcattcattt gtttacctta accaaccttg gagcaccagc tgccttcaaa tatttcgata   4620

ccacaattga tcgtaaacgg tatacaagta caaaagaagt cttggacgca accctcattc   4680

atcaatctat tactggatta tatgagacac gcattgatct ttcacagctg ggcggagaca   4740

agaagaaaaa actgaaactg caccatcatc accatcatca tcaccatcat tgataactcg   4800

agaaagctta cataaaaaac cggccttggc cccgccggtt ttttattatt tttcttcctc   4860

cgcatgttca atccgctcca taatcgacgg atggctccct ctgaaaattt taacgagaaa   4920

cggcgggttg acccggctca gtcccgtaac ggccaagtcc tgaaacgtct caatcgccgc   4980

ttcccggttt ccggtcagct caatgccgta acggtcggcg gcgttttcct gataccggga   5040

gacggcattc gtaatc                                                   5056
```

```
<210> SEQ ID NO 3
<211> LENGTH: 8
<212> TYPE: PRT
<213> ORGANISM: Artificial sequence
<220> FEATURE:
<223> OTHER INFORMATION: N-terminal NLS

<400> SEQUENCE: 3

Ala Pro Lys Lys Lys Arg Lys Val
1               5


<210> SEQ ID NO 4
<211> LENGTH: 6
<212> TYPE: PRT
```

<213> ORGANISM: Artificial sequence
<220> FEATURE:
<223> OTHER INFORMATION: C-terminal NLS

<400> SEQUENCE: 4

Lys Lys Lys Lys Leu Lys
1 5

<210> SEQ ID NO 5
<211> LENGTH: 10
<212> TYPE: PRT
<213> ORGANISM: Artificial sequence
<220> FEATURE:
<223> OTHER INFORMATION: deca-Histidine tag

<400> SEQUENCE: 5

His His His His His His His His His His
1 5 10

<210> SEQ ID NO 6
<211> LENGTH: 607
<212> TYPE: DNA
<213> ORGANISM: Bacillus subtilis

<400> SEQUENCE: 6
attcctccat tttcttctgc tatcaaaata acagactcgt gattttccaa acgagctttc 60
aaaaaagcct ctgccccttg caaatcggat gcctgtctat aaaattcccg atattggtta 120
aacagcggcg caatggcggc cgcatctgat gtctttgctt ggcgaatgtt catcttattt 180
cttcctccct ctcaataatt ttttcattct atccctttc tgtaaagttt atttttcaga 240
atacttttat catcatgctt tgaaaaaata tcacgataat atccattgtt ctcacggaag 300
cacacgcagg tcatttgaac gaattttttc gacaggaatt tgccgggact caggagcatt 360
taacctaaaa aagcatgaca tttcagcata atgaacattt actcatgtct attttcgttc 420
ttttctgtat gaaaatagtt atttcgagtc tctacggaaa tagcgagaga tgatatacct 480
aaatagagat aaaatcatct caaaaaaatg ggtctactaa aatattattc catctattac 540
aataaattca cagaatagtc ttttaagtaa gtctactctg aatttttta aaaggagagg 600 gtaacta 607

<210> SEQ ID NO 7
<211> LENGTH: 247
<212> TYPE: DNA
<213> ORGANISM: Artificial sequence
<220> FEATURE:
<223> OTHER INFORMATION: synthesized terminator DNA sequence

<400> SEQUENCE: 7
acataaaaaa ccggccttgg ccccgccggt tttttattat ttttcttcct ccgcatgttc 60
aatccgctcc ataatcgacg gatggctccc tctgaaaatt ttaacgagaa acggcgggtt 120
gacccggctc agtcccgtaa cggccaagtc ctgaaacgtc tcaatcgccg cttcccggtt 180
tccggtcagc tcaatgccgt aacggtcggc ggcgttttcc tgataccggg agacggcatt 240
cgtaatc 247

<210> SEQ ID NO 8
<211> LENGTH: 50
<212> TYPE: DNA
<213> ORGANISM: Artificial sequence
<220> FEATURE:
<223> OTHER INFORMATION: Cas9 forward primer

<400> SEQUENCE: 8
atatatgagt aaacttggtc tgacagaatt cctccatttt cttctgctat 50

<210> SEQ ID NO 9
<211> LENGTH: 35
<212> TYPE: DNA
<213> ORGANISM: Artificial sequence
<220> FEATURE:
<223> OTHER INFORMATION: Cas9 revers primer

<400> SEQUENCE: 9
tgcggccgcg aattcgatta cgaatgccgt ctccc 35

<210> SEQ ID NO 10
<211> LENGTH: 3290
<212> TYPE: DNA
<213> ORGANISM: Artificial sequence
<220> FEATURE:
<223> OTHER INFORMATION: plasmid pKB320 backbone

<400> SEQUENCE: 10
gaattcgcgg ccgcacgcgt ccatggggat ccccgcgggt cgacctcgag agttacgcta 60
gggataacag ggtaatatag gagctccagt cggcttaaac cagttttcgc tggtgcgaaa 120
aaagagtgtc ttgtgacacc taaattcaaa atctatcggt cagatttata ccgatttgat 180
tttatatatt cttgaataac atacgccgag ttatcacata aaagcgggaa ccaatcataa 240
aatttaaact tcattgcata atccattaaa ctcttaaatt ctacgattcc ttgttcatca 300
ataaactcaa tcatttcttt aattaattta tatctatctg ttgttgtttt ctttaataat 360
tcattaacat ctacaccgcc ataaactatc atatcttctt tttgatattt aaatttatta 420
ggatcgtcca tgtgaagcat atatctcaca agacctttca cacttcctgc aatctgcgga 480
atagtcgcat tcaattcttc tgttaattat ttttatctgt tcataagatt tattaccctc 540
atacatcact agaatatgat aatgctcttt tttcatccta ccttctgtat cagtatccct 600
atcatgtaat ggagacacta caaattgaat gtgtaactct tttaaatact ctaaccactc 660
ggcttttgct gattctggat ataaaacaaa tgtccaatta cgtcctcttg aatttttctt 720
gttttcagtt tcttttatta cattttcgct catgatataa taacggtgct aatacactta 780
acaaaattta gtcatagata ggcagcatgc cagtgctgtc tatctttttt tgtttaaaat 840
gcaccgtatt cctcctttgc atattttttt attagaatac cggttgcatc tgatttgcta 900
atattatatt tttctttgat tctatttaat atctcatttt cttctgttgt aagtcttaaa 960
gtaacagcaa ctttttttctc ttcttttcta tctacaacta tcactgtacc tcccaacatc 1020 tgttttttttc actttaacat aaaaaacaac cttttaacat taaaaaccca atatttattt 1080
atttgtttgg acaatggaca ctggacacct agggggggagg tcgtagtacc cccctatgtt 1140
ttctccccta aataacccca aaaatctaag aaaaaaagac ctcaaaaagg tctttaatta 1200
acatctcaaa tttcgcattt attccaattt cctttttgcg tgtgatgcga gctcatcggc 1260
tccgtcgata ctatgttata cgccaacttt caaaacaact ttgaaaaagc tgttttctgg 1320
tatttaaggt tttagaatgc aaggaacagt gaattggagt tcgtcttgtt ataattagct 1380
tcttggggta tctttaaata ctgtagaaaa gaggaaggaa ataataaatg gctaaaatga 1440
gaatatcacc ggaattgaaa aaactgatcg aaaaataccg ctgcgtaaaa gatacggaag 1500
gaatgtctcc tgctaaggta tataagctgg tgggagaaaa tgaaaaccta tatttaaaaa 1560

-continued

```
tgacggacag ccggtataaa gggaccacct atgatgtgga acgggaaaag gacatgatgc   1620

tatggctgga aggaaagctg cctgttccaa aggtcctgca ctttgaacgg catgatggct   1680

ggagcaatct gctcatgagt gaggccgatg gcgtcctttg ctcggaagag tatgaagatg   1740

aacaaagccc tgaaaagatt atcgagctgt atgcggagtg catcaggctc tttcactcca   1800

tcgacatatc ggattgtccc tatacgaata gcttagacag ccgcttagcc gaattggatt   1860

acttactgaa taacgatctg gccgatgtgg attgcgaaaa ctgggaagaa gacactccat   1920

ttaaagatcc gcgcgagctg tatgattttt taaagacgga aaagcccgaa gaggaacttg   1980

tcttttccca cggcgacctg ggagacagca acatctttgt gaaagatggc aaagtaagtg   2040

gctttattga tcttgggaga agcggcaggg cggacaagtg gtatgacatt gccttctgcg   2100

tccggtcgat cagggaggat atcggggaag aacagtatgt cgagctattt tttgacttac   2160

tggggatcaa gcctgattgg gagaaaataa aatattatat tttactggat gaattgtttt   2220

agtgactgca gtgagatctg gtaatgactc tctagcttga ggcatcaaat aaaacgaaag   2280

gctcagtcga aagactgggc ctttcgtttt atctgttgtt tgtcggtgaa cgctctcctg   2340

agtaggacaa atccgccgct ctagctaagc agaaggccat cctgacggat ggcctttttg   2400

cgtttctaca aactcttgtt aactctagag ctgcctgccg cgtttcggtg atgaagatct   2460

tcccgatgat taattaattc agaacgctcg gttgccgccg ggcgtttttt atgaagcttc   2520

gttgctggcg tttttccata ggctccgccc ccctgacgag catcacaaaa atcgacgctc   2580

aagtcagagg tggcgaaacc cgacaggact ataaagatac caggcgtttc cccctggaag   2640

ctccctcgtg cgctctcctg ttccgaccct gccgcttacc ggatacctgt ccgcctttct   2700

cccttcggga agcgtggcgc tttctcatag ctcacgctgt aggtatctca gttcggtgta   2760

ggtcgttcgc tccaagctgg gctgtgtgca cgaacccccc gttcagcccg accgctgcgc   2820

cttatccggt aactatcgtc ttgagtccaa cccggtaaga cacgacttat cgccactggc   2880

agcagccact ggtaacagga ttagcagagc gaggtatgta ggcggtgcta cagagttctt   2940

gaagtggtgg cctaactacg gctacactag aaggacagta tttggtatct gcgctctgct   3000

gaagccagtt accttcggaa aaagagttgg tagctcttga tccggcaaac aaaccaccgc   3060

tggtagcggt ggtttttttg tttgcaagca gcagattacg cgcagaaaaa aaggatctca   3120

agaagatcct ttgatctttt ctacggggtc tgacgctcag tggaacgaaa actcacgtta   3180

agggattttg gtcatgagat tatcaaaaag gatcttcacc tagatccttt taaattaaaa   3240

atgaagtttt aaatcaatct aaagtatata tgagtaaact tggtctgaca              3290
```

<210> SEQ ID NO 11
<211> LENGTH: 4204
<212> TYPE: DNA
<213> ORGANISM: Artificial sequence
<220> FEATURE:
<223> OTHER INFORMATION: pKB320 plasmid

<400> SEQUENCE: 11

```
gcggccgcac gcgtccatgg ggatccccgc gggtcgacct cgagagttac gctagggata     60

acagggtaat ataggagctc cagtcggctt aaaccagttt tcgctggtgc gaaaaaagag    120

tgtcttgtga cacctaaatt caaaatctat cggtcagatt tataccgatt tgattttata    180

tattcttgaa taacatacgc cgagttatca cataaaagcg ggaaccaatc ataaaattta    240

aacttcattg cataatccat taaactctta aattctacga ttccttgttc atcaataaac    300

tcaatcattt ctttaattaa tttatatcta tctgttgttg ttttctttaa taattcatta    360
```

-continued

```
acatctacac cgccataaac tatcatatct tctttttgat atttaaattt attaggatcg    420
tccatgtgaa gcatatatct cacaagacct ttcacacttc ctgcaatctg cggaatagtc    480
gcattcaatt cttctgttaa ttatttttat ctgttcataa gatttattac cctcatacat    540
cactagaata tgataatgct ctttttcat cctaccttct gtatcagtat ccctatcatg    600
taatggagac actacaaatt gaatgtgtaa ctcttttaaa tactctaacc actcggcttt    660
tgctgattct ggatataaaa caaatgtcca attacgtcct cttgaatttt tcttgttttc    720
agtttctttt attacatttt cgctcatgat ataataacgg tgctaataca cttaacaaaa    780
tttagtcata gataggcagc atgccagtgc tgtctatctt tttttgttta aaatgcaccg    840
tattcctcct ttgcatattt ttttattaga ataccggttg catctgattt gctaatatta    900
tatttttctt tgattctatt taatatctca ttttcttctg ttgtaagtct taaagtaaca    960
gcaacttttt tctcttcttt tctatctaca actatcactg tacctcccaa catctgtttt   1020
tttcacttta acataaaaaa caacctttta acattaaaaa cccaatattt atttatttgt   1080
ttggacaatg gacactggac acctaggggg gaggtcgtag taccccccta tgttttctcc   1140
cctaaataac cccaaaaatc taagaaaaaa agacctcaaa aaggtcttta attaacatct   1200
caaatttcgc atttattcca atttcctttt tgcgtgtgat gcgagctcat cggctccgtc   1260
gatactatgt tatacgccaa ctttcaaaac aactttgaaa aagctgtttt ctggtattta   1320
aggttttaga atgcaaggaa cagtgaattg gagttcgtct tgttataatt agcttcttgg   1380
ggtatcttta aatactgtag aaaagaggaa ggaaataata aatggctaaa atgagaatat   1440
caccggaatt gaaaaaactg atcgaaaaat accgctgcgt aaaagatacg gaaggaatgt   1500
ctcctgctaa ggtatataag ctggtgggag aaaatgaaaa cctatattta aaaatgacgg   1560
acagccggta taaagggacc acctatgatg tggaacggga aaggacatg atgctatggc   1620
tggaaggaaa gctgcctgtt ccaaaggtcc tgcactttga acggcatgat ggctggagca   1680
atctgctcat gagtgaggcc gatggcgtcc tttgctcgga agagtatgaa gatgaacaaa   1740
gccctgaaaa gattatcgag ctgtatgcgg agtgcatcag gctctttcac tccatcgaca   1800
tatcggattg tccctatacg aatagcttag acagccgctt agccgaattg gattacttac   1860
tgaataacga tctggccgat gtggattgcg aaaactggga agaagacact ccatttaaag   1920
atccgcgcga gctgtatgat tttttaaaga cggaaaagcc cgaagaggaa cttgtctttt   1980
cccacggcga cctgggagac agcaacatct ttgtgaaaga tggcaaagta agtggcttta   2040
ttgatcttgg gagaagcggc agggcggaca agtggtatga cattgccttc tgcgtccggt   2100
cgatcaggga ggatatcggg gaagaacagt atgtcgagct atttttttgac ttactgggga   2160
tcaagcctga ttgggagaaa ataaaatatt atattttact ggatgaattg ttttagtgac   2220
tgcagtgaga tctggtaatg actctctagc ttgaggcatc aaataaaacg aaaggctcag   2280
tcgaaagact gggcctttcg ttttatctgt tgtttgtcgg tgaacgctct cctgagtagg   2340
acaaatccgc cgctctagct aagcagaagg ccatcctgac ggatggcctt tttgcgtttc   2400
tacaaactct tgttaactct agagctgcct gccgcgtttc ggtgatgaag atcttcccga   2460
tgattaatta attcagaacg ctcggttgcc gccgggcgtt ttttatgaag cttcgttgct   2520
ggcgtttttc cataggctcc gcccccctga cgagcatcac aaaaatcgac gctcaagtca   2580
gaggtggcga aacccgacag gactataaag ataccaggcg tttccccctg gaagctccct   2640
cgtgcgctct cctgttccga ccctgccgct taccggatac ctgtccgcct ttctcccttc   2700
```

-continued

```
gggaagcgtg gcgctttctc atagctcacg ctgtaggtat ctcagttcgg tgtaggtcgt   2760
tcgctccaag ctgggctgtg tgcacgaacc ccccgttcag cccgaccgct gcgccttatc   2820
cggtaactat cgtcttgagt ccaacccggt aagacacgac ttatcgccac tggcagcagc   2880
cactggtaac aggattagca gagcgaggta tgtaggcggt gctacagagt tcttgaagtg   2940
gtggcctaac tacggctaca ctagaaggac agtatttggt atctgcgctc tgctgaagcc   3000
agttaccttc ggaaaaagag ttggtagctc ttgatccggc aaacaaacca ccgctggtag   3060
cggtggtttt tttgtttgca agcagcagat tacgcgcaga aaaaaaggat ctcaagaaga   3120
tcctttgatc ttttctacgg ggtctgacgc tcagtggaac gaaaactcac gttaagggat   3180
tttggtcatg agattatcaa aaaggatctt cacctagatc cttttaaatt aaaaatgaag   3240
ttttaaatca atctaaagta tatatgagta aacttggtct gacagttacc aatgcttaat   3300
cagtgaggca cctatctcag cgatctgtct atttcgttca tccatagttg cctgactccc   3360
cgtcgtgtag ataactacga tacgggaggg cttaccatct ggccccagtg ctgcaatgat   3420
accgcgagac ccacgctcac cggctccaga tttatcagca ataaaccagc cagccggaag   3480
ggccgagcgc agaagtggtc ctgcaacttt atccgcctcc atccagtcta ttaattgttg   3540
ccgggaagct agagtaagta gttcgccagt taatagtttg cgcaacgttg ttgccattgc   3600
tacaggcatc gtggtgtcac gctcgtcgtt tggtatggct tcattcagct ccggttccca   3660
acgatcaagg cgagttacat gatcccccat gttgtgcaaa aaagcggtta gctccttcgg   3720
tcctccgatc gttgtcagaa gtaagttggc cgcagtgtta tcactcatgg ttatggcagc   3780
actgcataat tctcttactg tcatgccatc cgtaagatgc ttttctgtga ctggtgagta   3840
ctcaaccaag tcattctgag aatagtgtat gcggcgaccg agttgctctt gcccggcgtc   3900
aatacgggat aataccgcgc cacatagcag aactttaaaa gtgctcatca ttggaaaacg   3960
ttcttcgggg cgaaaactct caaggatctt accgctgttg agatccagtt cgatgtaacc   4020
cactcgtgca cccaactgat cttcagcatc ttttactttc accagcgttt ctgggtgagc   4080
aaaaacagga aggcaaaatg ccgcaaaaaa gggaataagg gcgacacgga aatgttgaat   4140
actcatactc ttcctttttc aatattattg aagcatttat cagggttatt gtctcatgga   4200
attc                                                                4204
```

<210> SEQ ID NO 12
<211> LENGTH: 35
<212> TYPE: DNA
<213> ORGANISM: Artificial sequence
<220> FEATURE:
<223> OTHER INFORMATION: pKB320 forward primer

<400> SEQUENCE: 12

```
gggagacggc attcgtaatc gaattcgcgg ccgca                                35
```

<210> SEQ ID NO 13
<211> LENGTH: 50
<212> TYPE: DNA
<213> ORGANISM: Artificial sequence
<220> FEATURE:
<223> OTHER INFORMATION: pKB320 reverse primer

<400> SEQUENCE: 13

```
atagcagaag aaaatggagg aattctgtca gaccaagttt actcatatat                50
```

<210> SEQ ID NO 14
<211> LENGTH: 23

<212> TYPE: DNA
<213> ORGANISM: Artificial sequence
<220> FEATURE:
<223> OTHER INFORMATION: plasmid RSP1

<400> SEQUENCE: 14
ccgactggag ctcctatatt acc 23

<210> SEQ ID NO 15
<211> LENGTH: 20
<212> TYPE: DNA
<213> ORGANISM: Artificial sequence
<220> FEATURE:
<223> OTHER INFORMATION: plasmid RSP2

<400> SEQUENCE: 15
gctgtggcga tctgtattcc 20

<210> SEQ ID NO 16
<211> LENGTH: 22
<212> TYPE: DNA
<213> ORGANISM: Artificial sequence
<220> FEATURE:
<223> OTHER INFORMATION: plasmid FSP1

<400> SEQUENCE: 16
gtcttttaag taagtctact ct 22

<210> SEQ ID NO 17
<211> LENGTH: 20
<212> TYPE: DNA
<213> ORGANISM: Artificial sequence
<220> FEATURE:
<223> OTHER INFORMATION: plasmid FSP2

<400> SEQUENCE: 17
ccaaagcgat tttaagcgcg 20

<210> SEQ ID NO 18
<211> LENGTH: 20
<212> TYPE: DNA
<213> ORGANISM: Artificial sequence
<220> FEATURE:
<223> OTHER INFORMATION: plasmid FSP3

<400> SEQUENCE: 18
cctggcacgt ggtaattctc 20

<210> SEQ ID NO 19
<211> LENGTH: 20
<212> TYPE: DNA
<213> ORGANISM: Artificial sequence
<220> FEATURE:
<223> OTHER INFORMATION: plasmid FSP4

<400> SEQUENCE: 19
ggatttcctc aaatctgacg 20

<210> SEQ ID NO 20
<211> LENGTH: 21
<212> TYPE: DNA
<213> ORGANISM: Artificial sequence
<220> FEATURE:
<223> OTHER INFORMATION: plasmid FSP5

<400> SEQUENCE: 20
gtagaaacgc gccaaattac g 21

<210> SEQ ID NO 21
<211> LENGTH: 20
<212> TYPE: DNA
<213> ORGANISM: Artificial sequence
<220> FEATURE:
<223> OTHER INFORMATION: plasmid FSP6

<400> SEQUENCE: 21
gctggtggtt gctaaagtcg 20

<210> SEQ ID NO 22
<211> LENGTH: 20
<212> TYPE: DNA
<213> ORGANISM: Artificial sequence
<220> FEATURE:
<223> OTHER INFORMATION: plasmid FSP7

<400> SEQUENCE: 22
ggacgcaacc ctcattcatc 20

<210> SEQ ID NO 23
<211> LENGTH: 20
<212> TYPE: DNA
<213> ORGANISM: Artificial sequence
<220> FEATURE:
<223> OTHER INFORMATION: plasmid RSP3

<400> SEQUENCE: 23
caggcatccg atttgcaagg 20

<210> SEQ ID NO 24
<211> LENGTH: 19
<212> TYPE: DNA
<213> ORGANISM: Artificial sequence
<220> FEATURE:
<223> OTHER INFORMATION: plasmid FSP8

<400> SEQUENCE: 24
gcaagcagca gattacgcg 19

<210> SEQ ID NO 25
<211> LENGTH: 8347
<212> TYPE: DNA
<213> ORGANISM: Artificial sequence
<220> FEATURE:
<223> OTHER INFORMATION: plasmid pRF694

<400> SEQUENCE: 25
gaattcctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600

```
gggtaactag tggccccaaa aaagaaacgc aaggttatgg ataaaaaata cagcattggt    660
ctggatatcg gaaccaacag cgttgggtgg gcagtaataa cagatgaata caaagtgccg    720
tcaaaaaaat ttaaggttct ggggaataca gatcgccaca gcataaaaaa gaatctgatt    780
ggggcattgc tgtttgattc gggtgagaca gctgaggcca cgcgtctgaa acgtacagca    840
agaagacgtt acacacgtcg taaaaatcgt atttgctact tacaggaaat tttttctaac    900
gaaatggcca aggtagatga tagtttcttc catcgtctcg aagaatcttt tctggttgag    960
gaagataaaa aacacgaacg tcaccctatc tttggcaata tcgtggatga agtggcctat   1020
catgaaaaat accctacgat ttatcatctt cgcaagaagt tggttgatag tacggacaaa   1080
gcggatctgc gtttaatcta tcttgcgtta gcgcacatga tcaaatttcg tggtcatttc   1140
ttaattgaag gtgatctgaa tcctgataac tctgatgtgg acaaattgtt tatacaatta   1200
gtgcaaacct ataatcagct gttcgaggaa aaccccatta atgcctctgg agttgatgcc   1260
aaagcgattt taagcgcgag actttctaag tcccggcgtc tggagaatct gatcgcccag   1320
ttaccagggg aaaagaaaaa tggtctgttt ggtaatctga ttgccctcag tctggggctt   1380
accccgaact tcaaatccaa ttttgacctg gctgaggacg caaagctgca gctgagcaaa   1440
gatacttatg atgatgacct cgacaatctg ctcgcccaga ttggtgacca atatgcggat   1500
ctgtttctgg cagcgaagaa tctttcggat gctatcttgc tgtcggatat tctgcgtgtt   1560
aataccgaaa tcaccaaagc gcctctgtct gcaagtatga tcaagagata cgacgagcac   1620
caccaggacc tgactcttct taaggcactg gtacgccaac agcttccgga gaaatacaaa   1680
gaaatattct tcgaccagtc caagaatggt tacgcgggct acatcgatgg tggtgcatca   1740
caggaagagt tctataaatt tattaaacca atccttgaga aaatggatgg cacggaagag   1800
ttacttgtta aacttaaccg cgaagacttg cttagaaagc aacgtacatt cgacaacggc   1860
tccatcccac accagattca tttaggtgaa cttcacgcca tcttgcgcag acaagaagat   1920
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
cccaagcact ctcttttata tgagtacttt actgtgtaca acgaactgac taaagtgaaa   2220
tacgttacgg aaggtatgcg caaacctgcc tttcttagtg gcgagcagaa aaaagcaatt   2280
gtcgatcttc tctttaaaac gaatcgcaag gtaactgtaa aacagctgaa ggaagattat   2340
ttcaaaaaga tcgaatgctt tgattctgtc gagatctcgg gtgtcgaaga tcgtttcaac   2400
gcttccttag ggacctatca tgatttgctg aagataataa aagacaaaga ctttctcgac   2460
aatgaagaaa atgaagatat tctggaggat attgttttga ccttgacctt attcgaagat   2520
agagagatga tcgaggagcg cttaaaaacc tatgcccacc tgtttgatga caaagtcatg   2580
aagcaattaa agcgccgcag atatacgggg tggggccgct tgagccgcaa gttgattaac   2640
ggtattagag acaagcagag cggaaaaact atcctggatt tcctcaaatc tgacggattt   2700
gcgaaccgca attttatgca gcttatacat gatgattcgc ttacattcaa agaggatatt   2760
cagaaggctc aggtgtctgg gcaaggtgat tcactccacg aacatatagc aaatttggcc   2820
ggctctcctg cgattaagaa ggggatcctg caaacagtta aagttgtgga tgaacttgta   2880
aaagtaatgg gccgccacaa gccggagaat atcgtgatag aaatggcgcg cgagaatcaa   2940
```

-continued

```
acgacacaaa aaggtcaaaa gaactcaaga gagagaatga agcgcattga ggaggggata   3000
aaggaacttg gatctcaaat tctgaaagaa catccagttg aaaacactca gctgcaaaat   3060
gaaaaattgt acctgtacta cctgcagaat ggaagagaca tgtacgtgga tcaggaattg   3120
gatatcaata gactctcgga ctatgacgta gatcacattg tccctcagag cttcctcaag   3180
gatgattcta tagataataa agtacttacg agatcggaca aaaatcgcgg taaatcggat   3240
aacgtcccat cggaggaagt cgttaaaaag atgaaaaact attggcgtca actgctgaac   3300
gccaagctga tcacacagcg taagtttgat aatctgacta aagccgaacg cggtggtctt   3360
agtgaactcg ataaagcagg atttataaaa cggcagttag tagaaacgcg ccaaattacg   3420
aaacacgtgg ctcagatcct cgattctaga atgaatacaa agtacgatga aaacgataaa   3480
ctgatccgtg aagtaaaagt cattacctta aaatctaaac ttgtgtccga tttccgcaaa   3540
gattttcagt tttacaaggt ccgggaaatc aataactatc accatgcaca tgatgcatat   3600
ttaaatgcgg ttgtaggcac ggcccttatt aagaaatacc ctaaactcga aagtgagttt   3660
gtttatgggg attataaagt gtatgacgtt cgcaaaatga tcgcgaaatc agaacaggaa   3720
atcggtaagg ctaccgctaa atactttttt tattccaaca ttatgaattt ttttaagacc   3780
gaaataactc tcgcgaatgg tgaaatccgt aaacggcctc ttatagaaac caatggtgaa   3840
acgggagaaa tcgtttggga taaaggtcgt gactttgcca ccgttcgtaa agtcctctca   3900
atgccgcaag ttaacattgt caagaagacg gaagttcaaa caggggggatt ctccaaagaa   3960
tctatcctgc cgaagcgtaa cagtgataaa cttattgcca gaaaaaaaga ttgggatcca   4020
aaaaaatacg gaggctttga ttcccctacc gtcgcgtata gtgtgctggt ggttgctaaa   4080
gtcgagaaag ggaaaagcaa gaaattgaaa tcagttaaag aactgctggg tattacaatt   4140
atggaaagat cgtcctttga gaaaaatccg atcgactttt tagaggccaa ggggtataag   4200
gaagtgaaaa aagatctcat catcaaatta ccgaagtata gtctttttga gctggaaaac   4260
ggcagaaaaa gaatgctggc ctccgcgggc gagttacaga agggaaatga gctggcgctg   4320
ccttccaaat atgttaattt tctgtacctt gccagtcatt atgagaaact gaagggcagc   4380
cccgaagata acgaacagaa acaattattc gtggaacagc ataagcacta tttagatgaa   4440
attatagagc aaattagtga attttctaag cgcgttatcc tcgcggatgc taatttagac   4500
aaagtactgt cagcttataa taaacatcgg gataagccga ttagagaaca ggccgaaaat   4560
atcattcatt tgtttacctt aaccaacctt ggagcaccag ctgccttcaa atatttcgat   4620
accacaattg atcgtaaacg gtatacaagt acaaaagaag tcttggacgc aaccctcatt   4680
catcaatcta ttactggatt atatgagaca cgcattgatc tttcacagct gggcggagac   4740
aagaagaaaa aactgaaact gcaccatcat caccatcatc atcaccatca ttgataactc   4800
gagaaagctt acataaaaaa ccggccttgg ccccgccggt tttttattat ttttcttcct   4860
ccgcatgttc aatccgctcc ataatcgacg gatggctccc tctgaaaatt ttaacgagaa   4920
acggcgggtt gacccggctc agtcccgtaa cggccaagtc ctgaaacgtc tcaatcgccg   4980
cttcccggtt tccggtcagc tcaatgccgt aacggtcggc ggcgttttcc tgataccggg   5040
agacggcatt cgtaatcgaa ttcgcggccg cacgcgtcca tggggatccc cgcgggtcga   5100
cctcgagagt tacgctaggg ataacagggt aatataggag ctccagtcgg cttaaaccag   5160
ttttcgctgg tgcgaaaaaa gagtgtcttg tgacacctaa attcaaaatc tatcggtcag   5220
atttataccg atttgatttt atatattctt gaataacata cgccgagtta tcacataaaa   5280
gcgggaacca atcataaaat ttaaacttca ttgcataatc cattaaactc ttaaattcta   5340
```

-continued

```
cgattccttg ttcatcaata aactcaatca tttctttaat taatttatat ctatctgttg   5400
ttgttttctt taataattca ttaacatcta caccgccata aactatcata tcttcttttt   5460
gatatttaaa tttattagga tcgtccatgt gaagcatata tctcacaaga cctttcacac   5520
ttcctgcaat ctgcggaata gtcgcattca attcttctgt taattatttt tatctgttca   5580
taagatttat taccctcata catcactaga atatgataat gctctttttt catcctacct   5640
tctgtatcag tatccctatc atgtaatgga gacactacaa attgaatgtg taactctttt   5700
aaatactcta accactcggc ttttgctgat tctggatata aaacaaatgt ccaattacgt   5760
cctcttgaat tttcttgtt ttcagtttct tttattacat tttcgctcat gatataataa   5820
cggtgctaat acacttaaca aaatttagtc atagataggc agcatgccag tgctgtctat   5880
cttttttgt ttaaaatgca ccgtattcct cctttgcata tttttttatt agaataccgg   5940
ttgcatctga tttgctaata ttatattttt ctttgattct atttaatatc tcattttctt   6000
ctgttgtaag tcttaaagta acagcaactt ttttctcttc ttttctatct acaactatca   6060
ctgtacctcc caacatctgt tttttcact ttaacataaa aaacaacctt ttaacattaa   6120
aaacccaata tttatttatt tgtttggaca atggacactg gacacctagg ggggaggtcg   6180
tagtaccccc ctatgttttc tcccctaaat aaccccaaaa atctaagaaa aaaagacctc   6240
aaaaaggtct ttaattaaca tctcaaattt cgcatttatt ccaatttcct ttttgcgtgt   6300
gatgcgagct catcggctcc gtcgatacta tgttatacgc caactttcaa aacaactttg   6360
aaaaagctgt tttctggtat ttaaggtttt agaatgcaag gaacagtgaa ttggagttcg   6420
tcttgttata attagcttct tggggtatct ttaaatactg tagaaaagag gaaggaaata   6480
ataaatggct aaaatgagaa tatcaccgga attgaaaaaa ctgatcgaaa aataccgctg   6540
cgtaaaagat acggaaggaa tgtctcctgc taaggtatat aagctggtgg gagaaaatga   6600
aaacctatat ttaaaaatga cggacagccg gtataaaggg accacctatg atgtggaacg   6660
ggaaaaggac atgatgctat ggctggaagg aaagctgcct gttccaaagg tcctgcactt   6720
tgaacggcat gatggctgga gcaatctgct catgagtgag gccgatggcg tcctttgctc   6780
ggaagagtat gaagatgaac aaagccctga aaagattatc gagctgtatg cggagtgcat   6840
caggctcttt cactccatcg acatatcgga ttgtccctat acgaatagct tagacagccg   6900
cttagccgaa ttggattact tactgaataa cgatctggcc gatgtggatt gcgaaaactg   6960
ggaagaagac actccattta aagatccgcg cgagctgtat gattttttaa agacggaaaa   7020
gcccgaagag gaacttgtct tttcccacgg cgacctggga gacagcaaca tctttgtgaa   7080
agatggcaaa gtaagtggct ttattgatct tgggagaagc ggcagggcgg acaagtggta   7140
tgacattgcc ttctgcgtcc ggtcgatcag ggaggatatc ggggaagaac agtatgtcga   7200
gctatttttt gacttactgg ggatcaagcc tgattgggag aaaataaaat attatatttt   7260
actggatgaa ttgttttagt gactgcagtg agatctggta atgactctct agcttgaggc   7320
atcaaataaa acgaaaggct cagtcgaaag actgggcctt tcgttttatc tgttgtttgt   7380
cggtgaacgc tctcctgagt aggacaaatc cgccgctcta gctaagcaga aggccatcct   7440
gacggatggc ctttttgcgt ttctacaaac tcttgttaac tctagagctg cctgccgcgt   7500
ttcggtgatg aagatcttcc cgatgattaa ttaattcaga acgctcggtt gccgccgggc   7560
gtttttatg aagcttcgtt gctggcgttt ttccataggc tccgcccccc tgacgagcat   7620
cacaaaaatc gacgctcaag tcagaggtgg cgaaacccga caggactata aagataccag   7680
```

```
gcgtttcccc ctggaagctc cctcgtgcgc tctcctgttc cgaccctgcc gcttaccgga   7740
tacctgtccg cctttctccc ttcgggaagc gtggcgcttt ctcatagctc acgctgtagg   7800
tatctcagtt cggtgtaggt cgttcgctcc aagctgggct gtgtgcacga accccccgtt   7860
cagcccgacc gctgcgcctt atccggtaac tatcgtcttg agtccaaccc ggtaagacac   7920
gacttatcgc cactggcagc agccactggt aacaggatta gcagagcgag gtatgtaggc   7980
ggtgctacag agttcttgaa gtggtggcct aactacggct acactagaag gacagtattt   8040
ggtatctgcg ctctgctgaa gccagttacc ttcggaaaaa gagttggtag ctcttgatcc   8100
ggcaaacaaa ccaccgctgg tagcggtggt ttttttgttt gcaagcagca gattacgcgc   8160
agaaaaaaag gatctcaaga agatcctttg atcttttcta cggggtctga cgctcagtgg   8220
aacgaaaact cacgttaagg gattttggtc atgagattat caaaaaggat cttcacctag   8280
atccttttaa attaaaaatg aagttttaaa tcaatctaaa gtatatatga gtaaacttgg   8340
tctgaca                                                             8347
```

<210> SEQ ID NO 26
<211> LENGTH: 9724
<212> TYPE: DNA
<213> ORGANISM: Artificial sequence
<220> FEATURE:
<223> OTHER INFORMATION: plasmid pRF801

<400> SEQUENCE: 26

```
gggtgaagtg gtcaagacct cactaggcac cttaaaaata gcgcaccctg aagaagattt     60
atttgaggta gcccttgcct acctagcttc caagaaagat atcctaacag cacaagagcg    120
gaaagatgtt ttgttctaca tccagaacaa cctctgctaa aattcctgaa aaattttgca    180
aaaagttgtt gactttatct acaaggtgtg gcataatgtg tggactcgac ttcgaataca    240
tccagtttta gagctagaaa tagcaagtta aaataaggct agtccgttat caacttgaaa    300
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgttt ttcagtttct tttattacat tttcgctcat gatataataa   1140
cggtgctaat acacttaaca aaatttagtc atagataggc agcatgccag tgctgtctat   1200
cttttttttgt ttaaaatgca ccgtattcct cctttgcata ttttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
```

ctgtacctcc caacatctgt ttttttcact ttaacataaa aaacaacctt ttaacattaa 1440
aaacccaata tttatttatt tgtttggaca atggacactg gacacctagg ggggaggtcg 1500
tagtaccccc ctatgttttc tcccctaaat aaccccaaaa atctaagaaa aaaagacctc 1560
aaaaaggtct ttaattaaca tctcaaattt cgcatttatt ccaatttcct ttttgcgtgt 1620
gatgcgagct catcggctcc gtcgatacta tgttatacgc caactttcaa aacaactttg 1680
aaaaagctgt tttctggtat ttaaggtttt agaatgcaag gaacagtgaa ttggagttcg 1740
tcttgttata attagcttct tggggtatct ttaaatactg tagaaaagag gaaggaaata 1800
ataaatggct aaaatgagaa tatcaccgga attgaaaaaa ctgatcgaaa aataccgctg 1860
cgtaaaagat acggaaggaa tgtctcctgc taaggtatat aagctggtgg gagaaaatga 1920
aaacctatat ttaaaaatga cggacagccg gtataaaggg accacctatg atgtggaacg 1980
ggaaaaggac atgatgctat ggctggaagg aaagctgcct gttccaaagg tcctgcactt 2040
tgaacggcat gatggctgga gcaatctgct catgagtgag gccgatggcg tcctttgctc 2100
ggaagagtat gaagatgaac aaagccctga aaagattatc gagctgtatg cggagtgcat 2160
caggctcttt cactccatcg acatatcgga ttgtccctat acgaatagct tagacagccg 2220
cttagccgaa ttggattact tactgaataa cgatctggcc gatgtggatt gcgaaaactg 2280
ggaagaagac actccattta aagatccgcg cgagctgtat gattttttaa agacggaaaa 2340
gcccgaagag gaacttgtct ttcccacggc cgacctggga gacagcaaca tctttgtgaa 2400
agatggcaaa gtaagtggct ttattgatct tgggagaagc ggcagggcgg acaagtggta 2460
tgacattgcc ttctgcgtcc ggtcgatcag ggaggatatc ggggaagaac agtatgtcga 2520
gctatttttt gacttactgg ggatcaagcc tgattgggag aaaataaaat attatatttt 2580
actggatgaa ttgttttagt gactgcagtg agatctggta atgactctct agcttgaggc 2640
atcaaataaa acgaaaggct cagtcgaaag actgggcctt tcgttttatc tgttgtttgt 2700
cggtgaacgc tctcctgagt aggacaaatc cgccgctcta gctaagcaga aggccatcct 2760
gacggatggc ctttttgcgt ttctacaaac tcttgttaac tctagagctg cctgccgcgt 2820
ttcggtgatg aagatcttcc cgatgattaa ttaattcaga acgctcggtt gccgccgggc 2880
gtttttttatg aagcttcgtt gctggcgttt ttccataggc tccgcccccc tgacgagcat 2940
cacaaaaatc gacgctcaag tcagaggtgg cgaaacccga caggactata aagataccag 3000
gcgtttcccc ctggaagctc cctcgtgcgc tctcctgttc cgaccctgcc gcttaccgga 3060
tacctgtccg cctttctccc ttcgggaagc gtggcgcttt ctcatagctc acgctgtagg 3120
tatctcagtt cggtgtaggt cgttcgctcc aagctgggct gtgtgcacga accccccgtt 3180
cagcccgacc gctgcgcctt atccggtaac tatcgtcttg agtccaaccc ggtaagacac 3240
gacttatcgc cactggcagc agccactggt aacaggatta gcagagcgag gtatgtaggc 3300
ggtgctacag agttcttgaa gtggtggcct aactacggct acactagaag gacagtattt 3360
ggtatctgcg ctctgctgaa gccagttacc ttcggaaaaa gagttggtag ctcttgatcc 3420
ggcaaacaaa ccaccgctgg tagcggtggt ttttttgttt gcaagcagca gattacgcgc 3480
agaaaaaaag gatctcaaga agatcctttg atcttttcta cggggtctga cgctcagtgg 3540
aacgaaaact cacgttaagg gattttggtc atgagattat caaaaaggat cttcacctag 3600
atccttttaa attaaaaatg aagttttaaa tcaatctaaa gtatatatga gtaaacttgg 3660
tctgacaaat ggttctttcc cctgtcctaa acaaaaaacc cgctttattg aaaaagcggg 3720

-continued

```
gctgttttac agacaggtca aataaacgtt tgaaaatgtt catttcaaaa cgcgcggaac   3780
ctccatcttc tcccatccag actatactgt cggcttcgga atcgcaccga atcctgccca   3840
taaaaaggct cgcgggctta gagcgcttgc tcatcaccgc cggtagggaa tttcaccctg   3900
ccccgaagat tgatcttatt tatttttaat actgatatta ttataaatta attgtgaaaa   3960
aatgtacagg tgcaaagctt attgcgctgt tttgggacat cctgcacgat atttcggtaa   4020
actcactttt tccgcatact aaaaaccgca cattcacagt tatttcattt ttaattttcg   4080
tctttccgcg tgaaactcat tgacactctt tatggaatat ggtaaattat cagatattta   4140
tgacgcttat ttaggaggaa atcttacaca gaagctgcgg aacctgaaaa gaattccttt   4200
caggttccgt ttttttagg aattctccct gatctcaagc atctggcggg gataaatccg   4260
ctctcctttc aaatcgttcc attctttgag gcgctgtaca gttacgccca ttttttcggc   4320
gatatgatga agcgtatccc ctttccgcac tacatatgta ccggtcttcg attcatcgtc   4380
atgaaggcgg agtgtttggc cggccttgag atttgaatgt ttcaacccgt ttattctcat   4440
gatctcctcg atggatatac cgctatcctt gctgattctc cagagcgtgt cccctttttg   4500
aacggtcacc gcaccgctca ttgtcccggc gttttgataa acgtggatag aattttgccg   4560
gaacgcctcc tcacgaagca ccgtcagcgg attgattgca tatcttttat cttcagtcca   4620
tgaaccgtga tgcatttcaa aatgcaggtg ggttccggtc gatattcgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttttct gtaaagttta tttttcagaa tacttttatc   4920
atcatgcttt gaaaaaatat cacgataata tccattgttc tcacggaagc acacgcaggt   4980
catttgaacg aattttttcg acaggaattt gccgggactc aggagcattt aacctaaaaa   5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga attttttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatctttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatctatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
```

```
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcacccottg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
taggcacggc ccttattaag aaataccta aactcgaaag tgagtttgtt tatggggatt   8340
ataaagtgta tgacgttcgc aaaatgatcg cgaaatcaga acaggaaatc ggtaaggcta   8400
ccgctaaata ctttttttat tccaacatta tgaatttttt taagaccgaa ataactctcg   8460
```

```
cgaatggtga aatccgtaaa cggcctctta tagaaaccaa tggtgaaacg ggagaaatcg   8520

tttgggataa aggtcgtgac tttgccaccg ttcgtaaagt cctctcaatg ccgcaagtta   8580

acattgtcaa gaagacggaa gttcaaacag ggggattctc caaagaatct atcctgccga   8640

agcgtaacag tgataaactt attgccagaa aaaaagattg ggatccaaaa aaatacggag   8700

gctttgattc ccctaccgtc gcgtatagtg tgctggtggt tgctaaagtc gagaaaggga   8760

aaagcaagaa attgaaatca gttaaagaac tgctgggtat tacaattatg gaaagatcgt   8820

cctttgagaa aaatccgatc gactttttag aggccaaggg gtataaggaa gtgaaaaaag   8880

atctcatcat caaattaccg aagtatagtc tttttgagct ggaaaacggc agaaaaagaa   8940

tgctggcctc cgcgggcgag ttacagaagg gaaatgagct ggcgctgcct tccaaatatg   9000

ttaattttct gtaccttgcc agtcattatg agaaactgaa gggcagcccc gaagataacg   9060

aacagaaaca attattcgtg gaacagcata agcactattt agatgaaatt atagagcaaa   9120

ttagtgaatt ttctaagcgc gttatcctcg cggatgctaa tttagacaaa gtactgtcag   9180

cttataataa acatcgggat aagccgatta gagaacaggc cgaaaatatc attcatttgt   9240

ttaccttaac caaccttgga gcaccagctg ccttcaaata tttcgatacc acaattgatc   9300

gtaaacggta tacaagtaca aaagaagtct tggacgcaac cctcattcat caatctatta   9360

ctggattata tgagacacgc attgatcttt cacagctggg cggagacaag aagaaaaaac   9420

tgaaactgca ccatcatcac catcatcatc accatcattg ataactcgag aaagcttaca   9480

taaaaaaccg gccttggccc cgccggtttt ttattatttt tcttcctccg catgttcaat   9540

ccgctccata atcgacggat ggctccctct gaaaatttta acgagaaacg gcgggttgac   9600

ccggctcagt cccgtaacgg ccaagtcctg aaacgtctca atcgccgctt cccggtttcc   9660

ggtcagctca atgccgtaac ggtcggcggc gttttcctga taccgggaga cggcattcgt   9720

aatc                                                                9724
```

<210> SEQ ID NO 27
<211> LENGTH: 9724
<212> TYPE: DNA
<213> ORGANISM: Artificial sequence
<220> FEATURE:
<223> OTHER INFORMATION: pRF806 plasmid

<400> SEQUENCE: 27

```
gggtgaagtg gtcaagacct cactaggcac cttaaaaata gcgcaccctg aagaagattt     60

atttgaggta gcccttgcct acctagcttc caagaaagat atcctaacag cacaagagcg    120

gaaagatgtt ttgttctaca tccagaacaa cctctgctaa aattcctgaa aaattttgca    180

aaaagttgtt gactttatct acaaggtgtg gcataatgtg tggagatgcc atcagttcct    240

catagtttta gagctagaaa tagcaagtta aaataaggct agtccgttat caacttgaaa    300

aagtggcacc gagtcggtgc gactcctgtt gatagatcca gtaatgacct cagaactcca    360

tctggatttg ttcagaacgc tcggttgccg ccgggcgttt tttattggtg agaatgtcga    420

cctcgagagt tacgctaggg ataacagggt aatataggag ctccagtcgg cttaaaccag    480

ttttcgctgg tgcgaaaaaa gagtgtcttg tgacacctaa attcaaaatc tatcggtcag    540

atttataccg atttgatttt atatattctt gaataacata cgccgagtta tcacataaaa    600

gcgggaacca atcataaaat ttaaacttca ttgcataatc cattaaactc ttaaattcta    660

cgattccttg ttcatcaata aactcaatca tttctttaat taatttatat ctatctgttg    720

ttgttttctt taataattca ttaacatcta caccgccata aactatcata tcttcttttt    780
```

```
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgtt ttcagtttct tttattacat tttcgctcat gatataataa   1140
cggtgctaat acacttaaca aaatttagtc atagataggc agcatgccag tgctgtctat   1200
cttttttgt ttaaaatgca ccgtattcct cctttgcata tttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgtttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gattttttaa agacggaaaa   2340
gcccgaagag gaacttgtct ttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
```

```
tatctcagtt cggtgtaggt cgttcgctcc aagctgggct gtgtgcacga acccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacattg atattcagca ccctgcgcat ttcgaccggg agaacgactc tgccgagctc   3720
atcgattctc cggacaatcc cggtattttt cacgtttgaa aagcctcctt ttctcctttc   3780
tttattgact tttgtcaaca tctttataat aaaagagatc ttcaaatttt ttgttgaaat   3840
actgaatcat ctttccgatc acaagttgtc cgggcctcct ttcgccattt aaaactctgc   3900
tgagtgtcgc cggggatacg ccgatttcaa tggcaagctg atttaaggag agattgtgtt   3960
caatcatgta ctggagaaca aaatctcttt tgatatgaat ctttttttacc atgattactc   4020
ccctttctaa tctcttatgt ttctttttat ctacattgaa catatacgat ttgttaactt   4080
ttgtcaatac ttttaccatc catatgtttc ctataggcaa tattcgtact aaaatatttt   4140
ataataagag attgcgaggt tttggccata cttctccgcg gcacactctc ctctctatca   4200
ttttcgtctg tttacgatcc tgctgttatt ttatccctta tgttaacttt tgtcaatatt   4260
tttcctgtct aagtatttcc tatagtcaac atttgtatta aaatgttcat atcatgaatt   4320
tgcggggggg atggcgatga caaggttcgg cgagcggctc aaagagctga gggaacaaag   4380
aagcctgtcg gttaatcagc ttgccatgta tgccggtgtg agcgccgcag ccatttccag   4440
agccgcagcc atttccagaa tcgaaaacgg ccaccgcggc gttcccaagc ccgcgacgat   4500
cagaaaattg gccgaggctc tgaaaatgcc gtacgagcag ctcatggata ttgccggtta   4560
tatgagagct gacgagattc gcgaacagcc gcgcggctat gtcacgatgc aggagatcgc   4620
ggccaagcac ggcgtcgaag acctgtggct gtttaaaccc gagaaatgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttttct gtaaagttta tttttcagaa tacttttatc   4920
atcatgcttt gaaaaaatat cacgataata tccattgttc tcacggaagc acacgcaggt   4980
catttgaacg aatttttttcg acaggaattt gccgggactc aggagcattt aacctaaaaa   5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga atttttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
```

```
cacgtcgtaa aaatcgtatt tgctacttac aggaaatttt ttctaacgaa atggccaagg   5580
tagatgatag tttcttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatctatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcaccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
```

-continued

```
ataataaagt acttacgaga tcggacaaaa atcgcggtaa atcggataac gtcccatcgg   7920

aggaagtcgt taaaaagatg aaaaactatt ggcgtcaact gctgaacgcc aagctgatca   7980

cacagcgtaa gtttgataat ctgactaaag ccgaacgcgg tggtcttagt gaactcgata   8040

aagcaggatt tataaaacgg cagttagtag aaacgcgcca aattacgaaa cacgtggctc   8100

agatcctcga ttctagaatg aatacaaagt acgatgaaaa cgataaactg atccgtgaag   8160

taaaagtcat taccttaaaa tctaaacttg tgtccgattt ccgcaaagat tttcagtttt   8220

acaaggtccg ggaaatcaat aactatcacc atgcacatga tgcatattta aatgcggttg   8280

taggcacggc ccttattaag aaatacccta aactcgaaag tgagtttgtt tatggggatt   8340

ataaagtgta tgacgttcgc aaaatgatcg cgaaatcaga acaggaaatc ggtaaggcta   8400

ccgctaaata ctttttttat tccaacatta tgaatttttt taagaccgaa ataactctcg   8460

cgaatggtga aatccgtaaa cggcctctta tagaaaccaa tggtgaaacg ggagaaatcg   8520

tttgggataa aggtcgtgac tttgccaccg ttcgtaaagt cctctcaatg ccgcaagtta   8580

acattgtcaa gaagacggaa gttcaaacag gggattctc caaagaatct atcctgccga    8640

agcgtaacag tgataaactt attgccagaa aaaaagattg ggatccaaaa aaatacggag   8700

gctttgattc ccctaccgtc gcgtatagtg tgctggtggt tgctaaagtc gagaaaggga   8760

aaagcaagaa attgaaatca gttaaagaac tgctgggtat tacaattatg gaaagatcgt   8820

cctttgagaa aaatccgatc gactttttag aggccaaggg gtataaggaa gtgaaaaaag   8880

atctcatcat caaattaccg aagtatagtc tttttgagct ggaaaacggc agaaaaagaa   8940

tgctggcctc cgcgggcgag ttacagaagg gaaatgagct ggcgctgcct tccaaatatg   9000

ttaattttct gtaccttgcc agtcattatg agaaactgaa gggcagcccc gaagataacg   9060

aacagaaaca attattcgtg gaacagcata agcactattt agatgaaatt atagagcaaa   9120

ttagtgaatt ttctaagcgc gttatcctcg cggatgctaa tttagacaaa gtactgtcag   9180

cttataataa acatcgggat aagccgatta gagaacaggc cgaaaatatc attcatttgt   9240

ttaccttaac caaccttgga gcaccagctg ccttcaaata tttcgatacc acaattgatc   9300

gtaaacggta tacaagtaca aaagaagtct tggacgcaac cctcattcat caatctatta   9360

ctggattata tgagacacgc attgatcttt cacagctggg cggagacaag aagaaaaaac   9420

tgaaactgca ccatcatcac catcatcatc accatcattg ataactcgag aaagcttaca   9480

taaaaaaccg gccttggccc cgccggtttt ttattatttt tcttcctccg catgttcaat   9540

ccgctccata atcgacggat ggctccctct gaaaatttta acgagaaacg gcgggttgac   9600

ccggctcagt cccgtaacgg ccaagtcctg aaacgtctca atcgccgctt cccggtttcc   9660

ggtcagctca atgccgtaac ggtcggcggc gttttcctga taccgggaga cggcattcgt   9720

aatc                                                                9724
```

<210> SEQ ID NO 28
<211> LENGTH: 20
<212> TYPE: DNA
<213> ORGANISM: Bacillus licheniformis

<400> SEQUENCE: 28

```
ctcgacttcg aatacatcca                                                 20
```

<210> SEQ ID NO 29
<211> LENGTH: 20
<212> TYPE: DNA
<213> ORGANISM: Bacillus licheniformis

<400> SEQUENCE: 29
gatgccatca gttcctcata 20

<210> SEQ ID NO 30
<211> LENGTH: 1578
<212> TYPE: DNA
<213> ORGANISM: Bacillus licheniformis

<400> SEQUENCE: 30
atgtttcgag tattggtctc agataaaatg tccagcgacg gcctcaaacc attaatggaa 60
gcagatttta ttgaaattgt agaaaagaat gttgcggaag cggaagacga gcttcatacg 120
tttgacgcgc tcttggtgcg gagcgccacg aaggtaaccg aagagctgtt taaaaagatg 180
acttcgctga aaatcgtcgc cagagcaggt gtcggcgtcg acaatatcga tattgacgag 240
gcgacaaaac acggtgttat cgtcgtaaac gcgccaaacg ggaatacaat ttcaaccgct 300
gaacatacct ttgcaatgtt ttcagcgtta atgagacata ttccgcaggc aaacatctcc 360
gtgaaatcaa gggagtggaa tcgttcggct tacgtcggtt cagagcttta cggaaaaacg 420
ctcggcatca tcggaatggg ccgcatcgga agcgaaatcg cgagccgcgc aaaagcattc 480
ggtatgaccg ttcatgtatt tgacccgttc ctgacccaag aaagggcaag caagctcggc 540
gttaacgcga acagctttga agaagttctg gcatgcgccg acatcattac ggttcatacc 600
ccgctcacga aagaaacgaa gggacttttg aacaaagaaa ccatcgcaaa aacgaaaaaa 660
ggcgttcgtc tcgttaactg tgcaagaggc ggcatcatcg atgaagcagc gcttttggaa 720
gctctggaaa gcggacatgt cgctggcgct gccttggatg tattcgaagt cgagcctccg 780
gtcgattcaa aactgatcga tcatccgctt gtagtcgcga ctcctcactt gggcgcctca 840
acaaaagaag cccagctgaa tgtcgctgca caagtgtccg aagaagtcct tcagtatgcg 900
caaggaaacc ctgtgatgtc cgcgatcaac cttccggcca tgacaaagga ttcattcgaa 960
aaaatccagc cttatcatca gtttgccaat acgatcggaa accttgtgtc tcagtgcatg 1020
aatgagcctg ttcaagatgt agccatccaa tatgaaggct ccatcgccaa acttgaaacg 1080
tcatttatta cgaaaagcct tttggccgga tttctgaagc cgagggtcgc ggctaccgtt 1140
aacgaagtga atgccggcac cgttgcgaaa gagcgcggca tcagcttcag cgaaaaaatt 1200
tcttccaatg agtcaggcta tgaaaactgc atctctgtga ctgtcacggg agatgtaaca 1260
acattctctt taagagcgac gtacattccg cacttcggcg gacgcatcgt tgccttaaac 1320
ggctttgata ttgattttta tccggctgga caccttgtct acattcacca ccaggataaa 1380
ccaggggcta tcggccatgt cggacgaatt ttaggagacc atgacatcaa tatcgccact 1440
atgcaggtag gccgaaaaga aaaaggcgga gaagcgatca tgatgctttc ctttgaccgc 1500
caccttgagg acgatatttt agctgagctg aaaaacatcc cggatatcgt gtctgttaaa 1560
gccatcgacc ttccttaa 1578

<210> SEQ ID NO 31
<211> LENGTH: 23
<212> TYPE: DNA
<213> ORGANISM: Bacillus licheniformis

<400> SEQUENCE: 31
ctcgacttcg aatacatcca agg 23

<210> SEQ ID NO 32

<211> LENGTH: 20
<212> TYPE: DNA
<213> ORGANISM: Artificial sequence
<220> FEATURE:
<223> OTHER INFORMATION: synthesized DNA encoding variable targeting domain

<400> SEQUENCE: 32
ctcgacttcg aatacatcca 20

<210> SEQ ID NO 33
<211> LENGTH: 76
<212> TYPE: DNA
<213> ORGANISM: Artificial sequence
<220> FEATURE:
<223> OTHER INFORMATION: synthesized DNA encoding CER domain

<400> SEQUENCE: 33
gttttagagc tagaaatagc aagttaaaat aaggctagtc cgttatcaac ttgaaaaagt 60
ggcaccgagt cggtgc 76

<210> SEQ ID NO 34
<211> LENGTH: 96
<212> TYPE: RNA
<213> ORGANISM: Artificial sequence
<220> FEATURE:
<223> OTHER INFORMATION: synthesized gRNA targeting target site 1

<400> SEQUENCE: 34
cucgacuucg aauacaucca guuuuagagc uagaaauagc aaguuaaaau aaggcuaguc 60
cguuaucaac uugaaaaagu ggcaccgagu cggugc 96

<210> SEQ ID NO 35
<211> LENGTH: 224
<212> TYPE: DNA
<213> ORGANISM: artificial sequence
<220> FEATURE:
<223> OTHER INFORMATION: synthesized spac promoter

<400> SEQUENCE: 35
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tgga 224

<210> SEQ ID NO 36
<211> LENGTH: 95
<212> TYPE: DNA
<213> ORGANISM: Artificial sequence
<220> FEATURE:
<223> OTHER INFORMATION: synthesized  t0 terminator

<400> SEQUENCE: 36
gactcctgtt gatagatcca gtaatgacct cagaactcca tctggatttg ttcagaacgc 60
tcggttgccg ccgggcgttt tttattggtg agaat 95

<210> SEQ ID NO 37
<211> LENGTH: 500
<212> TYPE: DNA
<213> ORGANISM: Bacillus licheniformis

<400> SEQUENCE: 37

-continued

```
aatggttctt tcccctgtcc taaacaaaaa acccgcttta ttgaaaaagc ggggctgttt     60

tacagacagg tcaaataaac gtttgaaaat gttcatttca aaacgcgcgg aacctccatc    120

ttctcccatc cagactatac tgtcggcttc ggaatcgcac cgaatcctgc ccataaaaag    180

gctcgcgggc ttagagcgct tgctcatcac cgccggtagg gaatttcacc ctgccccgaa    240

gattgatctt atttattttt aatactgata ttattataaa ttaattgtga aaaaatgtac    300

aggtgcaaag cttattgcgc tgttttggga catcctgcac gatatttcgg taaactcact    360

ttttccgcat actaaaaacc gcacattcac agttatttca tttttaattt tcgtctttcc    420

gcgtgaaact cattgacact ctttatggaa tatggtaaat tatcagatat ttatgacgct    480

tatttaggag gaaatcttac                                                500


<210> SEQ ID NO 38
<211> LENGTH: 40
<212> TYPE: DNA
<213> ORGANISM: Artificial sequence
<220> FEATURE:
<223> OTHER INFORMATION: serA1 homology arm 1 forward primer

<400> SEQUENCE: 38

tgagtaaact tggtctgaca aatggttctt tcccctgtcc                           40


<210> SEQ ID NO 39
<211> LENGTH: 46
<212> TYPE: DNA
<213> ORGANISM: Artificial sequence
<220> FEATURE:
<223> OTHER INFORMATION: serA1 homology arm 1 forward primer

<400> SEQUENCE: 39

aggttccgca gcttctgtgt aagatttcct cctaaataag cgtcat                    46


<210> SEQ ID NO 40
<211> LENGTH: 500
<212> TYPE: DNA
<213> ORGANISM: Bacillus  licheniformis

<400> SEQUENCE: 40

acagaagctg cggaacctga aaagaattcc tttcaggttc cgtttttttt aggaattctc     60

cctgatctca agcatctggc ggggataaat ccgctctcct ttcaaatcgt tccattcttt    120

gaggcgctgt acagttacgc ccattttttc ggcgatatga tgaagcgtat cccctttccg    180

cactacatat gtaccggtct tcgattcatc gtcatgaagg cggagtgttt ggccggcctt    240

gagatttgaa tgtttcaacc cgtttattct catgatctcc tcgatggata taccgctatc    300

cttgctgatt ctccagagcg tgtccccttt ttgaacggtc accgcaccgc tcattgtccc    360

ggcgttttga taaacgtgga tagaattttg ccggaacgcc tcctcacgaa gcaccgtcag    420

cggattgatt gcatatcttt tatcttcagt ccatgaaccg tgatgcattt caaaatgcag    480

gtgggttccg gtcgatattc                                                500


<210> SEQ ID NO 41
<211> LENGTH: 46
<212> TYPE: DNA
<213> ORGANISM: Artificial sequence
<220> FEATURE:
<223> OTHER INFORMATION: serA1 homology arm 2 forward primer

<400> SEQUENCE: 41

atgacgctta tttaggagga aatcttacac agaagctgcg gaacct                    46
```

<210> SEQ ID NO 42
<211> LENGTH: 41
<212> TYPE: DNA
<213> ORGANISM: Artificial sequence
<220> FEATURE:
<223> OTHER INFORMATION: serA1 homology arm 2 reverse primer

<400> SEQUENCE: 42
cagaagaaaa tggaggaatt cgaatatcga ccggaaccca c 41

<210> SEQ ID NO 43
<211> LENGTH: 415
<212> TYPE: DNA
<213> ORGANISM: Artificial sequence
<220> FEATURE:
<223> OTHER INFORMATION: DNA encoding ts1 gRNA expression cassette

<400> SEQUENCE: 43
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggactcgac ttcgaataca 240
tccagtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaat 415

<210> SEQ ID NO 44
<211> LENGTH: 1000
<212> TYPE: DNA
<213> ORGANISM: Artificial sequence
<220> FEATURE:
<223> OTHER INFORMATION: serA1 deletion editing template

<400> SEQUENCE: 44
aatggttctt tcccctgtcc taaacaaaaa acccgcttta ttgaaaaagc ggggctgttt 60
tacagacagg tcaaataaac gtttgaaaat gttcatttca aaacgcgcgg aacctccatc 120
ttctcccatc cagactatac tgtcggcttc ggaatcgcac cgaatcctgc ccataaaaag 180
gctcgcgggc ttagagcgct tgctcatcac cgccggtagg gaatttcacc ctgccccgaa 240
gattgatctt atttattttt aatactgata ttattataaa ttaattgtga aaaaatgtac 300
aggtgcaaag cttattgcgc tgttttggga catcctgcac gatatttcgg taaactcact 360
ttttccgcat actaaaaacc gcacattcac agttatttca tttttaattt tcgtctttcc 420
gcgtgaaact cattgacact ctttatggaa tatggtaaat tatcagatat ttatgacgct 480
tatttaggag gaaatcttac acagaagctg cggaacctga aaagaattcc tttcaggttc 540
cgtttttttt aggaattctc cctgatctca agcatctggc ggggataaat ccgctctcct 600
ttcaaatcgt tccattcttt gaggcgctgt acagttacgc ccatttttttc ggcgatatga 660 tgaagcgtat cccctttccg cactacatat gtaccggtct tcgattcatc gtcatgaagg 720
cggagtgttt ggccggcctt gagatttgaa tgtttcaacc cgtttattct catgatctcc 780
tcgatggata taccgctatc cttgctgatt ctccagagcg tgtccccttt ttgaacggtc 840
accgcaccgc tcattgtccc ggcgttttga taaacgtgga tagaattttg ccggaacgcc 900
tcctcacgaa gcaccgtcag cggattgatt gcatatcttt tatcttcagt ccatgaaccg 960
tgatgcattt caaaatgcag gtgggttccg gtcgatattc 1000

<210> SEQ ID NO 45
<211> LENGTH: 402
<212> TYPE: DNA
<213> ORGANISM: Bacillus licheniformis

<400> SEQUENCE: 45
atgacgaact ttggacacca tttacgacaa ttaagggaac ggaaaaaact gaccgtcaat 60
caactggcga tgtattccgg cgtcagttcg gcaggcattt cgcgaatcga aaacggaaag 120
cgcggcgtgc cgaagccggc gacgatcaga aaactggcgg acgctttgaa agtcccgtat 180
gaggaactga tggcatctgc aggctatatc agcgcgtcta cagtccagga agcaagaagc 240
agctatgatt ccatttacga catcgtgtca cagtacgatt tagaggacct ttctctgttt 300
gacagcgaaa agtggaaggt gctttcaaaa aaagacatcg aaaacctgga caaatatttc 360
gactttctcg tgcaggaagc aagcagccga aacaaaaact ga 402

<210> SEQ ID NO 46
<211> LENGTH: 20
<212> TYPE: DNA
<213> ORGANISM: Bacillus licheniformis

<400> SEQUENCE: 46
gatgccatca gttcctcata 20

<210> SEQ ID NO 47
<211> LENGTH: 23
<212> TYPE: DNA
<213> ORGANISM: Bacillus licheniformis

<400> SEQUENCE: 47
gatgccatca gttcctcata cgg 23

<210> SEQ ID NO 48
<211> LENGTH: 20
<212> TYPE: DNA
<213> ORGANISM: Artificial sequence
<220> FEATURE:
<223> OTHER INFORMATION: synthesized DNA encoding variable targeting domain 2

<400> SEQUENCE: 48
gatgccatca gttcctcata 20

<210> SEQ ID NO 49
<211> LENGTH: 96
<212> TYPE: RNA
<213> ORGANISM: Artificial sequence
<220> FEATURE:
<223> OTHER INFORMATION: synthesized gRNA targeting target site 2

<400> SEQUENCE: 49
gaugccauca guuccucaua guuuuagagc uagaaauagc aaguuaaaau aaggcuaguc 60
cguuaucaac uugaaaaagu ggcaccgagu cggugc 96

<210> SEQ ID NO 50
<211> LENGTH: 500
<212> TYPE: DNA
<213> ORGANISM: Bacillus licheniformis

<400> SEQUENCE: 50

-continued ttgatattca gcaccctgcg catttcgacc gggagaacga ctctgccgag ctcatcgatt 60
ctccggacaa tcccggtatt tttcacgttt gaaaagcctc cttttctcct ttctttattg 120
acttttgtca acatctttat aataaaagag atcttcaaat tttttgttga aatactgaat 180
catctttccg atcacaagtt gtccgggcct cctttcgcca tttaaaactc tgctgagtgt 240
cgccggggat acgccgattt caatggcaag ctgatttaag gagagattgt gttcaatcat 300
gtactggaga acaaaatctc ttttgatatg aatctttttt accatgatta ctcccctttc 360
taatctctta tgtttctttt tatctacatt gaacatatac gatttgttaa cttttgtcaa 420
tacttttacc atccatatgt ttcctatagg caatattcgt actaaaatat tttataataa 480
gagattgcga ggttttggcc 500

<210> SEQ ID NO 51
<211> LENGTH: 40
<212> TYPE: DNA
<213> ORGANISM: artificial sequence
<220> FEATURE:
<223> OTHER INFORMATION: rghR1 homology arm 1 forward primer

<400> SEQUENCE: 51
tgagtaaact tggtctgaca ttgatattca gcaccctgcg 40

<210> SEQ ID NO 52
<211> LENGTH: 38
<212> TYPE: DNA
<213> ORGANISM: Artificial sequence
<220> FEATURE:
<223> OTHER INFORMATION: rghR1 homology arm 1 reverse primer

<400> SEQUENCE: 52
tgtgccgcgg agaagtatgg ccaaaacctc gcaatctc 38

<210> SEQ ID NO 53
<211> LENGTH: 500
<212> TYPE: DNA
<213> ORGANISM: Bacillus licheniformis

<400> SEQUENCE: 53
atacttctcc gcggcacact ctcctctcta tcattttcgt ctgtttacga tcctgctgtt 60
attttatccc ttatgttaac ttttgtcaat atttttcctg tctaagtatt tcctatagtc 120
aacatttgta ttaaaatgtt catatcatga atttgcgggg gggatggcga tgacaaggtt 180
cggcgagcgg ctcaaagagc tgagggaaca aagaagcctg tcggttaatc agcttgccat 240
gtatgccggt gtgagcgccg cagccatttc cagagccgca gccatttcca gaatcgaaaa 300
cggccaccgc ggcgttccca agcccgcgac gatcagaaaa ttggccgagg ctctgaaaat 360
gccgtacgag cagctcatgg atattgccgg ttatatgaga gctgacgaga ttcgcgaaca 420
gccgcgcggc tatgtcacga tgcaggagat cgcggccaag cacggcgtcg aagacctgtg 480
gctgtttaaa cccgagaaat 500

<210> SEQ ID NO 54
<211> LENGTH: 38
<212> TYPE: DNA
<213> ORGANISM: Artificial sequence
<220> FEATURE:
<223> OTHER INFORMATION: rghR1 homology arm 2 forward primer

<400> SEQUENCE: 54
gagattgcga ggttttggcc atacttctcc gcggcaca 38

<210> SEQ ID NO 55
<211> LENGTH: 44
<212> TYPE: DNA
<213> ORGANISM: Artificial sequence
<220> FEATURE:
<223> OTHER INFORMATION: rghR1 homology arm 2 reverse primer

<400> SEQUENCE: 55
cagaagaaaa tggaggaatt catttctcgg gtttaaacag ccac 44

<210> SEQ ID NO 56
<211> LENGTH: 415
<212> TYPE: DNA
<213> ORGANISM: Artificial sequence
<220> FEATURE:
<223> OTHER INFORMATION: DNA encoding ts2 expression cassette

<400> SEQUENCE: 56
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggagatgcc atcagttcct 240
catagtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaat 415

<210> SEQ ID NO 57
<211> LENGTH: 1000
<212> TYPE: DNA
<213> ORGANISM: Artificial sequence
<220> FEATURE:
<223> OTHER INFORMATION: synthesized rghR1 deletion editing template

<400> SEQUENCE: 57
ttgatattca gcaccctgcg catttcgacc gggagaacga ctctgccgag ctcatcgatt 60
ctccggacaa tcccggtatt tttcacgttt gaaaagcctc cttttctcct ttctttattg 120
acttttgtca acatctttat aataaaagag atcttcaaat tttttgttga aatactgaat 180
catctttccg atcacaagtt gtccgggcct cctttcgcca tttaaaactc tgctgagtgt 240
cgccggggat acgccgattt caatggcaag ctgatttaag gagagattgt gttcaatcat 300
gtactggaga acaaaatctc ttttgatatg aatctttttt accatgatta ctccccttc 360 taatctctta tgtttctttt tatctacatt gaacatatac gatttgttaa cttttgtcaa 420
tacttttacc atccatatgt ttcctatagg caatattcgt actaaaatat tttataataa 480
gagattgcga ggttttggcc atacttctcc gcggcacact ctcctctcta tcattttcgt 540
ctgtttacga tcctgctgtt attttatccc ttatgttaac ttttgtcaat atttttcctg 600
tctaagtatt tcctatagtc aacatttgta ttaaaatgtt catatcatga atttgcgggg 660
gggatggcga tgacaaggtt cggcgagcgg ctcaaagagc tgagggaaca aagaagcctg 720
tcggttaatc agcttgccat gtatgccggt gtgagcgccg cagccatttc cagagccgca 780
gccatttcca gaatcgaaaa cggccaccgc ggcgttccca agcccgcgac gatcagaaaa 840
ttggccgagg ctctgaaaat gccgtacgag cagctcatgg atattgccgg ttatatgaga 900
gctgacgaga ttcgcgaaca gccgcgcggc tatgtcacga tgcaggagat cgcggccaag 960

-continued

```
cacggcgtcg aagacctgtg gctgtttaaa cccgagaaat                        1000


<210> SEQ ID NO 58
<211> LENGTH: 1368
<212> TYPE: PRT
<213> ORGANISM: Artificial sequence
<220> FEATURE:
<223> OTHER INFORMATION: synthesized Cas9 Y155H variant

<400> SEQUENCE: 58

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile His Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

-continued 355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

Lys Gln Arg Thr Phe Asp Asn Gly Ser Ile Pro His Gln Ile His Leu
405 410 415

Gly Glu Leu His Ala Ile Leu Arg Arg Gln Glu Asp Phe Tyr Pro Phe
420 425 430

Leu Lys Asp Asn Arg Glu Lys Ile Glu Lys Ile Leu Thr Phe Arg Ile
435 440 445

Pro Tyr Tyr Val Gly Pro Leu Ala Arg Gly Asn Ser Arg Phe Ala Trp
450 455 460

Met Thr Arg Lys Ser Glu Glu Thr Ile Thr Pro Trp Asn Phe Glu Glu
465 470 475 480

Val Val Asp Lys Gly Ala Ser Ala Gln Ser Phe Ile Glu Arg Met Thr
485 490 495

Asn Phe Asp Lys Asn Leu Pro Asn Glu Lys Val Leu Pro Lys His Ser
500 505 510

Leu Leu Tyr Glu Tyr Phe Thr Val Tyr Asn Glu Leu Thr Lys Val Lys
515 520 525

Tyr Val Thr Glu Gly Met Arg Lys Pro Ala Phe Leu Ser Gly Glu Gln
530 535 540

Lys Lys Ala Ile Val Asp Leu Leu Phe Lys Thr Asn Arg Lys Val Thr
545 550 555 560

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

Arg His Lys Pro Glu Asn Ile Val Ile Glu Met Ala Arg Glu Asn Gln
755 760 765

Thr Thr Gln Lys Gly Gln Lys Asn Ser Arg Glu Arg Met Lys Arg Ile
770 775 780

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185
```

```
Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 59
<211> LENGTH: 33
<212> TYPE: DNA
<213> ORGANISM: Artificial sequence
<220> FEATURE:
<223> OTHER INFORMATION: Y155H forward primer

<400> SEQUENCE: 59

gatctgcgtt taatccatct tgcgttagcg cac                                 33


<210> SEQ ID NO 60
<211> LENGTH: 33
<212> TYPE: DNA
<213> ORGANISM: Artificial sequence
<220> FEATURE:
<223> OTHER INFORMATION: Y155H reverse primer

<400> SEQUENCE: 60

gtgcgctaac gcaagatgga ttaaacgcag atc                                 33


<210> SEQ ID NO 61
<211> LENGTH: 9724
<212> TYPE: DNA
<213> ORGANISM: Artificial sequence
<220> FEATURE:
<223> OTHER INFORMATION: plasmid pRF827

<400> SEQUENCE: 61

gggtgaagtg gtcaagacct cactaggcac cttaaaaata gcgcaccctg aagaagattt     60

atttgaggta gcccttgcct acctagcttc caagaaagat atcctaacag cacaagagcg    120

gaaagatgtt ttgttctaca tccagaacaa cctctgctaa aattcctgaa aaattttgca    180

aaaagttgtt gactttatct acaaggtgtg gcataatgtg tggactcgac ttcgaataca    240

tccagtttta gagctagaaa tagcaagtta aaataaggct agtccgttat caacttgaaa    300
```

```
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgttt ttcagtttct tttattacat tttcgctcat gatataataa   1140
cggtgctaat acacttaaca aaatttagtc atagataggc agcatgccag tgctgtctat   1200
ctttttttgt ttaaaatgca ccgtattcct cctttgcata ttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gattttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
```

atcaaataaa acgaaaggct cagtcgaaag actgggcctt tcgttttatc tgttgtttgt 2700
cggtgaacgc tctcctgagt aggacaaatc cgccgctcta gctaagcaga aggccatcct 2760
gacggatggc ctttttgcgt ttctacaaac tcttgttaac tctagagctg cctgccgcgt 2820
ttcggtgatg aagatcttcc cgatgattaa ttaattcaga acgctcggtt gccgccgggc 2880 gtttttttatg aagcttcgtt gctggcgttt ttccataggc tccgcccccc tgacgagcat 2940
cacaaaaatc gacgctcaag tcagaggtgg cgaaacccga caggactata aagataccag 3000
gcgtttcccc ctggaagctc cctcgtgcgc tctcctgttc cgaccctgcc gcttaccgga 3060
tacctgtccg cctttctccc ttcgggaagc gtggcgcttt ctcatagctc acgctgtagg 3120
tatctcagtt cggtgtaggt cgttcgctcc aagctgggct gtgtgcacga accccccgtt 3180
cagcccgacc gctgcgcctt atccggtaac tatcgtcttg agtccaaccc ggtaagacac 3240
gacttatcgc cactggcagc agccactggt aacaggatta gcagagcgag gtatgtaggc 3300
ggtgctacag agttcttgaa gtggtggcct aactacggct acactagaag gacagtattt 3360
ggtatctgcg ctctgctgaa gccagttacc ttcggaaaaa gagttggtag ctcttgatcc 3420
ggcaaacaaa ccaccgctgg tagcggtggt ttttttgttt gcaagcagca gattacgcgc 3480
agaaaaaaag gatctcaaga agatcctttg atcttttcta cggggtctga cgctcagtgg 3540
aacgaaaact cacgttaagg gattttggtc atgagattat caaaaaggat cttcacctag 3600
atccttttaa attaaaaatg aagttttaaa tcaatctaaa gtatatatga gtaaacttgg 3660
tctgacaaat ggttctttcc cctgtcctaa acaaaaaacc cgctttattg aaaaagcggg 3720
gctgttttac agacaggtca aataaacgtt tgaaaatgtt catttcaaaa cgcgcggaac 3780
ctccatcttc tcccatccag actatactgt cggcttcgga atcgcaccga atcctgccca 3840
taaaaaggct cgcgggctta gagcgcttgc tcatcaccgc cggtagggaa tttcaccctg 3900
ccccgaagat tgatcttatt tatttttaat actgatatta ttataaatta attgtgaaaa 3960
aatgtacagg tgcaaagctt attgcgctgt tttgggacat cctgcacgat atttcggtaa 4020
actcactttt tccgcatact aaaaaccgca cattcacagt tatttcattt ttaattttcg 4080
tctttccgcg tgaaactcat tgacactctt tatggaatat ggtaaattat cagatattta 4140
tgacgcttat ttaggaggaa atcttacaca gaagctgcgg aacctgaaaa gaattccttt 4200
caggttccgt ttttttagg aattctccct gatctcaagc atctggcggg gataaatccg 4260
ctctcctttc aaatcgttcc attctttgag gcgctgtaca gttacgccca ttttttcggc 4320
gatatgatga agcgtatccc ctttccgcac tacatatgta ccggtcttcg attcatcgtc 4380
atgaaggcgg agtgtttggc cggccttgag atttgaatgt ttcaacccgt ttattctcat 4440
gatctcctcg atggatatac cgctatcctt gctgattctc cagagcgtgt cccctttttg 4500
aacggtcacc gcaccgctca ttgtcccggc gttttgataa acgtggatag aattttgccg 4560
gaacgcctcc tcacgaagca ccgtcagcgg attgattgca tatcttttat cttcagtcca 4620
tgaaccgtga tgcatttcaa aatgcaggtg ggttccggtc gatattcgaa ttcctccatt 4680
ttcttctgct atcaaaataa cagactcgtg attttccaaa cgagctttca aaaaagcctc 4740
tgccccttgc aaatcggatg cctgtctata aaattcccga tattggttaa acagcggcgc 4800
aatggcggcc gcatctgatg tctttgcttg gcgaatgttc atcttatttc ttcctccctc 4860
tcaataattt tttcattcta tcccttttct gtaaagttta tttttcagaa tacttttatc 4920
atcatgcttt gaaaaaatat cacgataata tccattgttc tcacggaagc acacgcaggt 4980
catttgaacg aatttttttcg acaggaattt gccgggactc aggagcattt aacctaaaaa 5040

```
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga attttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatccatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcaccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
```

-continued

```
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
taggcacggc ccttattaag aaataccta aactcgaaag tgagtttgtt tatggggatt   8340
ataaagtgta tgacgttcgc aaaatgatcg cgaaatcaga acaggaaatc ggtaaggcta   8400
ccgctaaata cttttttat tccaacatta tgaatttttt taagaccgaa ataactctcg   8460
cgaatggtga aatccgtaaa cggcctctta tagaaaccaa tggtgaaacg ggagaaatcg   8520
tttgggataa aggtcgtgac tttgccaccg ttcgtaaagt cctctcaatg ccgcaagtta   8580
acattgtcaa gaagacggaa gttcaaacag gggattctc caaagaatct atcctgccga   8640
agcgtaacag tgataaactt attgccagaa aaaaagattg ggatccaaaa aaatacggag   8700
gctttgattc ccctaccgtc gcgtatagtg tgctggtggt tgctaaagtc gagaaaggga   8760
aaagcaagaa attgaaatca gttaaagaac tgctgggtat tacaattatg gaaagatcgt   8820
cctttgagaa aaatccgatc gactttttag aggccaaggg gtataaggaa gtgaaaaaag   8880
atctcatcat caaattaccg aagtatagtc tttttgagct ggaaaacggc agaaaaagaa   8940
tgctggcctc cgcgggcgag ttacagaagg gaaatgagct ggcgctgcct tccaaatatg   9000
ttaattttct gtaccttgcc agtcattatg agaaactgaa gggcagcccc gaagataacg   9060
aacagaaaca attattcgtg gaacagcata agcactattt agatgaaatt atagagcaaa   9120
ttagtgaatt ttctaagcgc gttatcctcg cggatgctaa tttagacaaa gtactgtcag   9180
cttataataa acatcgggat aagccgatta gagaacaggc cgaaaatatc attcatttgt   9240
ttaccttaac caaccttgga gcaccagctg ccttcaaata tttcgatacc acaattgatc   9300
gtaaacggta tacaagtaca aaagaagtct tggacgcaac cctcattcat caatctatta   9360
ctggattata tgagacacgc attgatcttt cacagctggg cggagacaag aagaaaaaac   9420
tgaaactgca ccatcatcac catcatcatc accatcattg ataactcgag aaagcttaca   9480
taaaaaaccg gccttggccc cgccggtttt ttattatttt tcttcctccg catgttcaat   9540
ccgctccata atcgacggat ggctccctct gaaaatttta acgagaaacg gcgggttgac   9600
ccggctcagt cccgtaacgg ccaagtcctg aaacgtctca atcgccgctt cccggtttcc   9660
ggtcagctca atgccgtaac ggtcggcggc gttttcctga taccgggaga cggcattcgt   9720
aatc                                                                9724
```

<210> SEQ ID NO 62
<211> LENGTH: 5042
<212> TYPE: DNA
<213> ORGANISM: Artificial sequence
<220> FEATURE:
<223> OTHER INFORMATION: synthesized Y155H variant expression cassette

<400> SEQUENCE: 62
attcctccat tttcttctgc tatcaaaata acagactcgt gattttccaa acgagctttc 60
aaaaaagcct ctgccccttg caaatcggat gcctgtctat aaaattcccg atattggtta 120
aacagcggcg caatggcggc cgcatctgat gtctttgctt ggcgaatgtt catcttattt 180
cttcctccct ctcaataatt ttttcattct atccctttc tgtaaagttt atttttcaga 240
atacttttat catcatgctt tgaaaaaata tcacgataat atccattgtt ctcacggaag 300
cacacgcagg tcatttgaac gaatttttc gacaggaatt tgccgggact caggagcatt 360
taacctaaaa aagcatgaca tttcagcata atgaacattt actcatgtct attttcgttc 420
ttttctgtat gaaaatagtt atttcgagtc tctacggaaa tagcgagaga tgatatacct 480
aaatagagat aaaatcatct caaaaaaatg ggtctactaa aatattattc catctattac 540
aataaattca cagaatagtc ttttaagtaa gtctactctg aattttttta aaaggagagg 600
gtaactagtg gccccaaaaa agaaacgcaa ggttatggat aaaaaataca gcattggtct 660
ggatatcgga accaacagcg ttgggtgggc agtaataaca gatgaataca aagtgccgtc 720
aaaaaaattt aaggttctgg ggaatacaga tcgccacagc ataaaaaaga atctgattgg 780
ggcattgctg tttgattcgg gtgagacagc tgaggccacg cgtctgaaac gtacagcaag 840
aagacgttac acacgtcgta aaaatcgtat ttgctactta caggaaattt tttctaacga 900
aatggccaag gtagatgata gtttcttcca tcgtctcgaa gaatcttttc tggttgagga 960
agataaaaaa cacgaacgtc accctatctt tggcaatatc gtggatgaag tggcctatca 1020
tgaaaaatac cctacgattt atcatcttcg caagaagttg gttgatagta cggacaaagc 1080
ggatctgcgt ttaatccatc ttgcgttagc gcacatgatc aaatttcgtg gtcatttctt 1140
aattgaaggt gatctgaatc ctgataactc tgatgtggac aaattgttta tacaattagt 1200
gcaaacctat aatcagctgt tcgaggaaaa ccccattaat gcctctggag ttgatgccaa 1260
agcgatttta agcgcgagac tttctaagtc ccggcgtctg gagaatctga tcgcccagtt 1320
accaggggaa aagaaaaatg gtctgtttgg taatctgatt gccctcagtc tggggcttac 1380
cccgaacttc aaatccaatt ttgacctggc tgaggacgca aagctgcagc tgagcaaaga 1440
tacttatgat gatgacctcg acaatctgct cgcccagatt ggtgaccaat atgcggatct 1500
gtttctggca gcgaagaatc tttcggatgc tatcttgctg tcggatattc tgcgtgttaa 1560
taccgaaatc accaaagcgc ctctgtctgc aagtatgatc aagagatacg acgagcacca 1620
ccaggacctg actcttctta aggcactggt acgccaacag cttccggaga aatacaaaga 1680
aatattcttc gaccagtcca agaatggtta cgcgggctac atcgatggtg gtgcatcaca 1740
ggaagagttc tataaattta ttaaaccaat ccttgagaaa atggatggca cggaagagtt 1800
acttgttaaa cttaaccgcg aagacttgct tagaaagcaa cgtacattcg acaacggctc 1860
catcccacac cagattcatt taggtgaact tcacgccatc ttgcgcagac aagaagattt 1920
ctatcccttc ttaaaagaca atcgggagaa aatcgagaag atcctgacgt tccgcattcc 1980
ctattatgtc ggtcccctgg cacgtggtaa ttctcggttt gcctggatga cgcgcaaaag 2040

-continued

```
tgaggaaacc atcacccctt ggaactttga agaagtcgtg gataaaggtg ctagcgcgca   2100
gtcttttata gaaagaatga cgaacttcga taaaaacttg cccaacgaaa aagtcctgcc   2160
caagcactct cttttatatg agtactttac tgtgtacaac gaactgacta aagtgaaata   2220
cgttacggaa ggtatgcgca aacctgcctt tcttagtggc gagcagaaaa aagcaattgt   2280
cgatcttctc tttaaaacga atcgcaaggt aactgtaaaa cagctgaagg aagattattt   2340
caaaaagatc gaatgctttg attctgtcga gatctcgggt gtcgaagatc gtttcaacgc   2400
ttccttaggg acctatcatg atttgctgaa gataataaaa gacaaagact ttctcgacaa   2460
tgaagaaaat gaagatattc tggaggatat tgttttgacc ttgaccttat tcgaagatag   2520
agagatgatc gaggagcgct taaaaaccta tgcccacctg tttgatgaca aagtcatgaa   2580
gcaattaaag cgccgcagat atacggggtg gggccgcttg agccgcaagt tgattaacgg   2640
tattagagac aagcagagcg gaaaaactat cctggatttc ctcaaatctg acggatttgc   2700
gaaccgcaat tttatgcagc ttatacatga tgattcgctt acattcaaag aggatattca   2760
gaaggctcag gtgtctgggc aaggtgattc actccacgaa catatagcaa atttggccgg   2820
ctctcctgcg attaagaagg ggatcctgca aacagttaaa gttgtggatg aacttgtaaa   2880
agtaatgggc cgccacaagc cggagaatat cgtgatagaa atggcgcgcg agaatcaaac   2940
gacacaaaaa ggtcaaaaga actcaagaga gagaatgaag cgcattgagg aggggataaa   3000
ggaacttgga tctcaaattc tgaaagaaca tccagttgaa aacactcagc tgcaaaatga   3060
aaaattgtac ctgtactacc tgcagaatgg aagagacatg tacgtggatc aggaattgga   3120
tatcaataga ctctcggact atgacgtaga tcacattgtc cctcagagct tcctcaagga   3180
tgattctata gataataaag tacttacgag atcggacaaa aatcgcggta aatcggataa   3240
cgtcccatcg gaggaagtcg ttaaaaagat gaaaaactat tggcgtcaac tgctgaacgc   3300
caagctgatc acacagcgta agtttgataa tctgactaaa gccgaacgcg gtggtcttag   3360
tgaactcgat aaagcaggat ttataaaacg gcagttagta gaaacgcgcc aaattacgaa   3420
acacgtggct cagatcctcg attctagaat gaatacaaag tacgatgaaa acgataaact   3480
gatccgtgaa gtaaaagtca ttaccttaaa atctaaactt gtgtccgatt tccgcaaaga   3540
ttttcagttt tacaaggtcc gggaaatcaa taactatcac catgcacatg atgcatattt   3600
aaatgcggtt gtaggcacgg cccttattaa gaaataccct aaactcgaaa gtgagtttgt   3660
ttatggggat tataaagtgt atgacgttcg caaaatgatc gcgaaatcag aacaggaaat   3720
cggtaaggct accgctaaat actttttta ttccaacatt atgaattttt ttaagaccga   3780
aataactctc gcgaatggtg aaatccgtaa acggcctctt atagaaacca atggtgaaac   3840
gggagaaatc gtttgggata aaggtcgtga ctttgccacc gttcgtaaag tcctctcaat   3900
gccgcaagtt aacattgtca agaagacgga agttcaaaca gggggattct ccaaagaatc   3960
tatcctgccg aagcgtaaca gtgataaact tattgccaga aaaaaagatt gggatccaaa   4020
aaaatacgga ggctttgatt cccctaccgt cgcgtatagt gtgctggtgg ttgctaaagt   4080
cgagaaaggg aaaagcaaga aattgaaatc agttaaagaa ctgctgggta ttacaattat   4140
ggaaagatcg tcctttgaga aaaatccgat cgacttttta gaggccaagg ggtataagga   4200
agtgaaaaaa gatctcatca tcaaattacc gaagtatagt ctttttgagc tggaaaacgg   4260
cagaaaaaga atgctggcct ccgcgggcga gttacagaag ggaaatgagc tggcgctgcc   4320
ttccaaatat gttaattttc tgtaccttgc cagtcattat gagaaactga agggcagccc   4380
cgaagataac gaacagaaac aattattcgt ggaacagcat aagcactatt tagatgaaat   4440
```

```
tatagagcaa attagtgaat tttctaagcg cgttatcctc gcggatgcta atttagacaa   4500

agtactgtca gcttataata aacatcggga taagccgatt agagaacagg ccgaaaatat   4560

cattcatttg tttaccttaa ccaaccttgg agcaccagct gccttcaaat atttcgatac   4620

cacaattgat cgtaaacggt atacaagtac aaaagaagtc ttggacgcaa ccctcattca   4680

tcaatctatt actggattat atgagacacg cattgatctt tcacagctgg gcggagacaa   4740

gaagaaaaaa ctgaaactgc accatcatca ccatcatcat caccatcatt gataaacata   4800

aaaaaccggc cttggccccg ccggtttttt attatttttc ttcctccgca tgttcaatcc   4860

gctccataat cgacggatgg ctccctctga aaattttaac gagaaacggc gggttgaccc   4920

ggctcagtcc cgtaacggcc aagtcctgaa acgtctcaat cgccgcttcc cggtttccgg   4980

tcagctcaat gccgtaacgg tcggcggcgt tttcctgata ccgggagacg gcattcgtaa   5040

tc                                                                  5042
```

<210> SEQ ID NO 63
<211> LENGTH: 9724
<212> TYPE: DNA
<213> ORGANISM: Artificial sequence
<220> FEATURE:
<223> OTHER INFORMATION: plasmid pRF856

<400> SEQUENCE: 63

```
gggtgaagtg gtcaagacct cactaggcac cttaaaaata gcgcaccctg aagaagattt     60

atttgaggta gcccttgcct acctagcttc caagaaagat atcctaacag cacaagagcg    120

gaaagatgtt ttgttctaca tccagaacaa cctctgctaa aattcctgaa aaattttgca    180

aaaagttgtt gactttatct acaaggtgtg gcataatgtg tggagatgcc atcagttcct    240

catagtttta gagctagaaa tagcaagtta aaataaggct agtccgttat caacttgaaa    300

aagtggcacc gagtcggtgc gactcctgtt gatagatcca gtaatgacct cagaactcca    360

tctggatttg ttcagaacgc tcggttgccg ccgggcgttt tttattggtg agaatgtcga    420

cctcgagagt tacgctaggg ataacagggt aatataggag ctccagtcgg cttaaaccag    480

ttttcgctgg tgcgaaaaaa gagtgtcttg tgacacctaa attcaaaatc tatcggtcag    540

atttataccg atttgatttt atatattctt gaataacata cgccgagtta tcacataaaa    600

gcgggaacca atcataaaat ttaaacttca ttgcataatc cattaaactc ttaaattcta    660

cgattccttg ttcatcaata aactcaatca tttctttaat taatttatat ctatctgttg    720

ttgttttctt taataattca ttaacatcta caccgccata aactatcata tcttcttttt    780

gatatttaaa tttattagga tcgtccatgt gaagcatata tctcacaaga cctttcacac    840

ttcctgcaat ctgcggaata gtcgcattca attcttctgt taattatttt tatctgttca    900

taagatttat taccctcata catcactaga atatgataat gctctttttt catcctacct    960

tctgtatcag tatccctatc atgtaatgga gacactacaa attgaatgtg taactctttt   1020

aaatactcta accactcggc ttttgctgat tctggatata aaacaaatgt ccaattacgt   1080

cctcttgaat tttcttgtt ttcagtttct tttattacat tttcgctcat gatataataa    1140

cggtgctaat acacttaaca aaatttagtc atagataggc agcatgccag tgctgtctat   1200

cttttttgt ttaaaatgca ccgtattcct cctttgcata tttttttatt agaataccgg    1260

ttgcatctga tttgctaata ttatattttt ctttgattct atttaatatc tcattttctt   1320

ctgttgtaag tcttaaagta acagcaactt ttttctcttc ttttctatct acaactatca   1380
```

-continued

```
ctgtacctcc caacatctgt tttttcact ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gatttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacattg atattcagca ccctgcgcat ttcgaccggg agaacgactc tgccgagctc   3720
atcgattctc cggacaatcc cggtattttt cacgtttgaa aagcctcctt ttctcctttc   3780
```

```
tttattgact tttgtcaaca tctttataat aaaagagatc ttcaaatttt ttgttgaaat   3840
actgaatcat ctttccgatc acaagttgtc cgggcctcct ttcgccattt aaaactctgc   3900
tgagtgtcgc cggggatacg ccgatttcaa tggcaagctg atttaaggag agattgtgtt   3960
caatcatgta ctggagaaca aaatctcttt tgatatgaat cttttttacc atgattactc   4020
ccctttctaa tctcttatgt ttctttttat ctacattgaa catatacgat ttgttaactt   4080
ttgtcaatac ttttaccatc catatgtttc ctataggcaa tattcgtact aaaatatttt   4140
ataataagag attgcgaggt tttggccata cttctccgcg gcacactctc ctctctatca   4200
ttttcgtctg tttacgatcc tgctgttatt ttatccctta tgttaacttt tgtcaatatt   4260
tttcctgtct aagtatttcc tatagtcaac atttgtatta aaatgttcat atcatgaatt   4320
tgcggggggg atggcgatga caaggttcgg cgagcggctc aaagagctga gggaacaaag   4380
aagcctgtcg gttaatcagc ttgccatgta tgccggtgtg agcgccgcag ccatttccag   4440
agccgcagcc atttccagaa tcgaaaacgg ccaccgcggc gttcccaagc ccgcgacgat   4500
cagaaaattg gccgaggctc tgaaaatgcc gtacgagcag ctcatggata ttgccggtta   4560
tatgagagct gacgagattc gcgaacagcc gcgcggctat gtcacgatgc aggagatcgc   4620
ggccaagcac ggcgtcgaag acctgtggct gtttaaaccc gagaaatgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttgct gtaaagttta tttttcagaa tacttttatc   4920
atcatgcttt gaaaaaatat cacgataata tccattgttc tcacggaagc acacgcaggt   4980
catttgaacg aatttttcg acaggaattt gccgggactc aggagcattt aacctaaaaa   5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga atttttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatctttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatccatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
```

-continued

```
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcaccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
taggcacggc ccttattaag aaataccct aactcgaaag tgagtttgtt tatggggatt   8340
ataaagtgta tgacgttcgc aaaatgatcg cgaaatcaga acaggaaatc ggtaaggcta   8400
ccgctaaata ctttttttat tccaacatta tgaatttttt taagaccgaa ataactctcg   8460
cgaatggtga aatccgtaaa cggcctctta tagaaaccaa tggtgaaacg ggagaaatcg   8520
```

tttgggataa aggtcgtgac tttgccaccg ttcgtaaagt cctctcaatg ccgcaagtta 8580
acattgtcaa gaagacggaa gttcaaacag ggggattctc caaagaatct atcctgccga 8640
agcgtaacag tgataaactt attgccagaa aaaaagattg ggatccaaaa aaatacggag 8700
gctttgattc ccctaccgtc gcgtatagtg tgctggtggt tgctaaagtc gagaaaggga 8760
aaagcaagaa attgaaatca gttaaagaac tgctgggtat tacaattatg gaaagatcgt 8820
cctttgagaa aaatccgatc gactttttag aggccaaggg gtataaggaa gtgaaaaaag 8880
atctcatcat caaattaccg aagtatagtc tttttgagct ggaaaacggc agaaaaagaa 8940
tgctggcctc cgcgggcgag ttacagaagg gaaatgagct ggcgctgcct tccaaatatg 9000
ttaattttct gtaccttgcc agtcattatg agaaactgaa gggcagcccc gaagataacg 9060
aacagaaaca attattcgtg gaacagcata agcactattt agatgaaatt atagagcaaa 9120
ttagtgaatt ttctaagcgc gttatcctcg cggatgctaa tttagacaaa gtactgtcag 9180
cttataataa acatcgggat aagccgatta gagaacaggc cgaaaatatc attcatttgt 9240
ttaccttaac caaccttgga gcaccagctg ccttcaaata tttcgatacc acaattgatc 9300
gtaaacggta tacaagtaca aaagaagtct tggacgcaac cctcattcat caatctatta 9360
ctggattata tgagacacgc attgatcttt cacagctggg cggagacaag aagaaaaaac 9420
tgaaactgca ccatcatcac catcatcatc accatcattg ataactcgag aaagcttaca 9480
taaaaaaccg gccttggccc cgccggtttt ttattatttt tcttcctccg catgttcaat 9540
ccgctccata atcgacggat ggctccctct gaaaatttta acgagaaacg gcgggttgac 9600
ccggctcagt cccgtaacgg ccaagtcctg aaacgtctca atcgccgctt cccggtttcc 9660
ggtcagctca atgccgtaac ggtcggcggc gttttcctga taccgggaga cggcattcgt 9720
aatc 9724

<210> SEQ ID NO 64
<211> LENGTH: 6393
<212> TYPE: DNA
<213> ORGANISM: Artificial sequence
<220> FEATURE:
<223> OTHER INFORMATION: synthesized pBL.comK-syn

<400> SEQUENCE: 64
aagcttcata tgcaagggtt tattgttttc taaaatctga ttaccaatta gaatgaatat 60
ttcccaaata ttaaataata aaacaaaaaa attgaaaaaa gtgtttccac catttttttca 120 attttttat aattttttta atctgttatt taaatagttt atagttaaat ttacattttc 180
attagtccat tcaatattct ctccaagata actacgaact gctaacaaaa ttctctccct 240
atgttctaat ggagaagatt cagccactgc atttcccgca atatcttttg gtatgatttt 300
acccgtgtcc atagttaaaa tcatacggca taaagttaat atagagttgg tttcatcatc 360
ctgataatta tctattaatt cctctgacga atccataatg gctcttctca catcagaaaa 420
tggaatatca ggtagtaatt cctctaagtc ataatttccg tatattcttt tattttttcg 480
ttttgcttgg taaagcatta tggttaaatc tgaatttaat tccttctgag gaatgtatcc 540
ttgttcataa agctcttgta accattctcc ataaataaat tcttgtttgg gaggatgatt 600
ccacggtacc atttcttgct gaataataat tgttaattca atatatcgta agttgctttt 660
atctcctatt ttttttgaaa taggtctaat tttttgtata agtatttctt tactttgatc 720
tgtcaatggt tcagatacga cgactaaaaa gtcaagatca ctatttggtt ttagtccact 780

-continued ctcaactcct gatccaaaca tgtaagtacc aataaggtta ttttttaaat gtttccgaag 840
tatttttttc actttattaa tttgttcgta tgtattcaaa tatatcctcc tcactatttt 900
gattagtacc tattttatat ccatagttgt taattaaata aacttaattt agtttattta 960
tggatttcat tggcttctaa attttttatc tagataataa ttattttagt taattttatt 1020
ctagattata tatgatatga tctttcattt ccataaaact aaagtaagtg taaacctatt 1080
cattgtttta aaaatatctc ttgccagtca cgttacgtta ttagttatag ttattataac 1140
atgtattcac gaacgggcgc gccggtatcc gcgcttcttg agcactattt attcaaagcc 1200
gctccagatc aatagcgctt tttcagctcc ctgaggatga attcgtatat cagctgattc 1260
cggtcttctt tcggatagag cataaattcc tgtttcttct gcatggggtt tccttcaatc 1320
ctgtcgataa attttgttct cagccatgcc gttcggtaaa cctggttttc gaaagatgag 1380
atggatacgg gcagctccag cgtttccccg ttgacaaacg tgacaaacgt gttgtcatac 1440
tttgccgcgc aaaactcgtg aacatgcgca tgggaaagcc acccgcactg aggacgagtt 1500
gaggaaaatg tggggaaaag aaaaatgttg tttgagtgat ccaccatgat cggcggttta 1560
tgggaaactt taatgacttc atatgtgccc gcttttcttc ccgcatagct cgatccgaaa 1620
tagcggcagc ttctttcgat aatttgaaac ggcttcatat tgacgcggaa agtcctgtcg 1680
gtctcaagta tttttgaggc ggatttctcc ccctcaccca gaggcaggac agccattgtc 1740
gaactgttta cttcatacgt atcctttgtc atatcctctg tgctcatgtg atttccccct 1800
taaaaataaa ttcattcaaa tacagatgca ttttatttca tatagtaagt acatcaccta 1860
ttagtttgtt gtttaaacaa actaacttat tttcatctta tataacctcg tcagtatttt 1920
caatattttt tttagttttt tatgaacaca ttagatttaa taaagggaag attcgctatg 1980
tactatgttg atacttaatt taaagattaa acaaatggag tggatgaagt ggatatcgct 2040
gatcaaacct ttgtcaaaaa agtaaatcaa aagttattat taaaagaaat ccttaaaaat 2100
tcacctattt caagagcaaa attatctgaa atgactggat taaataaatc aactgtctca 2160
tcacaggtaa acacgttaat gaaagaaagt atggtatttg aaataggtca aggacaatca 2220
agtggcggaa gaagacctgt catgcttgtt tttaataaaa aggcaggata ctccgttgga 2280
atagatgttg gtgtggatta tattaatggc attttaacag accttgaagg aacaatcgtt 2340
cttgatcaat accgccattt ggaatccaat tctccagaaa taacgaaaga cattttgatt 2400
gatatgattc atcactttat tacgcaaatg ccccaatctc cgtacgggtt tattggtata 2460
ggtacttgcg tgcctggact cattgataaa gatcaaaaaa ttgttttcac tccgaactcc 2520
aactggagag atattgactt aaaatcttcg atacaagaga agtacaatgt gtctgttttt 2580
attgaaaatg aggcaaatgc tggcgcatat ggagaaaaac tatttggagc tgcaaaaaat 2640
cacgataaca ttatttacgt aagtatcagc acaggaatag ggatcggtgt tattatcaac 2700
aatcatttat atagaggagt aagcggcttc tctggagaaa tgggacatat gacaatagac 2760
tttaatggtc ctaaatgcag ttgcggaaac cgaggatgct gggaattgta tgcttcagag 2820
aaggctttat ttaaatctct tcagaccaaa gagaaaaaac tgtcctatca agatatcata 2880
aacctcgccc atctgaatga tatcggaacc ttaaatgcat tacaaaattt tggattctat 2940
ttaggaatag gccttaccaa tattctaaat actctcaacc cacaagccgt aattttaaga 3000
aatagcataa ttgaatcgca tcctatggtt ttaaattcaa tgagaagtga agtatcatca 3060
agggtttatt cccaattagg caatagctat gaattattgc catcttcctt aggacagaat 3120
gcaccggcat taggaatgtc ctccattgtg attgatcatt ttctggacat gattacaatg 3180

```
taatttttta tggaatggac agctcatctt taaagatgag ttttttttatt ctaggagtat   3240
ttctgaagca atagtgacat ggcaccttct catatgaaaa aggagttcta aaataaaaat   3300
ctcctttttc atgtgcaaat tatttttctt tataacgaaa atatctaaat gacaatgcat   3360
atgcaagagg ggatcacata aatatatatt ttaaaaatat cccactttat ccaattttcg   3420
tttgttgaac taatgggtgc tttagttgaa gaataaaaga ccacattaaa aaatgtggtc   3480
ttttgtgttt ttttaaagga tttgagcgta gcgaaaaatc cttttctttc ttatcttgat   3540
actatataga aacaacatca tttttcaaaa ttaggtcaaa gccttgtgta tcaagggttt   3600
gatggttctt tgacaggtaa aaactccttc tgctattatt aaatactata tagaaacaac   3660
atcatttttc aaaattaggt caaagccttg tgtatcaagg gtttgatggt tctttgacag   3720
gtaaaaactc cttctgctat tattaaggtg tcgaatcaaa ataatagaat gctagagaac   3780
tagctcagaa ggagtttttt tgttgattta ttcatctgaa aatgattata gcatcctcga   3840
agataaaacc gcaacaggta aaaagcggga ttggaagggg aaaaagagac ggacgaacct   3900
catggcggag cattacgaag cgttagagag taagattggg gcaccttact atggcaaaaa   3960
ggctgaaaaa ctaattagtt gtgcagagta tctttcgttt aagagagacc cggagacggg   4020
caagttaaaa ctgtatcaag cccatttttg taaagtgagg ttatgtccga tgtgtgcgtg   4080
gcgcaggtcg ttaaaaattg cttatcacaa taagttgatc gtagaggaag ccaatagaca   4140
gtacggctgc ggatggattt ttctcacgct gacgattcga aatgtaaagg gagaacggct   4200
gaagccacaa atttctgcga tgatggaagg ctttaggaaa ctgttccagt acaaaaaagt   4260
aaaaacttcg gttcttggat ttttcagagc tttagagatt accaaaaatc atgaagaaga   4320
tacatatcat cctcattttc atgtgttgat accagtaagg aaaaattatt ttgggaaaaa   4380
ctatattaag caggcggagt ggacgagcct ttggaaaaag gcgatgaaat tggattacac   4440
tccaattgtc gatattcgtc gagtgaaagg taaagctaag attgacgctg aacagattga   4500
aaacgatgtg cggaacgcaa tgatggagca aaaagctgtt ctcgaaatct ctaaatatcc   4560
ggttaaggat acggatgttg tgcgcggtaa taaggtgact gaagacaatc tgaacacggt   4620
gctttacttg gatgatgcgt tggcagctcg aaggttaatt ggatacggtg gcattttgaa   4680
ggagatacat aaagagctga atcttggtga tgcggaggac ggcgatctgg tcaagattga   4740
ggaagaagat gacgaggttg caaatggtgc atttgaggtt atggcttatt ggcatcctgg   4800
cattaaaaat tacataatca aataaaaaaa gcagaccttt agaaggcctg ctttttttaac   4860
taacccattt gtattgtgtt gaaatatgtt ttgtatggtg cactctcagt acaatctgct   4920
ctgatgccgc atagttaagc cagccccgac acccgccaac acccgctgac gcgccctgac   4980
gggcttgtct gctcccggca tccgcttaca gacaagctgt gaccgtctcc gggagctgca   5040
tgtgtcagag gttttcaccg tcatcaccga aacgcgcgag acgaaagggc ctcgtgatac   5100
gcctattttt ataggttaat gtcatgataa taatggtttc ttagcgattc acaaaaaata   5160
ggcacacgaa aaacaagtta agggatgcag tttatgcatc ccttaactta aaatactaaa   5220
aatgcccata ttttttcctc cttataaaat tagtataatt atagcacgag atctaaaagg   5280
atctaggtga agatcctttt tgataatctc atgaccaaaa tcccttaacg tgagttttcg   5340
ttccactgag cgtcagaccc cgtagaaaag atcaaaggat cttcttgaga tccttttttt   5400
ctgcgcgtaa tctgctgctt gcaaacaaaa aaaccaccgc taccagcggt ggtttgtttg   5460
ccggatcaag agctaccaac tctttttccg aaggtaactg gcttcagcag agcgcagata   5520
```

ccaaatactg ttcttctagt gtagccgtag ttaggccacc acttcaagaa ctctgtagca 5580
ccgcctacat acctcgctct gctaatcctg ttaccagtgg ctgctgccag tggcgataag 5640
tcgtgtctta ccgggttgga ctcaagacga tagttaccgg ataaggcgca gcggtcgggc 5700
tgaacggggg gttcgtgcac acagcccagc ttggagcgaa cgacctacac cgaactgaga 5760
tacctacagc gtgagctatg agaaagcgcc acgcttcccg aagggagaaa ggcggacagg 5820
tatccggtaa gcggcagggt cggaacagga gagcgcacga gggagcttcc agggggaaac 5880
gcctggtatc tttatagtcc tgtcgggttt cgccacctct gacttgagcg tcgatttttg 5940
tgatgctcgt caggggggcg gagcctatgg aaaaacgcca gcaacgcggc ctttttacgg 6000
ttcctggcct tttgctggcc ttttgctcac atgttctttc ctgcgttatc ccctgattct 6060
gtggataacc gtattaccgc ctttgagtga gctgataccg ctcgccgcag ccgaacgacc 6120
gagcgcagcg agtcagtgag cgaggaagcg gaagagcgcc caatacgcaa accgcctctc 6180
cccgcgcgtt ggccgattca ttaatgcagc tggcacgaca ggtttcccga ctggaaagcg 6240
ggcagtgagc gcaacgcaat taatgtgagt tagctcactc attaggcacc ccaggcttta 6300
cactttatgc ttccggctcg tatgttgtgt ggaattgtga gcggataaca atttcacaca 6360
ggaaacagct atgaccatga ttacgccgga tcc 6393

<210> SEQ ID NO 65
<211> LENGTH: 2800
<212> TYPE: DNA
<213> ORGANISM: Bacillus licheniformis

<400> SEQUENCE: 65
tagagacgag acgtctcacc ttgttgtgtt tcattttgtc actctctcct tttcgatcac 60
atctcacgaa aagaggaatg gttctttccc ctgtcctaaa caaaaaaccc gctttattga 120
aaaagcgggg ctgttttaca gacaggtcaa ataaacgttt gaaaatgttc atttcaaaac 180
gcgcggaacc tccatcttct cccatccaga ctatactgtc ggcttcggaa tcgcaccgaa 240
tcctgcccat aaaaaggctc gcgggcttag agcgcttgct catcaccgcc ggtagggaat 300
ttcaccctgc cccgaagatt gatcttattt atttttaata ctgatattat tataaattaa 360
ttgtgaaaaa atgtacaggt gcaaagctta ttgcgctgtt ttgggacatc ctgcacgata 420
tttcggtaaa ctcacttttt ccgcatacta aaaaccgcac attcacagtt atttcatttt 480
taattttcgt ctttccgcgt gaaactcatt gacactcttt atggaatatg gtaaattatc 540
agatatttat gacgcttatt taggaggaaa tcttacatgt ttcgagtatt ggtctcagat 600
aaaatgtcca gcgacggcct caaaccatta atggaagcag attttattga aattgtagaa 660
aagaatgttg cggaagcgga agacgagctt catacgtttg acgcgctctt ggtgcggagc 720
gccacgaagg taaccgaaga gctgtttaaa aagatgactt cgctgaaaat cgtcgccaga 780
gcaggtgtcg gcgtcgacaa tatcgatatt gacgaggcga caaaacacgg tgttatcgtc 840
gtaaacgcgc caaacgggaa tacaatttca accgctgaac atacctttgc aatgttttca 900
gcgttaatga gacatattcc gcaggcaaac atctccgtga aatcaaggga gtggaatcgt 960
tcggcttacg tcggttcaga gctttacgga aaaacgctcg gcatcatcgg aatgggccgc 1020
atcggaagcg aaatcgcgag ccgcgcaaaa gcattcggta tgaccgttca tgtatttgac 1080
ccgttcctga cccaagaaag ggcaagcaag ctcggcgtta acgcgaacag ctttgaagaa 1140
gttctggcat gcgccgacat cattacggtt catacccgc tcacgaaaga aacgaaggga 1200
cttttgaaca aagaaaccat cgcaaaaacg aaaaaaggcg ttcgtctcgt taactgtgca 1260
agaggcggca tcatcgatga agcagcgctt ttggaagctc tggaaagcgg acatgtcgct 1320
ggcgctgcct tggatgtatt cgaagtcgag cctccggtcg attcaaaact gatcgatcat 1380
ccgcttgtag tcgcgactcc tcacttgggc gcctcaacaa aagaagccca gctgaatgtc 1440
gctgcacaag tgtccgaaga agtccttcag tatgcgcaag gaaaccctgt gatgtccgcg 1500
atcaaccttc cggccatgac aaaggattca ttcgaaaaaa tccagcctta tcatcagttt 1560
gccaatacga tcggaaacct tgtgtctcag tgcatgaatg agcctgttca agatgtagcc 1620
atccaatatg aaggctccat cgccaaactt gaaacgtcat ttattacgaa aagccttttg 1680
gccggatttc tgaagccgag ggtcgcggct accgttaacg aagtgaatgc cggcaccgtt 1740
gcgaaagagc gcggcatcag cttcagcgaa aaaatttctt ccaatgagtc aggctatgaa 1800
aactgcatct ctgtgactgt cacgggagat gtaacaacat tctctttaag agcgacgtac 1860
attccgcact tcggcggacg catcgttgcc ttaaacggct ttgatattga tttttatccg 1920
gctggacacc ttgtctacat tcaccaccag gataaaccag gggctatcgg ccatgtcgga 1980
cgaattttag gagaccatga catcaatatc gccactatgc aggtaggccg aaaagaaaaa 2040
ggcggagaag cgatcatgat gctttccttt gaccgccacc ttgaggacga tattttagct 2100
gagctgaaaa acatcccgga tatcgtgtct gttaaagcca tcgaccttcc ttaaacagaa 2160
gctgcggaac ctgaaaagaa ttcctttcag gttccgtttt ttttaggaat tctccctgat 2220
ctcaagcatc tggcggggat aaatccgctc tcctttcaaa tcgttccatt ctttgaggcg 2280
ctgtacagtt acgcccattt tttcggcgat atgatgaagc gtatcccctt tccgcactac 2340
atatgtaccg gtcttcgatt catcgtcatg aaggcggagt gtttggccgg ccttgagatt 2400
tgaatgtttc aacccgttta ttctcatgat ctcctcgatg gatataccgc tatccttgct 2460
gattctccag agcgtgtccc ctttttgaac ggtcaccgca ccgctcattg tcccggcgtt 2520
ttgataaacg tggatagaat tttgccggaa cgcctcctca cgaagcaccg tcagcggatt 2580
gattgcatat cttttatctt cagtccatga accgtgatgc atttcaaaat gcaggtgggt 2640
tccggtcgat attcccgtat tgccgatgat tccgatttgc tcgccttttt tcacccgctc 2700
cttttccttt ttcaggcgtt tgcttaagtg ggcataaacg gtttcatatc cgttgtcatg 2760
tttaataaat atcacttggc cgtaggagtc ggattgatac 2800

<210> SEQ ID NO 66
<211> LENGTH: 1222
<212> TYPE: DNA
<213> ORGANISM: Artificial sequence
<220> FEATURE:
<223> OTHER INFORMATION: target site 1 edited locus

<400> SEQUENCE: 66
tagagacgag acgtctcacc ttgttgtgtt tcattttgtc actctctcct tttcgatcac 60
atctcacgaa aagaggaatg gttctttccc ctgtcctaaa caaaaaaccc gctttattga 120
aaaagcgggg ctgttttaca gacaggtcaa ataaacgttt gaaaatgttc atttcaaaac 180
gcgcggaacc tccatcttct cccatccaga ctatactgtc ggcttcggaa tcgcaccgaa 240
tcctgcccat aaaaaggctc gcgggcttag agcgcttgct catcaccgcc ggtagggaat 300
ttcaccctgc cccgaagatt gatcttattt atttttaata ctgatattat tataaattaa 360
ttgtgaaaaa atgtacaggt gcaaagctta ttgcgctgtt ttgggacatc ctgcacgata 420
tttcggtaaa ctcacttttt ccgcatacta aaaaccgcac attcacagtt atttcatttt 480
taattttcgt ctttccgcgt gaaactcatt gacactcttt atggaatatg gtaaattatc 540
agatatttat gacgcttatt taggaggaaa tcttacacag aagctgcgga acctgaaaag 600
aattcctttc aggttccgtt ttttttagga attctccctg atctcaagca tctggcgggg 660
ataaatccgc tctcctttca aatcgttcca ttctttgagg cgctgtacag ttacgcccat 720
tttttcggcg atatgatgaa gcgtatcccc tttccgcact acatatgtac cggtcttcga 780
ttcatcgtca tgaaggcgga gtgtttggcc ggccttgaga tttgaatgtt tcaacccgtt 840
tattctcatg atctcctcga tggatatacc gctatccttg ctgattctcc agagcgtgtc 900 cccttttga acggtcaccg caccgctcat tgtcccggcg ttttgataaa cgtggataga 960
attttgccgg aacgcctcct cacgaagcac cgtcagcgga ttgattgcat atcttttatc 1020
ttcagtccat gaaccgtgat gcatttcaaa atgcaggtgg gttccggtcg atattcccgt 1080
attgccgatg attccgattt gctcgccttt tttcacccgc tccttttcct ttttcaggcg 1140
tttgcttaag tgggcataaa cggtttcata tccgttgtca tgtttaataa atatcacttg 1200
gccgtaggag tcggattgat ac 1222

<210> SEQ ID NO 67
<211> LENGTH: 20
<212> TYPE: DNA
<213> ORGANISM: Artificial sequence
<220> FEATURE:
<223> OTHER INFORMATION: primer

<400> SEQUENCE: 67
tagagacgag acgtctcacc 20

<210> SEQ ID NO 68
<211> LENGTH: 21
<212> TYPE: DNA
<213> ORGANISM: Artificial sequence
<220> FEATURE:
<223> OTHER INFORMATION: primer

<400> SEQUENCE: 68
gtatcaatcc gactcctacg g 21

<210> SEQ ID NO 69
<211> LENGTH: 1517
<212> TYPE: DNA
<213> ORGANISM: Bacillus licheniformis

<400> SEQUENCE: 69
atcaaacatg ccatgtttgc ggcgtatttt gtcaaaatga tattttcgcc gtcggtatat 60
atttcgagcg ggtccttttc attgatattc agcaccctgc gcatttcgac cgggagaacg 120
actctgccga gctcatcgat tctccggaca atcccggtat ttttcacgtt tgaaaagcct 180
ccttttctcc tttctttatt gacttttgtc aacatcttta taataaaaga gatcttcaaa 240
ttttttgttg aaatactgaa tcatctttcc gatcacaagt tgtccgggcc tcctttcgcc 300
atttaaaact ctgctgagtg tcgccgggga tacgccgatt tcaatggcaa gctgatttaa 360
ggagagattg tgttcaatca tgtactggag aacaaaatct cttttgatat gaatcttttt 420
taccatgatt actccccttt ctaatctctt atgtttcttt ttatctacat tgaacatata 480
cgatttgtta acttttgtca atacttttac catccatatg tttcctatag gcaatattcg 540
tactaaaata ttttataata agagattgcg aggttttggc catgacgaac tttggacacc 600
atttacgaca attaagggaa cggaaaaaac tgaccgtcaa tcaactggcg atgtattccg 660
gcgtcagttc ggcaggcatt tcgcgaatcg aaaacggaaa gcgcggcgtg ccgaagccgg 720
cgacgatcag aaaactggcg gacgctttga aagtcccgta tgaggaactg atggcatctg 780
caggctatat cagcgcgtct acagtccagg aagcaagaag cagctatgat tccatttacg 840
acatcgtgtc acagtacgat ttagaggacc tttctctgtt tgacagcgaa aagtggaagg 900
tgctttcaaa aaaagacatc gaaaacctgg acaaatattt cgactttctc gtgcaggaag 960
caagcagccg aaacaaaaac tgaatacttc tccgcggcac actctcctct ctatcatttt 1020
cgtctgttta cgatcctgct gttattttat ccctatgtt aacttttgtc aatatttttc 1080
ctgtctaagt atttcctata gtcaacattt gtattaaaat gttcatatca tgaatttgcg 1140
ggggggatgg cgatgacaag gttcggcgag cggctcaaag agctgaggga acaaagaagc 1200
ctgtcggtta atcagcttgc catgtatgcc ggtgtgagcg ccgcagccat ttccagagcc 1260
gcagccattt ccagaatcga aaacggccac cgcggcgttc ccaagcccgc gacgatcaga 1320
aaattggccg aggctctgaa aatgccgtac gagcagctca tggatattgc cggttatatg 1380
agagctgacg agattcgcga acagccgcgc ggctatgtca cgatgcagga gatcgcggcc 1440
aagcacggcg tcgaagacct gtggctgttt aaacccgaga aatgggactg tttgtcccgc 1500
gaagacctgc tcaacct 1517

<210> SEQ ID NO 70
<211> LENGTH: 1115
<212> TYPE: DNA
<213> ORGANISM: Artificial sequence
<220> FEATURE:
<223> OTHER INFORMATION: target site 2 edited locus

<400> SEQUENCE: 70
atcaaacatg ccatgtttgc ggcgtatttt gtcaaaatga tattttcgcc gtcggtatat 60
atttcgagcg ggtccttttc attgatattc agcaccctgc gcatttcgac cgggagaacg 120
actctgccga gctcatcgat tctccggaca atcccggtat ttttcacgtt tgaaaagcct 180
ccttttctcc tttctttatt gacttttgtc aacatcttta taataaaaga gatcttcaaa 240
ttttttgttg aaatactgaa tcatctttcc gatcacaagt tgtccgggcc tcctttcgcc 300
atttaaaact ctgctgagtg tcgccgggga tacgccgatt tcaatggcaa gctgatttaa 360
ggagagattg tgttcaatca tgtactggag aacaaaatct cttttgatat gaatcttttt 420
taccatgatt actccccttt ctaatctctt atgtttcttt ttatctacat tgaacatata 480
cgatttgtta acttttgtca atacttttac catccatatg tttcctatag gcaatattcg 540
tactaaaata ttttataata agagattgcg aggttttggc catacttctc cgcggcacac 600
tctcctctct atcattttcg tctgtttacg atcctgctgt tattttatcc cttatgttaa 660
cttttgtcaa tatttttcct gtctaagtat ttcctatagt caacatttgt attaaaatgt 720
tcatatcatg aatttgcggg ggggatggcg atgacaaggt tcggcgagcg gctcaaagag 780
ctgagggaac aaagaagcct gtcggttaat cagcttgcca tgtatgccgg tgtgagcgcc 840
gcagccattt ccagagccgc agccatttcc agaatcgaaa acggccaccg cggcgttccc 900
aagcccgcga cgatcagaaa attggccgag gctctgaaaa tgccgtacga gcagctcatg 960
gatattgccg gttatatgag agctgacgag attcgcgaac agccgcgcgg ctatgtcacg 1020
atgcaggaga tcgcggccaa gcacggcgtc gaagacctgt ggctgtttaa acccgagaaa 1080
tgggactgtt tgtcccgcga agacctgctc aacct 1115

<210> SEQ ID NO 71
<211> LENGTH: 20
<212> TYPE: DNA
<213> ORGANISM: Artificial sequence
<220> FEATURE:
<223> OTHER INFORMATION: primer

<400> SEQUENCE: 71
atcaaacatg ccatgtttgc 20

<210> SEQ ID NO 72
<211> LENGTH: 18
<212> TYPE: DNA
<213> ORGANISM: artificial sequence
<220> FEATURE:
<223> OTHER INFORMATION: primer

<400> SEQUENCE: 72
aggttgagca ggtcttcg 18

<210> SEQ ID NO 73
<211> LENGTH: 4272
<212> TYPE: DNA
<213> ORGANISM: Artificial sequence
<220> FEATURE:
<223> OTHER INFORMATION: Yarrowia codon optimized Cas9

<400> SEQUENCE: 73 atgggggggtt ctcatcatca tcatcatcat ggtatggcta gcatgactgg tggacagcaa 60
atgggtcggg atctgtacga cgatgacgat aaggatccga gctcgagatc tgcagctggt 120
accatatggg aattcgacaa gaaatactcc atcggcctgg acattggaac caactctgtc 180
ggctgggctg tcatcaccga cgagtacaag gtgccctcca agaaattcaa ggtcctcgga 240
aacaccgatc gacactccat caagaaaaac ctcattggtg ccctgttgtt cgattctggc 300
gagactgccg aagctaccag actcaagcga actgctcggc gacgttacac ccgacggaag 360
aaccgaatct gctacctgca ggagatcttt tccaacgaga tggccaaggt ggacgattcg 420
ttctttcatc gactggagga atccttcctc gtcgaggaag acaagaaaca cgagcgtcat 480
cccatctttg gcaacattgt ggacgaggtt gcttaccacg agaagtatcc taccatctac 540
cacctgcgaa agaaactcgt cgattccacc gacaaggcgg atctcagact tatctacctc 600
gctctggcac acatgatcaa gtttcgaggt catttcctca tcgagggcga tctcaatccc 660
gacaacagcg atgtggacaa gctgttcatt cagctcgttc agacctacaa ccagctgttc 720
gaggaaaacc ccatcaatgc ctccggagtc gatgcaaagg ccatcttgtc tgctcgactc 780
tcgaagagca gacgactgga gaacctcatt gcccaacttc ctggcgagaa aaagaacgga 840
ctgtttggca acctcattgc cctttctctt ggtctcacac ccaacttcaa gtccaacttc 900
gatctggcgg aggacgccaa gctccagctg tccaaggaca cctacgacga tgacctcgac 960
aacctgcttg cacagattgg cgatcagtac gccgacctgt ttctcgctgc caagaacctt 1020
tcggatgcta ttctcttgtc tgacattctg cgagtcaaca ccgagatcac aaaggctccc 1080
ctttctgcct ccatgatcaa gcgatacgac gagcaccatc aggatctcac actgctcaag 1140
gctcttgtcc gacagcaact gcccgagaag tacaaggaga tcttttttcga tcagtcgaag 1200 aacggctacg ctggatacat cgacggcgga gcctctcagg aagagttcta caagttcatc 1260
aagccaattc tcgagaagat ggacggaacc gaggaactgc ttgtcaagct caatcgagag 1320
gatctgcttc ggaagcaacg aaccttcgac aacggcagca ttcctcatca gatccacctc 1380

```
ggtgagctgc acgccattct tcgacgtcag gaagacttct accccttttct caaggacaac   1440
cgagagaaga tcgagaagat tcttaccttt cgaatcccct actatgttgg tcctcttgcc   1500
agaggaaact ctcgatttgc ttggatgact cgaaagtccg aggaaaccat cactccctgg   1560
aacttcgagg aagtcgtgga caagggtgcc tctgcacagt ccttcatcga gcgaatgacc   1620
aacttcgaca agaatctgcc caacgagaag gttcttccca agcattcgct gctctacgag   1680
tactttacag tctacaacga actcaccaaa gtcaagtacg ttaccgaggg aatgcgaaag   1740
cctgccttct tgtctggcga acagaagaaa gccattgtcg atctcctgtt caagaccaac   1800
cgaaaggtca ctgttaagca gctcaaggag gactacttca agaaaatcga gtgtttcgac   1860
agcgtcgaga tttccggagt tgaggaccga ttcaacgcct ctttgggcac ctatcacgat   1920
ctgctcaaga ttatcaagga caaggatttt ctcgacaacg aggaaaacga ggacattctg   1980
gaggacatcg tgctcactct taccctgttc gaagatcggg agatgatcga ggaacgactc   2040
aagacatacg ctcacctgtt cgacgacaag gtcatgaaac aactcaagcg acgtagatac   2100
accggctggg gaagactttc gcgaaagctc atcaacggca tcagagacaa gcagtccgga   2160
aagaccattc tggactttct caagtccgat ggctttgcca accgaaactt catgcagctc   2220
attcacgacg attctcttac cttcaaggag gacatccaga aggcacaagt gtccggtcag   2280
ggcgacagct tgcacgaaca tattgccaac ctggctggtt cgccagccat caagaaaggc   2340
attctccaga ctgtcaaggt tgtcgacgag ctggtgaagg tcatgggacg tcacaagccc   2400
gagaacattg tgatcgagat ggccagagag aaccagacaa ctcaaaaggg tcagaaaaac   2460
tcgcgagagc ggatgaagcg aatcgaggaa ggcatcaagg agctgggatc ccagattctc   2520
aaggagcatc ccgtcgagaa cactcaactg cagaacgaga agctgtatct ctactatctg   2580
cagaatggtc gagacatgta cgtggatcag gaactggaca tcaatcgtct cagcgactac   2640
gatgtggacc acattgtccc tcaatccttt ctcaaggacg attctatcga caacaaggtc   2700
cttacacgat ccgacaagaa cagaggcaag tcggacaacg ttcccagcga agaggtggtc   2760
aaaaagatga agaactactg gcgacagctg ctcaacgcca agctcattac ccagcgaaag   2820
ttcgacaatc ttaccaaggc cgagcgaggc ggtctgtccg agctcgacaa ggctggcttc   2880
atcaagcgtc aactcgtcga gaccagacag atcacaaagc acgtcgcaca gattctcgat   2940
tctcggatga acaccaagta cgacgagaac gacaagctca tccgagaggt caaggtgatt   3000
actctcaagt ccaaactggt ctccgatttc cgaaaggact ttcagttcta caaggtgcga   3060
gagatcaaca attaccacca tgcccacgat gcttacctca acgccgtcgt tggcactgcg   3120
ctcatcaaga aatacccaa gctcgaaagc gagttcgttt acggcgatta caaggtctac   3180
gacgttcgaa agatgattgc caagtccgaa caggagattg gcaaggctac tgccaagtac   3240
ttcttttact ccaacatcat gaactttttc aagaccgaga tcaccttggc caacggagag   3300
attcgaaaga gaccacttat cgagaccaac ggcgaaactg gagagatcgt gtgggacaag   3360
ggtcgagact ttgcaaccgt gcgaaaggtt ctgtcgatgc ctcaggtcaa catcgtcaag   3420
aaaaccgagg ttcagactgg cggattctcc aaggagtcga ttctgcccaa gcgaaactcc   3480
gacaagctca tcgctcgaaa gaaagactgg gatcccaaga aatacggtgg cttcgattct   3540
cctaccgtcg cctattccgt gcttgtcgtt gcgaaggtcg agaagggcaa gtccaaaaag   3600
ctcaagtccg tcaaggagct gctcggaatt accatcatgg agcgatcgag cttcgagaag   3660
aatcccatcg acttcttgga agccaagggt tacaaggagg tcaagaaaga cctcattatc   3720
```

```
aagctgccca agtactctct gttcgaactg gagaacggtc gaaagcgtat gctcgcctcc   3780

gctggcgagc tgcagaaggg aaacgagctt gccttgcctt cgaagtacgt caactttctc   3840

tatctggctt ctcactacga gaagctcaag ggttctcccg aggacaacga acagaagcaa   3900

ctcttcgttg agcagcacaa acattacctc gacgagatta tcgagcagat ttccgagttt   3960

tcgaagcgag tcatcctggc tgatgccaac ttggacaagg tgctctctgc ctacaacaag   4020

catcgggaca aacccattcg agaacaggcg gagaacatca ttcacctgtt tactcttacc   4080

aacctgggtg ctcctgcagc tttcaagtac ttcgatacca ctatcgaccg aaagcggtac   4140

acatccacca aggaggttct cgatgccacc ctgattcacc agtccatcac tggcctgtac   4200

gagacccgaa tcgacctgtc tcagcttggt ggcgactcca gagccgatcc caagaaaaag   4260

cgaaaggtct aa                                                       4272
```

```
<210> SEQ ID NO 74
<211> LENGTH: 9
<212> TYPE: PRT
<213> ORGANISM: Simian virus 40

<400> SEQUENCE: 74

Met Ala Pro Lys Lys Lys Arg Lys Val
1               5
```

```
<210> SEQ ID NO 75
<211> LENGTH: 546
<212> TYPE: DNA
<213> ORGANISM: Yarrowia lipolytica

<400> SEQUENCE: 75

tcgacgttta aaccatcatc taagggcctc aaaactacct cggaactgct gcgctgatct     60

ggacaccaca gaggttccga gcactttagg ttgcaccaaa tgtcccacca ggtgcaggca    120

gaaaacgctg gaacagcgtg tacagtttgt cttaacaaaa agtgagggcg ctgaggtcga    180

gcagggtggt gtgacttgtt atagccttta gagctgcgaa agcgcgtatg gatttggctc    240

atcaggccag attgagggtc tgtggacaca tgtcatgtta gtgtacttca atcgccccct    300

ggatatagcc ccgacaatag gccgtggcct catttttttg ccttccgcac atttccattg    360

ctcggtaccc acaccttgct tctcctgcac ttgccaacct taatactggt ttacattgac    420

caacatctta caagcggggg gcttgtctag ggtatatata aacagtggct ctcccaatcg    480

gttgccagtc tctttttcc tttctttccc cacagattcg aaatctaaac tacacatcac    540

accatg                                                               546
```

```
<210> SEQ ID NO 76
<211> LENGTH: 4683
<212> TYPE: DNA
<213> ORGANISM: Artificial sequence
<220> FEATURE:
<223> OTHER INFORMATION: Yarrowia Cas9 expression cassette

<400> SEQUENCE: 76

tcgacgttta aaccatcatc taagggcctc aaaactacct cggaactgct gcgctgatct     60

ggacaccaca gaggttccga gcactttagg ttgcaccaaa tgtcccacca ggtgcaggca    120

gaaaacgctg gaacagcgtg tacagtttgt cttaacaaaa agtgagggcg ctgaggtcga    180

gcagggtggt gtgacttgtt atagccttta gagctgcgaa agcgcgtatg gatttggctc    240

atcaggccag attgagggtc tgtggacaca tgtcatgtta gtgtacttca atcgccccct    300
```

-continued

```
ggatatagcc ccgacaatag gccgtggcct catttttttg ccttccgcac atttccattg    360
ctcggtaccc acaccttgct tctcctgcac ttgccaacct taatactggt ttacattgac    420
caacatctta caagcggggg gcttgtctag ggtatatata aacagtggct ctcccaatcg    480
gttgccagtc tctttttttcc tttctttccc cacagattcg aaatctaaac tacacatcac    540
accatggaca agaaatactc catcggcctg gacattggaa ccaactctgt cggctgggct    600
gtcatcaccg acgagtacaa ggtgccctcc aagaaattca aggtcctcgg aaacaccgat    660
cgacactcca tcaagaaaaa cctcattggt gccctgttgt tcgattctgg cgagactgcc    720
gaagctacca gactcaagcg aactgctcgg cgacgttaca cccgacggaa gaaccgaatc    780
tgctacctgc aggagatctt ttccaacgag atggccaagg tggacgattc gttctttcat    840
cgactggagg aatccttcct cgtcgaggaa gacaagaaac acgagcgtca tcccatcttt    900
ggcaacattg tggacgaggt tgcttaccac gagaagtatc ctaccatcta ccacctgcga    960
aagaaactcg tcgattccac cgacaaggcg gatctcagac ttatctacct cgctctggca   1020
cacatgatca agtttcgagg tcatttcctc atcgagggcg atctcaatcc cgacaacagc   1080
gatgtggaca agctgttcat tcagctcgtt cagacctaca accagctgtt cgaggaaaac   1140
cccatcaatg cctccggagt cgatgcaaag gccatcttgt ctgctcgact ctcgaagagc   1200
agacgactgg agaacctcat tgcccaactt cctggcgaga aaaagaacgg actgtttggc   1260
aacctcattg ccctttctct tggtctcaca cccaacttca agtccaactt cgatctggcg   1320
gaggacgcca agctccagct gtccaaggac acctacgacg atgacctcga caacctgctt   1380
gcacagattg gcgatcagta cgccgacctg tttctcgctg ccaagaacct ttcggatgct   1440
attctcttgt ctgacattct gcgagtcaac accgagatca caaaggctcc cctttctgcc   1500
tccatgatca agcgatacga cgagcaccat caggatctca cactgctcaa ggctcttgtc   1560
cgacagcaac tgcccgagaa gtacaaggag atctttttcg atcagtcgaa gaacggctac   1620
gctggataca tcgacggcgg agcctctcag gaagagttct acaagttcat caagccaatt   1680
ctcgagaaga tggacggaac cgaggaactg cttgtcaagc tcaatcgaga ggatctgctt   1740
cggaagcaac gaaccttcga caacggcagc attcctcatc agatccacct cggtgagctg   1800
cacgccattc ttcgacgtca ggaagacttc taccccttttc tcaaggacaa ccgagagaag   1860
atcgagaaga ttcttacctt tcgaatcccc tactatgttg gtcctcttgc cagaggaaac   1920
tctcgatttg cttggatgac tcgaaagtcc gaggaaacca tcactccctg gaacttcgag   1980
gaagtcgtgg acaagggtgc ctctgcacag tccttcatcg agcgaatgac caacttcgac   2040
aagaatctgc ccaacgagaa ggttcttccc aagcattcgc tgctctacga gtactttaca   2100
gtctacaacg aactcaccaa agtcaagtac gttaccgagg gaatgcgaaa gcctgccttc   2160
ttgtctggcg aacagaagaa agccattgtc gatctcctgt tcaagaccaa ccgaaaggtc   2220
actgttaagc agctcaagga ggactacttc aagaaaatcg agtgtttcga cagcgtcgag   2280
atttccggag ttgaggaccg attcaacgcc tctttgggca cctatcacga tctgctcaag   2340
attatcaagg acaaggattt tctcgacaac gaggaaaacg aggacattct ggaggacatc   2400
gtgctcactc ttaccctgtt cgaagatcgg gagatgatcg aggaacgact caagacatac   2460
gctcacctgt tcgacgacaa ggtcatgaaa caactcaagc gacgtagata caccggctgg   2520
ggaagacttt cgcgaaagct catcaacggc atcagagaca agcagtccgg aaagaccatt   2580
ctggactttc tcaagtccga tggctttgcc aaccgaaact tcatgcagct cattcacgac   2640
gattctctta ccttcaagga ggacatccag aaggcacaag tgtccggtca gggcgacagc   2700
```

ttgcacgaac atattgccaa cctggctggt tcgccagcca tcaagaaagg cattctccag 2760
actgtcaagg ttgtcgacga gctggtgaag gtcatgggac gtcacaagcc cgagaacatt 2820
gtgatcgaga tggccagaga gaaccagaca actcaaaagg gtcagaaaaa ctcgcgagag 2880
cggatgaagc gaatcgagga aggcatcaag gagctgggat cccagattct caaggagcat 2940
cccgtcgaga acactcaact gcagaacgag aagctgtatc tctactatct gcagaatggt 3000
cgagacatgt acgtggatca ggaactggac atcaatcgtc tcagcgacta cgatgtggac 3060
cacattgtcc ctcaatcctt tctcaaggac gattctatcg acaacaaggt ccttacacga 3120
tccgacaaga acagaggcaa gtcggacaac gttcccagcg aagaggtggt caaaaagatg 3180
aagaactact ggcgacagct gctcaacgcc aagctcatta cccagcgaaa gttcgacaat 3240
cttaccaagg ccgagcgagg cggtctgtcc gagctcgaca aggctggctt catcaagcgt 3300
caactcgtcg agaccagaca gatcacaaag cacgtcgcac agattctcga ttctcggatg 3360
aacaccaagt acgacgagaa cgacaagctc atccgagagg tcaaggtgat tactctcaag 3420
tccaaactgg tctccgattt ccgaaaggac tttcagttct acaaggtgcg agagatcaac 3480
aattaccacc atgcccacga tgcttacctc aacgccgtcg ttggcactgc gctcatcaag 3540
aaatacccca agctcgaaag cgagttcgtt tacggcgatt acaaggtcta cgacgttcga 3600
aagatgattg ccaagtccga acaggagatt ggcaaggcta ctgccaagta cttcttttac 3660
tccaacatca tgaacttttt caagaccgag atcaccttgg ccaacggaga gattcgaaag 3720
agaccactta tcgagaccaa cggcgaaact ggagagatcg tgtgggacaa gggtcgagac 3780
tttgcaaccg tgcgaaaggt tctgtcgatg cctcaggtca acatcgtcaa gaaaaccgag 3840
gttcagactg gcggattctc caaggagtcg attctgccca agcgaaactc cgacaagctc 3900
atcgctcgaa agaaagactg ggatcccaag aaatacggtg gcttcgattc tcctaccgtc 3960
gcctattccg tgcttgtcgt tgcgaaggtc gagaagggca agtccaaaaa gctcaagtcc 4020
gtcaaggagc tgctcggaat taccatcatg gagcgatcga gcttcgagaa gaatcccatc 4080
gacttcttgg aagccaaggg ttacaaggag gtcaagaaag acctcattat caagctgccc 4140
aagtactctc tgttcgaact ggagaacggt cgaaagcgta tgctcgcctc cgctggcgag 4200
ctgcagaagg gaaacgagct tgccttgcct tcgaagtacg tcaactttct ctatctggct 4260
tctcactacg agaagctcaa gggttctccc gaggacaacg aacagaagca actcttcgtt 4320
gagcagcaca aacattacct cgacgagatt atcgagcaga tttccgagtt ttcgaagcga 4380
gtcatcctgg ctgatgccaa cttggacaag gtgctctctg cctacaacaa gcatcgggac 4440
aaacccattc gagaacaggc ggagaacatc attcacctgt ttactcttac caacctgggt 4500
gctcctgcag ctttcaagta cttcgatacc actatcgacc gaaagcggta cacatccacc 4560
aaggaggttc tcgatgccac cctgattcac cagtccatca ctggcctgta cgagacccga 4620
atcgacctgt ctcagcttgg tggcgactcc agagccgatc ccaagaaaaa gcgaaaggtc 4680
taa 4683

<210> SEQ ID NO 77
<211> LENGTH: 10706
<212> TYPE: DNA
<213> ORGANISM: Artificial sequence
<220> FEATURE:
<223> OTHER INFORMATION: plasmid pZufCas9

<400> SEQUENCE: 77

-continued

```
catggacaag aaatactcca tcggcctgga cattggaacc aactctgtcg gctgggctgt     60
catcaccgac gagtacaagg tgccctccaa gaaattcaag gtcctcggaa acaccgatcg    120
acactccatc aagaaaaacc tcattggtgc cctgttgttc gattctggcg agactgccga    180
agctaccaga ctcaagcgaa ctgctcggcg acgttacacc cgacggaaga accgaatctg    240
ctacctgcag gagatctttt ccaacgagat ggccaaggtg gacgattcgt tctttcatcg    300
actggaggaa tccttcctcg tcgaggaaga caagaaacac gagcgtcatc ccatctttgg    360
caacattgtg gacgaggttg cttaccacga gaagtatcct accatctacc acctgcgaaa    420
gaaactcgtc gattccaccg acaaggcgga tctcagactt atctacctcg ctctggcaca    480
catgatcaag tttcgaggtc atttcctcat cgagggcgat ctcaatcccg acaacagcga    540
tgtggacaag ctgttcattc agctcgttca gacctacaac cagctgttcg aggaaaaccc    600
catcaatgcc tccggagtcg atgcaaaggc catcttgtct gctcgactct cgaagagcag    660
acgactggag aacctcattg cccaacttcc tggcgagaaa aagaacggac tgtttggcaa    720
cctcattgcc ctttctcttg gtctcacacc caacttcaag tccaacttcg atctggcgga    780
ggacgccaag ctccagctgt ccaaggacac ctacgacgat gacctcgaca acctgcttgc    840
acagattggc gatcagtacg ccgacctgtt tctcgctgcc aagaaccttt cggatgctat    900
tctcttgtct gacattctgc gagtcaacac cgagatcaca aaggctcccc tttctgcctc    960
catgatcaag cgatacgacg agcaccatca ggatctcaca ctgctcaagg ctcttgtccg   1020
acagcaactg cccgagaagt acaaggagat ctttttcgat cagtcgaaga acggctacgc   1080
tggatacatc gacggcggag cctctcagga agagttctac aagttcatca agccaattct   1140
cgagaagatg gacggaaccg aggaactgct tgtcaagctc aatcgagagg atctgcttcg   1200
gaagcaacga accttcgaca acggcagcat tcctcatcag atccacctcg gtgagctgca   1260
cgccattctt cgacgtcagg aagacttcta cccctttctc aaggacaacc gagagaagat   1320
cgagaagatt cttacctttc gaatccccta ctatgttggt cctcttgcca gaggaaactc   1380
tcgatttgct tggatgactc gaaagtccga ggaaaccatc actccctgga acttcgagga   1440
agtcgtggac aagggtgcct ctgcacagtc cttcatcgag cgaatgacca acttcgacaa   1500
gaatctgccc aacgagaagg ttcttcccaa gcattcgctg ctctacgagt actttacagt   1560
ctacaacgaa ctcaccaaag tcaagtacgt taccgaggga atgcgaaagc ctgccttctt   1620
gtctggcgaa cagaagaaag ccattgtcga tctcctgttc aagaccaacc gaaaggtcac   1680
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
```

```
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
```

-continued

```
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
```

-continued

```
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aattttttgc ttaaattcaa tcccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatttcg acagtaatta attaagtcat acacaagtca gctttcttcg   8700
agcctcatat aagtataagt agttcaacgt attagcactg tacccagcat ctccgtatcg   8760
agaaacacaa caacatgccc cattggacag atcatgcgga tacacaggtt gtgcagtatc   8820
atacatactc gatcagacag gtcgtctgac catcatacaa gctgaacaag cgctccatac   8880
ttgcacgctc tctatataca cagttaaatt acatatccat agtctaacct ctaacagtta   8940
atcttctggt aagcctccca gccagccttc tggtatcgct tggcctcctc aataggatct   9000
cggttctggc cgtacagacc tcggccgaca attatgatat ccgttccggt agacatgaca   9060
tcctcaacag ttcggtactg ctgtccgaga gcgtctccct tgtcgtcaag acccaccccg   9120
ggggtcagaa taagccagtc ctcagagtcg ccccttaggtc ggttctgggc aatgaagcca   9180
accacaaact cggggtcgga tcgggcaagc tcaatggtct gcttggagta ctcgccagtg   9240
gccagagagc ccttgcaaga cagctcggcc agcatgagca gacctctggc cagcttctcg   9300
ttgggagagg ggactaggaa ctccttgtac tgggagttct cgtagtcaga gacgtcctcc   9360
ttcttctgtt cagagacagt ttcctcggca ccagctcgca ggccagcaat gattccggtt   9420
ccgggtacac cgtgggcgtt ggtgatatcg gaccactcgg cgattcggtg acaccggtac   9480
```

```
tggtgcttga cagtgttgcc aatatctgcg aactttctgt cctcgaacag gaagaaaccg   9540

tgcttaagag caagttcctt gaggggggagc acagtgccgg cgtaggtgaa gtcgtcaatg   9600

atgtcgatat gggttttgat catgcacaca taaggtccga ccttatcggc aagctcaatg   9660

agctccttgg tggtggtaac atccagagaa gcacacaggt tggttttctt ggctgccacg   9720

agcttgagca ctcgagcggc aaaggcggac ttgtggacgt tagctcgagc ttcgtaggag   9780

ggcattttgg tggtgaagag gagactgaaa taaatttagt ctgcagaact ttttatcgga   9840

accttatctg gggcagtgaa gtatatgtta tggtaatagt tacgagttag ttgaacttat   9900

agatagactg gactatacgg ctatcggtcc aaattagaaa gaacgtcaat ggctctctgg   9960

gcgtcgcctt tgccgacaaa aatgtgatca tgatgaaagc cagcaatgac gttgcagctg  10020

atattgttgt cggccaaccg cgccgaaaac gcagctgtca gacccacagc ctccaacgaa  10080

gaatgtatcg tcaaagtgat ccaagcacac tcatagttgg agtcgtactc caaaggcggc  10140

aatgacgagt cagacagata ctcgtcgacg tttaaaccat catctaaggg cctcaaaact  10200

acctcggaac tgctgcgctg atctggacac cacagaggtt ccgagcactt taggttgcac  10260

caaatgtccc accaggtgca ggcagaaaac gctggaacag cgtgtacagt ttgtcttaac  10320

aaaaagtgag ggcgctgagg tcgagcaggg tggtgtgact tgttatagcc tttagagctg  10380

cgaaagcgcg tatggatttg gctcatcagg ccagattgag ggtctgtgga cacatgtcat  10440

gttagtgtac ttcaatcgcc ccctggatat agccccgaca ataggccgtg gcctcatttt  10500

tttgccttcc gcacatttcc attgctcggt acccacacct tgcttctcct gcacttgcca  10560

accttaatac tggtttacat tgaccaacat cttacaagcg gggggcttgt ctagggtata  10620

tataaacagt ggctctccca atcggttgcc agtctctttt ttcctttctt tccccacaga  10680

ttcgaaatct aaactacaca tcacac                                        10706
```

<210> SEQ ID NO 78
<211> LENGTH: 4144
<212> TYPE: DNA
<213> ORGANISM: Artificial sequence
<220> FEATURE:
<223> OTHER INFORMATION: Cas9-SV40 fusion

<400> SEQUENCE: 78

```
acaagaaata ctccatcggc ctggacattg gaaccaactc tgtcggctgg gctgtcatca     60

ccgacgagta caaggtgccc tccaagaaat tcaaggtcct cggaaacacc gatcgacact    120

ccatcaagaa aaacctcatt ggtgccctgt tgttcgattc tggcgagact gccgaagcta    180

ccagactcaa gcgaactgct cggcgacgtt acacccgacg gaagaaccga atctgctacc    240

tgcaggagat cttttccaac gagatggcca aggtggacga ttcgttcttt catcgactgg    300

aggaatcctt cctcgtcgag gaagacaaga aacacgagcg tcatcccatc tttggcaaca    360

ttgtggacga ggttgcttac cacgagaagt atcctaccat ctaccacctg cgaaagaaac    420

tcgtcgattc caccgacaag gcggatctca gacttatcta cctcgctctg gcacacatga    480

tcaagtttcg aggtcatttc ctcatcgagg gcgatctcaa tcccgacaac agcgatgtgg    540

acaagctgtt cattcagctc gttcagacct acaaccagct gttcgaggaa aaccccatca    600

atgcctccgg agtcgatgca aaggccatct tgtctgctcg actctcgaag agcagacgac    660

tggagaacct cattgcccaa cttcctggcg agaaaaagaa cggactgttt ggcaacctca    720

ttgccctttc tcttggtctc acacccaact tcaagtccaa cttcgatctg gcggaggacg    780

ccaagctcca gctgtccaag gacacctacg acgatgacct cgacaacctg cttgcacaga    840
```

-continued

```
ttggcgatca gtacgccgac ctgtttctcg ctgccaagaa cctttcggat gctattctct    900
tgtctgacat tctgcgagtc aacaccgaga tcacaaaggc tcccctttct gcctccatga    960
tcaagcgata cgacgagcac catcaggatc tcacactgct caaggctctt gtccgacagc   1020
aactgcccga gaagtacaag gagatctttt tcgatcagtc gaagaacggc tacgctggat   1080
acatcgacgg cggagcctct caggaagagt tctacaagtt catcaagcca attctcgaga   1140
agatggacgg aaccgaggaa ctgcttgtca agctcaatcg agaggatctg cttcggaagc   1200
aacgaacctt cgacaacggc agcattcctc atcagatcca cctcggtgag ctgcacgcca   1260
ttcttcgacg tcaggaagac ttctacccct ttctcaagga caaccgagag aagatcgaga   1320
agattcttac ctttcgaatc ccctactatg ttggtcctct tgccagagga aactctcgat   1380
ttgcttggat gactcgaaag tccgaggaaa ccatcactcc ctggaacttc gaggaagtcg   1440
tggacaaggg tgcctctgca cagtccttca tcgagcgaat gaccaacttc gacaagaatc   1500
tgcccaacga gaaggttctt cccaagcatt cgctgctcta cgagtacttt acagtctaca   1560
acgaactcac caaagtcaag tacgttaccg agggaatgcg aaagcctgcc ttcttgtctg   1620
gcgaacagaa gaaagccatt gtcgatctcc tgttcaagac caaccgaaag gtcactgtta   1680
agcagctcaa ggaggactac ttcaagaaaa tcgagtgttt cgacagcgtc gagatttccg   1740
gagttgagga ccgattcaac gcctctttgg gcacctatca cgatctgctc aagattatca   1800
aggacaagga ttttctcgac aacgaggaaa acgaggacat tctggaggac atcgtgctca   1860
ctcttaccct gttcgaagat cgggagatga tcgaggaacg actcaagaca tacgctcacc   1920
tgttcgacga caaggtcatg aaacaactca agcgacgtag atacaccggc tggggaagac   1980
tttcgcgaaa gctcatcaac ggcatcagag acaagcagtc cggaaagacc attctggact   2040
ttctcaagtc cgatggcttt gccaaccgaa acttcatgca gctcattcac gacgattctc   2100
ttaccttcaa ggaggacatc cagaaggcac aagtgtccgg tcagggcgac agcttgcacg   2160
aacatattgc caacctggct ggttcgccag ccatcaagaa aggcattctc cagactgtca   2220
aggttgtcga cgagctggtg aaggtcatgg gacgtcacaa gcccgagaac attgtgatcg   2280
agatggccag agagaaccag acaactcaaa agggtcagaa aaactcgcga gagcggatga   2340
agcgaatcga ggaaggcatc aaggagctgg gatcccagat tctcaaggag catcccgtcg   2400
agaacactca actgcagaac gagaagctgt atctctacta tctgcagaat ggtcgagaca   2460
tgtacgtgga tcaggaactg gacatcaatc gtctcagcga ctacgatgtg gaccacattg   2520
tccctcaatc ctttctcaag gacgattcta tcgacaacaa ggtccttaca cgatccgaca   2580
agaacagagg caagtcggac aacgttccca gcgaagaggt ggtcaaaaag atgaagaact   2640
actggcgaca gctgctcaac gccaagctca ttacccagcg aaagttcgac aatcttacca   2700
aggccgagcg aggcggtctg tccgagctcg acaaggctgg cttcatcaag cgtcaactcg   2760
tcgagaccag acagatcaca aagcacgtcg cacagattct cgattctcgg atgaacacca   2820
agtacgacga gaacgacaag ctcatccgag aggtcaaggt gattactctc aagtccaaac   2880
tggtctccga tttccgaaag gactttcagt tctacaaggt gcgagagatc aacaattacc   2940
accatgccca cgatgcttac ctcaacgccg tcgttggcac tgcgctcatc aagaaatacc   3000
ccaagctcga aagcgagttc gtttacggcg attacaaggt ctacgacgtt cgaaagatga   3060
ttgccaagtc cgaacaggag attggcaagg ctactgccaa gtacttcttt tactccaaca   3120
tcatgaactt tttcaagacc gagatcacct tggccaacgg agagattcga aagagaccac   3180
```

ttatcgagac caacggcgaa actggagaga tcgtgtggga caagggtcga gactttgcaa 3240
ccgtgcgaaa ggttctgtcg atgcctcagg tcaacatcgt caagaaaacc gaggttcaga 3300
ctggcggatt ctccaaggag tcgattctgc ccaagcgaaa ctccgacaag ctcatcgctc 3360
gaaagaaaga ctgggatccc aagaaatacg gtggcttcga ttctcctacc gtcgcctatt 3420
ccgtgcttgt cgttgcgaag gtcgagaagg gcaagtccaa aaagctcaag tccgtcaagg 3480
agctgctcgg aattaccatc atggagcgat cgagcttcga gaagaatccc atcgacttct 3540
tggaagccaa gggttacaag gaggtcaaga aagacctcat tatcaagctg cccaagtact 3600
ctctgttcga actggagaac ggtcgaaagc gtatgctcgc ctccgctggc gagctgcaga 3660
agggaaacga gcttgccttg ccttcgaagt acgtcaactt tctctatctg gcttctcact 3720
acgagaagct caagggttct cccgaggaca acgaacagaa gcaactcttc gttgagcagc 3780
acaaacatta cctcgacgag attatcgagc agatttccga gttttcgaag cgagtcatcc 3840
tggctgatgc caacttggac aaggtgctct ctgcctacaa caagcatcgg gacaaaccca 3900
ttcgagaaca ggcggagaac atcattcacc tgtttactct taccaacctg ggtgctcctg 3960
cagctttcaa gtacttcgat accactatcg accgaaagcg gtacacatcc accaaggagg 4020
ttctcgatgc caccctgatt caccagtcca tcactggcct gtacgagacc cgaatcgacc 4080
tgtctcagct tggtggcgac tccagagccg atcccaagaa aaagcgaaag gtctaagcgg 4140
ccgc 4144

<210> SEQ ID NO 79
<211> LENGTH: 35
<212> TYPE: DNA
<213> ORGANISM: Artificial sequence
<220> FEATURE:
<223> OTHER INFORMATION: Cas9-SV40 forward primer

<400> SEQUENCE: 79
gggggaattc gacaagaaat actccatcgg cctgg 35

<210> SEQ ID NO 80
<211> LENGTH: 31
<212> TYPE: DNA
<213> ORGANISM: Artificial sequence
<220> FEATURE:
<223> OTHER INFORMATION: Cas9-SV40 reverse primer

<400> SEQUENCE: 80
ccccaagctt agcggccgct tagacctttc g 31

<210> SEQ ID NO 81
<211> LENGTH: 4166
<212> TYPE: DNA
<213> ORGANISM: Artificial sequence
<220> FEATURE:
<223> OTHER INFORMATION: Cas9-SV40 PCR product

<400> SEQUENCE: 81
gggggaattc gacaagaaat actccatcgg cctggacatt ggaaccaact ctgtcggctg 60
ggctgtcatc accgacgagt acaaggtgcc ctccaagaaa ttcaaggtcc tcggaaacac 120
cgatcgacac tccatcaaga aaaacctcat tggtgccctg ttgttcgatt ctggcgagac 180
tgccgaagct accagactca agcgaactgc tcggcgacgt tacacccgac ggaagaaccg 240
aatctgctac ctgcaggaga tcttttccaa cgagatggcc aaggtggacg attcgttctt 300
tcatcgactg gaggaatcct tcctcgtcga ggaagacaag aaacacgagc gtcatcccat 360

-continued

```
ctttggcaac attgtggacg aggttgctta ccacgagaag tatcctacca tctaccacct    420
gcgaaagaaa ctcgtcgatt ccaccgacaa ggcggatctc agacttatct acctcgctct    480
ggcacacatg atcaagtttc gaggtcattt cctcatcgag ggcgatctca atcccgacaa    540
cagcgatgtg gacaagctgt tcattcagct cgttcagacc tacaaccagc tgttcgagga    600
aaaccccatc aatgcctccg gagtcgatgc aaaggccatc ttgtctgctc gactctcgaa    660
gagcagacga ctggagaacc tcattgccca acttcctggc gagaaaaaga acggactgtt    720
tggcaacctc attgcccttt ctcttggtct cacacccaac ttcaagtcca acttcgatct    780
ggcggaggac gccaagctcc agctgtccaa ggacacctac gacgatgacc tcgacaacct    840
gcttgcacag attggcgatc agtacgccga cctgtttctc gctgccaaga acctttcgga    900
tgctattctc ttgtctgaca ttctgcgagt caacaccgag atcacaaagg ctcccctttc    960
tgcctccatg atcaagcgat acgacgagca ccatcaggat ctcacactgc tcaaggctct   1020
tgtccgacag caactgcccg agaagtacaa ggagatcttt ttcgatcagt cgaagaacgg   1080
ctacgctgga tacatcgacg gcggagcctc tcaggaagag ttctacaagt tcatcaagcc   1140
aattctcgag aagatggacg gaaccgagga actgcttgtc aagctcaatc gagaggatct   1200
gcttcggaag caacgaacct tcgacaacgg cagcattcct catcagatcc acctcggtga   1260
gctgcacgcc attcttcgac gtcaggaaga cttctacccc tttctcaagg acaaccgaga   1320
gaagatcgag aagattctta cctttcgaat cccctactat gttggtcctc ttgccagagg   1380
aaactctcga tttgcttgga tgactcgaaa gtccgaggaa accatcactc cctggaactt   1440
cgaggaagtc gtggacaagg gtgcctctgc acagtccttc atcgagcgaa tgaccaactt   1500
cgacaagaat ctgcccaacg agaaggttct tcccaagcat tcgctgctct acgagtactt   1560
tacagtctac aacgaactca ccaaagtcaa gtacgttacc gagggaatgc gaaagcctgc   1620
cttcttgtct ggcgaacaga agaaagccat tgtcgatctc ctgttcaaga ccaaccgaaa   1680
ggtcactgtt aagcagctca aggaggacta cttcaagaaa atcgagtgtt tcgacagcgt   1740
cgagatttcc ggagttgagg accgattcaa cgcctctttg ggcacctatc acgatctgct   1800
caagattatc aaggacaagg attttctcga caacgaggaa aacgaggaca ttctggagga   1860
catcgtgctc actcttaccc tgttcgaaga tcgggagatg atcgaggaac gactcaagac   1920
atacgctcac ctgttcgacg acaaggtcat gaaacaactc aagcgacgta gatacaccgg   1980
ctggggaaga ctttcgcgaa agctcatcaa cggcatcaga gacaagcagt ccggaaagac   2040
cattctggac tttctcaagt ccgatggctt tgccaaccga aacttcatgc agctcattca   2100
cgacgattct cttaccttca aggaggacat ccagaaggca caagtgtccg gtcagggcga   2160
cagcttgcac gaacatattg ccaacctggc tggttcgcca gccatcaaga aaggcattct   2220
ccagactgtc aaggttgtcg acgagctggt gaaggtcatg ggacgtcaca agcccgagaa   2280
cattgtgatc gagatggcca gagagaacca gacaactcaa aagggtcaga aaaactcgcg   2340
agagcggatg aagcgaatcg aggaaggcat caaggagctg ggatcccaga ttctcaagga   2400
gcatcccgtc gagaacactc aactgcagaa cgagaagctg tatctctact atctgcagaa   2460
tggtcgagac atgtacgtgg atcaggaact ggacatcaat cgtctcagcg actacgatgt   2520
ggaccacatt gtccctcaat cctttctcaa ggacgattct atcgacaaca aggtccttac   2580
acgatccgac aagaacagag gcaagtcgga caacgttccc agcgaagagg tggtcaaaaa   2640
gatgaagaac tactggcgac agctgctcaa cgccaagctc attacccagc gaaagttcga   2700
```

```
caatcttacc aaggccgagc gaggcggtct gtccgagctc gacaaggctg gcttcatcaa   2760

gcgtcaactc gtcgagacca gacagatcac aaagcacgtc gcacagattc tcgattctcg   2820

gatgaacacc aagtacgacg agaacgacaa gctcatccga gaggtcaagg tgattactct   2880

caagtccaaa ctggtctccg atttccgaaa ggactttcag ttctacaagg tgcgagagat   2940

caacaattac caccatgccc acgatgctta cctcaacgcc gtcgttggca ctgcgctcat   3000

caagaaatac cccaagctcg aaagcgagtt cgtttacggc gattacaagg tctacgacgt   3060

tcgaaagatg attgccaagt ccgaacagga gattggcaag gctactgcca agtacttctt   3120

ttactccaac atcatgaact tttcaagac cgagatcacc ttggccaacg gagagattcg   3180

aaagagacca cttatcgaga ccaacggcga aactggagag atcgtgtggg acaagggtcg   3240

agactttgca accgtgcgaa aggttctgtc gatgcctcag gtcaacatcg tcaagaaaac   3300

cgaggttcag actggcggat tctccaagga gtcgattctg cccaagcgaa actccgacaa   3360

gctcatcgct cgaaagaaag actgggatcc caagaaatac ggtggcttcg attctcctac   3420

cgtcgcctat tccgtgcttg tcgttgcgaa ggtcgagaag ggcaagtcca aaaagctcaa   3480

gtccgtcaag gagctgctcg gaattaccat catggagcga tcgagcttcg agaagaatcc   3540

catcgacttc ttggaagcca agggttacaa ggaggtcaag aaagacctca ttatcaagct   3600

gcccaagtac tctctgttcg aactggagaa cggtcgaaag cgtatgctcg cctccgctgg   3660

cgagctgcag aagggaaacg agcttgcctt gccttcgaag tacgtcaact ttctctatct   3720

ggcttctcac tacgagaagc tcaagggttc tcccgaggac aacgaacaga agcaactctt   3780

cgttgagcag cacaaacatt acctcgacga gattatcgag cagatttccg agttttcgaa   3840

gcgagtcatc ctggctgatg ccaacttgga caaggtgctc tctgcctaca acaagcatcg   3900

ggacaaaccc attcgagaac aggcggagaa catcattcac ctgtttactc ttaccaacct   3960

gggtgctcct gcagctttca agtacttcga taccactatc gaccgaaagc ggtacacatc   4020

caccaaggag gttctcgatg ccaccctgat tcaccagtcc atcactggcc tgtacgagac   4080

ccgaatcgac ctgtctcagc ttggtggcga ctccagagcc gatcccaaga aaaagcgaaa   4140

ggtctaagcg gccgctaagc ttgggg                                        4166
```

<210> SEQ ID NO 82
<211> LENGTH: 4092
<212> TYPE: DNA
<213> ORGANISM: Artificial sequence
<220> FEATURE:
<223> OTHER INFORMATION: plasmid pBAD/HisB

<400> SEQUENCE: 82

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttgggc     300

taacaggagg aattaaccat gggggttct catcatcatc atcatcatgg tatggctagc     360

atgactggtg gacagcaaat gggtcgggat ctgtacgacg atgacgataa ggatccgagc    420

tcgagatctg cagctggtac catatgggaa ttcgaagctt ggctgttttg gcggatgaga    480

gaagattttc agcctgatac agattaaatc agaacgcaga agcggtctga taaaacagaa    540

tttgcctggc ggcagtagcg cggtggtccc acctgacccc atgccgaact cagaagtgaa    600
```

acgccgtagc gccgatggta gtgtggggtc tccccatgcg agagtaggga actgccaggc 660
atcaaataaa acgaaaggct cagtcgaaag actgggcctt tcgttttatc tgttgtttgt 720
cggtgaacgc tctcctgagt aggacaaatc cgccgggagc ggatttgaac gttgcgaagc 780
aacggcccgg agggtggcgg gcaggacgcc cgccataaac tgccaggcat caaattaagc 840
agaaggccat cctgacggat ggcctttttg cgtttctaca aactcttttg tttatttttc 900
taaatacatt caaatatgta tccgctcatg agacaataac cctgataaat gcttcaataa 960
tattgaaaaa ggaagagtat gagtattcaa catttccgtg tcgcccttat tccctttttt 1020
gcggcatttt gccttcctgt ttttgctcac ccagaaacgc tggtgaaagt aaaagatgct 1080
gaagatcagt tgggtgcacg agtgggttac atcgaactgg atctcaacag cggtaagatc 1140
cttgagagtt ttcgccccga agaacgtttt ccaatgatga gcacttttaa agttctgcta 1200
tgtggcgcgg tattatcccg tgttgacgcc gggcaagagc aactcggtcg ccgcatacac 1260
tattctcaga atgacttggt tgagtactca ccagtcacag aaaagcatct tacggatggc 1320
atgacagtaa gagaattatg cagtgctgcc ataaccatga gtgataacac tgcggccaac 1380
ttacttctga caacgatcgg aggaccgaag gagctaaccg cttttttgca caacatgggg 1440
gatcatgtaa ctcgccttga tcgttgggaa ccggagctga atgaagccat accaaacgac 1500
gagcgtgaca ccacgatgcc tgtagcaatg gcaacaacgt tgcgcaaact attaactggc 1560
gaactactta ctctagcttc ccggcaacaa ttaatagact ggatggaggc ggataaagtt 1620
gcaggaccac ttctgcgctc ggcccttccg gctggctggt ttattgctga taaatctgga 1680
gccggtgagc gtgggtctcg cggtatcatt gcagcactgg ggccagatgg taagccctcc 1740
cgtatcgtag ttatctacac gacggggagt caggcaacta tggatgaacg aaatagacag 1800
atcgctgaga taggtgcctc actgattaag cattggtaac tgtcagacca agtttactca 1860
tatatacttt agattgattt aaaacttcat ttttaattta aaaggatcta ggtgaagatc 1920
ctttttgata atctcatgac caaaatccct taacgtgagt tttcgttcca ctgagcgtca 1980
gaccccgtag aaaagatcaa aggatcttct tgagatcctt tttttctgcg cgtaatctgc 2040
tgcttgcaaa caaaaaaacc accgctacca gcggtggttt gtttgccgga tcaagagcta 2100
ccaactcttt ttccgaaggt aactggcttc agcagagcgc agataccaaa tactgtcctt 2160
ctagtgtagc cgtagttagg ccaccacttc aagaactctg tagcaccgcc tacatacctc 2220
gctctgctaa tcctgttacc agtggctgct gccagtggcg ataagtcgtg tcttaccggg 2280
ttggactcaa gacgatagtt accggataag gcgcagcggt cgggctgaac ggggggttcg 2340
tgcacacagc ccagcttgga gcgaacgacc tacaccgaac tgagatacct acagcgtgag 2400
ctatgagaaa gcgccacgct tcccgaaggg agaaaggcgg acaggtatcc ggtaagcggc 2460
agggtcggaa caggagagcg cacgagggag cttccagggg gaaacgcctg gtatctttat 2520
agtcctgtcg ggtttcgcca cctctgactt gagcgtcgat ttttgtgatg ctcgtcaggg 2580
gggcggagcc tatggaaaaa cgccagcaac gcggcctttt tacggttcct ggccttttgc 2640
tggccttttg ctcacatgtt ctttcctgcg ttatcccctg attctgtgga taaccgtatt 2700
accgcctttg agtgagctga taccgctcgc cgcagccgaa cgaccgagcg cagcgagtca 2760
gtgagcgagg aagcggaaga gcgcctgatg cggtattttc tccttacgca tctgtgcggt 2820
atttcacacc gcatatggtg cactctcagt acaatctgct ctgatgccgc atagttaagc 2880
cagtatacac tccgctatcg ctacgtgact gggtcatggc tgcgccccga cacccgccaa 2940
cacccgctga cgcgccctga cgggcttgtc tgctcccggc atccgcttac agacaagctg 3000
tgaccgtctc cgggagctgc atgtgtcaga ggttttcacc gtcatcaccg aaacgcgcga 3060
ggcagcagat caattcgcgc gcgaaggcga agcggcatgc ataatgtgcc tgtcaaatgg 3120
acgaagcagg gattctgcaa accctatgct actccgtcaa gccgtcaatt gtctgattcg 3180
ttaccaatta tgacaacttg acggctacat cattcacttt ttcttcacaa ccggcacgga 3240
actcgctcgg gctggccccg gtgcattttt taaatacccg cgagaaatag agttgatcgt 3300
caaaaccaac attgcgaccg acggtggcga taggcatccg ggtggtgctc aaaagcagct 3360
tcgcctggct gatacgttgg tcctcgcgcc agcttaagac gctaatccct aactgctggc 3420
ggaaaagatg tgacagacgc gacggcgaca agcaaacatg ctgtgcgacg ctggcgatat 3480
caaaattgct gtctgccagg tgatcgctga tgtactgaca agcctcgcgt acccgattat 3540
ccatcggtgg atggagcgac tcgttaatcg cttccatgcg ccgcagtaac aattgctcaa 3600
gcagatttat cgccagcagc tccgaatagc gcccttcccc ttgcccggcg ttaatgattt 3660
gcccaaacag gtcgctgaaa tgcggctggt gcgcttcatc cgggcgaaag aaccccgtat 3720
tggcaaatat tgacggccag ttaagccatt catgccagta ggcgcgcgga cgaaagtaaa 3780
cccactggtg ataccattcg cgagcctccg gatgacgacc gtagtgatga atctctcctg 3840
gcgggaacag caaaatatca cccggtcggc aaacaaattc tcgtccctga tttttcacca 3900
ccccctgacc gcgaatggtg agattgagaa tataaccttt cattcccagc ggtcggtcga 3960
taaaaaaatc gagataaccg ttggcctcaa tcggcgttaa acccgccacc agatgggcat 4020
taaacgagta tcccggcagc aggggatcat tttgcgcttc agccatactt ttcatactcc 4080
cgccattcag ag 4092

<210> SEQ ID NO 83
<211> LENGTH: 8237
<212> TYPE: DNA
<213> ORGANISM: Artificial sequence
<220> FEATURE:
<223> OTHER INFORMATION: plamsid pRF48

<400> SEQUENCE: 83
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840
cacagattgg cgatcagtac gccgacctgt ttctcgctgc caagaacctt tcggatgcta 900

```
ttctcttgtc tgacattctg cgagtcaaca ccgagatcac aaaggctccc ctttctgcct    960
ccatgatcaa gcgatacgac gagcaccatc aggatctcac actgctcaag gctcttgtcc   1020
gacagcaact gcccgagaag tacaaggaga tctttttcga tcagtcgaag aacggctacg   1080
ctggatacat cgacggcgga gcctctcagg aagagttcta caagttcatc aagccaattc   1140
tcgagaagat ggacggaacc gaggaactgc ttgtcaagct caatcgagag gatctgcttc   1200
ggaagcaacg aaccttcgac aacggcagca ttcctcatca gatccacctc ggtgagctgc   1260
acgccattct tcgacgtcag gaagacttct accccttttct caaggacaac cgagagaaga   1320
tcgagaagat tcttaccttt cgaatcccct actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca agcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca agaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca accgaaactt catgcagctc attcacgacg   2100
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaacttttc aagaccgaga tcaccttggc caacggagag attcgaaaga    3180
gaccacttat cgagaccaac ggcgaaactg gagagatcgt gtgggacaag ggtcgagact   3240
```

-continued

```
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
```

aatcccttaa cgtgagtttt cgttccactg agcgtcagac cccgtagaaa agatcaaagg 5700
atcttcttga gatccttttt ttctgcgcgt aatctgctgc ttgcaaacaa aaaaaccacc 5760
gctaccagcg gtggtttgtt tgccggatca agagctacca actctttttc cgaaggtaac 5820
tggcttcagc agagcgcaga taccaaatac tgtccttcta gtgtagccgt agttaggcca 5880
ccacttcaag aactctgtag caccgcctac atacctcgct ctgctaatcc tgttaccagt 5940
ggctgctgcc agtggcgata agtcgtgtct taccgggttg gactcaagac gatagttacc 6000
ggataaggcg cagcggtcgg gctgaacggg gggttcgtgc acacagccca gcttggagcg 6060
aacgacctac accgaactga gatacctaca gcgtgagcta tgagaaagcg ccacgcttcc 6120
cgaagggaga aaggcggaca ggtatccggt aagcggcagg gtcggaacag gagagcgcac 6180
gagggagctt ccagggggaa acgcctggta tctttatagt cctgtcgggt ttcgccacct 6240
ctgacttgag cgtcgatttt tgtgatgctc gtcagggggg cggagcctat ggaaaaacgc 6300
cagcaacgcg gcctttttac ggttcctggc cttttgctgg ccttttgctc acatgttctt 6360
tcctgcgtta tcccctgatt ctgtggataa ccgtattacc gcctttgagt gagctgatac 6420
cgctcgccgc agccgaacga ccgagcgcag cgagtcagtg agcgaggaag cggaagagcg 6480
cctgatgcgg tattttctcc ttacgcatct gtgcggtatt tcacaccgca tatggtgcac 6540
tctcagtaca atctgctctg atgccgcata gttaagccag tatacactcc gctatcgcta 6600
cgtgactggg tcatggctgc gccccgacac ccgccaacac ccgctgacgc gccctgacgg 6660
gcttgtctgc tcccggcatc cgcttacaga caagctgtga ccgtctccgg gagctgcatg 6720
tgtcagaggt tttcaccgtc atcaccgaaa cgcgcgaggc agcagatcaa ttcgcgcgcg 6780
aaggcgaagc ggcatgcata atgtgcctgt caaatggacg aagcagggat tctgcaaacc 6840
ctatgctact ccgtcaagcc gtcaattgtc tgattcgtta ccaattatga caacttgacg 6900
gctacatcat tcactttttc ttcacaaccg gcacggaact cgctcgggct ggccccggtg 6960
catttttaa atacccgcga gaaatagagt tgatcgtcaa aaccaacatt gcgaccgacg 7020
gtggcgatag gcatccgggt ggtgctcaaa agcagcttcg cctggctgat acgttggtcc 7080
tcgcgccagc ttaagacgct aatccctaac tgctggcgga aaagatgtga cagacgcgac 7140
ggcgacaagc aaacatgctg tgcgacgctg gcgatatcaa aattgctgtc tgccaggtga 7200
tcgctgatgt actgacaagc ctcgcgtacc cgattatcca tcggtggatg gagcgactcg 7260
ttaatcgctt ccatgcgccg cagtaacaat tgctcaagca gatttatcgc cagcagctcc 7320
gaatagcgcc cttccccttg cccggcgtta atgatttgcc caaacaggtc gctgaaatgc 7380
ggctggtgcg cttcatccgg gcgaaagaac cccgtattgg caaatattga cggccagtta 7440
agccattcat gccagtaggc gcgcggacga aagtaaaccc actggtgata ccattcgcga 7500
gcctccggat gacgaccgta gtgatgaatc tctcctggcg ggaacagcaa aatatcaccc 7560
ggtcggcaaa caaattctcg tccctgattt ttcaccaccc cctgaccgcg aatggtgaga 7620
ttgagaatat aacctttcat tcccagcggt cggtcgataa aaaaatcgag ataaccgttg 7680
gcctcaatcg gcgttaaacc cgccaccaga tgggcattaa acgagtatcc cggcagcagg 7740
ggatcatttt gcgcttcagc catacttttc atactcccgc cattcagaga agaaaccaat 7800
tgtccatatt gcatcagaca ttgccgtcac tgcgtctttt actggctctt ctcgctaacc 7860
aaaccggtaa ccccgcttat taaaagcatt ctgtaacaaa gcgggaccaa agccatgaca 7920
aaaacgcgta acaaaagtgt ctataatcac ggcagaaaag tccacattga ttatttgcac 7980

```
ggcgtcacac tttgctatgc catagcattt ttatccataa gattagcgga tcctacctga   8040

cgctttttat cgcaactctc tactgtttct ccatacccgt tttttgggct aacaggagga   8100

attaaccatg gggggttctc atcatcatca tcatcatggt atggctagca tgactggtgg   8160

acagcaaatg ggtcgggatc tgtacgacga tgacgataag gatccgagct cgagatctgc   8220

agctggtacc atatggg                                                   8237
```

<210> SEQ ID NO 84
<211> LENGTH: 6493
<212> TYPE: DNA
<213> ORGANISM: Artificial sequence
<220> FEATURE:
<223> OTHER INFORMATION: E.Coli Cas9 expression cassette

<400> SEQUENCE: 84

```
tgcactctca gtacaatctg ctctgatgcc gcatagttaa gccagtatac actccgctat     60

cgctacgtga ctgggtcatg gctgcgcccc gacacccgcc aacacccgct gacgcgccct    120

gacgggcttg tctgctcccg gcatccgctt acagacaagc tgtgaccgtc tccgggagct    180

gcatgtgtca gaggttttca ccgtcatcac cgaaacgcgc gaggcagcag atcaattcgc    240

gcgcgaaggc gaagcggcat gcataatgtg cctgtcaaat ggacgaagca gggattctgc    300

aaaccctatg ctactccgtc aagccgtcaa ttgtctgatt cgttaccaat tatgacaact    360

tgacggctac atcattcact ttttcttcac aaccggcacg gaactcgctc gggctggccc    420

cggtgcattt tttaaatacc cgcgagaaat agagttgatc gtcaaaacca acattgcgac    480

cgacggtggc gataggcatc cgggtggtgc tcaaaagcag cttcgcctgg ctgatacgtt    540

ggtcctcgcg ccagcttaag acgctaatcc ctaactgctg gcggaaaaga tgtgacagac    600

gcgacggcga caagcaaaca tgctgtgcga cgctggcgat atcaaaattg ctgtctgcca    660

ggtgatcgct gatgtactga caagcctcgc gtacccgatt atccatcggt ggatggagcg    720

actcgttaat cgcttccatg cgccgcagta acaattgctc aagcagattt atcgccagca    780

gctccgaata gcgcccttcc ccttgcccgg cgttaatgat ttgcccaaac aggtcgctga    840

aatgcggctg gtgcgcttca tccgggcgaa agaaccccgt attggcaaat attgacggcc    900

agttaagcca ttcatgccag taggcgcgcg gacgaaagta aacccactgg tgataccatt    960

cgcgagcctc cggatgacga ccgtagtgat gaatctctcc tggcgggaac agcaaaatat   1020

cacccggtcg gcaaacaaat tctcgtccct gatttttcac cacccctga ccgcgaatgg   1080

tgagattgag aatataacct ttcattccca gcggtcggtc gataaaaaaa tcgagataac   1140

cgttggcctc aatcggcgtt aaacccgcca ccagatgggc attaaacgag tatcccggca   1200

gcaggggatc attttgcgct tcagccatac ttttcatact cccgccattc agagaagaaa   1260

ccaattgtcc atattgcatc agacattgcc gtcactgcgt cttttactgg ctcttctcgc   1320

taaccaaacc ggtaaccccg cttattaaaa gcattctgta acaaagcggg accaaagcca   1380

tgacaaaaac gcgtaacaaa agtgtctata atcacggcag aaaagtccac attgattatt   1440

tgcacggcgt cacactttgc tatgccatag catttttatc cataagatta gcggatccta   1500

cctgacgctt tttatcgcaa ctctctactg tttctccata cccgtttttt gggctaacag   1560

gaggaattaa ccatgggggg ttctcatcat catcatcatc atggtatggc tagcatgact   1620

ggtggacagc aaatgggtcg ggatctgtac gacgatgacg ataaggatcc gagctcgaga   1680

tctgcagctg gtaccatatg ggaattcgac aagaaatact ccatcggcct ggacattgga   1740

accaactctg tcggctgggc tgtcatcacc gacgagtaca aggtgccctc caagaaattc   1800
```

-continued

```
aaggtcctcg gaaacaccga tcgacactcc atcaagaaaa acctcattgg tgccctgttg   1860
ttcgattctg gcgagactgc cgaagctacc agactcaagc gaactgctcg gcgacgttac   1920
acccgacgga agaaccgaat ctgctacctg caggagatct tttccaacga gatggccaag   1980
gtggacgatt cgttctttca tcgactggag gaatccttcc tcgtcgagga agacaagaaa   2040
cacgagcgtc atcccatctt tggcaacatt gtggacgagg ttgcttacca cgagaagtat   2100
cctaccatct accacctgcg aaagaaactc gtcgattcca ccgacaaggc ggatctcaga   2160
cttatctacc tcgctctggc acacatgatc aagtttcgag gtcatttcct catcgagggc   2220
gatctcaatc ccgacaacag cgatgtggac aagctgttca ttcagctcgt tcagacctac   2280
aaccagctgt tcgaggaaaa ccccatcaat gcctccggag tcgatgcaaa ggccatcttg   2340
tctgctcgac tctcgaagag cagacgactg gagaacctca ttgcccaact tcctggcgag   2400
aaaaagaacg gactgtttgg caacctcatt gccctttctc ttggtctcac acccaacttc   2460
aagtccaact tcgatctggc ggaggacgcc aagctccagc tgtccaagga cacctacgac   2520
gatgacctcg acaacctgct tgcacagatt ggcgatcagt acgccgacct gtttctcgct   2580
gccaagaacc tttcggatgc tattctcttg tctgacattc tgcgagtcaa caccgagatc   2640
acaaaggctc ccctttctgc ctccatgatc aagcgatacg acgagcacca tcaggatctc   2700
acactgctca aggctcttgt ccgacagcaa ctgcccgaga agtacaagga gatctttttc   2760
gatcagtcga agaacggcta cgctggatac atcgacggcg gagcctctca ggaagagttc   2820
tacaagttca tcaagccaat tctcgagaag atggacggaa ccgaggaact gcttgtcaag   2880
ctcaatcgag aggatctgct tcggaagcaa cgaaccttcg acaacggcag cattcctcat   2940
cagatccacc tcggtgagct gcacgccatt cttcgacgtc aggaagactt ctaccccttt   3000
ctcaaggaca accgagagaa gatcgagaag attcttacct ttcgaatccc ctactatgtt   3060
ggtcctcttg ccagaggaaa ctctcgattt gcttggatga ctcgaaagtc cgaggaaacc   3120
atcactccct ggaacttcga ggaagtcgtg gacaagggtg cctctgcaca gtccttcatc   3180
gagcgaatga ccaacttcga caagaatctg cccaacgaga aggttcttcc caagcattcg   3240
ctgctctacg agtactttac agtctacaac gaactcacca aagtcaagta cgttaccgag   3300
ggaatgcgaa agcctgcctt cttgtctggc gaacagaaga aagccattgt cgatctcctg   3360
ttcaagacca accgaaaggt cactgttaag cagctcaagg aggactactt caagaaaatc   3420
gagtgtttcg acagcgtcga gatttccgga gttgaggacc gattcaacgc ctctttgggc   3480
acctatcacg atctgctcaa gattatcaag gacaaggatt ttctcgacaa cgaggaaaac   3540
gaggacattc tggaggacat cgtgctcact cttaccctgt tcgaagatcg ggagatgatc   3600
gaggaacgac tcaagacata cgctcacctg ttcgacgaca aggtcatgaa acaactcaag   3660
cgacgtagat acaccggctg gggaagactt tcgcgaaagc tcatcaacgg catcagagac   3720
aagcagtccg gaaagaccat tctggacttt ctcaagtccg atggctttgc caaccgaaac   3780
ttcatgcagc tcattcacga cgattctctt accttcaagg aggacatcca gaaggcacaa   3840
gtgtccggtc agggcgacag cttgcacgaa catattgcca acctggctgg ttcgccagcc   3900
atcaagaaag gcattctcca gactgtcaag gttgtcgacg agctggtgaa ggtcatggga   3960
cgtcacaagc ccgagaacat tgtgatcgag atggccagag agaaccagac aactcaaaag   4020
ggtcagaaaa actcgcgaga gcggatgaag cgaatcgagg aaggcatcaa ggagctggga   4080
tcccagattc tcaaggagca tcccgtcgag aacactcaac tgcagaacga gaagctgtat   4140
```

```
ctctactatc tgcagaatgg tcgagacatg tacgtggatc aggaactgga catcaatcgt   4200
ctcagcgact acgatgtgga ccacattgtc cctcaatcct ttctcaagga cgattctatc   4260
gacaacaagg tccttacacg atccgacaag aacagaggca agtcggacaa cgttcccagc   4320
gaagaggtgg tcaaaaagat gaagaactac tggcgacagc tgctcaacgc caagctcatt   4380
acccagcgaa agttcgacaa tcttaccaag gccgagcgag gcggtctgtc cgagctcgac   4440
aaggctggct tcatcaagcg tcaactcgtc gagaccagac agatcacaaa gcacgtcgca   4500
cagattctcg attctcggat gaacaccaag tacgacgaga acgacaagct catccgagag   4560
gtcaaggtga ttactctcaa gtccaaactg gtctccgatt tccgaaagga ctttcagttc   4620
tacaaggtgc gagagatcaa caattaccac catgcccacg atgcttacct caacgccgtc   4680
gttggcactg cgctcatcaa gaaatacccc aagctcgaaa gcgagttcgt ttacggcgat   4740
tacaaggtct acgacgttcg aaagatgatt gccaagtccg aacaggagat tggcaaggct   4800
actgccaagt acttctttta ctccaacatc atgaactttt tcaagaccga gatcaccttg   4860
gccaacggag agattcgaaa gagaccactt atcgagacca acggcgaaac tggagagatc   4920
gtgtgggaca agggtcgaga ctttgcaacc gtgcgaaagg ttctgtcgat gcctcaggtc   4980
aacatcgtca agaaaaccga ggttcagact ggcggattct ccaaggagtc gattctgccc   5040
aagcgaaact ccgacaagct catcgctcga aagaaagact gggatcccaa gaaatacggt   5100
ggcttcgatt ctcctaccgt cgcctattcc gtgcttgtcg ttgcgaaggt cgagaagggc   5160
aagtccaaaa agctcaagtc cgtcaaggag ctgctcggaa ttaccatcat ggagcgatcg   5220
agcttcgaga agaatcccat cgacttcttg gaagccaagg gttacaagga ggtcaagaaa   5280
gacctcatta tcaagctgcc caagtactct ctgttcgaac tggagaacgg tcgaaagcgt   5340
atgctcgcct ccgctggcga gctgcagaag ggaaacgagc ttgccttgcc ttcgaagtac   5400
gtcaactttc tctatctggc ttctcactac gagaagctca agggttctcc cgaggacaac   5460
gaacagaagc aactcttcgt tgagcagcac aaacattacc tcgacgagat tatcgagcag   5520
atttccgagt tttcgaagcg agtcatcctg gctgatgcca acttggacaa ggtgctctct   5580
gcctacaaca agcatcggga caaacccatt cgagaacagg cggagaacat cattcacctg   5640
tttactctta ccaacctggg tgctcctgca gctttcaagt acttcgatac cactatcgac   5700
cgaaagcggt acacatccac caaggaggtt ctcgatgcca ccctgattca ccagtccatc   5760
actggcctgt acgagacccg aatcgacctg tctcagcttg gtggcgactc cagagccgat   5820
cccaagaaaa agcgaaaggt ctaagcggcc gctaagcttg gctgttttgg cggatgagag   5880
aagattttca gcctgataca gattaaatca gaacgcagaa gcggtctgat aaaacagaat   5940
ttgcctggcg gcagtagcgc ggtggtccca cctgacccca tgccgaactc agaagtgaaa   6000
cgccgtagcg ccgatggtag tgtggggtct ccccatgcga gagtagggaa ctgccaggca   6060
tcaaataaaa cgaaaggctc agtcgaaaga ctgggccttt cgttttatct gttgtttgtc   6120
ggtgaacgct ctcctgagta ggacaaatcc gccgggagcg gatttgaacg ttgcgaagca   6180
acggcccgga gggtggcggg caggacgccc gccataaact gccaggcatc aaattaagca   6240
gaaggccatc ctgacggatg gcctttttgc gtttctacaa actcttttgt ttatttttct   6300
aaatacattc aaatatgtat ccgctcatga gacaataacc ctgataaatg cttcaataat   6360
attgaaaaag gaagagtatg agtattcaac atttccgtgt cgcccttatt cccttttttg   6420
cggcattttg ccttcctgtt tttgctcacc cagaaacgct ggtgaaagta aaagatgctg   6480
aagatcagtt ggg                                                      6493
```

<210> SEQ ID NO 85
<211> LENGTH: 5681
<212> TYPE: DNA
<213> ORGANISM: Artificial sequence
<220> FEATURE:
<223> OTHER INFORMATION: plasmid pKO3
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1109)..(1109)
<223> OTHER INFORMATION: n is a, c, g, or t
<220> FEATURE:
<221> NAME/KEY: misc_feature
<222> LOCATION: (1661)..(1662)
<223> OTHER INFORMATION: n is a, c, g, or t
<220> FEATURE:
<221> NAME/KEY: misc_feature
<222> LOCATION: (1665)..(1665)
<223> OTHER INFORMATION: n is a, c, g, or t
<220> FEATURE:
<221> NAME/KEY: misc_feature
<222> LOCATION: (3573)..(3574)
<223> OTHER INFORMATION: n is a, c, g, or t
<220> FEATURE:
<221> NAME/KEY: misc_feature
<222> LOCATION: (5648)..(5648)
<223> OTHER INFORMATION: n is a, c, g, or t

<400> SEQUENCE: 85

```
ccctttcgtc ttcgaataaa tacctgtgac ggaagatcac ttcgcagaat aaataaatcc     60

tggtgtccct gttgataccg ggaagccctg ggccaacttt tggcgaaaat gagacgttga    120

tcggcacgta agaggttcca actttcacca taatgaaata agatcactac cgggcgtatt    180

ttttgagtta tcgagatttt caggagctaa ggaagctaaa atggagaaaa aaatcactgg    240

atataccacc gttgatatat cccaatggca tcgtaaagaa cattttgagg catttcagtc    300

agttgctcaa tgtacctata accagaccgt tcagctggat attacggcct ttttaaagac    360

cgtaaagaaa aataagcaca agttttatcc ggcctttatt cacattcttg cccgcctgat    420

gaatgctcat ccggaattcc gtatggcaat gaaagacggt gagctggtga tatgggatag    480

tgttcaccct tgttacaccg ttttccatga gcaaactgaa acgttttcat cgctctggag    540

tgaataccac gacgatttcc ggcagtttct acacatatat tcgcaagatg tggcgtgtta    600

cggtgaaaac ctggcctatt tccctaaagg gtttattgag aatatgtttt tcgtctcagc    660

caatccctgg gtgagtttca ccagttttga tttaaacgtg gccaatatgg acaacttctt    720

cgcccccgtt ttcaccatgg gcaaatatta tacgcaaggc gacaaggtgc tgatgccgct    780

ggcgattcag gttcatcatg ccgtttgtga tggcttccat gtcggcagaa tgcttaatga    840

attacaacag tactgcgatg agtggcaggg cggggcgtaa tttttttaag gcagttattg    900

gtgcccttaa acgcctggtg ctacgcctga ataagtgata ataagcggat gaatggcaga    960

aattcgaaag caaattcgac ccggtcgtcg gttcagggca gggtcgttaa atagccgctt   1020

atgtctattg ctggtttant cggtacccgg ggatcgcggc cgcggaccgg atcctctaga   1080

gcggccgcga tcctctagag tcgaccggng aatggcgaat gggacgcgcc ctgtagcggc   1140

gcattaagcg cggcgggtgt ggtggttacg cgcagcgtga ccgctacact tgccagcgcc   1200

ctagcgcccg ctcctttcgc tttcttccct tcctttctcg ccacgttcgc cggctttccc   1260

cgtcaagctc taaatcgggg gctcccttta gggttccgat ttagtgcttt acggcacctc   1320
```

-continued

```
gaccccaaaa aacttgatta gggtgatggt tcacgtagtg ggccatcgcc ctgatagacg   1380
gtttttcgcc ctttgacgtt ggagtccacg ttctttaata gtggactctt gttccaaact   1440
ggaacaacac tcaaccctat ctcggtctat tcttttgatt tataagggat tttgccgatt   1500
tcggcctatt ggttaaaaaa tgagctgatt taacaaaaat ttaacgcgaa ttttaacaaa   1560
atattaacgc ttacaattta ggtggcactt ttcggggaaa tgtgcgcgga acccctattt   1620
gtttattttt ctaaatacat tcaaatatgt atccgctcat nncangatcc tttttaaccc   1680
atcacatata cctgccgttc actattattt agtgaaatga gatattatga tattttctga   1740
attgtgatta aaaaggcaac tttatgccca tgcaacagaa actataaaaa atacagagaa   1800
tgaaaagaaa cagatagatt ttttagttct ttaggcccgt agtctgcaaa tccttttatg   1860
attttctatc aaacaaaaga ggaaaataga ccagttgcaa tccaaacgag agtctaatag   1920
aatgaggtcg aaaagtaaat cgcgcgggtt tgttactgat aaagcaggca agacctaaaa   1980
tgtgtaaagg gcaaagtgta tactttggcg tcacccctta catattttag gtcttttttt   2040
attgtgcgta actaacttgc catcttcaaa caggagggct ggaagaagca gaccgctaac   2100
acagtacata aaaaaggaga catgaacgat gaacatcaaa aagtttgcaa aacaagcaac   2160
agtattaacc tttactaccg cactgctggc aggaggcgca actcaagcgt ttgcgaaaga   2220
aacgaaccaa aagccatata aggaaacata cggcatttcc catattacac gccatgatat   2280
gctgcaaatc cctgaacagc aaaaaaatga aaaatatcaa gttcctgaat tcgattcgtc   2340
cacaattaaa aatatctctt ctgcaaaagg cctggacgtt tgggacagct ggccattaca   2400
aaacgctgac ggcactgtcg caaactatca cggctaccac atcgtctttg cattagccgg   2460
agatcctaaa aatgcggatg acacatcgat ttacatgttc tatcaaaaag tcggcgaaac   2520
ttctattgac agctggaaaa acgctggccg cgtctttaaa gacagcgaca aattcgatgc   2580
aaatgattct atcctaaaag accaaacaca agaatggtca ggttcagcca catttacatc   2640
tgacggaaaa atccgtttat tctacactga tttctccggt aaacattacg gcaaacaaac   2700
actgacaact gcacaagtta acgtatcagc atcagacagc tctttgaaca tcaacggtgt   2760
agaggattat aaatcaatct ttgacggtga cggaaaaacg tatcaaaatg tacagcagtt   2820
catcgatgaa ggcaactaca gctcaggcga caaccatacg ctgagagatc ctcactacgt   2880
agaagataaa ggccacaaat acttagtatt tgaagcaaac actggaactg aagatggcta   2940
ccaaggcgaa gaatctttat ttaacaaagc atactatggc aaaagcacat cattcttccg   3000
tcaagaaagt caaaaacttc tgcaaagcga taaaaaacgc acggctgagt tagcaaacgg   3060
cgctctcggt atgattgagc taaacgatga ttacacactg aaaaaagtga tgaaaccgct   3120
gattgcatct aacacagtaa cagatgaaat tgaacgcgcg aacgtcttta aaatgaacgg   3180
caaatggtac ctgttcactg actcccgcgg atcaaaaatg acgattgacg gcattacgtc   3240
taacgatatt tacatgcttg gttatgtttc taattcttta actggcccat acaagccgct   3300
gaacaaaact ggccttgtgt taaaaatgga tcttgatcct aacgatgtaa cctttactta   3360
ctcacacttc gctgtacctc aagcgaaagg aaacaatgtc gtgattacaa gctatatgac   3420
aaacagagga ttctacgcag acaaacaatc aacgtttgcg ccaagcttcc tgctgaacat   3480
caaaggcaag aaaacatctg ttgtcaaaga cagcatcctt gaacaaggac aattaacagt   3540
taacaaataa aaacgcaaaa gaaaatgccg atnnccggtt tattgactac cggaagcagt   3600
gtgaccgtgt gcttctcaaa tgcctcaggc tgtctatgtg tgactgttga gctgtaacaa   3660
gttgtctcag gtgttcaatt tcatgttcta gttgctttgt tttactggtt tcacctgttc   3720
```

```
tattaggtgt tacatgctgt tcatctgtta cattgtcgat ctgttcatgg tgaacagctt   3780

taaatgcacc aaaaactcgt aaaagctctg atgtatctat ctttttttaca ccgttttcat   3840

ctgtgcatat ggacagtttt ccctttgata tctaacggtg aacagttgtt ctacttttgt   3900

ttgttagtct tgatgcttca ctgatagata caagagccat aagaacctca gatccttccg   3960

tatttagcca gtatgttctc tagtgtggtt cgttgttttt gcgtgagcca tgagaacgaa   4020

ccattgagat catgcttact ttgcatgtca ctcaaaaatt ttgcctcaaa actggtgagc   4080

tgaatttttg cagttaaagc atcgtgtagt gtttttctta gtccgttacg taggtaggaa   4140

tctgatgtaa tggttgttgg tattttgtca ccattcattt ttatctggtt gttctcaagt   4200

tcggttacga gatccatttg tctatctagt tcaacttgga aaatcaacgt atcagtcggg   4260

cggcctcgct tatcaaccac caatttcata ttgctgtaag tgtttaaatc tttacttatt   4320

ggtttcaaaa cccattggtt aagcctttta aactcatggt agttattttc aagcattaac   4380

atgaacttaa attcatcaag gctaatctct atatttgcct tgtgagtttt cttttgtgtt   4440

agttctttta ataaccactc ataaatcctc atagagtatt tgttttcaaa agacttaaca   4500

tgttccagat tatattttat gaattttttt aactggaaaa gataaggcaa tatctcttca   4560

ctaaaaacta attctaattt ttcgcttgag aacttggcat agtttgtcca ctggaaaatc   4620

tcaaagcctt taaccaaagg attcctgatt tccacagttc tcgtcatcag ctctctggtt   4680

gctttagcta atacaccata agcattttcc ctactgatgt tcatcatctg agcgtattgg   4740

ttataagtga acgataccgt ccgttctttc cttgtagggt tttcaatcgt ggggttgagt   4800

agtgccacac agcataaaat tagcttggtt tcatgctccg ttaagtcata gcgactaatc   4860

gctagttcat ttgctttgaa aacaactaat tcagacatac atctcaattg gtctaggtga   4920

ttttaatcac tataccaatt gagatgggct agtcaatgat aattactagt ccttttcctt   4980

tgagttgtgg gtatctgtaa attctgctag acctttgctg gaaaacttgt aaattctgct   5040

agaccctctg taaattccgc tagacctttg tgtgtttttt ttgtttatat tcaagtggtt   5100

ataatttata gaataaagaa agaataaaaa aagataaaaa gaatagatcc cagccctgtg   5160

tataactcac tactttagtc agttccgcag tattacaaaa ggatgtcgca aacgctgttt   5220

gctcctctac aaaacagacc ttaaaaccct aaaggcttaa gtagcaccct cgcaagctcg   5280

ggcaaatcgc tgaatattcc ttttgtctcc gaccatcagg cacctgagtc gctgtctttt   5340

tcgtgacatt cagttcgctg cgctcacggc tctggcagtg aatgggggta aatggcacta   5400

caggcgcctt ttatggattc atgcaaggaa actacccata atacaagaaa agcccgtcac   5460

gggcttctca gggcgtttta tggcgggtct gctatgtggt gctatctgac tttttgctgt   5520

tcagcagttc ctgccctctg attttccagt ctgaccactt cggattatcc cgtgacaggt   5580

cattcagact ggctaatgca cccagtaagg cagcggtatc atcaacaggc ttacccgtct   5640

tactgtcngg atcgacgctc tcccttatgc gactcctgca t                      5681
```

<210> SEQ ID NO 86
<211> LENGTH: 12166
<212> TYPE: DNA
<213> ORGANISM: Artificial sequence
<220> FEATURE:
<223> OTHER INFORMATION: plasmid pRF97

<400> SEQUENCE: 86

```
ccctttcgtc ttcgaataaa tacctgtgac ggaagatcac ttcgcagaat aaataaatcc     60
```

-continued

```
tggtgtccct gttgataccg ggaagccctg ggccaacttt tggcgaaaat gagacgttga    120
tcggcacgta agaggttcca actttcacca taatgaaata agatcactac cgggcgtatt    180
ttttgagtta tcgagatttt caggagctaa ggaagctaaa atggagaaaa aaatcactgg    240
atataccacc gttgatatat cccaatggca tcgtaaagaa cattttgagg catttcagtc    300
agttgctcaa tgtacctata accagaccgt tcagctggat attacggcct ttttaaagac    360
cgtaaagaaa aataagcaca agttttatcc ggcctttatt cacattcttg cccgcctgat    420
gaatgctcat ccggaattcc gtatggcaat gaaagacggt gagctggtga tatgggatag    480
tgttcaccct tgttacaccg ttttccatga gcaaactgaa acgttttcat cgctctggag    540
tgaataccac gacgatttcc ggcagtttct acacatatat tcgcaagatg tggcgtgtta    600
cggtgaaaac ctggcctatt tccctaaagg gtttattgag aatatgtttt tcgtctcagc    660
caatccctgg gtgagtttca ccagttttga tttaaacgtg gccaatatgg acaacttctt    720
cgcccccgtt ttcaccatgg gcaaatatta tacgcaaggc gacaaggtgc tgatgccgct    780
ggcgattcag gttcatcatg ccgtttgtga tggcttccat gtcggcagaa tgcttaatga    840
attacaacag tactgcgatg agtggcaggg cggggcgtaa tttttttaag gcagttattg    900
gtgcccttaa acgcctggtg ctacgcctga ataagtgata ataagcggat gaatggcaga    960
aattcgaaag caaattcgac ccggtcgtcg gttcagggca gggtcgttaa atagccgctt   1020
atgtctattg ctggtttatc ggtacccccc aactgatctt cagcatcttt tactttcacc   1080
agcgtttctg ggtgagcaaa aacaggaagg caaaatgccg caaaaaaggg aataagggcg   1140
acacggaaat gttgaatact catactcttc ctttttcaat attattgaag catttatcag   1200
ggttattgtc tcatgagcgg atacatattt gaatgtattt agaaaaataa acaaaagagt   1260
ttgtagaaac gcaaaaaggc catccgtcag gatggccttc tgcttaattt gatgcctggc   1320
agtttatggc gggcgtcctg cccgccaccc tccgggccgt tgcttcgcaa cgttcaaatc   1380
cgctcccggc ggatttgtcc tactcaggag agcgttcacc gacaaacaac agataaaacg   1440
aaaggcccag tctttcgact gagcctttcg ttttatttga tgcctggcag ttccctactc   1500
tcgcatgggg agaccccaca ctaccatcgg cgctacggcg tttcacttct gagttcggca   1560
tggggtcagg tgggaccacc gcgctactgc cgccaggcaa attctgtttt atcagaccgc   1620
ttctgcgttc tgatttaatc tgtatcaggc tgaaaatctt ctctcatccg ccaaaacagc   1680
caagcttagc ggccgcttag acctttcgct tttcttgggg atcggctctg gagtcgccac   1740
caagctgaga caggtcgatt cggtctcgt acaggccagt gatggactgg tgaatcaggg    1800
tggcatcgag aacctccttg gtggatgtgt accgctttcg gtcgatagtg gtatcgaagt   1860
acttgaaagc tgcaggagca cccaggttgg taagagtaaa caggtgaatg atgttctccg   1920
cctgttctcg aatgggtttg tcccgatgct tgttgtaggc agagagcacc ttgtccaagt   1980
tggcatcagc caggatgact cgcttcgaaa actcggaaat ctgctcgata atctcgtcga   2040
ggtaatgttt gtgctgctca acgaagagtt gcttctgttc gttgtcctcg ggagaaccct   2100
tgagcttctc gtagtgagaa gccagataga gaaagttgac gtacttcgaa ggcaaggcaa   2160
gctcgtttcc cttctgcagc tcgccagcgg aggcgagcat acgctttcga ccgttctcca   2220
gttcgaacag agagtacttg ggcagcttga taatgaggtc tttcttgacc tccttgtaac   2280
ccttggcttc caagaagtcg atgggattct tctcgaagct cgatcgctcc atgatggtaa   2340
ttccgagcag ctccttgacg gacttgagct ttttggactt gcccttctcg accttcgcaa   2400
cgacaagcac ggaataggcg acggtaggag aatcgaagcc accgtatttc ttgggatccc   2460
```

```
agtctttctt tcgagcgatg agcttgtcgg agtttcgctt gggcagaatc gactccttgg   2520
agaatccgcc agtctgaacc tcggttttct tgacgatgtt gacctgaggc atcgacagaa   2580
cctttcgcac ggttgcaaag tctcgaccct tgtcccacac gatctctcca gtttcgccgt   2640
tggtctcgat aagtggtctc tttcgaatct ctccgttggc caaggtgatc tcggtcttga   2700
aaaagttcat gatgttggag taaaagaagt acttggcagt agccttgcca atctcctgtt   2760
cggacttggc aatcatcttt cgaacgtcgt agaccttgta atcgccgtaa acgaactcgc   2820
tttcgagctt ggggtatttc ttgatgagcg cagtgccaac gacggcgttg aggtaagcat   2880
cgtgggcatg gtggtaattg ttgatctctc gcaccttgta gaactgaaag tcctttcgga   2940
aatcggagac cagtttggac ttgagagtaa tcaccttgac ctctcggatg agcttgtcgt   3000
tctcgtcgta cttggtgttc atccgagaat cgagaatctg tgcgacgtgc tttgtgatct   3060
gtctggtctc gacgagttga cgcttgatga agccagcctt gtcgagctcg gacagaccgc   3120
ctcgctcggc cttggtaaga ttgtcgaact ttcgctgggt aatgagcttg gcgttgagca   3180
gctgtcgcca gtagttcttc atctttttga ccacctcttc gctgggaacg ttgtccgact   3240
tgcctctgtt cttgtcggat cgtgtaagga ccttgttgtc gatagaatcg tccttgagaa   3300
aggattgagg gacaatgtgg tccacatcgt agtcgctgag acgattgatg tccagttcct   3360
gatccacgta catgtctcga ccattctgca gatagtagag atacagcttc tcgttctgca   3420
gttgagtgtt ctcgacggga tgctccttga gaatctggga tcccagctcc ttgatgcctt   3480
cctcgattcg cttcatccgc tctcgcgagt tttctgacc cttttgagtt gtctggttct   3540
ctctggccat ctcgatcaca atgttctcgg gcttgtgacg tcccatgacc ttcaccagct   3600
cgtcgacaac cttgacagtc tggagaatgc ctttcttgat ggctggcgaa ccagccaggt   3660
tggcaatatg ttcgtgcaag ctgtcgccct gaccggacac ttgtgccttc tggatgtcct   3720
ccttgaaggt aagagaatcg tcgtgaatga gctgcatgaa gtttcggttg gcaaagccat   3780
cggacttgag aaagtccaga atggtctttc cggactgctt gtctctgatg ccgttgatga   3840
gctttcgcga aagtcttccc cagccggtgt atctacgtcg cttgagttgt ttcatgacct   3900
tgtcgtcgaa caggtgagcg tatgtcttga gtcgttcctc gatcatctcc cgatcttcga   3960
acagggtaag agtgagcacg atgtcctcca gaatgtcctc gttttcctcg ttgtcgagaa   4020
aatccttgtc cttgataatc ttgagcagat cgtgataggt gcccaaagag gcgttgaatc   4080
ggtcctcaac tccggaaatc tcgacgctgt cgaaacactc gattttcttg aagtagtcct   4140
ccttgagctg cttaacagtg acctttcggt tggtcttgaa caggagatcg acaatggctt   4200
tcttctgttc gccagacaag aaggcaggct ttcgcattcc ctcggtaacg tacttgactt   4260
tggtgagttc gttgtagact gtaaagtact cgtagagcag cgaatgcttg ggaagaacct   4320
tctcgttggg cagattcttg tcgaagttgg tcattcgctc gatgaaggac tgtgcagagg   4380
caccccttgtc cacgacttcc tcgaagttcc agggagtgat ggtttcctcg gactttcgag   4440
tcatccaagc aaatcgagag tttcctctgg caagaggacc aacatagtag gggattcgaa   4500
aggtaagaat cttctcgatc ttctctcggt tgtccttgag aaaggggtag aagtcttcct   4560
gacgtcgaag aatggcgtgc agctcaccga ggtggatctg atgaggaatg ctgccgttgt   4620
cgaaggttcg ttgcttccga agcagatcct ctcgattgag cttgacaagc agttcctcgg   4680
ttccgtccat cttctcgaga attggcttga tgaacttgta gaactcttcc tgagaggctc   4740
cgccgtcgat gtatccagcg tagccgttct tcgactgatc gaaaaagatc tccttgtact   4800
```

-continued tctcgggcag ttgctgtcgg acaagagcct tgagcagtgt gagatcctga tggtgctcgt 4860
cgtatcgctt gatcatggag gcagaaaggg gagcctttgt gatctcggtg ttgactcgca 4920
gaatgtcaga caagagaata gcatccgaaa ggttcttggc agcgagaaac aggtcggcgt 4980
actgatcgcc aatctgtgca agcaggttgt cgaggtcatc gtcgtaggtg tccttggaca 5040
gctggagctt ggcgtcctcc gccagatcga agttggactt gaagttgggt gtgagaccaa 5100
gagaaagggc aatgaggttg ccaaacagtc cgttcttttt ctcgccagga agttgggcaa 5160
tgaggttctc cagtcgtctg ctcttcgaga gtcgagcaga caagatggcc tttgcatcga 5220
ctccggaggc attgatgggg ttttcctcga acagctggtt gtaggtctga acgagctgaa 5280
tgaacagctt gtccacatcg ctgttgtcgg gattgagatc gccctcgatg aggaaatgac 5340
ctcgaaactt gatcatgtgt gccagagcga ggtagataag tctgagatcc gccttgtcgg 5400
tggaatcgac gagtttcttt cgcaggtggt agatggtagg atacttctcg tggtaagcaa 5460
cctcgtccac aatgttgcca aagatgggat gacgctcgtg tttcttgtct tcctcgacga 5520
ggaaggattc ctccagtcga tgaaagaacg aatcgtccac cttggccatc tcgttggaaa 5580
agatctcctg caggtagcag attcggttct tccgtcgggt gtaacgtcgc cgagcagttc 5640
gcttgagtct ggtagcttcg gcagtctcgc cagaatcgaa caacagggca ccaatgaggt 5700
ttttcttgat ggagtgtcga tcggtgtttc cgaggacctt gaatttcttg gagggcacct 5760
tgtactcgtc ggtgatgaca gcccagccga cagagttggt tccaatgtcc aggccgatgg 5820
agtatttctt gtcgaattcc catatggtac cagctgcaga tctcgagctc ggatccttat 5880
cgtcatcgtc gtacagatcc cgacccattt gctgtccacc agtcatgcta gccataccat 5940
gatgatgatg atgatgagaa ccccccatgg ttaattcctc ctgttagccc aaaaaacggg 6000
tatggagaaa cagtagagag ttgcgataaa aagcgtcagg taggatccgc taatcttatg 6060
gataaaaatg ctatggcata gcaaagtgtg acgccgtgca aataatcaat gtggactttt 6120
ctgccgtgat tatagacact tttgttacgc gtttttgtca tggctttggt cccgctttgt 6180
tacagaatgc ttttaataag cggggttacc ggtttggtta gcgagaagag ccagtaaaag 6240
acgcagtgac ggcaatgtct gatgcaatat ggacaattgg tttcttctct gaatggcggg 6300
agtatgaaaa gtatggctga agcgcaaaat gatcccctgc tgccgggata ctcgtttaat 6360
gcccatctgg tggcgggttt aacgccgatt gaggccaacg gttatctcga ttttttttatc 6420 gaccgaccgc tgggaatgaa aggttatatt ctcaatctca ccattcgcgg tcagggggtg 6480
gtgaaaaatc agggacgaga atttgtttgc cgaccgggtg atattttgct gttcccgcca 6540
ggagagattc atcactacgg tcgtcatccg gaggctcgcg aatggtatca ccagtgggtt 6600
tactttcgtc cgcgcgccta ctggcatgaa tggcttaact ggccgtcaat atttgccaat 6660
acggggttct ttcgcccgga tgaagcgcac cagccgcatt tcagcgacct gtttgggcaa 6720
atcattaacg ccgggcaagg ggaagggcgc tattcggagc tgctggcgat aaatctgctt 6780
gagcaattgt tactgcggcg catggaagcg attaacgagt cgctccatcc accgatggat 6840
aatcgggtac gcgaggcttg tcagtacatc agcgatcacc tggcagacag caattttgat 6900
atcgccagcg tcgcacagca tgtttgcttg tcgccgtcgc gtctgtcaca tcttttccgc 6960
cagcagttag ggattagcgt cttaagctgg cgcgaggacc aacgtatcag ccaggcgaag 7020
ctgcttttga gcaccacccg gatgcctatc gccaccgtcg gtcgcaatgt tggttttgac 7080
gatcaactct atttctcgcg ggtatttaaa aaatgcaccg gggccagccc gagcgagttc 7140
cgtgccggtt gtgaagaaaa agtgaatgat gtagccgtca agttgtcata attggtaacg 7200

```
aatcagacaa ttgacggctt gacggagtag catagggttt gcagaatccc tgcttcgtcc   7260
atttgacagg cacattatgc atgccgcttc gccttcgcgc gcgaattgat ctgctgcctc   7320
gcgcgtttcg gtgatgacgg tgaaaacctc tgacacatgc agctcccgga gacggtcaca   7380
gcttgtctgt aagcggatgc cgggagcaga caagcccgtc agggcgcgtc agcgggtgtt   7440
ggcgggtgtc ggggcgcagc catgacccag tcacgtagcg atagcggagt gtatactggc   7500
ttaactatgc ggcatcagag cagattgtac tgagagtgca ggggatcgcg gccgcggacc   7560
ggatcctcta gagcggccgc gatcctctag agtcgaccgg gaatggcgaa tgggacgcgc   7620
cctgtagcgg cgcattaagc gcggcgggtg tggtggttac gcgcagcgtg accgctacac   7680
ttgccagcgc cctagcgccc gctcctttcg ctttcttccc ttcctttctc gccacgttcg   7740
ccggctttcc ccgtcaagct ctaaatcggg ggctcccttt agggttccga tttagtgctt   7800
tacggcacct cgaccccaaa aaacttgatt agggtgatgg ttcacgtagt gggccatcgc   7860
cctgatagac ggtttttcgc cctttgacgt tggagtccac gttctttaat agtggactct   7920
tgttccaaac tggaacaaca ctcaacccta tctcggtcta ttcttttgat ttataaggga   7980
ttttgccgat ttcggcctat tggttaaaaa atgagctgat ttaacaaaaa tttaacgcga   8040
attttaacaa aatattaacg cttacaattt aggtggcact tttcggggaa atgtgcgcgg   8100
aacccctatt tgtttatttt tctaaataca ttcaaatatg tatccgctca tcagatcctt   8160
tttaacccat cacatatacc tgccgttcac tattatttag tgaaatgaga tattatgata   8220
ttttctgaat tgtgattaaa aaggcaactt tatgcccatg caacagaaac tataaaaaat   8280
acagagaatg aaaagaaaca gatagatttt ttagttcttt aggcccgtag tctgcaaatc   8340
cttttatgat ttttctatcaa acaaaagagg aaaatagacc agttgcaatc caaacgagag   8400
tctaatagaa tgaggtcgaa aagtaaatcg cgcgggtttg ttactgataa agcaggcaag   8460
acctaaaatg tgtaaagggc aaagtgtata ctttggcgtc accccttaca tattttaggt   8520
ctttttttat tgtgcgtaac taacttgcca tcttcaaaca ggagggctgg aagaagcaga   8580
ccgctaacac agtacataaa aaaggagaca tgaacgatga acatcaaaaa gtttgcaaaa   8640
caagcaacag tattaacctt tactaccgca ctgctggcag gaggcgcaac tcaagcgttt   8700
gcgaaagaaa cgaaccaaaa gccatataag gaaacatacg gcatttccca tattacacgc   8760
catgatatgc tgcaaatccc tgaacagcaa aaaaatgaaa aatatcaagt tcctgaattc   8820
gattcgtcca caattaaaaa tatctcttct gcaaaaggcc tggacgtttg ggacagctgg   8880
ccattacaaa acgctgacgg cactgtcgca aactatcacg gctaccacat cgtctttgca   8940
ttagccggag atcctaaaaa tgcggatgac acatcgattt acatgttcta tcaaaaagtc   9000
ggcgaaactt ctattgacag ctggaaaaac gctggccgcg tctttaaaga cagcgacaaa   9060
ttcgatgcaa atgattctat cctaaaagac caaacacaag aatggtcagg ttcagccaca   9120
tttacatctg acggaaaaat ccgtttattc tacactgatt tctccggtaa acattacggc   9180
aaacaaacac tgacaactgc acaagttaac gtatcagcat cagacagctc tttgaacatc   9240
aacggtgtag aggattataa atcaatcttt gacggtgacg gaaaaacgta tcaaaatgta   9300
cagcagttca tcgatgaagg caactacagc tcaggcgaca accatacgct gagagatcct   9360
cactacgtag aagataaagg ccacaaatac ttagtatttg aagcaaacac tggaactgaa   9420
gatggctacc aaggcgaaga atctttattt aacaaagcat actatggcaa aagcacatca   9480
ttcttccgtc aagaaagtca aaaacttctg caaagcgata aaaaacgcac ggctgagtta   9540
```

-continued

```
gcaaacggcg ctctcggtat gattgagcta aacgatgatt acacactgaa aaaagtgatg   9600
aaaccgctga ttgcatctaa cacagtaaca gatgaaattg aacgcgcgaa cgtctttaaa   9660
atgaacggca aatggtacct gttcactgac tcccgcggat caaaaatgac gattgacggc   9720
attacgtcta acgatattta catgcttggt tatgtttcta attctttaac tggcccatac   9780
aagccgctga acaaaactgg ccttgtgtta aaaatggatc ttgatcctaa cgatgtaacc   9840
tttacttact cacacttcgc tgtacctcaa gcgaaaggaa acaatgtcgt gattacaagc   9900
tatatgacaa acagaggatt ctacgcagac aaacaatcaa cgtttgcgcc aagcttcctg   9960
ctgaacatca aaggcaagaa aacatctgtt gtcaaagaca gcatccttga acaaggacaa  10020
ttaacagtta acaaataaaa acgcaaaaga aaatgccgat ccggtttatt gactaccgga  10080
agcagtgtga ccgtgtgctt ctcaaatgcc tcaggctgtc tatgtgtgac tgttgagctg  10140
taacaagttg tctcaggtgt tcaatttcat gttctagttg ctttgtttta ctggtttcac  10200
ctgttctatt aggtgttaca tgctgttcat ctgttacatt gtcgatctgt tcatggtgaa  10260
cagctttaaa tgcaccaaaa actcgtaaaa gctctgatgt atctatcttt tttacaccgt  10320
tttcatctgt gcatatggac agttttccct ttgatatcta acggtgaaca gttgttctac  10380
ttttgtttgt tagtcttgat gcttcactga tagatacaag agccataaga acctcagatc  10440
cttccgtatt tagccagtat gttctctagt gtggttcgtt gtttttgcgt gagccatgag  10500
aacgaaccat tgagatcatg cttactttgc atgtcactca aaaattttgc ctcaaaactg  10560
gtgagctgaa tttttgcagt taaagcatcg tgtagtgttt ttcttagtcc gttacgtagg  10620
taggaatctg atgtaatggt tgttggtatt ttgtcaccat tcatttttat ctggttgttc  10680
tcaagttcgg ttacgagatc catttgtcta tctagttcaa cttggaaaat caacgtatca  10740
gtcgggcggc ctcgcttatc aaccaccaat ttcatattgc tgtaagtgtt taaatcttta  10800
cttattggtt tcaaaaccca ttggttaagc cttttaaact catggtagtt attttcaagc  10860
attaacatga acttaaattc atcaaggcta atctctatat ttgccttgtg agttttcttt  10920
tgtgttagtt cttttaataa ccactcataa atcctcatag agtatttgtt ttcaaaagac  10980
ttaacatgtt ccagattata ttttatgaat ttttttaact ggaaaagata aggcaatatc  11040
tcttcactaa aaactaattc taatttttcg cttgagaact tggcatagtt tgtccactgg  11100
aaaatctcaa agcctttaac caaaggattc ctgatttcca cagttctcgt catcagctct  11160
ctggttgctt tagctaatac accataagca ttttccctac tgatgttcat catctgagcg  11220
tattggttat aagtgaacga taccgtccgt tctttccttg tagggttttc aatcgtgggg  11280
ttgagtagtg ccacacagca taaaattagc ttggtttcat gctccgttaa gtcatagcga  11340
ctaatcgcta gttcatttgc tttgaaaaca actaattcag acatacatct caattggtct  11400
aggtgatttt aatcactata ccaattgaga tgggctagtc aatgataatt actagtcctt  11460
ttcctttgag ttgtgggtat ctgtaaattc tgctagacct ttgctggaaa acttgtaaat  11520
tctgctagac cctctgtaaa ttccgctaga cctttgtgtg ttttttttgt ttatattcaa  11580
gtggttataa tttatagaat aaagaaagaa taaaaaaaga taaaaagaat agatcccagc  11640
cctgtgtata actcactact ttagtcagtt ccgcagtatt acaaaaggat gtcgcaaacg  11700
ctgtttgctc ctctacaaaa cagaccttaa aaccctaaag gcttaagtag caccctcgca  11760
agctcgggca aatcgctgaa tattcctttt gtctccgacc atcaggcacc tgagtcgctg  11820
tctttttcgt gacattcagt tcgctgcgct cacggctctg gcagtgaatg ggggtaaatg  11880
gcactacagg cgccttttat ggattcatgc aaggaaacta cccataatac aagaaaagcc  11940
```

cgtcacgggc ttctcagggc gttttatggc gggtctgcta tgtggtgcta tctgactttt 12000
tgctgttcag cagttcctgc cctctgattt tccagtctga ccacttcgga ttatcccgtg 12060
acaggtcatt cagactggct aatgcaccca gtaaggcagc ggtatcatca acaggcttac 12120
ccgtcttact gtcggatcga cgctctccct tatgcgactc ctgcat 12166

<210> SEQ ID NO 87
<211> LENGTH: 410
<212> TYPE: DNA
<213> ORGANISM: Artificial sequence
<220> FEATURE:
<223> OTHER INFORMATION: Y155H encoding synthetic fragment

<400> SEQUENCE: 87
ctccagtcgt ctgctcttcg agagtcgagc agacaagatg gcctttgcat cgactccgga 60
ggcattgatg gggttttcct cgaacagctg gttgtaggtc tgaacgagct gaatgaacag 120
cttgtccaca tcgctgttgt cgggattgag atcgccctcg atgaggaaat gacctcgaaa 180
cttgatcatg tgtgccagag cgagatggat aagtctgaga tccgccttgt cggtggaatc 240
gacgagtttc tttcgcaggt ggtagatggt aggatacttc tcgtggtaag caacctcgtc 300
cacaatgttg ccaaagatgg gatgacgctc gtgtttcttg tcttcctcga cgaggaagga 360
ttcctccagt cgatgaaaga acgaatcgtc caccttggcc atctcgttgg 410

<210> SEQ ID NO 88
<211> LENGTH: 20
<212> TYPE: DNA
<213> ORGANISM: Artificial sequence
<220> FEATURE:
<223> OTHER INFORMATION: Y155H synthetic fragment forward primer

<400> SEQUENCE: 88
ccaacgagat ggccaaggtg 20

<210> SEQ ID NO 89
<211> LENGTH: 20
<212> TYPE: DNA
<213> ORGANISM: Artificial sequence
<220> FEATURE:
<223> OTHER INFORMATION: Y155H synthetic fragment reverse primer

<400> SEQUENCE: 89
ccaacgagat ggccaaggtg 20

<210> SEQ ID NO 90
<211> LENGTH: 11794
<212> TYPE: DNA
<213> ORGANISM: Artificial sequence
<220> FEATURE:
<223> OTHER INFORMATION: pRF97-Y155H fragment of plasmid

<400> SEQUENCE: 90
caccttggcc atctcgttgg aaaagatctc ctgcaggtag cagattcggt tcttccgtcg 60
ggtgtaacgt cgccgagcag ttcgcttgag tctggtagct tcggcagtct cgccagaatc 120
gaacaacagg gcaccaatga ggtttttctt gatggagtgt cgatcggtgt ttccgaggac 180
cttgaatttc ttggagggca ccttgtactc gtcggtgatg acagcccagc cgacagagtt 240
ggttccaatg tccaggccga tggagtattt cttgtcgaat tcccatatgg taccagctgc 300
agatctcgag ctcggatcct tatcgtcatc gtcgtacaga tcccgaccca tttgctgtcc 360

-continued

```
accagtcatg ctagccatac catgatgatg atgatgatga gaacccccca tggttaattc    420
ctcctgttag cccaaaaaac gggtatggag aaacagtaga gagttgcgat aaaaagcgtc    480
aggtaggatc cgctaatctt atggataaaa atgctatggc atagcaaagt gtgacgccgt    540
gcaaataatc aatgtggact ttctgccgt gattatagac acttttgtta cgcgtttttg    600
tcatggcttt ggtcccgctt tgttacagaa tgcttttaat aagcggggtt accggtttgg    660
ttagcgagaa gagccagtaa aagacgcagt gacggcaatg tctgatgcaa tatggacaat    720
tggtttcttc tctgaatggc gggagtatga aaagtatggc tgaagcgcaa aatgatcccc    780
tgctgccggg atactcgttt aatgcccatc tggtggcggg tttaacgccg attgaggcca    840
acggttatct cgattttttt atcgaccgac cgctgggaat gaaaggttat attctcaatc    900
tcaccattcg cggtcagggg gtggtgaaaa atcagggacg agaatttgtt tgccgaccgg    960
gtgatatttt gctgttcccg ccaggagaga ttcatcacta cggtcgtcat ccggaggctc   1020
gcgaatggta tcaccagtgg gtttactttc gtccgcgcgc ctactggcat gaatggctta   1080
actggccgtc aatatttgcc aatacggggt tctttcgccc ggatgaagcg caccagccgc   1140
atttcagcga cctgtttggg caaatcatta acgccgggca aggggaaggg cgctattcgg   1200
agctgctggc gataaatctg cttgagcaat tgttactgcg gcgcatggaa gcgattaacg   1260
agtcgctcca tccaccgatg gataatcggg tacgcgaggc ttgtcagtac atcagcgatc   1320
acctggcaga cagcaatttt gatatcgcca gcgtcgcaca gcatgtttgc ttgtcgccgt   1380
cgcgtctgtc acatcttttc cgccagcagt tagggattag cgtcttaagc tggcgcgagg   1440
accaacgtat cagccaggcg aagctgcttt tgagcaccac ccggatgcct atcgccaccg   1500
tcggtcgcaa tgttggtttt gacgatcaac tctatttctc gcgggtattt aaaaaatgca   1560
ccggggccag cccgagcgag ttccgtgccg gttgtgaaga aaaagtgaat gatgtagccg   1620
tcaagttgtc ataattggta acgaatcaga caattgacgg cttgacggag tagcataggg   1680
tttgcagaat ccctgcttcg tccatttgac aggcacatta tgcatgccgc ttcgccttcg   1740
cgcgcgaatt gatctgctgc ctcgcgcgtt tcggtgatga cggtgaaaac ctctgacaca   1800
tgcagctccc ggagacggtc acagcttgtc tgtaagcgga tgccgggagc agacaagccc   1860
gtcagggcgc gtcagcgggt gttggcgggt gtcggggcgc agccatgacc cagtcacgta   1920
gcgatagcgg agtgtatact ggcttaacta tgcggcatca gagcagattg tactgagagt   1980
gcaggggatc gcggccgcgg accggatcct ctagagcggc cgcgatcctc tagagtcgac   2040
cggtggcgaa tgggacgcgc cctgtagcgg cgcattaagc gcggcgggtg tggtggttac   2100
gcgcagcgtg accgctacac ttgccagcgc cctagcgccc gctcctttcg ctttcttccc   2160
ttcctttctc gccacgttcg ccggctttcc ccgtcaagct ctaaatcggg ggctcccttt   2220
agggttccga tttagtgctt tacggcacct cgaccccaaa aaacttgatt agggtgatgg   2280
ttcacgtagt gggccatcgc cctgatagac ggtttttcgc cctttgacgt tggagtccac   2340
gttctttaat agtggactct tgttccaaac tggaacaaca ctcaacccta tctcggtcta   2400
ttcttttgat ttataaggga ttttgccgat ttcggcctat tggttaaaaa atgagctgat   2460
ttaacaaaaa tttaacgcga attttaacaa aatattaacg cttacaattt aggtggcact   2520
tttcggggaa atgtgcgcgg aacccctatt tgtttatttt tctaaataca ttcaaatatg   2580
tatccgctca ccgcgatcct ttttaaccca tcacatatac ctgccgttca ctattattta   2640
gtgaaatgag atattatgat attttctgaa ttgtgattaa aaaggcaact ttatgcccat   2700
gcaacagaaa ctataaaaaa tacagagaat gaaaagaaac agatagattt tttagttctt   2760
```

taggcccgta gtctgcaaat ccttttatga ttttctatca aacaaaagag gaaaatagac 2820
cagttgcaat ccaaacgaga gtctaataga atgaggtcga aaagtaaatc gcgcgggttt 2880
gttactgata aagcaggcaa gacctaaaat gtgtaaaggg caaagtgtat actttggcgt 2940
cacccccttac atattttagg tcttttttta ttgtgcgtaa ctaacttgcc atcttcaaac 3000
aggagggctg gaagaagcag accgctaaca cagtacataa aaaaggagac atgaacgatg 3060
aacatcaaaa agtttgcaaa acaagcaaca gtattaacct ttactaccgc actgctggca 3120
ggaggcgcaa ctcaagcgtt tgcgaaagaa acgaaccaaa agccatataa ggaaacatac 3180
ggcatttccc atattacacg ccatgatatg ctgcaaatcc ctgaacagca aaaaaatgaa 3240
aaatatcaag ttcctgagtt cgattcgtcc acaattaaaa atatctcttc tgcaaaaggc 3300
ctggacgttt gggacagctg gccattacaa aacgctgacg gcactgtcgc aaactatcac 3360
ggctaccaca tcgtctttgc attagccgga gatcctaaaa atgcggatga cacatcgatt 3420
tacatgttct atcaaaaagt cggcgaaact tctattgaca gctggaaaaa cgctggccgc 3480
gtctttaaag acagcgacaa attcgatgca aatgattcta tcctaaaaga ccaaacacaa 3540
gaatggtcag gttcagccac atttacatct gacggaaaaa tccgtttatt ctacactgat 3600
ttctccggta aacattacgg caaacaaaca ctgacaactg cacaagttaa cgtatcagca 3660
tcagacagct ctttgaacat caacggtgta gaggattata aatcaatctt tgacggtgac 3720
ggaaaaacgt atcaaaatgt acagcagttc atcgatgaag gcaactacag ctcaggcgac 3780
aaccatacgc tgagagatcc tcactacgta gaagataaag gccacaaata cttagtattt 3840
gaagcaaaca ctggaactga agatggctac caaggcgaag aatctttatt taacaaagca 3900
tactatggca aaagcacatc attcttccgt caagaaagtc aaaaacttct gcaaagcgat 3960
aaaaaacgca cggctgagtt agcaaacggc gctctcggta tgattgagct aaacgatgat 4020
tacacactga aaaaagtgat gaaaccgctg attgcatcta acacagtaac agatgaaatt 4080
gaacgcgcga acgtctttaa aatgaacggc aaatggtacc tgttcactga ctcccgcgga 4140
tcaaaaatga cgattgacgg cattacgtct aacgatattt acatgcttgg ttatgtttct 4200
aattctttaa ctggcccata caagccgctg aacaaaactg gccttgtgtt aaaaatggat 4260
cttgatccta acgatgtaac ctttacttac tcacacttcg ctgtacctca agcgaaagga 4320
aacaatgtcg tgattacaag ctatatgaca aacagaggat tctacgcaga caaacaatca 4380
acgtttgcgc caagcttcct gctgaacatc aaaggcaaga aaacatctgt tgtcaaagac 4440
agcatccttg aacaaggaca attaacagtt aacaaataaa aacgcaaaag aaaatgccga 4500
tattgactac cggaagcagt gtgaccgtgt gcttctcaaa tgcctgattc aggctgtcta 4560
tgtgtgactg ttgagctgta acaagttgtc tcaggtgttc aatttcatgt tctagttgct 4620
ttgttttact ggtttcacct gttctattag gtgttacatg ctgttcatct gttacattgt 4680
cgatctgttc atggtgaaca gctttaaatg caccaaaaac tcgtaaaagc tctgatgtat 4740
ctatcttttt tacaccgttt tcatctgtgc atatggacag ttttcccttt gatatgtaac 4800
ggtgaacagt tgttctactt ttgtttgtta gtcttgatgc ttcactgata gatacaagag 4860
ccataagaac ctcagatcct tccgtattta gccagtatgt tctctagtgt ggttcgttgt 4920
ttttgcgtga gccatgagaa cgaaccattg agatcatact tactttgcat gtcactcaaa 4980
aattttgcct caaaactggt gagctgaatt tttgcagtta aagcatcgtg tagtgttttt 5040
cttagtccgt tatgtaggta ggaatctgat gtaatggttg ttggtatttt gtcaccattc 5100

-continued

```
atttttatct ggttgttctc aagttcggtt acgagatcca tttgtctatc tagttcaact   5160
tggaaaatca acgtatcagt cgggcggcct cgcttatcaa ccaccaattt catattgctg   5220
taagtgttta aatctttact tattggtttc aaaacccatt ggttaagcct tttaaactca   5280
tggtagttat tttcaagcat taacatgaac ttaaattcat caaggctaat ctctatattt   5340
gccttgtgag ttttcttttg tgttagttct tttaataacc actcataaat cctcatagag   5400
tatttgtttt caaaagactt aacatgttcc agattatatt ttatgaattt ttttaactgg   5460
aaaagataag gcaatatctc ttcactaaaa actaattcta atttttcgct tgagaacttg   5520
gcatagtttg tccactggaa aatctcaaag cctttaacca aaggattcct gatttccaca   5580
gttctcgtca tcagctctct ggttgcttta gctaatacac cataagcatt ttccctactg   5640
atgttcatca tctgaacgta ttggttataa gtgaacgata ccgtccgttc tttccttgta   5700
gggttttcaa tcgtggggtt gagtagtgcc acacagcata aaattagctt ggtttcatgc   5760
tccgttaagt catagcgact aatcgctagt tcatttgctt tgaaaacaac taattcagac   5820
atacatctca attggtctag gtgattttaa tcactatacc aattgagatg ggctagtcaa   5880
tgataattac tagtcctttt cctttgagtt gtgggtatct gtaaattctg ctagaccttt   5940
gctggaaaac ttgtaaattc tgctagaccc tctgtaaatt ccgctagacc tttgtgtgtt   6000
tttttgttt atattcaagt ggttataatt tatagaataa agaaagaata aaaaaagata   6060
aaaagaatag atcccagccc tgtgtataac tcactacttt agtcagttcc gcagtattac   6120
aaaaggatgt cgcaaacgct gtttgctcct ctacaaaaca gaccttaaaa ccctaaaggc   6180
ttaagtagca ccctcgcaag ctcgggcaaa tcgctgaata ttccttttgt ctccgaccat   6240
caggcacctg agtcgctgtc tttttcgtga cattcagttc gctgcgctca cggctctggc   6300
agtgaatggg ggtaaatggc actacaggcg ccttttatgg attcatgcaa ggaaactacc   6360
cataatacaa gaaaagcccg tcacgggctt ctcagggcgt tttatggcgg gtctgctatg   6420
tggtgctatc tgactttttg ctgttcagca gttcctgccc tctgattttc cagtctgacc   6480
acttcggatt atcccgtgac aggtcattca gactggctaa tgcacccagt aaggcagcgg   6540
tatcatcaac aggcttaccc gtcttactgt cggggatcga cgctctccct tatgcgactc   6600
ctgcaccttt cgtcttcgaa taaatacctg tgacggaaga tcacttcgca gaataaataa   6660
atcctggtgt ccctgttgat accgggaagc cctgggccaa cttttggcga aaatgagacg   6720
ttgatcggca cgtaagaggt tccaactttc accataatga aataagatca ctaccgggcg   6780
tatttttga gttatcgaga ttttcaggag ctaaggaagc taaaatggag aaaaaaatca   6840
ctggatatac caccgttgat atatcccaat ggcatcgtaa agaacatttt gaggcatttc   6900
agtcagttgc tcaatgtacc tataaccaga ccgttcagct ggatattacg gcctttttaa   6960
agaccgtaaa gaaaaataag cacaagtttt atccggcctt tattcacatt cttgcccgcc   7020
tgatgaatgc tcatccggaa ttccgtatgg caatgaaaga cggtgagctg gtgatatggg   7080
atagtgttca cccttgttac accgttttcc atgagcaaac tgaaacgttt tcatcgctct   7140
ggagtgaata ccacgacgat ttccggcagt ttctacacat atattcgcaa gatgtggcgt   7200
gttacggtga aaacctggcc tatttcccta aagggtttat tgagaatatg tttttcgtct   7260
cagccaatcc ctgggtgagt ttcaccagtt ttgatttaaa cgtggccaat atggacaact   7320
tcttcgcccc cgttttcacc atgggcaaat attatacgca aggcgacaag gtgctgatgc   7380
cgctggcgat tcaggttcat catgccgttt gtgatggctt ccatgtcggc agaatgctta   7440
atgaattaca acagtactgc gatgagtggc agggcggggc gtaatttttt taaggcagtt   7500
```

```
attggtgccc ttaaacgcct ggttgctacg cctgaataag tgataataag cggatgaatg   7560
gcagaaattc gaaagcaaat tcgacccggt cgtcggttca gggcagggtc gttaaatagc   7620
cgcttatgtc tattgctggt ctcggtaccc tgcacccaac tgatcttcag catcttttac   7680
tttcaccagc gtttctgggt gagcaaaaac aggaaggcaa aatgccgcaa aaaagggaat   7740
aagggcgaca cggaaatgtt gaatactcat actcttcctt tttcaatatt attgaagcat   7800
ttatcagggt tattgtctca tgagcggata catatttgaa tgtatttaga aaaataaaca   7860
aaagagtttg tagaaacgca aaaaggccat ccgtcaggat ggccttctgc ttaatttgat   7920
gcctggcagt ttatggcggg cgtcctgccc gccaccctcc gggccgttgc ttcgcaacgt   7980
tcaaatccgc tcccggcgga tttgtcctac tcaggagagc gttcaccgac aaacaacaga   8040
taaaacgaaa ggcccagtct ttcgactgag cctttcgttt tatttgatgc ctggcagttc   8100
cctactctcg catggggaga ccccacacta ccatcggcgc tacggcgttt cacttctgag   8160
ttcggcatgg ggtcaggtgg gaccaccgcg ctactgccgc caggcaaatt ctgttttatc   8220
agaccgcttc tgcgttctga tttaatctgt atcaggctga aaatcttctc tcatccgcca   8280
aaacagccaa gcttagcggc cgcttagacc tttcgctttt tcttgggatc ggctctggag   8340
tcgccaccaa gctgagacag gtcgattcgg gtctcgtaca ggccagtgat ggactggtga   8400
atcagggtgg catcgagaac ctccttggtg gatgtgtacc gctttcggtc gatagtggta   8460
tcgaagtact tgaaagctgc aggagcaccc aggttggtaa gagtaaacag gtgaatgatg   8520
ttctccgcct gttctcgaat gggtttgtcc cgatgcttgt tgtaggcaga gagcaccttg   8580
tccaagttgg catcagccag gatgactcgc ttcgaaaact cggaaatctg ctcgataatc   8640
tcgtcgaggt aatgtttgtg ctgctcaacg aagagttgct tctgttcgtt gtcctcggga   8700
gaacccttga gcttctcgta gtgagaagcc agatagagaa agttgacgta cttcgaaggc   8760
aaggcaagct cgtttccctt ctgcagctcg ccagcggagg cgagcatacg ctttcgaccg   8820
ttctccagtt cgaacagaga gtacttgggc agcttgataa tgaggtcttt cttgacctcc   8880
ttgtaaccct tggcttccaa gaagtcgatg ggattcttct cgaagctcga tcgctccatg   8940
atggtaattc cgagcagctc cttgacggac ttgagctttt tggacttgcc cttctcgacc   9000
ttcgcaacga caagcacgga ataggcgacg gtaggagaat cgaagccacc gtatttcttg   9060
ggatcccagt ctttctttcg agcgatgagc ttgtcggagt ttcgcttggg cagaatcgac   9120
tccttggaga atccgccagt ctgaacctcg gttttcttga cgatgttgac ctgaggcatc   9180
gacagaacct ttcgcacggt tgcaaagtct cgacccttgt cccacacgat ctctccagtt   9240
tcgccgttgg tctcgataag tggtctcttt cgaatctctc cgttggccaa ggtgatctcg   9300
gtcttgaaaa agttcatgat gttggagtaa aagaagtact tggcagtagc cttgccaatc   9360
tcctgttcgg acttggcaat catctttcga acgtcgtaga ccttgtaatc gccgtaaacg   9420
aactcgcttt cgagcttggg gtatttcttg atgagcgcag tgccaacgac ggcgttgagg   9480
taagcatcgt gggcatggtg gtaattgttg atctctcgca ccttgtagaa ctgaaagtcc   9540
tttcggaaat cggagaccag tttggacttg agagtaatca ccttgacctc tcggatgagc   9600
ttgtcgttct cgtcgtactt ggtgttcatc cgagaatcga gaatctgtgc gacgtgcttt   9660
gtgatctgtc tggtctcgac gagttgacgc ttgatgaagc cagccttgtc gagctcggac   9720
agaccgcctc gctcggcctt ggtaagattg tcgaactttc gctgggtaat gagcttggcg   9780
ttgagcagct gtcgccagta gttcttcatc tttttgacca cctcttcgct gggaacgttg   9840
```

-continued

```
tccgacttgc ctctgttctt gtcggatcgt gtaaggacct tgttgtcgat agaatcgtcc   9900

ttgagaaagg attgagggac aatgtggtcc acatcgtagt cgctgagacg attgatgtcc   9960

agttcctgat ccacgtacat gtctcgacca ttctgcagat agtagagata cagcttctcg  10020

ttctgcagtt gagtgttctc gacgggatgc tccttgagaa tctgggatcc cagctccttg  10080

atgccttcct cgattcgctt catccgctct cgcgagtttt tctgaccctt ttgagttgtc  10140

tggttctctc tggccatctc gatcacaatg ttctcgggct tgtgacgtcc catgaccttc  10200

accagctcgt cgacaacctt gacagtctgg agaatgcctt tcttgatggc tggcgaacca  10260

gccaggttgg caatatgttc gtgcaagctg tcgccctgac cggacacttg tgccttctgg  10320

atgtcctcct tgaaggtaag agaatcgtcg tgaatgagct gcatgaagtt tcggttggca  10380

aagccatcgg acttgagaaa gtccagaatg gtctttccgg actgcttgtc tctgatgccg  10440

ttgatgagct ttcgcgaaag tcttccccag ccggtgtatc tacgtcgctt gagttgtttc  10500

atgaccttgt cgtcgaacag gtgagcgtat gtcttgagtc gttcctcgat catctcccga  10560

tcttcgaaca gggtaagagt gagcacgatg tcctccagaa tgtcctcgtt ttcctcgttg  10620

tcgagaaaat ccttgtcctt gataatcttg agcagatcgt gataggtgcc caaagaggcg  10680

ttgaatcggt cctcaactcc ggaaatctcg acgctgtcga aacactcgat tttcttgaag  10740

tagtcctcct tgagctgctt aacagtgacc tttcggttgg tcttgaacag gagatcgaca  10800

atggctttct tctgttcgcc agacaagaag gcaggctttc gcattccctc ggtaacgtac  10860

ttgactttgg tgagttcgtt gtagactgta aagtactcgt agagcagcga atgcttggga  10920

agaaccttct cgttgggcag attcttgtcg aagttggtca ttcgctcgat gaaggactgt  10980

gcagaggcac ccttgtccac gacttcctcg aagttccagg gagtgatggt ttcctcggac  11040

tttcgagtca tccaagcaaa tcgagagttt cctctggcaa gaggaccaac atagtagggg  11100

attcgaaagg taagaatctt ctcgatcttc tctcggttgt ccttgagaaa ggggtagaag  11160

tcttcctgac gtcgaagaat ggcgtgcagc tcaccgaggt ggatctgatg aggaatgctg  11220

ccgttgtcga aggttcgttg cttccgaagc agatcctctc gattgagctt gacaagcagt  11280

tcctcggttc cgtccatctt ctcgagaatt ggcttgatga acttgtagaa ctcttcctga  11340

gaggctccgc cgtcgatgta tccagcgtag ccgttcttcg actgatcgaa aaagatctcc  11400

ttgtacttct cgggcagttg ctgtcggaca agagccttga gcagtgtgag atcctgatgg  11460

tgctcgtcgt atcgcttgat catggaggca gaaaggggag cctttgtgat ctcggtgttg  11520

actcgcagaa tgtcagacaa gagaatagca tccgaaaggt tcttggcagc gagaaacagg  11580

tcggcgtact gatcgccaat ctgtgcaagc aggttgtcga ggtcatcgtc gtaggtgtcc  11640

ttggacagct ggagcttggc gtcctccgcc agatcgaagt tggacttgaa gttgggtgtg  11700

agaccaagag aaagggcaat gaggttgcca aacagtccgt tctttttctc gccaggaagt  11760

tgggcaatga ggttctccag tcgtctgctc ttcg                              11794
```

<210> SEQ ID NO 91
<211> LENGTH: 20
<212> TYPE: DNA
<213> ORGANISM: Artificial sequence
<220> FEATURE:
<223> OTHER INFORMATION: pRF97-Y155H fragment forward primer

<400> SEQUENCE: 91

```
caccttggcc atctcgttgg                                                20
```

<210> SEQ ID NO 92
<211> LENGTH: 20
<212> TYPE: DNA
<213> ORGANISM: Artificial sequence
<220> FEATURE:
<223> OTHER INFORMATION: pRF97-Y155H fragment reverse primer

<400> SEQUENCE: 92
cgaagagcag acgactggag 20

<210> SEQ ID NO 93
<211> LENGTH: 12164
<212> TYPE: DNA
<213> ORGANISM: Artificial sequence
<220> FEATURE:
<223> OTHER INFORMATION: plasmid pRF861

<400> SEQUENCE: 93
cctttcgtct tcgaataaat acctgtgacg gaagatcact tcgcagaata aataaatcct 60
ggtgtccctg ttgataccgg gaagccctgg gccaactttt ggcgaaaatg agacgttgat 120
cggcacgtaa gaggttccaa ctttcaccat aatgaaataa gatcactacc gggcgtattt 180
tttgagttat cgagattttc aggagctaag gaagctaaaa tggagaaaaa aatcactgga 240
tataccaccg ttgatatatc ccaatggcat cgtaaagaac attttgaggc atttcagtca 300
gttgctcaat gtacctataa ccagaccgtt cagctggata ttacggcctt tttaaagacc 360
gtaaagaaaa ataagcacaa gttttatccg gcctttattc acattcttgc ccgcctgatg 420
aatgctcatc cggaattccg tatggcaatg aaagacggtg agctggtgat atgggatagt 480
gttcaccctt gttacaccgt tttccatgag caaactgaaa cgttttcatc gctctggagt 540
gaataccacg acgatttccg gcagtttcta cacatatatt cgcaagatgt ggcgtgttac 600
ggtgaaaacc tggcctattt ccctaaaggg tttattgaga atatgttttt cgtctcagcc 660
aatccctggg tgagtttcac cagttttgat ttaaacgtgg ccaatatgga caacttcttc 720
gcccccgttt tcaccatggg caaatattat acgcaaggcg acaaggtgct gatgccgctg 780
gcgattcagg ttcatcatgc cgtttgtgat ggcttccatg tcggcagaat gcttaatgaa 840
ttacaacagt actgcgatga gtggcagggc ggggcgtaat ttttttaagg cagttattgg 900
tgcccttaaa cgcctggttg ctacgcctga ataagtgata ataagcggat gaatggcaga 960
aattcgaaag caaattcgac ccggtcgtcg gttcagggca gggtcgttaa atagccgctt 1020
atgtctattg ctggtctcgg taccctgcac ccaactgatc ttcagcatct tttactttca 1080
ccagcgtttc tgggtgagca aaaacaggaa ggcaaaatgc cgcaaaaaag ggaataaggg 1140
cgacacggaa atgttgaata ctcatactct tcctttttca atattattga agcatttatc 1200
agggttattg tctcatgagc ggatacatat ttgaatgtat ttagaaaaat aaacaaaaga 1260
gtttgtagaa acgcaaaaag gccatccgtc aggatggcct tctgcttaat ttgatgcctg 1320
gcagtttatg gcgggcgtcc tgcccgccac cctccgggcc gttgcttcgc aacgttcaaa 1380
tccgctcccg gcggatttgt cctactcagg agagcgttca ccgacaaaca acagataaaa 1440
cgaaaggccc agtctttcga ctgagccttt cgttttattt gatgcctggc agttccctac 1500
tctcgcatgg ggagacccca cactaccatc ggcgctacgg cgtttcactt ctgagttcgg 1560
catggggtca ggtgggacca ccgcgctact gccgccaggc aaattctgtt ttatcagacc 1620
gcttctgcgt tctgatttaa tctgtatcag gctgaaaatc ttctctcatc cgccaaaaca 1680
gccaagctta gcggccgctt agacctttcg ctttttcttg ggatcggctc tggagtcgcc 1740

```
accaagctga gacaggtcga ttcgggtctc gtacaggcca gtgatggact ggtgaatcag   1800
ggtggcatcg agaacctcct tggtggatgt gtaccgcttt cggtcgatag tggtatcgaa   1860
gtacttgaaa gctgcaggag cacccaggtt ggtaagagta aacaggtgaa tgatgttctc   1920
cgcctgttct cgaatgggtt tgtcccgatg cttgttgtag gcagagagca ccttgtccaa   1980
gttggcatca gccaggatga ctcgcttcga aaactcggaa atctgctcga taatctcgtc   2040
gaggtaatgt ttgtgctgct caacgaagag ttgcttctgt tcgttgtcct cgggagaacc   2100
cttgagcttc tcgtagtgag aagccagata gagaaagttg acgtacttcg aaggcaaggc   2160
aagctcgttt cccttctgca gctcgccagc ggaggcgagc atacgctttc gaccgttctc   2220
cagttcgaac agagagtact tgggcagctt gataatgagg tctttcttga cctccttgta   2280
acccttggct tccaagaagt cgatgggatt cttctcgaag ctcgatcgct ccatgatggt   2340
aattccgagc agctccttga cggacttgag ctttttggac ttgcccttct cgaccttcgc   2400
aacgacaagc acggaatagg cgacggtagg agaatcgaag ccaccgtatt tcttgggatc   2460
ccagtctttc tttcgagcga tgagcttgtc ggagtttcgc ttgggcagaa tcgactcctt   2520
ggagaatccg ccagtctgaa cctcggtttt cttgacgatg ttgacctgag gcatcgacag   2580
aacctttcgc acggttgcaa agtctcgacc cttgtcccac acgatctctc cagtttcgcc   2640
gttggtctcg ataagtggtc tctttcgaat ctctccgttg gccaaggtga tctcggtctt   2700
gaaaaagttc atgatgttgg agtaaaagaa gtacttggca gtagccttgc caatctcctg   2760
ttcggacttg gcaatcatct ttcgaacgtc gtagaccttg taatcgccgt aaacgaactc   2820
gctttcgagc ttggggtatt tcttgatgag cgcagtgcca acgacggcgt tgaggtaagc   2880
atcgtgggca tggtggtaat tgttgatctc tcgcaccttg tagaactgaa agtcctttcg   2940
gaaatcggag accagtttgg acttgagagt aatcaccttg acctctcgga tgagcttgtc   3000
gttctcgtcg tacttggtgt tcatccgaga atcgagaatc tgtgcgacgt gctttgtgat   3060
ctgtctggtc tcgacgagtt gacgcttgat gaagccagcc ttgtcgagct cggacagacc   3120
gcctcgctcg gccttggtaa gattgtcgaa ctttcgctgg gtaatgagct tggcgttgag   3180
cagctgtcgc cagtagttct tcatcttttt gaccacctct tcgctgggaa cgttgtccga   3240
cttgcctctg ttcttgtcgg atcgtgtaag gaccttgttg tcgatagaat cgtccttgag   3300
aaaggattga gggacaatgt ggtccacatc gtagtcgctg agacgattga tgtccagttc   3360
ctgatccacg tacatgtctc gaccattctg cagatagtag agatacagct tctcgttctg   3420
cagttgagtg ttctcgacgg gatgctcctt gagaatctgg gatcccagct ccttgatgcc   3480
ttcctcgatt cgcttcatcc gctctcgcga gtttttctga cccttttgag ttgtctggtt   3540
ctctctggcc atctcgatca caatgttctc gggcttgtga cgtcccatga ccttcaccag   3600
ctcgtcgaca accttgacag tctggagaat gcctttcttg atggctggcg aaccagccag   3660
gttggcaata tgttcgtgca agctgtcgcc ctgaccggac acttgtgcct tctggatgtc   3720
ctccttgaag gtaagagaat cgtcgtgaat gagctgcatg aagtttcggt tggcaaagcc   3780
atcggacttg agaaagtcca gaatggtctt tccggactgc ttgtctctga tgccgttgat   3840
gagctttcgc gaaagtcttc cccagccggt gtatctacgt cgcttgagtt gtttcatgac   3900
cttgtcgtcg aacaggtgag cgtatgtctt gagtcgttcc tcgatcatct cccgatcttc   3960
gaacagggta agagtgagca cgatgtcctc cagaatgtcc tcgttttcct cgttgtcgag   4020
aaaatccttg tccttgataa tcttgagcag atcgtgatag gtgcccaaag aggcgttgaa   4080
tcggtcctca actccggaaa tctcgacgct gtcgaaacac tcgattttct tgaagtagtc   4140
```

-continued

```
ctccttgagc tgcttaacag tgacctttcg gttggtcttg aacaggagat cgacaatggc   4200
tttcttctgt tcgccagaca agaaggcagg ctttcgcatt ccctcggtaa cgtacttgac   4260
tttggtgagt tcgttgtaga ctgtaaagta ctcgtagagc agcgaatgct tgggaagaac   4320
cttctcgttg ggcagattct tgtcgaagtt ggtcattcgc tcgatgaagg actgtgcaga   4380
ggcacccttg tccacgactt cctcgaagtt ccagggagtg atggtttcct cggactttcg   4440
agtcatccaa gcaaatcgag agtttcctct ggcaagagga ccaacatagt aggggattcg   4500
aaaggtaaga atcttctcga tcttctctcg gttgtccttg agaaaggggt agaagtcttc   4560
ctgacgtcga agaatggcgt gcagctcacc gaggtggatc tgatgaggaa tgctgccgtt   4620
gtcgaaggtt cgttgcttcc gaagcagatc ctctcgattg agcttgacaa gcagttcctc   4680
ggttccgtcc atcttctcga gaattggctt gatgaacttg tagaactctt cctgagaggc   4740
tccgccgtcg atgtatccag cgtagccgtt cttcgactga tcgaaaaaga tctccttgta   4800
cttctcgggc agttgctgtc ggacaagagc cttgagcagt gtgagatcct gatggtgctc   4860
gtcgtatcgc ttgatcatgg aggcagaaag gggagccttt gtgatctcgg tgttgactcg   4920
cagaatgtca gacaagagaa tagcatccga aaggttcttg gcagcgagaa acaggtcggc   4980
gtactgatcg ccaatctgtg caagcaggtt gtcgaggtca tcgtcgtagg tgtccttgga   5040
cagctggagc ttggcgtcct ccgccagatc gaagttggac ttgaagttgg gtgtgagacc   5100
aagagaaagg gcaatgaggt tgccaaacag tccgttcttt ttctcgccag gaagttgggc   5160
aatgaggttc tccagtcgtc tgctcttcga gagtcgagca gacaagatgg cctttgcatc   5220
gactccggag gcattgatgg ggttttcctc gaacagctgg ttgtaggtct gaacgagctg   5280
aatgaacagc ttgtccacat cgctgttgtc gggattgaga tcgccctcga tgaggaaatg   5340
acctcgaaac ttgatcatgt gtgccagagc gagatggata agtctgagat ccgccttgtc   5400
ggtggaatcg acgagtttct ttcgcaggtg gtagatggta ggatacttct cgtggtaagc   5460
aacctcgtcc acaatgttgc caaagatggg atgacgctcg tgtttcttgt cttcctcgac   5520
gaggaaggat tcctccagtc gatgaaagaa cgaatcgtcc accttggcca tctcgttgga   5580
aaagatctcc tgcaggtagc agattcggtt cttccgtcgg gtgtaacgtc gccgagcagt   5640
tcgcttgagt ctggtagctt cggcagtctc gccagaatcg aacaacaggg caccaatgag   5700
gtttttcttg atggagtgtc gatcggtgtt tccgaggacc ttgaatttct tggagggcac   5760
cttgtactcg tcggtgatga cagcccagcc gacagagttg gttccaatgt ccaggccgat   5820
ggagtatttc ttgtcgaatt cccatatggt accagctgca gatctcgagc tcggatcctt   5880
atcgtcatcg tcgtacagat cccgacccat ttgctgtcca ccagtcatgc tagccatacc   5940
atgatgatga tgatgatgag aacccccccat ggttaattcc tcctgttagc ccaaaaaacg   6000
ggtatggaga aacagtagag agttgcgata aaaagcgtca ggtaggatcc gctaatctta   6060
tggataaaaa tgctatggca tagcaaagtg tgacgccgtg caaataatca atgtggactt   6120
ttctgccgtg attatagaca cttttgttac gcgtttttgt catggctttg gtcccgcttt   6180
gttacagaat gcttttaata agcggggtta ccggtttggt tagcgagaag agccagtaaa   6240
agacgcagtg acggcaatgt ctgatgcaat atggacaatt ggtttcttct ctgaatggcg   6300
ggagtatgaa aagtatggct gaagcgcaaa atgatcccct gctgccggga tactcgttta   6360
atgcccatct ggtggcgggt ttaacgccga ttgaggccaa cggttatctc gatttttta   6420
tcgaccgacc gctgggaatg aaaggttata ttctcaatct caccattcgc ggtcaggggg   6480
```

-continued

```
tggtgaaaaa tcagggacga gaatttgttt gccgaccggg tgatattttg ctgttcccgc   6540
caggagagat tcatcactac ggtcgtcatc cggaggctcg cgaatggtat caccagtggg   6600
tttactttcg tccgcgcgcc tactggcatg aatggcttaa ctggccgtca atatttgcca   6660
atacggggtt ctttcgcccg gatgaagcgc accagccgca tttcagcgac ctgtttgggc   6720
aaatcattaa cgccgggcaa ggggaagggc gctattcgga gctgctggcg ataaatctgc   6780
ttgagcaatt gttactgcgg cgcatggaag cgattaacga gtcgctccat ccaccgatgg   6840
ataatcgggt acgcgaggct tgtcagtaca tcagcgatca cctggcagac agcaattttg   6900
atatcgccag cgtcgcacag catgtttgct tgtcgccgtc gcgtctgtca catcttttcc   6960
gccagcagtt agggattagc gtcttaagct ggcgcgagga ccaacgtatc agccaggcga   7020
agctgctttt gagcaccacc cggatgccta tcgccaccgt cggtcgcaat gttggttttg   7080
acgatcaact ctatttctcg cgggtattta aaaaatgcac cggggccagc ccgagcgagt   7140
tccgtgccgg ttgtgaagaa aaagtgaatg atgtagccgt caagttgtca taattggtaa   7200
cgaatcagac aattgacggc ttgacggagt agcatagggt ttgcagaatc cctgcttcgt   7260
ccatttgaca ggcacattat gcatgccgct tcgccttcgc gcgcgaattg atctgctgcc   7320
tcgcgcgttt cggtgatgac ggtgaaaacc tctgacacat gcagctcccg gagacggtca   7380
cagcttgtct gtaagcggat gccgggagca gacaagcccg tcagggcgcg tcagcgggtg   7440
ttggcgggtg tcggggcgca gccatgaccc agtcacgtag cgatagcgga gtgtatactg   7500
gcttaactat gcggcatcag agcagattgt actgagagtg caggggatcg cggccgcgga   7560
ccggatcctc tagagcggcc gcgatcctct agagtcgacc ggtggcgaat gggacgcgcc   7620
ctgtagcggc gcattaagcg cggcgggtgt ggtggttacg cgcagcgtga ccgctacact   7680
tgccagcgcc ctagcgcccg ctcctttcgc tttcttccct tcctttctcg ccacgttcgc   7740
cggctttccc cgtcaagctc taaatcgggg gctcccttta gggttccgat ttagtgcttt   7800
acggcacctc gaccccaaaa aacttgatta gggtgatggt tcacgtagtg ggccatcgcc   7860
ctgatagacg gtttttcgcc ctttgacgtt ggagtccacg ttctttaata gtggactctt   7920
gttccaaact ggaacaacac tcaaccctat ctcggtctat tcttttgatt tataagggat   7980
tttgccgatt tcggcctatt ggttaaaaaa tgagctgatt taacaaaaat ttaacgcgaa   8040
ttttaacaaa atattaacgc ttacaattta ggtggcactt ttcggggaaa tgtgcgcgga   8100
acccctattt gtttattttt ctaaatacat tcaaatatgt atccgctcac cgcgatcctt   8160
tttaacccat cacatatacc tgccgttcac tattatttag tgaaatgaga tattatgata   8220
ttttctgaat tgtgattaaa aaggcaactt tatgcccatg caacagaaac tataaaaaat   8280
acagagaatg aaaagaaaca gatagatttt ttagttcttt aggcccgtag tctgcaaatc   8340
cttttatgat ttctatcaa acaaaagagg aaaatagacc agttgcaatc caaacgagag   8400
tctaatagaa tgaggtcgaa aagtaaatcg cgcgggtttg ttactgataa agcaggcaag   8460
acctaaaatg tgtaaagggc aaagtgtata ctttggcgtc accccttaca tattttaggt   8520
cttttttat tgtgcgtaac taacttgcca tcttcaaaca ggagggctgg aagaagcaga   8580
ccgctaacac agtacataaa aaggagaca tgaacgatga acatcaaaaa gtttgcaaaa   8640
caagcaacag tattaacctt tactaccgca ctgctggcag gaggcgcaac tcaagcgttt   8700
gcgaaagaaa cgaaccaaaa gccatataag gaaacatacg gcatttccca tattacacgc   8760
catgatatgc tgcaaatccc tgaacagcaa aaaaatgaaa aatatcaagt tcctgagttc   8820
gattcgtcca caattaaaaa tatctcttct gcaaaaggcc tggacgtttg ggacagctgg   8880
```

ccattacaaa acgctgacgg cactgtcgca aactatcacg gctaccacat cgtctttgca 8940
ttagccggag atcctaaaaa tgcggatgac acatcgattt acatgttcta tcaaaaagtc 9000
ggcgaaactt ctattgacag ctggaaaaac gctggccgcg tctttaaaga cagcgacaaa 9060
ttcgatgcaa atgattctat cctaaaagac caaacacaag aatggtcagg ttcagccaca 9120
tttacatctg acggaaaaat ccgtttattc tacactgatt tctccggtaa acattacggc 9180
aaacaaacac tgacaactgc acaagttaac gtatcagcat cagacagctc tttgaacatc 9240
aacggtgtag aggattataa atcaatcttt gacggtgacg gaaaaacgta tcaaaatgta 9300
cagcagttca tcgatgaagg caactacagc tcaggcgaca accatacgct gagagatcct 9360
cactacgtag aagataaagg ccacaaatac ttagtatttg aagcaaacac tggaactgaa 9420
gatggctacc aaggcgaaga atctttattt aacaaagcat actatggcaa aagcacatca 9480
ttcttccgtc aagaaagtca aaaacttctg caaagcgata aaaaacgcac ggctgagtta 9540
gcaaacggcg ctctcggtat gattgagcta aacgatgatt acacactgaa aaaagtgatg 9600
aaaccgctga ttgcatctaa cacagtaaca gatgaaattg aacgcgcgaa cgtctttaaa 9660
atgaacggca aatggtacct gttcactgac tcccgcggat caaaaatgac gattgacggc 9720
attacgtcta acgatattta catgcttggt tatgtttcta attctttaac tggcccatac 9780
aagccgctga acaaaactgg ccttgtgtta aaaatggatc ttgatcctaa cgatgtaacc 9840
tttacttact cacacttcgc tgtacctcaa gcgaaaggaa acaatgtcgt gattacaagc 9900
tatatgacaa acagaggatt ctacgcagac aaacaatcaa cgtttgcgcc aagcttcctg 9960
ctgaacatca aaggcaagaa aacatctgtt gtcaaagaca gcatccttga acaaggacaa 10020
ttaacagtta acaaataaaa acgcaaaaga aaatgccgat attgactacc ggaagcagtg 10080
tgaccgtgtg cttctcaaat gcctgattca ggctgtctat gtgtgactgt tgagctgtaa 10140
caagttgtct caggtgttca atttcatgtt ctagttgctt tgttttactg gtttcacctg 10200
ttctattagg tgttacatgc tgttcatctg ttacattgtc gatctgttca tggtgaacag 10260
ctttaaatgc accaaaaact cgtaaaagct ctgatgtatc tatctttttt acaccgtttt 10320
catctgtgca tatggacagt tttccctttg atatgtaacg gtgaacagtt gttctacttt 10380
tgtttgttag tcttgatgct tcactgatag atacaagagc cataagaacc tcagatcctt 10440
ccgtatttag ccagtatgtt ctctagtgtg gttcgttgtt tttgcgtgag ccatgagaac 10500
gaaccattga gatcatactt actttgcatg tcactcaaaa attttgcctc aaaactggtg 10560
agctgaattt ttgcagttaa agcatcgtgt agtgtttttc ttagtccgtt atgtaggtag 10620
gaatctgatg taatggttgt tggtattttg tcaccattca tttttatctg gttgttctca 10680
agttcggtta cgagatccat ttgtctatct agttcaactt ggaaaatcaa cgtatcagtc 10740
gggcggcctc gcttatcaac caccaatttc atattgctgt aagtgtttaa atctttactt 10800
attggtttca aaacccattg gttaagcctt ttaaactcat ggtagttatt ttcaagcatt 10860
aacatgaact taaattcatc aaggctaatc tctatatttg ccttgtgagt tttcttttgt 10920
gttagttctt ttaataacca ctcataaatc ctcatagagt atttgttttc aaaagactta 10980
acatgttcca gattatattt tatgaatttt tttaactgga aagataaggc caatatctct 11040
tcactaaaaa ctaattctaa tttttcgctt gagaacttgg catagtttgt ccactggaaa 11100
atctcaaagc ctttaaccaa aggattcctg atttccacag ttctcgtcat cagctctctg 11160
gttgctttag ctaatacacc ataagcattt tccctactga tgttcatcat ctgaacgtat 11220

```
tggttataag tgaacgatac cgtccgttct ttccttgtag ggttttcaat cgtggggttg  11280

agtagtgcca cacagcataa aattagcttg gtttcatgct ccgttaagtc atagcgacta  11340

atcgctagtt catttgcttt gaaaacaact aattcagaca tacatctcaa ttggtctagg  11400

tgattttaat cactatacca attgagatgg gctagtcaat gataattact agtccttttc  11460

ctttgagttg tgggtatctg taaattctgc tagacctttg ctggaaaact tgtaaattct  11520

gctagaccct ctgtaaattc cgctagacct ttgtgtgttt tttttgttta tattcaagtg  11580

gttataattt atagaataaa gaaagaataa aaaaagataa aaagaataga tcccagccct  11640

gtgtataact cactacttta gtcagttccg cagtattaca aaaggatgtc gcaaacgctg  11700

tttgctcctc tacaaaacag accttaaaac cctaaaggct taagtagcac cctcgcaagc  11760

tcgggcaaat cgctgaatat tccttttgtc tccgaccatc aggcacctga gtcgctgtct  11820

ttttcgtgac attcagttcg ctgcgctcac ggctctggca gtgaatgggg gtaaatggca  11880

ctacaggcgc cttttatgga ttcatgcaag gaaactaccc ataatacaag aaaagcccgt  11940

cacgggcttc tcagggcgtt ttatggcggg tctgctatgt ggtgctatct gactttttgc  12000

tgttcagcag ttcctgccct ctgattttcc agtctgacca cttcggatta tcccgtgaca  12060

ggtcattcag actggctaat gcacccagta aggcagcggt atcatcaaca ggcttacccg  12120

tcttactgtc ggggatcgac gctctccctt atgcgactcc tgca                  12164
```

<210> SEQ ID NO 94
<211> LENGTH: 918
<212> TYPE: DNA
<213> ORGANISM: E. coli

<400> SEQUENCE: 94

```
atgaacttca gacgcctgaa atacttcgta aaaattgtag atattggtag cctgacccag    60

gctgctgaag tattgcatat cgcacaacca gcgctcagcc agcaggttgc cacactggaa   120

ggtgagttaa atcaacaact tttgatccgt acaaagcggg gcgttacacc aacagacgcc   180

ggaaaaattc tctataccca tgcgcgggcc attttacgtc agtgtgaaca ggcccaactg   240

gcggtgcata acgttggtca ggcattatcg gggcaagtct cgattggctt tgcaccagga   300

accgctgcgt catccatcac catgccctta ttacaggcgg ttcgcgctga atttccggag   360

atcgttatct atcttcatga aaatagtggt gcagtgctta acgaaaaatt gataaatcac   420

caactcgata tggcggtgat ttatgagcat tcccctgtgg ctggtgtatc cagtcaggct   480

ttgctgaaag aagatctttt tctggtagga actcaagatt gcccggggca aagcgttgat   540

gtgaatgcta ttgcgcaaat gaacctcttt ctccccagtg attacagtgc tattagactt   600

cgtgttgatg aggctttttc cctacggcga ctcacggcaa aagttattgg tgaaattgag   660

tctattgcca cgcttaccgc agcgattgcc agcggcatgg gcgttgcagt attacccgaa   720

tcggccgcgc gttcgttatg tggcgcagta aatgggtgga tgtcacgcat taccactcct   780

tccatgagtc tctctttgtc attaaattta cccgccagag cgaacttatc gccacaggca   840

caggcagtga aagagttgtt aatgtcagtg attagttctc cagtgatgga aaaaaggcag   900

tggcaattgg tgagctaa                                                 918
```

<210> SEQ ID NO 95
<211> LENGTH: 20
<212> TYPE: DNA
<213> ORGANISM: E. coli

<400> SEQUENCE: 95
tatgcaatac ttcagcagcc 20

<210> SEQ ID NO 96
<211> LENGTH: 23
<212> TYPE: DNA
<213> ORGANISM: E. coli

<400> SEQUENCE: 96
tatgcaatac ttcagcagcc tgg 23

<210> SEQ ID NO 97
<211> LENGTH: 20
<212> TYPE: DNA
<213> ORGANISM: E. coli

<400> SEQUENCE: 97
acaaccagcg ctcagccagc 20

<210> SEQ ID NO 98
<211> LENGTH: 23
<212> TYPE: DNA
<213> ORGANISM: E. coli

<400> SEQUENCE: 98
acaaccagcg ctcagccagc agg 23

<210> SEQ ID NO 99
<211> LENGTH: 56
<212> TYPE: DNA
<213> ORGANISM: N25 phage

<400> SEQUENCE: 99
aagaatcata aaaaatttat ttgctttcag gaaaattttt ctgtataata gattca 56

<210> SEQ ID NO 100
<211> LENGTH: 247
<212> TYPE: DNA
<213> ORGANISM: Artificial sequence
<220> FEATURE:
<223> OTHER INFORMATION: synthesized nac target site 1 gRNA expression
cassette

<400> SEQUENCE: 100
aagaatcata aaaaatttat ttgctttcag gaaaattttt ctgtataata gattcatatg 60
caatacttca gcagccgttt tagagctaga aatagcaagt taaaataagg ctagtccgtt 120
atcaacttga aaaagtggca ccgagtcggt gcgactcctg ttgatagatc cagtaatgac 180
ctcagaactc catctggatt tgttcagaac gctcggttgc cgccgggcgt tttttattgg 240
tgagaat 247

<210> SEQ ID NO 101
<211> LENGTH: 247
<212> TYPE: DNA
<213> ORGANISM: Artificial sequence
<220> FEATURE:
<223> OTHER INFORMATION: synthesized nac target site 2 gRNA expression
cassette

<400> SEQUENCE: 101
aagaatcata aaaaatttat ttgctttcag gaaaattttt ctgtataata gattcaacaa 60
ccagcgctca gccagcgttt tagagctaga aatagcaagt taaaataagg ctagtccgtt 120

-continued

```
atcaacttga aaaagtggca ccgagtcggt gcgactcctg ttgatagatc cagtaatgac    180

ctcagaactc catctggatt tgttcagaac gctcggttgc cgccgggcgt tttttattgg    240

tgagaat                                                              247
```

<210> SEQ ID NO 102
<211> LENGTH: 500
<212> TYPE: DNA
<213> ORGANISM: E. coli

<400> SEQUENCE: 102

```
gaagttcatg ttgcctccgg tttttaagaa tcggcccaag tgccgccatt acttacaacc     60

agattgcaag atgcttgcca gttttatttt ggtgttgatg tacaagctaa ccaactgtca    120

aataagagat tatgatagat tcgtcatttg ctcctttaat cagctgtcgc gttcccctgc    180

cctataaaag gagggtatgc accacgatgg ttcattaccc aataagattg aaagctcacc    240

actttgttga aattgacagc aaacaaacaa aaaaatgcat ttcacccttt gacatcacca    300

tgcactgcca ttaatatgcg ccccgttcac acgattcctc tgtagttcag tcggtagaac    360

ggcggactgt taatccgtat gtcactggtt cgagtccagt cagaggagcc aaattcaaaa    420

aagcctgctt tctagcaggc tttttgcttt ctaattacca acgctcttaa aacatctgtc    480

ttgaaccaga actaatttgc                                                500
```

<210> SEQ ID NO 103
<211> LENGTH: 500
<212> TYPE: DNA
<213> ORGANISM: E. coli

<400> SEQUENCE: 103

```
cgtcccctgg attagctcga gccgaacctc cgggaaaagt tcgcgaaaag ctttaatgac     60

ctctggcaag ctataacgtg cctgagtatg cgtcgttgca atagtgagaa cgccagacgt    120

atcgttggta aacaggtctg caagccgacg aacattactg gcttcattca gaatacgttc    180

tgcaatgacc agtaatgctt tgcccggttc agtcatgccc agcagtcgct tacctcgtcg    240

aacaaatatt tcgatgccaa gttcatcctc cagttcccga atatgacggc tgacgcctga    300

ctgtgaggta aaaagcatat tcgcaacctc tgtcaggttg taatcctgac gtgcagcctc    360

gcggattatc tttagttgtt ggaaattcac ggtaaactcc gggcagttca gatttcccgt    420

tattgttaaa gtctaatgcc cggcataaca aataataaaa acccgcatct tattccatcc    480

cgatataaca cttagctcac                                                500
```

<210> SEQ ID NO 104
<211> LENGTH: 1000
<212> TYPE: DNA
<213> ORGANISM: Artificial sequence
<220> FEATURE:
<223> OTHER INFORMATION: synthesized nac deletion editing template

<400> SEQUENCE: 104

```
cgtcccctgg attagctcga gccgaacctc cgggaaaagt tcgcgaaaag ctttaatgac     60

ctctggcaag ctataacgtg cctgagtatg cgtcgttgca atagtgagaa cgccagacgt    120

atcgttggta aacaggtctg caagccgacg aacattactg gcttcattca gaatacgttc    180

tgcaatgacc agtaatgctt tgcccggttc agtcatgccc agcagtcgct tacctcgtcg    240

aacaaatatt tcgatgccaa gttcatcctc cagttcccga atatgacggc tgacgcctga    300

ctgtgaggta aaaagcatat tcgcaacctc tgtcaggttg taatcctgac gtgcagcctc    360
```

gcggattatc tttagttgtt ggaaattcac ggtaaactcc gggcagttca gatttcccgt 420
tattgttaaa gtctaatgcc cggcataaca aataataaaa acccgcatct tattccatcc 480
cgatataaca cttagctcac gaagttcatg ttgcctccgg tttttaagaa tcggcccaag 540
tgccgccatt acttacaacc agattgcaag atgcttgcca gttttatttt ggtgttgatg 600
tacaagctaa ccaactgtca aataagagat tatgatagat tcgtcatttg ctcctttaat 660
cagctgtcgc gttcccctgc cctataaaag gagggtatgc accacgatgg ttcattaccc 720
aataagattg aaagctcacc actttgttga aattgacagc aaacaaacaa aaaaatgcat 780
ttcacccttt gacatcacca tgcactgcca ttaatatgcg ccccgttcac acgattcctc 840
tgtagttcag tcggtagaac ggcggactgt taatccgtat gtcactggtt cgagtccagt 900
cagaggagcc aaattcaaaa aagcctgctt tctagcaggc tttttgcttt ctaattacca 960
acgctcttaa aacatctgtc ttgaaccaga actaatttgc 1000

<210> SEQ ID NO 105
<211> LENGTH: 20
<212> TYPE: DNA
<213> ORGANISM: Artificial sequence
<220> FEATURE:
<223> OTHER INFORMATION: 5' pRF97 or pRF861 identity fragment

<400> SEQUENCE: 105
cgaatcagac aattgacggc 20

<210> SEQ ID NO 106
<211> LENGTH: 21
<212> TYPE: DNA
<213> ORGANISM: Artificial sequence
<220> FEATURE:
<223> OTHER INFORMATION: 3' pRF97 or pRF861 identity fragment

<400> SEQUENCE: 106
gcttccggta gtcaataaac c 21

<210> SEQ ID NO 107
<211> LENGTH: 1288
<212> TYPE: DNA
<213> ORGANISM: artificial sequence
<220> FEATURE:
<223> OTHER INFORMATION: nacETsite1

<400> SEQUENCE: 107
cgaatcagac aattgacggc cgtcccctgg attagctcga gccgaacctc cgggaaaagt 60
tcgcgaaaag ctttaatgac ctctggcaag ctataacgtg cctgagtatg cgtcgttgca 120
atagtgagaa cgccagacgt atcgttggta aacaggtctg caagccgacg aacattactg 180
gcttcattca gaatacgttc tgcaatgacc agtaatgctt tgcccggttc agtcatgccc 240
agcagtcgct tacctcgtcg aacaaatatt tcgatgccaa gttcatcctc cagttcccga 300
atatgacggc tgacgcctga ctgtgaggta aaaagcatat tcgcaacctc tgtcaggttg 360
taatcctgac gtgcagcctc gcggattatc tttagttgtt ggaaattcac ggtaaactcc 420
gggcagttca gatttcccgt tattgttaaa gtctaatgcc cggcataaca aataataaaa 480
acccgcatct tattccatcc cgatataaca cttagctcac gaagttcatg ttgcctccgg 540
tttttaagaa tcggcccaag tgccgccatt acttacaacc agattgcaag atgcttgcca 600
gttttatttt ggtgttgatg tacaagctaa ccaactgtca aataagagat tatgatagat 660

```
tcgtcatttg ctcctttaat cagctgtcgc gttcccctgc cctataaaag gagggtatgc    720

accacgatgg ttcattaccc aataagattg aaagctcacc actttgttga aattgacagc    780

aaacaaacaa aaaaatgcat ttcacccttt gacatcacca tgcactgcca ttaatatgcg    840

ccccgttcac acgattcctc tgtagttcag tcggtagaac ggcggactgt taatccgtat    900

gtcactggtt cgagtccagt cagaggagcc aaattcaaaa aagcctgctt tctagcaggc    960

tttttgcttt ctaattacca acgctcttaa aacatctgtc ttgaaccaga actaatttgc   1020

aagaatcata aaaaatttat ttgctttcag gaaaattttt ctgtataata gattcatatg   1080

caatacttca gcagccgttt tagagctaga aatagcaagt taaaataagg ctagtccgtt   1140

atcaacttga aaaagtggca ccgagtcggt gcgactcctg ttgatagatc cagtaatgac   1200

ctcagaactc catctggatt tgttcagaac gctcggttgc cgccgggcgt tttttattgg   1260

tgagaatggt ttattgacta ccggaagc                                      1288
```

```
<210> SEQ ID NO 108
<211> LENGTH: 1288
<212> TYPE: DNA
<213> ORGANISM: artificial sequence
<220> FEATURE:
<223> OTHER INFORMATION: nacETsite2

<400> SEQUENCE: 108
```

```
cgaatcagac aattgacggc cgtcccctgg attagctcga gccgaacctc cgggaaaagt     60

tcgcgaaaag ctttaatgac ctctggcaag ctataacgtg cctgagtatg cgtcgttgca    120

atagtgagaa cgccagacgt atcgttggta aacaggtctg caagccgacg aacattactg    180

gcttcattca gaatacgttc tgcaatgacc agtaatgctt tgcccggttc agtcatgccc    240

agcagtcgct tacctcgtcg aacaaatatt tcgatgccaa gttcatcctc cagttcccga    300

atatgacggc tgacgcctga ctgtgaggta aaaagcatat tcgcaacctc tgtcaggttg    360

taatcctgac gtgcagcctc gcggattatc tttagttgtt ggaaattcac ggtaaactcc    420

gggcagttca gatttcccgt tattgttaaa gtctaatgcc cggcataaca aataataaaa    480

acccgcatct tattccatcc cgatataaca cttagctcac gaagttcatg ttgcctccgg    540

tttttaagaa tcggcccaag tgccgccatt acttacaacc agattgcaag atgcttgcca    600

gttttatttt ggtgttgatg tacaagctaa ccaactgtca aataagagat tatgatagat    660

tcgtcatttg ctcctttaat cagctgtcgc gttcccctgc cctataaaag gagggtatgc    720

accacgatgg ttcattaccc aataagattg aaagctcacc actttgttga aattgacagc    780

aaacaaacaa aaaaatgcat ttcacccttt gacatcacca tgcactgcca ttaatatgcg    840

ccccgttcac acgattcctc tgtagttcag tcggtagaac ggcggactgt taatccgtat    900

gtcactggtt cgagtccagt cagaggagcc aaattcaaaa aagcctgctt tctagcaggc    960

tttttgcttt ctaattacca acgctcttaa aacatctgtc ttgaaccaga actaatttgc   1020

aagaatcata aaaaatttat ttgctttcag gaaaattttt ctgtataata gattcaacaa   1080

ccagcgctca gccagcgttt tagagctaga aatagcaagt taaaataagg ctagtccgtt   1140

atcaacttga aaaagtggca ccgagtcggt gcgactcctg ttgatagatc cagtaatgac   1200

ctcagaactc catctggatt tgttcagaac gctcggttgc cgccgggcgt tttttattgg   1260

tgagaatggt ttattgacta ccggaagc                                      1288
```

```
<210> SEQ ID NO 109
<211> LENGTH: 9322
```

<212> TYPE: DNA
<213> ORGANISM: Artificial sequence
<220> FEATURE:
<223> OTHER INFORMATION: pRF97-cassette

<400> SEQUENCE: 109
ggtttattga ctaccggaag cagtgtgacc gtgtgcttct caaatgcctc aggctgtcta 60
tgtgtgactg ttgagctgta acaagttgtc tcaggtgttc aatttcatgt tctagttgct 120
ttgttttact ggtttcacct gttctattag gtgttacatg ctgttcatct gttacattgt 180
cgatctgttc atggtgaaca gctttaaatg caccaaaaac tcgtaaaagc tctgatgtat 240
ctatcttttt tacaccgttt tcatctgtgc atatggacag ttttcccttt gatatctaac 300
ggtgaacagt tgttctactt ttgtttgtta gtcttgatgc ttcactgata gatacaagag 360
ccataagaac ctcagatcct tccgtattta gccagtatgt tctctagtgt ggttcgttgt 420
ttttgcgtga gccatgagaa cgaaccattg agatcatgct tactttgcat gtcactcaaa 480
aattttgcct caaaactggt gagctgaatt tttgcagtta aagcatcgtg tagtgttttt 540
cttagtccgt tacgtaggta ggaatctgat gtaatggttg ttggtatttt gtcaccattc 600
atttttatct ggttgttctc aagttcggtt acgagatcca tttgtctatc tagttcaact 660
tggaaaatca acgtatcagt cgggcggcct cgcttatcaa ccaccaattt catattgctg 720
taagtgttta aatctttact tattggtttc aaaacccatt ggttaagcct tttaaactca 780
tggtagttat tttcaagcat taacatgaac ttaaattcat caaggctaat ctctatattt 840
gccttgtgag ttttcttttg tgttagttct tttaataacc actcataaat cctcatagag 900
tatttgtttt caaaagactt aacatgttcc agattatatt ttatgaattt ttttaactgg 960
aaaagataag gcaatatctc ttcactaaaa actaattcta atttttcgct tgagaacttg 1020
gcatagtttg tccactggaa aatctcaaag cctttaacca aaggattcct gatttccaca 1080
gttctcgtca tcagctctct ggttgcttta gctaatacac cataagcatt ttccctactg 1140
atgttcatca tctgagcgta ttggttataa gtgaacgata ccgtccgttc tttccttgta 1200
gggttttcaa tcgtggggtt gagtagtgcc acacagcata aaattagctt ggtttcatgc 1260
tccgttaagt catagcgact aatcgctagt tcatttgctt tgaaaacaac taattcagac 1320
atacatctca attggtctag gtgattttaa tcactatacc aattgagatg ggctagtcaa 1380
tgataattac tagtcctttt cctttgagtt gtgggtatct gtaaattctg ctagaccttt 1440
gctggaaaac ttgtaaattc tgctagaccc tctgtaaatt ccgctagacc tttgtgtgtt 1500
ttttttgttt atattcaagt ggttataatt tatagaataa agaaagaata aaaaaagata 1560
aaaagaatag atcccagccc tgtgtataac tcactacttt agtcagttcc gcagtattac 1620
aaaaggatgt cgcaaacgct gtttgctcct ctacaaaaca gaccttaaaa ccctaaaggc 1680
ttaagtagca ccctcgcaag ctcgggcaaa tcgctgaata ttccttttgt ctccgaccat 1740
caggcacctg agtcgctgtc tttttcgtga cattcagttc gctgcgctca cggctctggc 1800
agtgaatggg ggtaaatggc actacaggcg ccttttatgg attcatgcaa ggaaactacc 1860
cataatacaa gaaaagcccg tcacgggctt ctcagggcgt tttatggcgg gtctgctatg 1920
tggtgctatc tgactttttg ctgttcagca gttcctgccc tctgattttc cagtctgacc 1980
acttcggatt atcccgtgac aggtcattca gactggctaa tgcacccagt aaggcagcgg 2040
tatcatcaac aggcttaccc gtcttactgt cggatcgacg ctctccctta tgcgactcct 2100
gcatcccttt cgtcttcgaa taaatacctg tgacggaaga tcacttcgca gaataaataa 2160

```
atcctggtgt ccctgttgat accgggaagc cctgggccaa cttttggcga aaatgagacg   2220
ttgatcggca cgtaagaggt tccaactttc accataatga aataagatca ctaccgggcg   2280
tattttttga gttatcgaga ttttcaggag ctaaggaagc taaaatggag aaaaaaatca   2340
ctggatatac caccgttgat atatcccaat ggcatcgtaa agaacatttt gaggcatttc   2400
agtcagttgc tcaatgtacc tataaccaga ccgttcagct ggatattacg gcctttttaa   2460
agaccgtaaa gaaaaataag cacaagtttt atccggcctt tattcacatt cttgcccgcc   2520
tgatgaatgc tcatccggaa ttccgtatgg caatgaaaga cggtgagctg gtgatatggg   2580
atagtgttca cccttgttac accgttttcc atgagcaaac tgaaacgttt tcatcgctct   2640
ggagtgaata ccacgacgat ttccggcagt ttctacacat atattcgcaa gatgtggcgt   2700
gttacggtga aaacctggcc tatttcccta aagggtttat tgagaatatg tttttcgtct   2760
cagccaatcc ctgggtgagt ttcaccagtt ttgatttaaa cgtggccaat atggacaact   2820
tcttcgcccc cgttttcacc atgggcaaat attatacgca aggcgacaag gtgctgatgc   2880
cgctggcgat tcaggttcat catgccgttt gtgatggctt ccatgtcggc agaatgctta   2940
atgaattaca acagtactgc gatgagtggc agggcggggc gtaatttttt taaggcagtt   3000
attggtgccc ttaaacgcct ggtgctacgc ctgaataagt gataataagc ggatgaatgg   3060
cagaaattcg aaagcaaatt cgacccggtc gtcggttcag ggcagggtcg ttaaatagcc   3120
gcttatgtct attgctggtt tatcggtacc ccccaactga tcttcagcat cttttacttt   3180
caccagcgtt tctgggtgag caaaaacagg aaggcaaaat gccgcaaaaa agggaataag   3240
ggcgacacgg aaatgttgaa tactcatact cttccttttt caatattatt gaagcattta   3300
tcagggttat tgtctcatga gcggatacat atttgaatgt atttagaaaa ataaacaaaa   3360
gagtttgtag aaacgcaaaa aggccatccg tcaggatggc cttctgctta atttgatgcc   3420
tggcagttta tggcgggcgt cctgcccgcc accctccggg ccgttgcttc gcaacgttca   3480
aatccgctcc cggcggattt gtcctactca ggagagcgtt caccgacaaa caacagataa   3540
aacgaaaggc ccagtctttc gactgagcct ttcgttttat ttgatgcctg gcagttccct   3600
actctcgcat ggggagaccc cacactacca tcggcgctac ggcgtttcac ttctgagttc   3660
ggcatggggt caggtgggac caccgcgcta ctgccgccag gcaaattctg ttttatcaga   3720
ccgcttctgc gttctgattt aatctgtatc aggctgaaaa tcttctctca tccgccaaaa   3780
cagccaagct tagcggccgc ttagaccttt cgcttttt ct tgggatcggc tctggagtcg   3840
ccaccaagct gagacaggtc gattcgggtc tcgtacaggc cagtgatgga ctggtgaatc   3900
agggtggcat cgagaacctc cttggtggat gtgtaccgct ttcggtcgat agtggtatcg   3960
aagtacttga aagctgcagg agcacccagg ttggtaagag taaacaggtg aatgatgttc   4020
tccgcctgtt ctcgaatggg tttgtcccga tgcttgttgt aggcagagag caccttgtcc   4080
aagttggcat cagccaggat gactcgcttc gaaaactcgg aaatctgctc gataatctcg   4140
tcgaggtaat gtttgtgctg ctcaacgaag agttgcttct gttcgttgtc ctcgggagaa   4200
cccttgagct tctcgtagtg agaagccaga tagagaaagt tgacgtactt cgaaggcaag   4260
gcaagctcgt ttcccttctg cagctcgcca gcggaggcga gcatacgctt tcgaccgttc   4320
tccagttcga acagagagta cttgggcagc ttgataatga ggtctttctt gacctccttg   4380
taacccttgg cttccaagaa gtcgatggga ttcttctcga agctcgatcg ctccatgatg   4440
gtaattccga gcagctcctt gacggacttg agctttttgg acttgccctt ctcgaccttc   4500
gcaacgacaa gcacggaata ggcgacggta ggagaatcga agccaccgta tttcttggga   4560
```

-continued

```
tcccagtctt tctttcgagc gatgagcttg tcggagtttc gcttgggcag aatcgactcc   4620
ttggagaatc cgccagtctg aacctcggtt ttcttgacga tgttgacctg aggcatcgac   4680
agaacctttc gcacggttgc aaagtctcga cccttgtccc acacgatctc tccagtttcg   4740
ccgttggtct cgataagtgg tctctttcga atctctccgt tggccaaggt gatctcggtc   4800
ttgaaaaagt tcatgatgtt ggagtaaaag aagtacttgg cagtagcctt gccaatctcc   4860
tgttcggact tggcaatcat ctttcgaacg tcgtagacct tgtaatcgcc gtaaacgaac   4920
tcgctttcga gcttggggta tttcttgatg agcgcagtgc caacgacggc gttgaggtaa   4980
gcatcgtggg catggtggta attgttgatc tctcgcacct tgtagaactg aaagtccttt   5040
cggaaatcgg agaccagttt ggacttgaga gtaatcacct tgacctctcg gatgagcttg   5100
tcgttctcgt cgtacttggt gttcatccga gaatcgagaa tctgtgcgac gtgctttgtg   5160
atctgtctgg tctcgacgag ttgacgcttg atgaagccag ccttgtcgag ctcggacaga   5220
ccgcctcgct cggccttggt aagattgtcg aactttcgct gggtaatgag cttggcgttg   5280
agcagctgtc gccagtagtt cttcatcttt ttgaccacct cttcgctggg aacgttgtcc   5340
gacttgcctc tgttcttgtc ggatcgtgta aggaccttgt tgtcgataga atcgtccttg   5400
agaaaggatt gagggacaat gtggtccaca tcgtagtcgc tgagacgatt gatgtccagt   5460
tcctgatcca cgtacatgtc tcgaccattc tgcagatagt agagatacag cttctcgttc   5520
tgcagttgag tgttctcgac gggatgctcc ttgagaatct gggatcccag ctccttgatg   5580
ccttcctcga ttcgcttcat ccgctctcgc gagtttttct gacccttttg agttgtctgg   5640
ttctctctgg ccatctcgat cacaatgttc tcgggcttgt gacgtcccat gaccttcacc   5700
agctcgtcga caaccttgac agtctggaga atgcctttct tgatggctgg cgaaccagcc   5760
aggttggcaa tatgttcgtg caagctgtcg ccctgaccgg acacttgtgc cttctggatg   5820
tcctccttga aggtaagaga atcgtcgtga atgagctgca tgaagtttcg gttggcaaag   5880
ccatcggact tgagaaagtc cagaatggtc tttccggact gcttgtctct gatgccgttg   5940
atgagctttc gcgaaagtct tccccagccg gtgtatctac gtcgcttgag ttgtttcatg   6000
accttgtcgt cgaacaggtg agcgtatgtc ttgagtcgtt cctcgatcat ctcccgatct   6060
tcgaacaggg taagagtgag cacgatgtcc tccagaatgt cctcgttttc ctcgttgtcg   6120
agaaaatcct tgtccttgat aatcttgagc agatcgtgat aggtgcccaa agaggcgttg   6180
aatcggtcct caactccgga aatctcgacg ctgtcgaaac actcgatttt cttgaagtag   6240
tcctccttga gctgcttaac agtgaccttt cggttggtct tgaacaggag atcgacaatg   6300
gctttcttct gttcgccaga caagaaggca ggctttcgca ttccctcggt aacgtacttg   6360
actttggtga gttcgttgta gactgtaaag tactcgtaga gcagcgaatg cttgggaaga   6420
accttctcgt tgggcagatt cttgtcgaag ttggtcattc gctcgatgaa ggactgtgca   6480
gaggcaccct tgtccacgac ttcctcgaag ttccagggag tgatggtttc ctcggacttt   6540
cgagtcatcc aagcaaatcg agagtttcct ctggcaagag gaccaacata gtaggggatt   6600
cgaaaggtaa gaatcttctc gatcttctct cggttgtcct tgagaaaggg gtagaagtct   6660
tcctgacgtc gaagaatggc gtgcagctca ccgaggtgga tctgatgagg aatgctgccg   6720
ttgtcgaagg ttcgttgctt ccgaagcaga tcctctcgat tgagcttgac aagcagttcc   6780
tcggttccgt ccatcttctc gagaattggc ttgatgaact tgtagaactc ttcctgagag   6840
gctccgccgt cgatgtatcc agcgtagccg ttcttcgact gatcgaaaaa gatctccttg   6900
```

-continued

```
tacttctcgg gcagttgctg tcggacaaga gccttgagca gtgtgagatc ctgatggtgc   6960
tcgtcgtatc gcttgatcat ggaggcagaa aggggagcct ttgtgatctc ggtgttgact   7020
cgcagaatgt cagacaagag aatagcatcc gaaaggttct tggcagcgag aaacaggtcg   7080
gcgtactgat cgccaatctg tgcaagcagg ttgtcgaggt catcgtcgta ggtgtccttg   7140
gacagctgga gcttggcgtc ctccgccaga tcgaagttgg acttgaagtt gggtgtgaga   7200
ccaagagaaa gggcaatgag gttgccaaac agtccgttct ttttctcgcc aggaagttgg   7260
gcaatgaggt tctccagtcg tctgctcttc gagagtcgag cagacaagat ggcctttgca   7320
tcgactccgg aggcattgat ggggttttcc tcgaacagct ggttgtaggt ctgaacgagc   7380
tgaatgaaca gcttgtccac atcgctgttg tcgggattga gatcgccctc gatgaggaaa   7440
tgacctcgaa acttgatcat gtgtgccaga gcgaggtaga taagtctgag atccgccttg   7500
tcggtggaat cgacgagttt ctttcgcagg tggtagatgg taggatactt ctcgtggtaa   7560
gcaacctcgt ccacaatgtt gccaaagatg ggatgacgct cgtgtttctt gtcttcctcg   7620
acgaggaagg attcctccag tcgatgaaag aacgaatcgt ccaccttggc catctcgttg   7680
gaaaagatct cctgcaggta gcagattcgg ttcttccgtc gggtgtaacg tcgccgagca   7740
gttcgcttga gtctggtagc ttcggcagtc tcgccagaat cgaacaacag ggcaccaatg   7800
aggtttttct tgatggagtg tcgatcggtg tttccgagga ccttgaattt cttggagggc   7860
accttgtact cgtcggtgat gacagcccag ccgacagagt tggttccaat gtccaggccg   7920
atggagtatt tcttgtcgaa ttcccatatg gtaccagctg cagatctcga gctcggatcc   7980
ttatcgtcat cgtcgtacag atcccgaccc atttgctgtc caccagtcat gctagccata   8040
ccatgatgat gatgatgatg agaacccccc atggttaatt cctcctgtta gcccaaaaaa   8100
cgggtatgga gaaacagtag agagttgcga taaaaagcgt caggtaggat ccgctaatct   8160
tatggataaa aatgctatgg catagcaaag tgtgacgccg tgcaaataat caatgtggac   8220
ttttctgccg tgattataga cacttttgtt acgcgttttt gtcatggctt tggtcccgct   8280
ttgttacaga atgcttttaa taagcggggt taccggtttg gttagcgaga agagccagta   8340
aaagacgcag tgacggcaat gtctgatgca atatggacaa ttggtttctt ctctgaatgg   8400
cgggagtatg aaaagtatgg ctgaagcgca aaatgatccc ctgctgccgg gatactcgtt   8460
taatgcccat ctggtggcgg gtttaacgcc gattgaggcc aacggttatc tcgatttttt   8520
tatcgaccga ccgctgggaa tgaaaggtta tattctcaat ctcaccattc gcggtcaggg   8580
ggtggtgaaa aatcagggac gagaatttgt ttgccgaccg ggtgatattt tgctgttccc   8640
gccaggagag attcatcact acggtcgtca tccggaggct cgcgaatggt atcaccagtg   8700
ggtttacttt cgtccgcgcg cctactggca tgaatggctt aactggccgt caatatttgc   8760
caatacgggg ttctttcgcc cggatgaagc gcaccagccg catttcagcg acctgtttgg   8820
gcaaatcatt aacgccgggc aaggggaagg gcgctattcg gagctgctgg cgataaatct   8880
gcttgagcaa ttgttactgc ggcgcatgga agcgattaac gagtcgctcc atccaccgat   8940
ggataatcgg gtacgcgagg cttgtcagta catcagcgat cacctggcag acagcaattt   9000
tgatatcgcc agcgtcgcac agcatgtttg cttgtcgccg tcgcgtctgt cacatctttt   9060
ccgccagcag ttagggatta gcgtcttaag ctggcgcgag gaccaacgta tcagccaggc   9120
gaagctgctt ttgagcacca cccggatgcc tatcgccacc gtcggtcgca atgttggttt   9180
tgacgatcaa ctctatttct cgcgggtatt taaaaaatgc accggggcca gcccgagcga   9240
gttccgtgcc ggttgtgaag aaaaagtgaa tgatgtagcc gtcaagttgt cataattggt   9300
```

aacgaatcag acaattgacg gc 9322

<210> SEQ ID NO 110
<211> LENGTH: 9322
<212> TYPE: DNA
<213> ORGANISM: Artificial sequence
<220> FEATURE:
<223> OTHER INFORMATION: pRF861-cassette

<400> SEQUENCE: 110
ggtttattga ctaccggaag cagtgtgacc gtgtgcttct caaatgcctc aggctgtcta 60
tgtgtgactg ttgagctgta acaagttgtc tcaggtgttc aatttcatgt tctagttgct 120
ttgttttact ggtttcacct gttctattag gtgttacatg ctgttcatct gttacattgt 180
cgatctgttc atggtgaaca gctttaaatg caccaaaaac tcgtaaaagc tctgatgtat 240
ctatcttttt tacaccgttt tcatctgtgc atatggacag ttttcccttt gatatctaac 300
ggtgaacagt tgttctactt ttgtttgtta gtcttgatgc ttcactgata gatacaagag 360
ccataagaac ctcagatcct tccgtattta gccagtatgt tctctagtgt ggttcgttgt 420
ttttgcgtga gccatgagaa cgaaccattg agatcatgct tactttgcat gtcactcaaa 480
aattttgcct caaaactggt gagctgaatt tttgcagtta aagcatcgtg tagtgttttt 540
cttagtccgt tacgtaggta ggaatctgat gtaatggttg ttggtatttt gtcaccattc 600
atttttatct ggttgttctc aagttcggtt acgagatcca tttgtctatc tagttcaact 660
tggaaaatca acgtatcagt cgggcggcct cgcttatcaa ccaccaattt catattgctg 720
taagtgttta aatctttact tattggtttc aaaacccatt ggttaagcct tttaaactca 780
tggtagttat tttcaagcat taacatgaac ttaaattcat caaggctaat ctctatattt 840
gccttgtgag ttttcttttg tgttagttct tttaataacc actcataaat cctcatagag 900
tatttgtttt caaaagactt aacatgttcc agattatatt ttatgaattt ttttaactgg 960
aaaagataag gcaatatctc ttcactaaaa actaattcta atttttcgct tgagaacttg 1020
gcatagtttg tccactggaa aatctcaaag cctttaacca aaggattcct gatttccaca 1080
gttctcgtca tcagctctct ggttgcttta gctaatacac cataagcatt ttccctactg 1140
atgttcatca tctgagcgta ttggttataa gtgaacgata ccgtccgttc tttccttgta 1200
gggttttcaa tcgtggggtt gagtagtgcc acacagcata aaattagctt ggtttcatgc 1260
tccgttaagt catagcgact aatcgctagt tcatttgctt tgaaaacaac taattcagac 1320
atacatctca attggtctag gtgattttaa tcactatacc aattgagatg ggctagtcaa 1380
tgataattac tagtcctttt cctttgagtt gtgggtatct gtaaattctg ctagaccttt 1440
gctggaaaac ttgtaaattc tgctagaccc tctgtaaatt ccgctagacc tttgtgtgtt 1500
ttttttgttt atattcaagt ggttataatt tatagaataa agaaagaata aaaaaagata 1560
aaaagaatag atcccagccc tgtgtataac tcactacttt agtcagttcc gcagtattac 1620
aaaaggatgt cgcaaacgct gtttgctcct ctacaaaaca gaccttaaaa ccctaaaggc 1680
ttaagtagca ccctcgcaag ctcgggcaaa tcgctgaata ttccttttgt ctccgaccat 1740
caggcacctg agtcgctgtc tttttcgtga cattcagttc gctgcgctca cggctctggc 1800
agtgaatggg ggtaaatggc actacaggcg cctttttatgg attcatgcaa ggaaactacc 1860
cataatacaa gaaaagcccg tcacgggctt ctcagggcgt tttatggcgg gtctgctatg 1920
tggtgctatc tgactttttg ctgttcagca gttcctgccc tctgattttc cagtctgacc 1980

-continued

```
acttcggatt atcccgtgac aggtcattca gactggctaa tgcacccagt aaggcagcgg   2040
tatcatcaac aggcttaccc gtcttactgt cggatcgacg ctctccctta tgcgactcct   2100
gcatcccttt cgtcttcgaa taaatacctg tgacggaaga tcacttcgca gaataaataa   2160
atcctggtgt ccctgttgat accgggaagc cctgggccaa cttttggcga aaatgagacg   2220
ttgatcggca cgtaagaggt tccaactttc accataatga aataagatca ctaccgggcg   2280
tatttttga gttatcgaga ttttcaggag ctaaggaagc taaaatggag aaaaaaatca    2340
ctggatatac caccgttgat atatcccaat ggcatcgtaa agaacatttt gaggcatttc   2400
agtcagttgc tcaatgtacc tataaccaga ccgttcagct ggatattacg gcctttttaa   2460
agaccgtaaa gaaaaataag cacaagtttt atccggcctt tattcacatt cttgcccgcc   2520
tgatgaatgc tcatccggaa ttccgtatgg caatgaaaga cggtgagctg gtgatatggg   2580
atagtgttca cccttgttac accgttttcc atgagcaaac tgaaacgttt tcatcgctct   2640
ggagtgaata ccacgacgat ttccggcagt ttctacacat atattcgcaa gatgtggcgt   2700
gttacggtga aaacctggcc tatttcccta aagggtttat tgagaatatg tttttcgtct   2760
cagccaatcc ctgggtgagt ttcaccagtt ttgatttaaa cgtggccaat atggacaact   2820
tcttcgcccc cgttttcacc atgggcaaat attatacgca aggcgacaag gtgctgatgc   2880
cgctggcgat tcaggttcat catgccgttt gtgatggctt ccatgtcggc agaatgctta   2940
atgaattaca acagtactgc gatgagtggc agggcggggc gtaatttttt taaggcagtt   3000
attggtgccc ttaaacgcct ggtgctacgc ctgaataagt gataataagc ggatgaatgg   3060
cagaaattcg aaagcaaatt cgacccggtc gtcggttcag ggcagggtcg ttaaatagcc   3120
gcttatgtct attgctggtt tatcggtacc ccccaactga tcttcagcat cttttacttt   3180
caccagcgtt tctgggtgag caaaaacagg aaggcaaaat gccgcaaaaa agggaataag   3240
ggcgacacgg aaatgttgaa tactcatact cttccttttt caatattatt gaagcattta   3300
tcagggttat tgtctcatga gcggatacat atttgaatgt atttagaaaa ataaacaaaa   3360
gagtttgtag aaacgcaaaa aggccatccg tcaggatggc cttctgctta atttgatgcc   3420
tggcagttta tggcgggcgt cctgcccgcc accctccggg ccgttgcttc gcaacgttca   3480
aatccgctcc cggcggattt gtcctactca ggagagcgtt caccgacaaa caacagataa   3540
aacgaaaggc ccagtctttc gactgagcct ttcgttttat ttgatgcctg gcagttccct   3600
actctcgcat ggggagaccc cacactacca tcggcgctac ggcgtttcac ttctgagttc   3660
ggcatggggt caggtgggac caccgcgcta ctgccgccag gcaaattctg ttttatcaga   3720
ccgcttctgc gttctgattt aatctgtatc aggctgaaaa tcttctctca tccgccaaaa   3780
cagccaagct tagcggccgc ttagaccttt cgctttttct tgggatcggc tctggagtcg   3840
ccaccaagct gagacaggtc gattcgggtc tcgtacaggc cagtgatgga ctggtgaatc   3900
agggtggcat cgagaacctc cttggtggat gtgtaccgct ttcggtcgat agtggtatcg   3960
aagtacttga aagctgcagg agcacccagg ttggtaagag taaacaggtg aatgatgttc   4020
tccgcctgtt ctcgaatggg tttgtcccga tgcttgttgt aggcagagag caccttgtcc   4080
aagttggcat cagccaggat gactcgcttc gaaaactcgg aaatctgctc gataatctcg   4140
tcgaggtaat gtttgtgctg ctcaacgaag agttgcttct gttcgttgtc ctcgggagaa   4200
cccttgagct tctcgtagtg agaagccaga tagagaaagt tgacgtactt cgaaggcaag   4260
gcaagctcgt ttcccttctg cagctcgcca gcggaggcga gcatacgctt tcgaccgttc   4320
tccagttcga acagagagta cttgggcagc ttgataatga ggtctttctt gacctccttg   4380
```

-continued

```
taacccttgg cttccaagaa gtcgatggga ttcttctcga agctcgatcg ctccatgatg   4440
gtaattccga gcagctcctt gacggacttg agctttttgg acttgccctt ctcgaccttc   4500
gcaacgacaa gcacggaata ggcgacggta ggagaatcga agccaccgta tttcttggga   4560
tcccagtctt tctttcgagc gatgagcttg tcggagtttc gcttgggcag aatcgactcc   4620
ttggagaatc cgccagtctg aacctcggtt ttcttgacga tgttgacctg aggcatcgac   4680
agaacctttc gcacggttgc aaagtctcga cccttgtccc acacgatctc tccagtttcg   4740
ccgttggtct cgataagtgg tctctttcga atctctccgt tggccaaggt gatctcggtc   4800
ttgaaaaagt tcatgatgtt ggagtaaaag aagtacttgg cagtagcctt gccaatctcc   4860
tgttcggact tggcaatcat ctttcgaacg tcgtagacct tgtaatcgcc gtaaacgaac   4920
tcgctttcga gcttggggta tttcttgatg agcgcagtgc caacgacggc gttgaggtaa   4980
gcatcgtggg catggtggta attgttgatc tctcgcacct tgtagaactg aaagtccttt   5040
cggaaatcgg agaccagttt ggacttgaga gtaatcacct tgacctctcg gatgagcttg   5100
tcgttctcgt cgtacttggt gttcatccga gaatcgagaa tctgtgcgac gtgctttgtg   5160
atctgtctgg tctcgacgag ttgacgcttg atgaagccag ccttgtcgag ctcggacaga   5220
ccgcctcgct cggccttggt aagattgtcg aactttcgct gggtaatgag cttggcgttg   5280
agcagctgtc gccagtagtt cttcatcttt ttgaccacct cttcgctggg aacgttgtcc   5340
gacttgcctc tgttcttgtc ggatcgtgta aggaccttgt tgtcgataga atcgtccttg   5400
agaaaggatt gagggacaat gtggtccaca tcgtagtcgc tgagacgatt gatgtccagt   5460
tcctgatcca cgtacatgtc tcgaccattc tgcagatagt agagatacag cttctcgttc   5520
tgcagttgag tgttctcgac gggatgctcc ttgagaatct gggatcccag ctccttgatg   5580
ccttcctcga ttcgcttcat ccgctctcgc gagtttttct gacccttttg agttgtctgg   5640
ttctctctgg ccatctcgat cacaatgttc tcgggcttgt gacgtcccat gaccttcacc   5700
agctcgtcga caaccttgac agtctggaga atgcctttct tgatggctgg cgaaccagcc   5760
aggttggcaa tatgttcgtg caagctgtcg ccctgaccgg acacttgtgc cttctggatg   5820
tcctccttga aggtaagaga atcgtcgtga atgagctgca tgaagtttcg gttggcaaag   5880
ccatcggact tgagaaagtc cagaatggtc tttccggact gcttgtctct gatgccgttg   5940
atgagctttc gcgaaagtct tccccagccg gtgtatctac gtcgcttgag ttgtttcatg   6000
accttgtcgt cgaacaggtg agcgtatgtc ttgagtcgtt cctcgatcat ctcccgatct   6060
tcgaacaggg taagagtgag cacgatgtcc tccagaatgt cctcgttttc ctcgttgtcg   6120
agaaaatcct tgtccttgat aatcttgagc agatcgtgat aggtgcccaa agaggcgttg   6180
aatcggtcct caactccgga aatctcgacg ctgtcgaaac actcgatttt cttgaagtag   6240
tcctccttga gctgcttaac agtgaccttt cggttggtct tgaacaggag atcgacaatg   6300
gctttcttct gttcgccaga caagaaggca ggctttcgca ttccctcggt aacgtacttg   6360
actttggtga gttcgttgta gactgtaaag tactcgtaga gcagcgaatg cttgggaaga   6420
accttctcgt tgggcagatt cttgtcgaag ttggtcattc gctcgatgaa ggactgtgca   6480
gaggcaccct tgtccacgac ttcctcgaag ttccagggag tgatggtttc ctcggacttt   6540
cgagtcatcc aagcaaatcg agagtttcct ctggcaagag gaccaacata gtaggggatt   6600
cgaaaggtaa gaatcttctc gatcttctct cggttgtcct tgagaaaggg gtagaagtct   6660
tcctgacgtc gaagaatggc gtgcagctca ccgaggtgga tctgatgagg aatgctgccg   6720
```

-continued

```
ttgtcgaagg ttcgttgctt ccgaagcaga tcctctcgat tgagcttgac aagcagttcc   6780
tcggttccgt ccatcttctc gagaattggc ttgatgaact tgtagaactc ttcctgagag   6840
gctccgccgt cgatgtatcc agcgtagccg ttcttcgact gatcgaaaaa gatctccttg   6900
tacttctcgg gcagttgctg tcggacaaga gccttgagca gtgtgagatc ctgatggtgc   6960
tcgtcgtatc gcttgatcat ggaggcagaa aggggagcct ttgtgatctc ggtgttgact   7020
cgcagaatgt cagacaagag aatagcatcc gaaaggttct tggcagcgag aaacaggtcg   7080
gcgtactgat cgccaatctg tgcaagcagg ttgtcgaggt catcgtcgta ggtgtccttg   7140
gacagctgga gcttggcgtc ctccgccaga tcgaagttgg acttgaagtt gggtgtgaga   7200
ccaagagaaa gggcaatgag gttgccaaac agtccgttct tttctcgcc aggaagttgg   7260
gcaatgaggt tctccagtcg tctgctcttc gagagtcgag cagacaagat ggcctttgca   7320
tcgactccgg aggcattgat ggggttttcc tcgaacagct ggttgtaggt ctgaacgagc   7380
tgaatgaaca gcttgtccac atcgctgttg tcgggattga gatcgccctc gatgaggaaa   7440
tgacctcgaa acttgatcat gtgtgccaga gcgagatgga taagtctgag atccgccttg   7500
tcggtggaat cgacgagttt ctttcgcagg tggtagatgg taggatactt ctcgtggtaa   7560
gcaacctcgt ccacaatgtt gccaaagatg ggatgacgct cgtgtttctt gtcttcctcg   7620
acgaggaagg attcctccag tcgatgaaag aacgaatcgt ccaccttggc catctcgttg   7680
gaaaagatct cctgcaggta gcagattcgg ttcttccgtc gggtgtaacg tcgccgagca   7740
gttcgcttga gtctggtagc ttcggcagtc tcgccagaat cgaacaacag ggcaccaatg   7800
aggtttttct tgatggagtg tcgatcggtg tttccgagga ccttgaattt cttggagggc   7860
accttgtact cgtcggtgat gacagcccag ccgacagagt tggttccaat gtccaggccg   7920
atggagtatt tcttgtcgaa ttcccatatg gtaccagctg cagatctcga gctcggatcc   7980
ttatcgtcat cgtcgtacag atcccgaccc atttgctgtc caccagtcat gctagccata   8040
ccatgatgat gatgatgatg agaacccccc atggttaatt cctcctgtta gcccaaaaaa   8100
cgggtatgga gaaacagtag agagttgcga taaaaagcgt caggtaggat ccgctaatct   8160
tatggataaa aatgctatgg catagcaaag tgtgacgccg tgcaaataat caatgtggac   8220
ttttctgccg tgattataga cacttttgtt acgcgttttt gtcatggctt tggtcccgct   8280
ttgttacaga atgcttttaa taagcggggt taccggtttg gttagcgaga agagccagta   8340
aaagacgcag tgacggcaat gtctgatgca atatggacaa ttggtttctt ctctgaatgg   8400
cgggagtatg aaaagtatgg ctgaagcgca aaatgatccc ctgctgccgg gatactcgtt   8460
taatgcccat ctggtggcgg gtttaacgcc gattgaggcc aacggttatc tcgatttttt   8520
tatcgaccga ccgctgggaa tgaaaggtta tattctcaat ctcaccattc gcggtcaggg   8580
ggtggtgaaa aatcagggac gagaatttgt ttgccgaccg ggtgatattt tgctgttccc   8640
gccaggagag attcatcact acggtcgtca tccggaggct cgcgaatggt atcaccagtg   8700
ggtttacttt cgtccgcgcg cctactggca tgaatggctt aactggccgt caatatttgc   8760
caatacgggg ttctttcgcc cggatgaagc gcaccagccg catttcagcg acctgtttgg   8820
gcaaatcatt aacgccgggc aaggggaagg gcgctattcg gagctgctgg cgataaatct   8880
gcttgagcaa ttgttactgc ggcgcatgga agcgattaac gagtcgctcc atccaccgat   8940
ggataatcgg gtacgcgagg cttgtcagta catcagcgat cacctggcag acagcaattt   9000
tgatatcgcc agcgtcgcac agcatgtttg cttgtcgccg tcgcgtctgt cacatctttt   9060
ccgccagcag ttagggatta gcgtcttaag ctggcgcgag gaccaacgta tcagccaggc   9120
```

```
gaagctgctt ttgagcacca cccggatgcc tatcgccacc gtcggtcgca atgttggttt   9180

tgacgatcaa ctctatttct cgcgggtatt taaaaaatgc accggggcca gcccgagcga   9240

gttccgtgcc ggttgtgaag aaaaagtgaa tgatgtagcc gtcaagttgt cataattggt   9300

aacgaatcag acaattgacg gc                                            9322
```

<210> SEQ ID NO 111
<211> LENGTH: 21
<212> TYPE: DNA
<213> ORGANISM: Artificial sequence
<220> FEATURE:
<223> OTHER INFORMATION: primer

<400> SEQUENCE: 111

```
ggtttattga ctaccggaag c                                               21
```

<210> SEQ ID NO 112
<211> LENGTH: 20
<212> TYPE: DNA
<213> ORGANISM: Artificial sequence
<220> FEATURE:
<223> OTHER INFORMATION: primer

<400> SEQUENCE: 112

```
gccgtcaatt gtctgattcg                                                 20
```

<210> SEQ ID NO 113
<211> LENGTH: 10569
<212> TYPE: DNA
<213> ORGANISM: Artificial sequence
<220> FEATURE:
<223> OTHER INFORMATION: pRF97-nacETsite1 plasmid

<400> SEQUENCE: 113

```
ccctttcgtc ttcgaataaa tacctgtgac ggaagatcac ttcgcagaat aaataaatcc     60

tggtgtccct gttgataccg ggaagccctg ggccaacttt tggcgaaaat gagacgttga    120

tcggcacgta agaggttcca actttcacca taatgaaata agatcactac cgggcgtatt    180

ttttgagtta tcgagatttt caggagctaa ggaagctaaa atggagaaaa aaatcactgg    240

atataccacc gttgatatat cccaatggca tcgtaaagaa cattttgagg catttcagtc    300

agttgctcaa tgtacctata accagaccgt tcagctggat attacggcct ttttaaagac    360

cgtaaagaaa aataagcaca agttttatcc ggcctttatt cacattcttg cccgcctgat    420

gaatgctcat ccggaattcc gtatggcaat gaaagacggt gagctggtga tatgggatag    480

tgttcaccct tgttacaccg ttttccatga gcaaactgaa acgttttcat cgctctggag    540

tgaataccac gacgatttcc ggcagtttct acacatatat tcgcaagatg tggcgtgtta    600

cggtgaaaac ctggcctatt tccctaaagg gtttattgag aatatgtttt tcgtctcagc    660

caatccctgg gtgagtttca ccagttttga tttaaacgtg gccaatatgg acaacttctt    720

cgcccccgtt ttcaccatgg gcaaatatta tacgcaaggc gacaaggtgc tgatgccgct    780

ggcgattcag gttcatcatg ccgtttgtga tggcttccat gtcggcagaa tgcttaatga    840

attacaacag tactgcgatg agtggcaggg cggggcgtaa tttttttaag gcagttattg    900

gtgcccttaa acgcctggtg ctacgcctga ataagtgata ataagcggat gaatggcaga    960

aattcgaaag caaattcgac ccggtcgtcg gttcagggca gggtcgttaa atagccgctt   1020

atgtctattg ctggtttatc ggtacccccc aactgatctt cagcatcttt tactttcacc   1080
```

-continued

```
agcgtttctg ggtgagcaaa aacaggaagg caaaatgccg caaaaaaggg aataagggcg   1140
acacggaaat gttgaatact catactcttc ctttttcaat attattgaag catttatcag   1200
ggttattgtc tcatgagcgg atacatattt gaatgtattt agaaaaataa acaaaagagt   1260
ttgtagaaac gcaaaaaggc catccgtcag gatggccttc tgcttaattt gatgcctggc   1320
agtttatggc gggcgtcctg cccgccaccc tccgggccgt tgcttcgcaa cgttcaaatc   1380
cgctcccggc ggatttgtcc tactcaggag agcgttcacc gacaaacaac agataaaacg   1440
aaaggcccag tctttcgact gagcctttcg ttttatttga tgcctggcag ttccctactc   1500
tcgcatgggg agaccccaca ctaccatcgg cgctacggcg tttcacttct gagttcggca   1560
tggggtcagg tgggaccacc gcgctactgc cgccaggcaa attctgtttt atcagaccgc   1620
ttctgcgttc tgatttaatc tgtatcaggc tgaaaatctt ctctcatccg ccaaaacagc   1680
caagcttagc ggccgcttag acctttcgct tttcttggg atcggctctg gagtcgccac    1740
caagctgaga caggtcgatt cgggtctcgt acaggccagt gatggactgg tgaatcaggg   1800
tggcatcgag aacctccttg gtggatgtgt accgctttcg gtcgatagtg gtatcgaagt   1860
acttgaaagc tgcaggagca cccaggttgg taagagtaaa caggtgaatg atgttctccg   1920
cctgttctcg aatgggtttg tcccgatgct tgttgtaggc agagagcacc ttgtccaagt   1980
tggcatcagc caggatgact cgcttcgaaa actcggaaat ctgctcgata atctcgtcga   2040
ggtaatgttt gtgctgctca acgaagagtt gcttctgttc gttgtcctcg ggagaaccct   2100
tgagcttctc gtagtgagaa gccagataga gaaagttgac gtacttcgaa ggcaaggcaa   2160
gctcgtttcc cttctgcagc tcgccagcgg aggcgagcat acgctttcga ccgttctcca   2220
gttcgaacag agagtacttg ggcagcttga taatgaggtc tttcttgacc tccttgtaac   2280
ccttggcttc caagaagtcg atgggattct tctcgaagct cgatcgctcc atgatggtaa   2340
ttccgagcag ctccttgacg gacttgagct tttggactt gcccttctcg accttcgcaa    2400
cgacaagcac ggaataggcg acggtaggag aatcgaagcc accgtatttc ttgggatccc   2460
agtctttctt tcgagcgatg agcttgtcgg agtttcgctt gggcagaatc gactccttgg   2520
agaatccgcc agtctgaacc tcggttttct tgacgatgtt gacctgaggc atcgacagaa   2580
cctttcgcac ggttgcaaag tctcgaccct tgtcccacac gatctctcca gtttcgccgt   2640
tggtctcgat aagtggtctc tttcgaatct ctccgttggc caaggtgatc tcggtcttga   2700
aaaagttcat gatgttggag taaaagaagt acttggcagt agccttgcca atctcctgtt   2760
cggacttggc aatcatcttt cgaacgtcgt agaccttgta atcgccgtaa acgaactcgc   2820
tttcgagctt ggggtatttc ttgatgagcg cagtgccaac gacggcgttg aggtaagcat   2880
cgtgggcatg gtggtaattg ttgatctctc gcaccttgta gaactgaaag tcctttcgga   2940
aatcggagac cagtttggac ttgagagtaa tcaccttgac ctctcggatg agcttgtcgt   3000
tctcgtcgta cttggtgttc atccgagaat cgagaatctg tgcgacgtgc tttgtgatct   3060
gtctggtctc gacgagttga cgcttgatga agccagcctt gtcgagctcg gacagaccgc   3120
ctcgctcggc cttggtaaga ttgtcgaact ttcgctgggt aatgagcttg gcgttgagca   3180
gctgtcgcca gtagttcttc atctttttga ccacctcttc gctgggaacg ttgtccgact   3240
tgcctctgtt cttgtcggat cgtgtaagga ccttgttgtc gatagaatcg tccttgagaa   3300
aggattgagg gacaatgtgg tccacatcgt agtcgctgag acgattgatg tccagttcct   3360
gatccacgta catgtctcga ccattctgca gatagtagag atacagcttc tcgttctgca   3420
gttgagtgtt ctcgacggga tgctccttga gaatctggga tcccagctcc ttgatgcctt   3480
```

cctcgattcg cttcatccgc tctcgcgagt ttttctgacc cttttgagtt gtctggttct 3540
ctctggccat ctcgatcaca atgttctcgg gcttgtgacg tcccatgacc ttcaccagct 3600
cgtcgacaac cttgacagtc tggagaatgc ctttcttgat ggctggcgaa ccagccaggt 3660
tggcaatatg ttcgtgcaag ctgtcgccct gaccggacac ttgtgccttc tggatgtcct 3720
ccttgaaggt aagagaatcg tcgtgaatga gctgcatgaa gtttcggttg gcaaagccat 3780
cggacttgag aaagtccaga atggtctttc cggactgctt gtctctgatg ccgttgatga 3840
gctttcgcga aagtcttccc cagccggtgt atctacgtcg cttgagttgt ttcatgacct 3900
tgtcgtcgaa caggtgagcg tatgtcttga gtcgttcctc gatcatctcc cgatcttcga 3960
acagggtaag agtgagcacg atgtcctcca gaatgtcctc gttttcctcg ttgtcgagaa 4020
aatccttgtc cttgataatc ttgagcagat cgtgataggt gcccaaagag gcgttgaatc 4080
ggtcctcaac tccggaaatc tcgacgctgt cgaaacactc gattttcttg aagtagtcct 4140
ccttgagctg cttaacagtg acctttcggt tggtcttgaa caggagatcg acaatggctt 4200
tcttctgttc gccagacaag aaggcaggct ttcgcattcc ctcggtaacg tacttgactt 4260
tggtgagttc gttgtagact gtaaagtact cgtagagcag cgaatgcttg ggaagaacct 4320
tctcgttggg cagattcttg tcgaagttgg tcattcgctc gatgaaggac tgtgcagagg 4380
cacccttgtc cacgacttcc tcgaagttcc agggagtgat ggtttcctcg gactttcgag 4440
tcatccaagc aaatcgagag tttcctctgg caagaggacc aacatagtag ggattcgaa 4500
aggtaagaat cttctcgatc ttctctcggt tgtccttgag aaaggggtag aagtcttcct 4560
gacgtcgaag aatggcgtgc agctcaccga ggtggatctg atgaggaatg ctgccgttgt 4620
cgaaggttcg ttgcttccga agcagatcct ctcgattgag cttgacaagc agttcctcgg 4680
ttccgtccat cttctcgaga attggcttga tgaacttgta gaactcttcc tgagaggctc 4740
cgccgtcgat gtatccagcg tagccgttct tcgactgatc gaaaaagatc tccttgtact 4800
tctcgggcag ttgctgtcgg acaagagcct tgagcagtgt gagatcctga tggtgctcgt 4860
cgtatcgctt gatcatggag gcagaaaggg gagcctttgt gatctcggtg ttgactcgca 4920
gaatgtcaga caagagaata gcatccgaaa ggttcttggc agcgagaaac aggtcggcgt 4980
actgatcgcc aatctgtgca agcaggttgt cgaggtcatc gtcgtaggtg tccttggaca 5040
gctggagctt ggcgtcctcc gccagatcga agttggactt gaagttgggt gtgagaccaa 5100
gagaaagggc aatgaggttg ccaaacagtc cgttcttttt ctcgccagga agttgggcaa 5160
tgaggttctc cagtcgtctg ctcttcgaga gtcgagcaga caagatggcc tttgcatcga 5220
ctccggaggc attgatgggg ttttcctcga acagctggtt gtaggtctga acgagctgaa 5280
tgaacagctt gtccacatcg ctgttgtcgg gattgagatc gccctcgatg aggaaatgac 5340
ctcgaaactt gatcatgtgt gccagagcga ggtagataag tctgagatcc gccttgtcgg 5400
tggaatcgac gagtttcttt cgcaggtggt agatggtagg atacttctcg tggtaagcaa 5460
cctcgtccac aatgttgcca aagatgggat gacgctcgtg tttcttgtct tcctcgacga 5520
ggaaggattc ctccagtcga tgaaagaacg aatcgtccac cttggccatc tcgttggaaa 5580
agatctcctg caggtagcag attcggttct tccgtcgggt gtaacgtcgc cgagcagttc 5640
gcttgagtct ggtagcttcg gcagtctcgc cagaatcgaa caacagggca ccaatgaggt 5700
ttttcttgat ggagtgtcga tcggtgtttc cgaggacctt gaatttcttg gagggcacct 5760
tgtactcgtc ggtgatgaca gcccagccga cagagttggt tccaatgtcc aggccgatgg 5820
agtatttctt gtcgaattcc catatggtac cagctgcaga tctcgagctc ggatccttat 5880
cgtcatcgtc gtacagatcc cgacccattt gctgtccacc agtcatgcta gccataccat 5940
gatgatgatg atgatgagaa ccccccatgg ttaattcctc ctgttagccc aaaaaacggg 6000
tatggagaaa cagtagagag ttgcgataaa aagcgtcagg taggatccgc taatcttatg 6060
gataaaaatg ctatggcata gcaaagtgtg acgccgtgca aataatcaat gtggactttt 6120
ctgccgtgat tatagacact tttgttacgc gtttttgtca tggctttggt cccgctttgt 6180
tacagaatgc ttttaataag cggggttacc ggtttggtta gcgagaagag ccagtaaaag 6240
acgcagtgac ggcaatgtct gatgcaatat ggacaattgg tttcttctct gaatggcggg 6300
agtatgaaaa gtatggctga agcgcaaaat gatcccctgc tgccgggata ctcgtttaat 6360
gcccatctgg tggcgggttt aacgccgatt gaggccaacg gttatctcga ttttttttatc 6420
gaccgaccgc tgggaatgaa aggttatatt ctcaatctca ccattcgcgg tcagggggtg 6480
gtgaaaaatc agggacgaga atttgtttgc cgaccgggtg atattttgct gttcccgcca 6540
ggagagattc atcactacgg tcgtcatccg gaggctcgcg aatggtatca ccagtgggtt 6600
tactttcgtc cgcgcgccta ctggcatgaa tggcttaact ggccgtcaat atttgccaat 6660
acggggttct ttcgcccgga tgaagcgcac cagccgcatt tcagcgacct gtttgggcaa 6720
atcattaacg ccgggcaagg ggaagggcgc tattcggagc tgctggcgat aaatctgctt 6780
gagcaattgt tactgcggcg catggaagcg attaacgagt cgctccatcc accgatggat 6840
aatcgggtac gcgaggcttg tcagtacatc agcgatcacc tggcagacag caattttgat 6900
atcgccagcg tcgcacagca tgtttgcttg tcgccgtcgc gtctgtcaca tcttttccgc 6960
cagcagttag ggattagcgt cttaagctgg cgcgaggacc aacgtatcag ccaggcgaag 7020
ctgcttttga gcaccacccg gatgcctatc gccaccgtcg gtcgcaatgt tggttttgac 7080
gatcaactct atttctcgcg ggtatttaaa aaatgcaccg ggccagcccc gagcgagttc 7140
cgtgccggtt gtgaagaaaa agtgaatgat gtagccgtca agttgtcata attggtaacg 7200
aatcagacaa ttgacggccg tcccctggat tagctcgagc cgaacctccg ggaaaagttc 7260
gcgaaaagct ttaatgacct ctggcaagct ataacgtgcc tgagtatgcg tcgttgcaat 7320
agtgagaacg ccagacgtat cgttggtaaa caggtctgca agccgacgaa cattactggc 7380
ttcattcaga atacgttctg caatgaccag taatgctttg cccggttcag tcatgcccag 7440
cagtcgctta cctcgtcgaa caaatatttc gatgccaagt tcatcctcca gttcccgaat 7500
atgacggctg acgcctgact gtgaggtaaa aagcatattc gcaacctctg tcaggttgta 7560
atcctgacgt gcagcctcgc ggattatctt tagttgttgg aaattcacgg taaactccgg 7620
gcagttcaga tttcccgtta ttgttaaagt ctaatgcccg gcataacaaa taataaaaac 7680
ccgcatctta ttccatcccg atataacact tagctcacga agttcatgtt gcctccggtt 7740
tttaagaatc ggcccaagtg ccgccattac ttacaaccag attgcaagat gcttgccagt 7800
tttattttgg tgttgatgta caagctaacc aactgtcaaa taagagatta tgatagattc 7860
gtcatttgct cctttaatca gctgtcgcgt tcccctgccc tataaaagga gggtatgcac 7920
cacgatggtt cattacccaa taagattgaa agctcaccac tttgttgaaa ttgacagcaa 7980
acaaacaaaa aaatgcattt caccctttga catcaccatg cactgccatt aatatgcgcc 8040
ccgttcacac gattcctctg tagttcagtc ggtagaacgg cggactgtta atccgtatgt 8100
cactggttcg agtccagtca gaggagccaa attcaaaaaa gcctgctttc tagcaggctt 8160
tttgctttct aattaccaac gctcttaaaa catctgtctt gaaccagaac taatttgcaa 8220
gaatcataaa aaatttattt gctttcagga aaatttttct gtataataga ttcatatgca 8280
atacttcagc agccgtttta gagctagaaa tagcaagtta aaataaggct agtccgttat 8340
caacttgaaa aagtggcacc gagtcggtgc gactcctgtt gatagatcca gtaatgacct 8400
cagaactcca tctggatttg ttcagaacgc tcggttgccg ccgggcgttt tttattggtg 8460
agaatggttt attgactacc ggaagcagtg tgaccgtgtg cttctcaaat gcctcaggct 8520
gtctatgtgt gactgttgag ctgtaacaag ttgtctcagg tgttcaattt catgttctag 8580
ttgctttgtt ttactggttt cacctgttct attaggtgtt acatgctgtt catctgttac 8640
attgtcgatc tgttcatggt gaacagcttt aaatgcacca aaaactcgta aaagctctga 8700
tgtatctatc tttttacac cgttttcatc tgtgcatatg gacagttttc cctttgatat 8760
ctaacggtga acagttgttc tacttttgtt tgttagtctt gatgcttcac tgatagatac 8820
aagagccata agaacctcag atccttccgt atttagccag tatgttctct agtgtggttc 8880
gttgtttttg cgtgagccat gagaacgaac cattgagatc atgcttactt tgcatgtcac 8940
tcaaaaattt tgcctcaaaa ctggtgagct gaatttttgc agttaaagca tcgtgtagtg 9000
tttttcttag tccgttacgt aggtaggaat ctgatgtaat ggttgttggt attttgtcac 9060
cattcatttt tatctggttg ttctcaagtt cggttacgag atccatttgt ctatctagtt 9120
caacttggaa aatcaacgta tcagtcgggc ggcctcgctt atcaaccacc aatttcatat 9180
tgctgtaagt gtttaaatct ttacttattg gtttcaaaac ccattggtta agccttttaa 9240
actcatggta gttattttca agcattaaca tgaacttaaa ttcatcaagg ctaatctcta 9300
tatttgcctt gtgagttttc ttttgtgtta gttcttttaa taaccactca taaatcctca 9360
tagagtattt gttttcaaaa gacttaacat gttccagatt atattttatg aattttttta 9420
actggaaaag ataaggcaat atctcttcac taaaaactaa ttctaatttt tcgcttgaga 9480
acttggcata gtttgtccac tggaaaatct caaagccttt aaccaaagga ttcctgattt 9540
ccacagttct cgtcatcagc tctctggttg ctttagctaa tacaccataa gcattttccc 9600
tactgatgtt catcatctga gcgtattggt tataagtgaa cgataccgtc cgttctttcc 9660
ttgtagggtt ttcaatcgtg gggttgagta gtgccacaca gcataaaatt agcttggttt 9720
catgctccgt taagtcatag cgactaatcg ctagttcatt tgctttgaaa acaactaatt 9780
cagacataca tctcaattgg tctaggtgat tttaatcact ataccaattg agatgggcta 9840
gtcaatgata attactagtc cttttccttt gagttgtggg tatctgtaaa ttctgctaga 9900
cctttgctgg aaaacttgta aattctgcta gaccctctgt aaattccgct agacctttgt 9960
gtgttttttt tgtttatatt caagtggtta taatttatag aataaagaaa gaataaaaaa 10020
agataaaaag aatagatccc agccctgtgt ataactcact actttagtca gttccgcagt 10080
attacaaaag gatgtcgcaa acgctgtttg ctcctctaca aaacagacct taaaacccta 10140
aaggcttaag tagcaccctc gcaagctcgg gcaaatcgct gaatattcct tttgtctccg 10200
accatcaggc acctgagtcg ctgtcttttt cgtgacattc agttcgctgc gctcacggct 10260
ctggcagtga atgggggtaa atggcactac aggcgccttt tatggattca tgcaaggaaa 10320
ctacccataa tacaagaaaa gcccgtcacg ggcttctcag ggcgttttat ggcgggtctg 10380
ctatgtggtg ctatctgact tttgctgtt cagcagttcc tgccctctga ttttccagtc 10440
tgaccacttc ggattatccc gtgacaggtc attcagactg gctaatgcac ccagtaaggc 10500
agcggtatca tcaacaggct tacccgtctt actgtcggat cgacgctctc ccttatgcga 10560
ctcctgcat 10569

<210> SEQ ID NO 114
<211> LENGTH: 10569
<212> TYPE: DNA
<213> ORGANISM: Artificial sequence
<220> FEATURE:
<223> OTHER INFORMATION: pRF97-nacETsite2 plasmid

<400> SEQUENCE: 114
ccctttcgtc ttcgaataaa tacctgtgac ggaagatcac ttcgcagaat aaataaatcc 60
tggtgtccct gttgataccg ggaagccctg ggccaacttt tggcgaaaat gagacgttga 120
tcggcacgta agaggttcca actttcacca taatgaaata agatcactac cgggcgtatt 180
ttttgagtta tcgagatttt caggagctaa ggaagctaaa atggagaaaa aaatcactgg 240
atataccacc gttgatatat cccaatggca tcgtaaagaa cattttgagg catttcagtc 300
agttgctcaa tgtacctata accagaccgt tcagctggat attacggcct ttttaaagac 360
cgtaaagaaa aataagcaca agttttatcc ggcctttatt cacattcttg cccgcctgat 420
gaatgctcat ccggaattcc gtatggcaat gaaagacggt gagctggtga tatgggatag 480
tgttcaccct tgttacaccg ttttccatga gcaaactgaa acgttttcat cgctctggag 540
tgaataccac gacgatttcc ggcagtttct acacatatat tcgcaagatg tggcgtgtta 600
cggtgaaaac ctggcctatt tccctaaagg gtttattgag aatatgtttt tcgtctcagc 660
caatccctgg gtgagtttca ccagttttga tttaaacgtg gccaatatgg acaacttctt 720
cgcccccgtt ttcaccatgg gcaaatatta tacgcaaggc gacaaggtgc tgatgccgct 780
ggcgattcag gttcatcatg ccgtttgtga tggcttccat gtcggcagaa tgcttaatga 840
attacaacag tactgcgatg agtggcaggg cggggcgtaa tttttttaag gcagttattg 900
gtgcccttaa acgcctggtg ctacgcctga ataagtgata ataagcggat gaatggcaga 960
aattcgaaag caaattcgac ccggtcgtcg gttcagggca gggtcgttaa atagccgctt 1020
atgtctattg ctggtttatc ggtacccccc aactgatctt cagcatcttt tactttcacc 1080
agcgtttctg ggtgagcaaa aacaggaagg caaaatgccg caaaaaaggg aataagggcg 1140
acacggaaat gttgaatact catactcttc ctttttcaat attattgaag catttatcag 1200
ggttattgtc tcatgagcgg atacatattt gaatgtattt agaaaaataa acaaaagagt 1260
ttgtagaaac gcaaaaaggc catccgtcag gatggccttc tgcttaattt gatgcctggc 1320
agtttatggc gggcgtcctg cccgccaccc tccgggccgt tgcttcgcaa cgttcaaatc 1380
cgctcccggc ggatttgtcc tactcaggag agcgttcacc gacaaacaac agataaaacg 1440
aaaggcccag tctttcgact gagcctttcg ttttatttga tgcctggcag ttccctactc 1500
tcgcatgggg agaccccaca ctaccatcgg cgctacggcg tttcacttct gagttcggca 1560
tggggtcagg tgggaccacc gcgctactgc cgccaggcaa attctgtttt atcagaccgc 1620
ttctgcgttc tgatttaatc tgtatcaggc tgaaaatctt ctctcatccg ccaaaacagc 1680
caagcttagc ggccgcttag acctttcgct tttcttggg atcggctctg gagtcgccac 1740
caagctgaga caggtcgatt cgggtctcgt acaggccagt gatggactgg tgaatcaggg 1800
tggcatcgag aacctccttg gtggatgtgt accgctttcg gtcgatagtg gtatcgaagt 1860
acttgaaagc tgcaggagca cccaggttgg taagagtaaa caggtgaatg atgttctccg 1920
cctgttctcg aatgggtttg tcccgatgct tgttgtaggc agagagcacc ttgtccaagt 1980
tggcatcagc caggatgact cgcttcgaaa actcggaaat ctgctcgata atctcgtcga 2040
ggtaatgttt gtgctgctca acgaagagtt gcttctgttc gttgtcctcg ggagaaccct 2100
tgagcttctc gtagtgagaa gccagataga gaaagttgac gtacttcgaa ggcaaggcaa 2160
gctcgtttcc cttctgcagc tcgccagcgg aggcgagcat acgctttcga ccgttctcca 2220
gttcgaacag agagtacttg ggcagcttga taatgaggtc tttcttgacc tccttgtaac 2280
ccttggcttc caagaagtcg atgggattct tctcgaagct cgatcgctcc atgatggtaa 2340
ttccgagcag ctccttgacg gacttgagct tttggactt gcccttctcg accttcgcaa 2400
cgacaagcac ggaataggcg acggtaggag aatcgaagcc accgtatttc ttgggatccc 2460
agtctttctt tcgagcgatg agcttgtcgg agtttcgctt gggcagaatc gactccttgg 2520
agaatccgcc agtctgaacc tcggttttct tgacgatgtt gacctgaggc atcgacagaa 2580
cctttcgcac ggttgcaaag tctcgaccct tgtcccacac gatctctcca gtttcgccgt 2640
tggtctcgat aagtggtctc tttcgaatct ctccgttggc caaggtgatc tcggtcttga 2700
aaaagttcat gatgttggag taaaagaagt acttggcagt agccttgcca atctcctgtt 2760
cggacttggc aatcatcttt cgaacgtcgt agaccttgta atcgccgtaa acgaactcgc 2820
tttcgagctt ggggtatttc ttgatgagcg cagtgccaac gacggcgttg aggtaagcat 2880
cgtgggcatg gtggtaattg ttgatctctc gcaccttgta gaactgaaag tcctttcgga 2940
aatcggagac cagtttggac ttgagagtaa tcaccttgac ctctcggatg agcttgtcgt 3000
tctcgtcgta cttggtgttc atccgagaat cgagaatctg tgcgacgtgc tttgtgatct 3060
gtctggtctc gacgagttga cgcttgatga agccagcctt gtcgagctcg gacagaccgc 3120
ctcgctcggc cttggtaaga ttgtcgaact ttcgctgggt aatgagcttg gcgttgagca 3180
gctgtcgcca gtagttcttc atctttttga ccacctcttc gctgggaacg ttgtccgact 3240
tgcctctgtt cttgtcggat cgtgtaagga ccttgttgtc gatagaatcg tccttgagaa 3300
aggattgagg gacaatgtgg tccacatcgt agtcgctgag acgattgatg tccagttcct 3360
gatccacgta catgtctcga ccattctgca gatagtagag atacagcttc tcgttctgca 3420
gttgagtgtt ctcgacggga tgctccttga gaatctggga tcccagctcc ttgatgcctt 3480
cctcgattcg cttcatccgc tctcgcgagt tttctgacc cttttgagtt gtctggttct 3540
ctctggccat ctcgatcaca atgttctcgg gcttgtgacg tcccatgacc ttcaccagct 3600
cgtcgacaac cttgacagtc tggagaatgc ctttcttgat ggctggcgaa ccagccaggt 3660
tggcaatatg ttcgtgcaag ctgtcgccct gaccggacac ttgtgccttc tggatgtcct 3720
ccttgaaggt aagagaatcg tcgtgaatga gctgcatgaa gtttcggttg gcaaagccat 3780
cggacttgag aaagtccaga atggtctttc cggactgctt gtctctgatg ccgttgatga 3840
gctttcgcga aagtcttccc cagccggtgt atctacgtcg cttgagttgt ttcatgacct 3900
tgtcgtcgaa caggtgagcg tatgtcttga gtcgttcctc gatcatctcc cgatcttcga 3960
acagggtaag agtgagcacg atgtcctcca gaatgtcctc gttttcctcg ttgtcgagaa 4020
aatccttgtc cttgataatc ttgagcagat cgtgataggt gcccaaagag gcgttgaatc 4080
ggtcctcaac tccggaaatc tcgacgctgt cgaaacactc gattttcttg aagtagtcct 4140
ccttgagctg cttaacagtg acctttcggt tggtcttgaa caggagatcg acaatggctt 4200
tcttctgttc gccagacaag aaggcaggct ttcgcattcc ctcggtaacg tacttgactt 4260
tggtgagttc gttgtagact gtaaagtact cgtagagcag cgaatgcttg ggaagaacct 4320
tctcgttggg cagattcttg tcgaagttgg tcattcgctc gatgaaggac tgtgcagagg 4380

-continued

```
caccottgtc cacgacttcc tcgaagttcc agggagtgat ggtttcctcg gactttcgag   4440
tcatccaagc aaatcgagag tttcctctgg caagaggacc aacatagtag gggattcgaa   4500
aggtaagaat cttctcgatc ttctctcggt tgtccttgag aaaggggtag aagtcttcct   4560
gacgtcgaag aatggcgtgc agctcaccga ggtggatctg atgaggaatg ctgccgttgt   4620
cgaaggttcg ttgcttccga agcagatcct ctcgattgag cttgacaagc agttcctcgg   4680
ttccgtccat cttctcgaga attggcttga tgaacttgta gaactcttcc tgagaggctc   4740
cgccgtcgat gtatccagcg tagccgttct tcgactgatc gaaaaagatc tccttgtact   4800
tctcgggcag ttgctgtcgg acaagagcct tgagcagtgt gagatcctga tggtgctcgt   4860
cgtatcgctt gatcatggag gcagaaaggg gagcctttgt gatctcggtg ttgactcgca   4920
gaatgtcaga caagagaata gcatccgaaa ggttcttggc agcgagaaac aggtcggcgt   4980
actgatcgcc aatctgtgca agcaggttgt cgaggtcatc gtcgtaggtg tccttggaca   5040
gctggagctt ggcgtcctcc gccagatcga agttggactt gaagttgggt gtgagaccaa   5100
gagaaagggc aatgaggttg ccaaacagtc cgttcttttt ctcgccagga agttgggcaa   5160
tgaggttctc cagtcgtctg ctcttcgaga gtcgagcaga caagatggcc tttgcatcga   5220
ctccggaggc attgatgggg ttttcctcga acagctggtt gtaggtctga acgagctgaa   5280
tgaacagctt gtccacatcg ctgttgtcgg gattgagatc gccctcgatg aggaaatgac   5340
ctcgaaactt gatcatgtgt gccagagcga ggtagataag tctgagatcc gccttgtcgg   5400
tggaatcgac gagtttcttt cgcaggtggt agatggtagg atacttctcg tggtaagcaa   5460
cctcgtccac aatgttgcca aagatgggat gacgctcgtg tttcttgtct tcctcgacga   5520
ggaaggattc ctccagtcga tgaaagaacg aatcgtccac cttggccatc tcgttggaaa   5580
agatctcctg caggtagcag attcggttct tccgtcgggt gtaacgtcgc cgagcagttc   5640
gcttgagtct ggtagcttcg gcagtctcgc cagaatcgaa caacagggca ccaatgaggt   5700
ttttcttgat ggagtgtcga tcggtgtttc cgaggacctt gaatttcttg gagggcacct   5760
tgtactcgtc ggtgatgaca gcccagccga cagagttggt tccaatgtcc aggccgatgg   5820
agtatttctt gtcgaattcc catatggtac cagctgcaga tctcgagctc ggatccttat   5880
cgtcatcgtc gtacagatcc cgacccattt gctgtccacc agtcatgcta gccataccat   5940
gatgatgatg atgatgagaa ccccccatgg ttaattcctc ctgttagccc aaaaaacggg   6000
tatggagaaa cagtagagag ttgcgataaa aagcgtcagg taggatccgc taatcttatg   6060
gataaaaatg ctatggcata gcaaagtgtg acgccgtgca aataatcaat gtggactttt   6120
ctgccgtgat tatagacact tttgttacgc gtttttgtca tggctttggt cccgctttgt   6180
tacagaatgc ttttaataag cggggttacc ggtttggtta gcgagaagag ccagtaaaag   6240
acgcagtgac ggcaatgtct gatgcaatat ggacaattgg tttcttctct gaatggcggg   6300
agtatgaaaa gtatggctga agcgcaaaat gatcccctgc tgccgggata ctcgtttaat   6360
gcccatctgg tggcgggttt aacgccgatt gaggccaacg gttatctcga ttttttttatc   6420
gaccgaccgc tgggaatgaa aggttatatt ctcaatctca ccattcgcgg tcagggggtg   6480
gtgaaaaatc agggacgaga atttgtttgc cgaccgggtg atattttgct gttcccgcca   6540
ggagagattc atcactacgg tcgtcatccg gaggctcgcg aatggtatca ccagtgggtt   6600
tactttcgtc cgcgcgccta ctggcatgaa tggcttaact ggccgtcaat atttgccaat   6660
acggggttct ttcgcccgga tgaagcgcac cagccgcatt tcagcgacct gtttgggcaa   6720
atcattaacg ccgggcaagg ggaagggcgc tattcggagc tgctggcgat aaatctgctt   6780
```

gagcaattgt tactgcggcg catggaagcg attaacgagt cgctccatcc accgatggat 6840
aatcgggtac gcgaggcttg tcagtacatc agcgatcacc tggcagacag caattttgat 6900
atcgccagcg tcgcacagca tgtttgcttg tcgccgtcgc gtctgtcaca tcttttccgc 6960
cagcagttag ggattagcgt cttaagctgg cgcgaggacc aacgtatcag ccaggcgaag 7020
ctgcttttga gcaccacccg gatgcctatc gccaccgtcg gtcgcaatgt tggttttgac 7080
gatcaactct atttctcgcg ggtatttaaa aaatgcaccg ggccagccc gagcgagttc 7140 cgtgccggtt gtgaagaaaa agtgaatgat gtagccgtca agttgtcata attggtaacg 7200
aatcagacaa ttgacggccg tcccctggat tagctcgagc cgaacctccg ggaaaagttc 7260
gcgaaaagct ttaatgacct ctggcaagct ataacgtgcc tgagtatgcg tcgttgcaat 7320
agtgagaacg ccagacgtat cgttggtaaa caggtctgca agccgacgaa cattactggc 7380
ttcattcaga atacgttctg caatgaccag taatgctttg cccggttcag tcatgcccag 7440
cagtcgctta cctcgtcgaa caaatatttc gatgccaagt tcatcctcca gttcccgaat 7500
atgacggctg acgcctgact gtgaggtaaa aagcatattc gcaacctctg tcaggttgta 7560
atcctgacgt gcagcctcgc ggattatctt tagttgttgg aaattcacgg taaactccgg 7620
gcagttcaga tttcccgtta ttgttaaagt ctaatgcccg gcataacaaa taataaaaac 7680
ccgcatctta ttccatcccg atataacact tagctcacga agttcatgtt gcctccggtt 7740
tttaagaatc ggcccaagtg ccgccattac ttacaaccag attgcaagat gcttgccagt 7800
tttattttgg tgttgatgta caagctaacc aactgtcaaa taagagatta tgatagattc 7860
gtcatttgct cctttaatca gctgtcgcgt tcccctgccc tataaaagga gggtatgcac 7920
cacgatggtt cattacccaa taagattgaa agctcaccac tttgttgaaa ttgacagcaa 7980
acaaacaaaa aaatgcattt caccctttga catcaccatg cactgccatt aatatgcgcc 8040
ccgttcacac gattcctctg tagttcagtc ggtagaacgg cggactgtta atccgtatgt 8100
cactggttcg agtccagtca gaggagccaa attcaaaaaa gcctgctttc tagcaggctt 8160
tttgctttct aattaccaac gctcttaaaa catctgtctt gaaccagaac taatttgcaa 8220
gaatcataaa aaatttattt gctttcagga aaatttttct gtataataga ttcaacaacc 8280
agcgctcagc cagcgtttta gagctagaaa tagcaagtta aaataaggct agtccgttat 8340
caacttgaaa aagtggcacc gagtcggtgc gactcctgtt gatagatcca gtaatgacct 8400
cagaactcca tctggatttg ttcagaacgc tcggttgccg ccgggcgttt tttattggtg 8460
agaatggttt attgactacc ggaagcagtg tgaccgtgtg cttctcaaat gcctcaggct 8520
gtctatgtgt gactgttgag ctgtaacaag ttgtctcagg tgttcaattt catgttctag 8580
ttgctttgtt ttactggttt cacctgttct attaggtgtt acatgctgtt catctgttac 8640
attgtcgatc tgttcatggt gaacagcttt aaatgcacca aaaactcgta aaagctctga 8700
tgtatctatc ttttttacac cgttttcatc tgtgcatatg gacagttttc cctttgatat 8760
ctaacggtga acagttgttc tacttttgtt tgttagtctt gatgcttcac tgatagatac 8820
aagagccata agaacctcag atccttccgt atttagccag tatgttctct agtgtggttc 8880 gttgttttg cgtgagccat gagaacgaac cattgagatc atgcttactt tgcatgtcac 8940
tcaaaaattt tgcctcaaaa ctggtgagct gaatttttgc agttaaagca tcgtgtagtg 9000
tttttcttag tccgttacgt aggtaggaat ctgatgtaat ggttgttggt attttgtcac 9060
cattcatttt tatctggttg ttctcaagtt cggttacgag atccatttgt ctatctagtt 9120

-continued

```
caacttggaa aatcaacgta tcagtcgggc ggcctcgctt atcaaccacc aatttcatat   9180

tgctgtaagt gtttaaatct ttacttattg gtttcaaaac ccattggtta agccttttaa   9240

actcatggta gttattttca agcattaaca tgaacttaaa ttcatcaagg ctaatctcta   9300

tatttgcctt gtgagttttc ttttgtgtta gttcttttaa taaccactca taaatcctca   9360

tagagtattt gttttcaaaa gacttaacat gttccagatt atattttatg aatttttttta   9420

actggaaaag ataaggcaat atctcttcac taaaaactaa ttctaatttt tcgcttgaga   9480

acttggcata gtttgtccac tggaaaatct caaagccttt aaccaaagga ttcctgattt   9540

ccacagttct cgtcatcagc tctctggttg ctttagctaa tacaccataa gcattttccc   9600

tactgatgtt catcatctga gcgtattggt tataagtgaa cgataccgtc cgttctttcc   9660

ttgtagggtt ttcaatcgtg gggttgagta gtgccacaca gcataaaatt agcttggttt   9720

catgctccgt taagtcatag cgactaatcg ctagttcatt tgctttgaaa acaactaatt   9780

cagacataca tctcaattgg tctaggtgat tttaatcact ataccaattg agatgggcta   9840

gtcaatgata attactagtc cttttccttt gagttgtggg tatctgtaaa ttctgctaga   9900

cctttgctgg aaaacttgta aattctgcta gaccctctgt aaattccgct agacctttgt   9960

gtgttttttt tgtttatatt caagtggtta taatttatag aataaagaaa gaataaaaaa  10020

agataaaaag aatagatccc agccctgtgt ataactcact actttagtca gttccgcagt  10080

attacaaaag gatgtcgcaa acgctgtttg ctcctctaca aaacagacct taaaacccta  10140

aaggcttaag tagcaccctc gcaagctcgg gcaaatcgct gaatattcct tttgtctccg  10200

accatcaggc acctgagtcg ctgtcttttt cgtgacattc agttcgctgc gctcacggct  10260

ctggcagtga atgggggtaa atggcactac aggcgccttt tatggattca tgcaaggaaa  10320

ctacccataa tacaagaaaa gcccgtcacg ggcttctcag ggcgttttat ggcgggtctg  10380

ctatgtggtg ctatctgact ttttgctgtt cagcagttcc tgccctctga ttttccagtc  10440

tgaccacttc ggattatccc gtgacaggtc attcagactg gctaatgcac ccagtaaggc  10500

agcggtatca tcaacaggct tacccgtctt actgtcggat cgacgctctc ccttatgcga  10560

ctcctgcat                                                          10569
```

<210> SEQ ID NO 115
<211> LENGTH: 10569
<212> TYPE: DNA
<213> ORGANISM: Artificial sequence
<220> FEATURE:
<223> OTHER INFORMATION: pRF861-nacETsite1 plasmid

<400> SEQUENCE: 115

```
ccctttcgtc ttcgaataaa tacctgtgac ggaagatcac ttcgcagaat aaataaatcc     60

tggtgtccct gttgataccg ggaagccctg ggccaacttt tggcgaaaat gagacgttga    120

tcggcacgta agaggttcca actttcacca taatgaaata agatcactac cgggcgtatt    180

ttttgagtta tcgagatttt caggagctaa ggaagctaaa atggagaaaa aaatcactgg    240

atataccacc gttgatatat cccaatggca tcgtaaagaa cattttgagg catttcagtc    300

agttgctcaa tgtacctata accagaccgt tcagctggat attacggcct ttttaaagac    360

cgtaaagaaa aataagcaca agttttatcc ggcctttatt cacattcttg cccgcctgat    420

gaatgctcat ccggaattcc gtatggcaat gaaagacggt gagctggtga tatgggatag    480

tgttcaccct tgttacaccg ttttccatga gcaaactgaa acgttttcat cgctctggag    540

tgaataccac gacgatttcc ggcagtttct acacatatat tcgcaagatg tggcgtgtta    600
```

```
cggtgaaaac ctggcctatt tccctaaagg gtttattgag aatatgtttt tcgtctcagc    660
caatccctgg gtgagtttca ccagttttga tttaaacgtg gccaatatgg acaacttctt    720
cgcccccgtt ttcaccatgg gcaaatatta tacgcaaggc gacaaggtgc tgatgccgct    780
ggcgattcag gttcatcatg ccgtttgtga tggcttccat gtcggcagaa tgcttaatga    840
attacaacag tactgcgatg agtggcaggg cggggcgtaa ttttttttaag gcagttattg    900
gtgcccttaa acgcctggtg ctacgcctga ataagtgata ataagcggat gaatggcaga    960
aattcgaaag caaattcgac ccggtcgtcg gttcagggca gggtcgttaa atagccgctt   1020
atgtctattg ctggtttatc ggtacccccc aactgatctt cagcatcttt tactttcacc   1080
agcgtttctg ggtgagcaaa aacaggaagg caaaatgccg caaaaaaggg aataagggcg   1140
acacggaaat gttgaatact catactcttc ctttttcaat attattgaag catttatcag   1200
ggttattgtc tcatgagcgg atacatattt gaatgtattt agaaaaataa acaaaagagt   1260
ttgtagaaac gcaaaaaggc catccgtcag gatggccttc tgcttaattt gatgcctggc   1320
agtttatggc gggcgtcctg cccgccaccc tccgggccgt tgcttcgcaa cgttcaaatc   1380
cgctcccggc ggatttgtcc tactcaggag agcgttcacc gacaaacaac agataaaacg   1440
aaaggcccag tctttcgact gagcctttcg ttttatttga tgcctggcag ttccctactc   1500
tcgcatgggg agaccccaca ctaccatcgg cgctacggcg tttcacttct gagttcggca   1560
tggggtcagg tgggaccacc gcgctactgc cgccaggcaa attctgtttt atcagaccgc   1620
ttctgcgttc tgatttaatc tgtatcaggc tgaaaatctt ctctcatccg ccaaaacagc   1680
caagcttagc ggccgcttag acctttcgct tttcttggg atcggctctg gagtcgccac   1740
caagctgaga caggtcgatt cgggtctcgt acaggccagt gatggactgg tgaatcaggg   1800
tggcatcgag aacctccttg gtggatgtgt accgctttcg gtcgatagtg gtatcgaagt   1860
acttgaaagc tgcaggagca cccaggttgg taagagtaaa caggtgaatg atgttctccg   1920
cctgttctcg aatgggtttg tcccgatgct tgttgtaggc agagagcacc ttgtccaagt   1980
tggcatcagc caggatgact cgcttcgaaa actcggaaat ctgctcgata atctcgtcga   2040
ggtaatgttt gtgctgctca acgaagagtt gcttctgttc gttgtcctcg ggagaaccct   2100
tgagcttctc gtagtgagaa gccagataga gaaagttgac gtacttcgaa ggcaaggcaa   2160
gctcgtttcc cttctgcagc tcgccagcgg aggcgagcat acgctttcga ccgttctcca   2220
gttcgaacag agagtacttg ggcagcttga taatgaggtc tttcttgacc tccttgtaac   2280
ccttggcttc caagaagtcg atgggattct tctcgaagct cgatcgctcc atgatggtaa   2340
ttccgagcag ctccttgacg gacttgagct ttttggactt gcccttctcg accttcgcaa   2400
cgacaagcac ggaataggcg acggtaggag aatcgaagcc accgtatttc ttgggatccc   2460
agtctttctt tcgagcgatg agcttgtcgg agtttcgctt gggcagaatc gactccttgg   2520
agaatccgcc agtctgaacc tcggttttct tgacgatgtt gacctgaggc atcgacagaa   2580
cctttcgcac ggttgcaaag tctcgaccct tgtcccacac gatctctcca gtttcgccgt   2640
tggtctcgat aagtggtctc tttcgaatct ctccgttggc caaggtgatc tcggtcttga   2700
aaaagttcat gatgttggag taaaagaagt acttggcagt agccttgcca atctcctgtt   2760
cggacttggc aatcatcttt cgaacgtcgt agaccttgta atcgccgtaa acgaactcgc   2820
tttcgagctt ggggtatttc ttgatgagcg cagtgccaac gacggcgttg aggtaagcat   2880
cgtgggcatg gtggtaattg ttgatctctc gcaccttgta gaactgaaag tcctttcgga   2940
```

-continued

```
aatcggagac cagtttggac ttgagagtaa tcaccttgac ctctcggatg agcttgtcgt   3000
tctcgtcgta cttggtgttc atccgagaat cgagaatctg tgcgacgtgc tttgtgatct   3060
gtctggtctc gacgagttga cgcttgatga agccagcctt gtcgagctcg gacagaccgc   3120
ctcgctcggc cttggtaaga ttgtcgaact ttcgctgggt aatgagcttg gcgttgagca   3180
gctgtcgcca gtagttcttc atctttttga ccacctcttc gctgggaacg ttgtccgact   3240
tgcctctgtt cttgtcggat cgtgtaagga ccttgttgtc gatagaatcg tccttgagaa   3300
aggattgagg gacaatgtgg tccacatcgt agtcgctgag acgattgatg tccagttcct   3360
gatccacgta catgtctcga ccattctgca gatagtagag atacagcttc tcgttctgca   3420
gttgagtgtt ctcgacggga tgctccttga gaatctggga tcccagctcc ttgatgcctt   3480
cctcgattcg cttcatccgc tctcgcgagt tttctgacc  cttttgagtt gtctggttct   3540
ctctggccat ctcgatcaca atgttctcgg gcttgtgacg tcccatgacc ttcaccagct   3600
cgtcgacaac cttgacagtc tggagaatgc ctttcttgat ggctggcgaa ccagccaggt   3660
tggcaatatg ttcgtgcaag ctgtcgccct gaccggacac ttgtgccttc tggatgtcct   3720
ccttgaaggt aagagaatcg tcgtgaatga gctgcatgaa gtttcggttg gcaaagccat   3780
cggacttgag aaagtccaga atggtctttc cggactgctt gtctctgatg ccgttgatga   3840
gctttcgcga aagtcttccc cagccggtgt atctacgtcg cttgagttgt ttcatgacct   3900
tgtcgtcgaa caggtgagcg tatgtcttga gtcgttcctc gatcatctcc cgatcttcga   3960
acagggtaag agtgagcacg atgtcctcca gaatgtcctc gttttcctcg ttgtcgagaa   4020
aatccttgtc cttgataatc ttgagcagat cgtgataggt gcccaaagag gcgttgaatc   4080
ggtcctcaac tccggaaatc tcgacgctgt cgaaacactc gattttcttg aagtagtcct   4140
ccttgagctg cttaacagtg acctttcggt tggtcttgaa caggagatcg acaatggctt   4200
tcttctgttc gccagacaag aaggcaggct ttcgcattcc ctcggtaacg tacttgactt   4260
tggtgagttc gttgtagact gtaaagtact cgtagagcag cgaatgcttg ggaagaacct   4320
tctcgttggg cagattcttg tcgaagttgg tcattcgctc gatgaaggac tgtgcagagg   4380
cacccttgtc cacgacttcc tcgaagttcc agggagtgat ggtttcctcg gactttcgag   4440
tcatccaagc aaatcgagag tttcctctgg caagaggacc aacatagtag gggattcgaa   4500
aggtaagaat cttctcgatc ttctctcggt tgtccttgag aaaggggtag aagtcttcct   4560
gacgtcgaag aatggcgtgc agctcaccga ggtggatctg atgaggaatg ctgccgttgt   4620
cgaaggttcg ttgcttccga agcagatcct ctcgattgag cttgacaagc agttcctcgg   4680
ttccgtccat cttctcgaga attggcttga tgaacttgta gaactcttcc tgagaggctc   4740
cgccgtcgat gtatccagcg tagccgttct tcgactgatc gaaaaagatc tccttgtact   4800
tctcgggcag ttgctgtcgg acaagagcct tgagcagtgt gagatcctga tggtgctcgt   4860
cgtatcgctt gatcatggag gcagaaaggg gagcctttgt gatctcggtg ttgactcgca   4920
gaatgtcaga caagagaata gcatccgaaa ggttcttggc agcgagaaac aggtcggcgt   4980
actgatcgcc aatctgtgca agcaggttgt cgaggtcatc gtcgtaggtg tccttggaca   5040
gctggagctt ggcgtcctcc gccagatcga agttggactt gaagttgggt gtgagaccaa   5100
gagaaagggc aatgaggttg ccaaacagtc cgttcttttt ctcgccagga agttgggcaa   5160
tgaggttctc cagtcgtctg ctcttcgaga gtcgagcaga caagatggcc tttgcatcga   5220
ctccggaggc attgatgggg ttttcctcga acagctggtt gtaggtctga acgagctgaa   5280
tgaacagctt gtccacatcg ctgttgtcgg gattgagatc gccctcgatg aggaaatgac   5340
```

ctcgaaactt gatcatgtgt gccagagcga gatggataag tctgagatcc gccttgtcgg 5400
tggaatcgac gagtttcttt cgcaggtggt agatggtagg atacttctcg tggtaagcaa 5460
cctcgtccac aatgttgcca aagatgggat gacgctcgtg tttcttgtct tcctcgacga 5520
ggaaggattc ctccagtcga tgaaagaacg aatcgtccac cttggccatc tcgttggaaa 5580
agatctcctg caggtagcag attcggttct tccgtcgggt gtaacgtcgc cgagcagttc 5640
gcttgagtct ggtagcttcg gcagtctcgc cagaatcgaa caacagggca ccaatgaggt 5700
ttttcttgat ggagtgtcga tcggtgtttc cgaggacctt gaatttcttg gagggcacct 5760
tgtactcgtc ggtgatgaca gcccagccga cagagttggt tccaatgtcc aggccgatgg 5820
agtatttctt gtcgaattcc catatggtac cagctgcaga tctcgagctc ggatccttat 5880
cgtcatcgtc gtacagatcc cgacccattt gctgtccacc agtcatgcta gccataccat 5940
gatgatgatg atgatgagaa ccccccatgg ttaattcctc ctgttagccc aaaaaacggg 6000
tatggagaaa cagtagagag ttgcgataaa aagcgtcagg taggatccgc taatcttatg 6060
gataaaaatg ctatggcata gcaaagtgtg acgccgtgca aataatcaat gtggactttt 6120
ctgccgtgat tatagacact tttgttacgc gtttttgtca tggctttggt cccgctttgt 6180
tacagaatgc ttttaataag cggggttacc ggtttggtta gcgagaagag ccagtaaaag 6240
acgcagtgac ggcaatgtct gatgcaatat ggacaattgg tttcttctct gaatggcggg 6300
agtatgaaaa gtatggctga agcgcaaaat gatcccctgc tgccgggata ctcgtttaat 6360
gcccatctgg tggcgggttt aacgccgatt gaggccaacg gttatctcga ttttttttatc 6420
gaccgaccgc tgggaatgaa aggttatatt ctcaatctca ccattcgcgg tcagggggtg 6480
gtgaaaaatc agggacgaga atttgtttgc cgaccgggtg atattttgct gttcccgcca 6540
ggagagattc atcactacgg tcgtcatccg gaggctcgcg aatggtatca ccagtgggtt 6600
tactttcgtc cgcgcgccta ctggcatgaa tggcttaact ggccgtcaat atttgccaat 6660
acggggttct ttcgcccgga tgaagcgcac cagccgcatt tcagcgacct gtttgggcaa 6720
atcattaacg ccgggcaagg ggaagggcgc tattcggagc tgctggcgat aaatctgctt 6780
gagcaattgt tactgcggcg catggaagcg attaacgagt cgctccatcc accgatggat 6840
aatcgggtac gcgaggcttg tcagtacatc agcgatcacc tggcagacag caattttgat 6900
atcgccagcg tcgcacagca tgtttgcttg tcgccgtcgc gtctgtcaca tcttttccgc 6960
cagcagttag ggattagcgt cttaagctgg cgcgaggacc aacgtatcag ccaggcgaag 7020
ctgcttttga gcaccacccg gatgcctatc gccaccgtcg gtcgcaatgt tggttttgac 7080
gatcaactct atttctcgcg ggtatttaaa aaatgcaccg gggccagccc gagcgagttc 7140
cgtgccggtt gtgaagaaaa agtgaatgat gtagccgtca agttgtcata attggtaacg 7200
aatcagacaa ttgacggccg tcccctggat tagctcgagc cgaacctccg ggaaaagttc 7260
gcgaaaagct ttaatgacct ctggcaagct ataacgtgcc tgagtatgcg tcgttgcaat 7320
agtgagaacg ccagacgtat cgttggtaaa caggtctgca agccgacgaa cattactggc 7380
ttcattcaga atacgttctg caatgaccag taatgctttg cccggttcag tcatgcccag 7440
cagtcgctta cctcgtcgaa caaatatttc gatgccaagt tcatcctcca gttcccgaat 7500
atgacggctg acgcctgact gtgaggtaaa aagcatattc gcaacctctg tcaggttgta 7560
atcctgacgt gcagcctcgc ggattatctt tagttgttgg aaattcacgg taaactccgg 7620
gcagttcaga tttcccgtta ttgttaaagt ctaatgcccg gcataacaaa taataaaaac 7680

-continued

```
ccgcatctta ttccatcccg atataacact tagctcacga agttcatgtt gcctccggtt   7740
tttaagaatc ggcccaagtg ccgccattac ttacaaccag attgcaagat gcttgccagt   7800
tttattttgg tgttgatgta caagctaacc aactgtcaaa taagagatta tgatagattc   7860
gtcatttgct cctttaatca gctgtcgcgt tcccctgccc tataaaagga gggtatgcac   7920
cacgatggtt cattacccaa taagattgaa agctcaccac tttgttgaaa ttgacagcaa   7980
acaaacaaaa aaatgcattt caccctttga catcaccatg cactgccatt aatatgcgcc   8040
ccgttcacac gattcctctg tagttcagtc ggtagaacgg cggactgtta atccgtatgt   8100
cactggttcg agtccagtca gaggagccaa attcaaaaaa gcctgctttc tagcaggctt   8160
tttgctttct aattaccaac gctcttaaaa catctgtctt gaaccagaac taatttgcaa   8220
gaatcataaa aaatttattt gctttcagga aaatttttct gtataataga ttcatatgca   8280
atacttcagc agccgtttta gagctagaaa tagcaagtta aaataaggct agtccgttat   8340
caacttgaaa aagtggcacc gagtcggtgc gactcctgtt gatagatcca gtaatgacct   8400
cagaactcca tctggatttg ttcagaacgc tcggttgccg ccgggcgttt tttattggtg   8460
agaatggttt attgactacc ggaagcagtg tgaccgtgtg cttctcaaat gcctcaggct   8520
gtctatgtgt gactgttgag ctgtaacaag ttgtctcagg tgttcaattt catgttctag   8580
ttgctttgtt ttactggttt cacctgttct attaggtgtt acatgctgtt catctgttac   8640
attgtcgatc tgttcatggt gaacagcttt aaatgcacca aaaactcgta aaagctctga   8700
tgtatctatc ttttttacac cgttttcatc tgtgcatatg gacagttttc cctttgatat   8760
ctaacggtga acagttgttc tacttttgtt tgttagtctt gatgcttcac tgatagatac   8820
aagagccata agaacctcag atccttccgt atttagccag tatgttctct agtgtggttc   8880
gttgtttttg cgtgagccat gagaacgaac cattgagatc atgcttactt tgcatgtcac   8940
tcaaaaattt tgcctcaaaa ctggtgagct gaatttttgc agttaaagca tcgtgtagtg   9000
tttttcttag tccgttacgt aggtaggaat ctgatgtaat ggttgttggt attttgtcac   9060
cattcatttt tatctggttg ttctcaagtt cggttacgag atccatttgt ctatctagtt   9120
caacttggaa aatcaacgta tcagtcgggc ggcctcgctt atcaaccacc aatttcatat   9180
tgctgtaagt gtttaaatct ttacttattg gtttcaaaac ccattggtta agccttttaa   9240
actcatggta gttattttca agcattaaca tgaacttaaa ttcatcaagg ctaatctcta   9300
tatttgcctt gtgagttttc ttttgtgtta gttcttttaa taaccactca taaatcctca   9360
tagagtattt gttttcaaaa gacttaacat gttccagatt atattttatg aattttttta   9420
actggaaaag ataaggcaat atctcttcac taaaaactaa ttctaatttt tcgcttgaga   9480
acttggcata gtttgtccac tggaaaatct caaagccttt aaccaaagga ttcctgattt   9540
ccacagttct cgtcatcagc tctctggttg ctttagctaa tacaccataa gcattttccc   9600
tactgatgtt catcatctga gcgtattggt tataagtgaa cgataccgtc cgttctttcc   9660
ttgtagggtt ttcaatcgtg gggttgagta gtgccacaca gcataaaatt agcttggttt   9720
catgctccgt taagtcatag cgactaatcg ctagttcatt tgctttgaaa acaactaatt   9780
cagacataca tctcaattgg tctaggtgat tttaatcact ataccaattg agatgggcta   9840
gtcaatgata attactagtc cttttccttt gagttgtggg tatctgtaaa ttctgctaga   9900
cctttgctgg aaaacttgta aattctgcta gaccctctgt aaattccgct agacctttgt   9960
gtgttttttt tgtttatatt caagtggtta taatttatag aataaagaaa gaataaaaaa  10020
agataaaaag aatagatccc agccctgtgt ataactcact actttagtca gttccgcagt  10080
```

```
attacaaaag gatgtcgcaa acgctgtttg ctcctctaca aaacagacct taaaacccta  10140

aaggcttaag tagcaccctc gcaagctcgg gcaaatcgct gaatattcct tttgtctccg  10200

accatcaggc acctgagtcg ctgtcttttt cgtgacattc agttcgctgc gctcacggct  10260

ctggcagtga atgggggtaa atggcactac aggcgccttt tatggattca tgcaaggaaa  10320

ctacccataa tacaagaaaa gcccgtcacg ggcttctcag ggcgttttat ggcgggtctg  10380

ctatgtggtg ctatctgact ttttgctgtt cagcagttcc tgccctctga ttttccagtc  10440

tgaccacttc ggattatccc gtgacaggtc attcagactg gctaatgcac ccagtaaggc  10500

agcggtatca tcaacaggct tacccgtctt actgtcggat cgacgctctc ccttatgcga  10560

ctcctgcat                                                          10569
```

<210> SEQ ID NO 116
<211> LENGTH: 10569
<212> TYPE: DNA
<213> ORGANISM: Artificial sequence
<220> FEATURE:
<223> OTHER INFORMATION: pRF861-nacETsite2 plasmid

<400> SEQUENCE: 116

```
ccctttcgtc ttcgaataaa tacctgtgac ggaagatcac ttcgcagaat aaataaatcc     60

tggtgtccct gttgataccg ggaagccctg ggccaacttt tggcgaaaat gagacgttga    120

tcggcacgta agaggttcca actttcacca taatgaaata agatcactac cgggcgtatt    180

ttttgagtta tcgagatttt caggagctaa ggaagctaaa atggagaaaa aaatcactgg    240

atataccacc gttgatatat cccaatggca tcgtaaagaa cattttgagg catttcagtc    300

agttgctcaa tgtacctata accagaccgt tcagctggat attacggcct ttttaaagac    360

cgtaaagaaa aataagcaca agttttatcc ggcctttatt cacattcttg cccgcctgat    420

gaatgctcat ccggaattcc gtatggcaat gaaagacggt gagctggtga tatgggatag    480

tgttcaccct tgttacaccg ttttccatga gcaaactgaa acgttttcat cgctctggag    540

tgaataccac gacgatttcc ggcagtttct acacatatat tcgcaagatg tggcgtgtta    600

cggtgaaaac ctggcctatt tccctaaagg gtttattgag aatatgtttt tcgtctcagc    660

caatccctgg gtgagtttca ccagttttga tttaaacgtg gccaatatgg acaacttctt    720

cgcccccgtt ttcaccatgg gcaaatatta tacgcaaggc gacaaggtgc tgatgccgct    780

ggcgattcag gttcatcatg ccgtttgtga tggcttccat gtcggcagaa tgcttaatga    840

attacaacag tactgcgatg agtggcaggg cggggcgtaa tttttttaag gcagttattg    900

gtgcccttaa acgcctggtg ctacgcctga ataagtgata ataagcggat gaatggcaga    960

aattcgaaag caaattcgac ccggtcgtcg gttcagggca gggtcgttaa atagccgctt   1020

atgtctattg ctggtttatc ggtacccccc aactgatctt cagcatcttt tactttcacc   1080

agcgtttctg ggtgagcaaa aacaggaagg caaaatgccg caaaaaaggg aataagggcg   1140

acacggaaat gttgaatact catactcttc ctttttcaat attattgaag catttatcag   1200

ggttattgtc tcatgagcgg atacatattt gaatgtattt agaaaaataa acaaaagagt   1260

ttgtagaaac gcaaaaaggc catccgtcag gatggccttc tgcttaattt gatgcctggc   1320

agtttatggc gggcgtcctg cccgccaccc tccgggccgt tgcttcgcaa cgttcaaatc   1380

cgctcccggc ggatttgtcc tactcaggag agcgttcacc gacaaacaac agataaaacg   1440

aaaggcccag tctttcgact gagcctttcg ttttatttga tgcctggcag ttccctactc   1500
```

```
tcgcatgggg agaccccaca ctaccatcgg cgctacggcg tttcacttct gagttcggca      1560

tggggtcagg tgggaccacc gcgctactgc cgccaggcaa attctgtttt atcagaccgc      1620

ttctgcgttc tgatttaatc tgtatcaggc tgaaaatctt ctctcatccg ccaaaacagc      1680

caagcttagc ggccgcttag acctttcgct ttttcttggg atcggctctg gagtcgccac      1740

caagctgaga caggtcgatt cgggtctcgt acaggccagt gatggactgg tgaatcaggg      1800

tggcatcgag aacctccttg gtggatgtgt accgctttcg gtcgatagtg gtatcgaagt      1860

acttgaaagc tgcaggagca cccaggttgg taagagtaaa caggtgaatg atgttctccg      1920

cctgttctcg aatgggtttg tcccgatgct tgttgtaggc agagagcacc ttgtccaagt      1980

tggcatcagc caggatgact cgcttcgaaa actcggaaat ctgctcgata atctcgtcga      2040

ggtaatgttt gtgctgctca acgaagagtt gcttctgttc gttgtcctcg ggagaaccct      2100

tgagcttctc gtagtgagaa gccagataga gaaagttgac gtacttcgaa ggcaaggcaa      2160

gctcgtttcc cttctgcagc tcgccagcgg aggcgagcat acgctttcga ccgttctcca      2220

gttcgaacag agagtacttg ggcagcttga taatgaggtc tttcttgacc tccttgtaac      2280

ccttggcttc caagaagtcg atgggattct tctcgaagct cgatcgctcc atgatggtaa      2340

ttccgagcag ctccttgacg gacttgagct ttttggactt gcccttctcg accttcgcaa      2400

cgacaagcac ggaataggcg acggtaggag aatcgaagcc accgtatttc ttgggatccc      2460

agtctttctt tcgagcgatg agcttgtcgg agtttcgctt gggcagaatc gactccttgg      2520

agaatccgcc agtctgaacc tcggttttct tgacgatgtt gacctgaggc atcgacagaa      2580

cctttcgcac ggttgcaaag tctcgaccct tgtcccacac gatctctcca gtttcgccgt      2640

tggtctcgat aagtggtctc tttcgaatct ctccgttggc caaggtgatc tcggtcttga      2700

aaaagttcat gatgttggag taaaagaagt acttggcagt agccttgcca atctcctgtt      2760

cggacttggc aatcatcttt cgaacgtcgt agaccttgta atcgccgtaa cgaactcgc       2820

tttcgagctt ggggtatttc ttgatgagcg cagtgccaac gacggcgttg aggtaagcat      2880

cgtgggcatg gtggtaattg ttgatctctc gcaccttgta gaactgaaag tcctttcgga      2940

aatcggagac cagtttggac ttgagagtaa tcaccttgac ctctcggatg agcttgtcgt      3000

tctcgtcgta cttggtgttc atccgagaat cgagaatctg tgcgacgtgc tttgtgatct      3060

gtctggtctc gacgagttga cgcttgatga agccagcctt gtcgagctcg acagaccgc       3120

ctcgctcggc cttggtaaga ttgtcgaact ttcgctgggt aatgagcttg gcgttgagca      3180

gctgtcgcca gtagttcttc atctttttga ccacctcttc gctgggaacg ttgtccgact      3240

tgcctctgtt cttgtcggat cgtgtaagga ccttgttgtc gatagaatcg tccttgagaa      3300

aggattgagg gacaatgtgg tccacatcgt agtcgctgag acgattgatg tccagttcct      3360

gatccacgta catgtctcga ccattctgca gatagtagag atacagcttc tcgttctgca      3420

gttgagtgtt ctcgacggga tgctccttga gaatctggga tcccagctcc ttgatgcctt      3480

cctcgattcg cttcatccgc tctcgcgagt ttttctgacc cttttgagtt gtctggttct      3540

ctctggccat ctcgatcaca atgttctcgg gcttgtgacg tcccatgacc ttcaccagct      3600

cgtcgacaac cttgacagtc tggagaatgc ctttcttgat ggctggcgaa ccagccaggt      3660

tggcaatatg ttcgtgcaag ctgtcgccct gaccggacac ttgtgccttc tggatgtcct      3720

ccttgaaggt aagagaatcg tcgtgaatga gctgcatgaa gtttcggttg gcaaagccat      3780

cggacttgag aaagtccaga atggtctttc cggactgctt gtctctgatg ccgttgatga      3840

gctttcgcga aagtcttccc cagccggtgt atctacgtcg cttgagttgt ttcatgacct      3900
```

```
tgtcgtcgaa caggtgagcg tatgtcttga gtcgttcctc gatcatctcc cgatcttcga   3960
acagggtaag agtgagcacg atgtcctcca gaatgtcctc gttttcctcg ttgtcgagaa   4020
aatccttgtc cttgataatc ttgagcagat cgtgataggt gcccaaagag gcgttgaatc   4080
ggtcctcaac tccggaaatc tcgacgctgt cgaaacactc gattttcttg aagtagtcct   4140
ccttgagctg cttaacagtg acctttcggt tggtcttgaa caggagatcg acaatggctt   4200
tcttctgttc gccagacaag aaggcaggct ttcgcattcc ctcggtaacg tacttgactt   4260
tggtgagttc gttgtagact gtaaagtact cgtagagcag cgaatgcttg ggaagaacct   4320
tctcgttggg cagattcttg tcgaagttgg tcattcgctc gatgaaggac tgtgcagagg   4380
cacccttgtc cacgacttcc tcgaagttcc agggagtgat ggtttcctcg gactttcgag   4440
tcatccaagc aaatcgagag tttcctctgg caagaggacc aacatagtag ggattcgaa    4500
aggtaagaat cttctcgatc ttctctcggt tgtccttgag aaaggggtag aagtcttcct   4560
gacgtcgaag aatggcgtgc agctcaccga ggtggatctg atgaggaatg ctgccgttgt   4620
cgaaggttcg ttgcttccga agcagatcct ctcgattgag cttgacaagc agttcctcgg   4680
ttccgtccat cttctcgaga attggcttga tgaacttgta gaactcttcc tgagaggctc   4740
cgccgtcgat gtatccagcg tagccgttct tcgactgatc gaaaaagatc tccttgtact   4800
tctcgggcag ttgctgtcgg acaagagcct tgagcagtgt gagatcctga tggtgctcgt   4860
cgtatcgctt gatcatggag gcagaaaggg gagcctttgt gatctcggtg ttgactcgca   4920
gaatgtcaga caagagaata gcatccgaaa ggttcttggc agcgagaaac aggtcggcgt   4980
actgatcgcc aatctgtgca agcaggttgt cgaggtcatc gtcgtaggtg tccttggaca   5040
gctggagctt ggcgtcctcc gccagatcga agttggactt gaagttgggt gtgagaccaa   5100
gagaaagggc aatgaggttg ccaaacagtc cgttcttttt ctcgccagga agttgggcaa   5160
tgaggttctc cagtcgtctg ctcttcgaga gtcgagcaga caagatggcc tttgcatcga   5220
ctccggaggc attgatgggg ttttcctcga acagctggtt gtaggtctga acgagctgaa   5280
tgaacagctt gtccacatcg ctgttgtcgg gattgagatc gccctcgatg aggaaatgac   5340
ctcgaaactt gatcatgtgt gccagagcga gatggataag tctgagatcc gccttgtcgg   5400
tggaatcgac gagtttcttt cgcaggtggt agatggtagg atacttctcg tggtaagcaa   5460
cctcgtccac aatgttgcca aagatgggat gacgctcgtg tttcttgtct tcctcgacga   5520
ggaaggattc ctccagtcga tgaaagaacg aatcgtccac cttggccatc tcgttggaaa   5580
agatctcctg caggtagcag attcggttct tccgtcgggt gtaacgtcgc cgagcagttc   5640
gcttgagtct ggtagcttcg gcagtctcgc cagaatcgaa caacagggca ccaatgaggt   5700
ttttcttgat ggagtgtcga tcggtgtttc cgaggacctt gaatttcttg gagggcacct   5760
tgtactcgtc ggtgatgaca gcccagccga cagagttggt tccaatgtcc aggccgatgg   5820
agtatttctt gtcgaattcc catatggtac cagctgcaga tctcgagctc ggatccttat   5880
cgtcatcgtc gtacagatcc cgacccattt gctgtccacc agtcatgcta gccataccat   5940
gatgatgatg atgatgagaa ccccccatgg ttaattcctc ctgttagccc aaaaaacggg   6000
tatggagaaa cagtagagag ttgcgataaa aagcgtcagg taggatccgc taatcttatg   6060
gataaaaatg ctatggcata gcaaagtgtg acgccgtgca aataatcaat gtggactttt   6120
ctgccgtgat tatagacact tttgttacgc gtttttgtca tggctttggt cccgctttgt   6180
tacagaatgc ttttaataag cggggttacc ggtttggtta gcgagaagag ccagtaaaag   6240
```

-continued

```
acgcagtgac ggcaatgtct gatgcaatat ggacaattgg tttcttctct gaatggcggg   6300
agtatgaaaa gtatggctga agcgcaaaat gatcccctgc tgccgggata ctcgtttaat   6360
gcccatctgg tggcgggttt aacgccgatt gaggccaacg gttatctcga tttttttatc   6420
gaccgaccgc tgggaatgaa aggttatatt ctcaatctca ccattcgcgg tcagggggtg   6480
gtgaaaaatc agggacgaga atttgtttgc cgaccgggtg atattttgct gttcccgcca   6540
ggagagattc atcactacgg tcgtcatccg gaggctcgcg aatggtatca ccagtgggtt   6600
tactttcgtc cgcgcgccta ctggcatgaa tggcttaact ggccgtcaat atttgccaat   6660
acggggttct ttcgcccgga tgaagcgcac cagccgcatt tcagcgacct gtttgggcaa   6720
atcattaacg ccgggcaagg ggaagggcgc tattcggagc tgctggcgat aaatctgctt   6780
gagcaattgt tactgcggcg catggaagcg attaacgagt cgctccatcc accgatggat   6840
aatcgggtac gcgaggcttg tcagtacatc agcgatcacc tggcagacag caattttgat   6900
atcgccagcg tcgcacagca tgtttgcttg tcgccgtcgc gtctgtcaca tcttttccgc   6960
cagcagttag ggattagcgt cttaagctgg cgcgaggacc aacgtatcag ccaggcgaag   7020
ctgcttttga gcaccacccg gatgcctatc gccaccgtcg gtcgcaatgt tggttttgac   7080
gatcaactct atttctcgcg ggtatttaaa aaatgcaccg gggccagccc gagcgagttc   7140
cgtgccggtt gtgaagaaaa agtgaatgat gtagccgtca agttgtcata attggtaacg   7200
aatcagacaa ttgacggccg tcccctggat tagctcgagc cgaacctccg ggaaaagttc   7260
gcgaaaagct ttaatgacct ctggcaagct ataacgtgcc tgagtatgcg tcgttgcaat   7320
agtgagaacg ccagacgtat cgttggtaaa caggtctgca agccgacgaa cattactggc   7380
ttcattcaga atacgttctg caatgaccag taatgctttg cccggttcag tcatgcccag   7440
cagtcgctta cctcgtcgaa caaatatttc gatgccaagt tcatcctcca gttcccgaat   7500
atgacggctg acgcctgact gtgaggtaaa aagcatattc gcaacctctg tcaggttgta   7560
atcctgacgt gcagcctcgc ggattatctt tagttgttgg aaattcacgg taaactccgg   7620
gcagttcaga tttcccgtta ttgttaaagt ctaatgcccg gcataacaaa taataaaaac   7680
ccgcatctta ttccatcccg atataacact tagctcacga agttcatgtt gcctccggtt   7740
tttaagaatc ggcccaagtg ccgccattac ttacaaccag attgcaagat gcttgccagt   7800
tttattttgg tgttgatgta caagctaacc aactgtcaaa taagagatta tgatagattc   7860
gtcatttgct cctttaatca gctgtcgcgt tcccctgccc tataaaagga gggtatgcac   7920
cacgatggtt cattacccaa taagattgaa agctcaccac tttgttgaaa ttgacagcaa   7980
acaaacaaaa aaatgcattt caccctttga catcaccatg cactgccatt aatatgcgcc   8040
ccgttcacac gattcctctg tagttcagtc ggtagaacgg cggactgtta atccgtatgt   8100
cactggttcg agtccagtca gaggagccaa attcaaaaaa gcctgctttc tagcaggctt   8160
tttgctttct aattaccaac gctcttaaaa catctgtctt gaaccagaac taatttgcaa   8220
gaatcataaa aaatttattt gctttcagga aaatttttct gtataataga ttcaacaacc   8280
agcgctcagc cagcgtttta gagctagaaa tagcaagtta aaataaggct agtccgttat   8340
caacttgaaa aagtggcacc gagtcggtgc gactcctgtt gatagatcca gtaatgacct   8400
cagaactcca tctggatttg ttcagaacgc tcggttgccg ccgggcgttt tttattggtg   8460
agaatggttt attgactacc ggaagcagtg tgaccgtgtg cttctcaaat gcctcaggct   8520
gtctatgtgt gactgttgag ctgtaacaag ttgtctcagg tgttcaattt catgttctag   8580
ttgctttgtt ttactggttt cacctgttct attaggtgtt acatgctgtt catctgttac   8640
```

attgtcgatc tgttcatggt gaacagcttt aaatgcacca aaaactcgta aaagctctga 8700
tgtatctatc ttttttacac cgttttcatc tgtgcatatg gacagttttc cctttgatat 8760
ctaacggtga acagttgttc tacttttgtt tgttagtctt gatgcttcac tgatagatac 8820
aagagccata agaacctcag atccttccgt atttagccag tatgttctct agtgtggttc 8880
gttgtttttg cgtgagccat gagaacgaac cattgagatc atgcttactt tgcatgtcac 8940
tcaaaaattt tgcctcaaaa ctggtgagct gaatttttgc agttaaagca tcgtgtagtg 9000
tttttcttag tccgttacgt aggtaggaat ctgatgtaat ggttgttggt attttgtcac 9060
cattcatttt tatctggttg ttctcaagtt cggttacgag atccatttgt ctatctagtt 9120
caacttggaa aatcaacgta tcagtcgggc ggcctcgctt atcaaccacc aatttcatat 9180
tgctgtaagt gtttaaatct ttacttattg gtttcaaaac ccattggtta agccttttaa 9240
actcatggta gttattttca agcattaaca tgaacttaaa ttcatcaagg ctaatctcta 9300
tatttgcctt gtgagttttc ttttgtgtta gttcttttaa taaccactca taaatcctca 9360
tagagtattt gttttcaaaa gacttaacat gttccagatt atattttatg aattttttta 9420
actggaaaag ataaggcaat atctcttcac taaaaactaa ttctaatttt tcgcttgaga 9480
acttggcata gtttgtccac tggaaaatct caaagccttt aaccaaagga ttcctgattt 9540
ccacagttct cgtcatcagc tctctggttg ctttagctaa tacaccataa gcattttccc 9600
tactgatgtt catcatctga gcgtattggt tataagtgaa cgataccgtc cgttctttcc 9660
ttgtagggtt ttcaatcgtg gggttgagta gtgccacaca gcataaaatt agcttggttt 9720
catgctccgt taagtcatag cgactaatcg ctagttcatt tgctttgaaa acaactaatt 9780
cagacataca tctcaattgg tctaggtgat tttaatcact ataccaattg agatgggcta 9840
gtcaatgata attactagtc cttttccttt gagttgtggg tatctgtaaa ttctgctaga 9900
cctttgctgg aaaacttgta aattctgcta gaccctctgt aaattccgct agacctttgt 9960
gtgttttttt tgtttatatt caagtggtta taatttatag aataaagaaa gaataaaaaa 10020
agataaaaag aatagatccc agccctgtgt ataactcact actttagtca gttccgcagt 10080
attacaaaag gatgtcgcaa acgctgtttg ctcctctaca aaacagacct taaaacccta 10140
aaggcttaag tagcaccctc gcaagctcgg gcaaatcgct gaatattcct tttgtctccg 10200
accatcaggc acctgagtcg ctgtcttttt cgtgacattc agttcgctgc gctcacggct 10260
ctggcagtga atgggggtaa atggcactac aggcgccttt tatggattca tgcaaggaaa 10320
ctacccataa tacaagaaaa gcccgtcacg ggcttctcag ggcgttttat ggcgggtctg 10380
ctatgtggtg ctatctgact tttgctgttt cagcagttcc tgccctctga ttttccagtc 10440
tgaccacttc ggattatccc gtgacaggtc attcagactg gctaatgcac ccagtaaggc 10500
agcggtatca tcaacaggct tacccgtctt actgtcggat cgacgctctc ccttatgcga 10560
ctcctgcat 10569

<210> SEQ ID NO 117
<211> LENGTH: 1958
<212> TYPE: DNA
<213> ORGANISM: E. coli

<400> SEQUENCE: 117
caatgtcgca atttcctgtg gcgtcccctg gattagctcg agccgaacct ccgggaaaag 60
ttcgcgaaaa gctttaatga cctctggcaa gctataacgt gcctgagtat gcgtcgttgc 120

```
aatagtgaga acgccagacg tatcgttggt aaacaggtct gcaagccgac gaacattact    180

ggcttcattc agaatacgtt ctgcaatgac cagtaatgct ttgcccggtt cagtcatgcc    240

cagcagtcgc ttacctcgtc gaacaaatat ttcgatgcca agttcatcct ccagttcccg    300

aatatgacgg ctgacgcctg actgtgaggt aaaaagcata ttcgcaacct ctgtcaggtt    360

gtaatcctga cgtgcagcct cgcggattat ctttagttgt tggaaattca cggtaaactc    420

cgggcagttc agatttcccg ttattgttaa agtctaatgc ccggcataac aaataataaa    480

aacccgcatc ttattccatc ccgatataac acttagctca ccaattgcca ctgccttttt    540

tccatcactg gagaactaat cactgacatt aacaactctt tcactgcctg tgcctgtggc    600

gataagttcg ctctggcggg taaatttaat gacaaagaga gactcatgga aggagtggta    660

atgcgtgaca tccacccatt tactgcgcca cataacgaac gcgcggccga ttcgggtaat    720

actgcaacgc ccatgccgct ggcaatcgct gcggtaagcg tggcaataga ctcaatttca    780

ccaataactt ttgccgtgag tcgccgtagg gaaaaagcct catcaacacg aagtctaata    840

gcactgtaat cactggggag aaagaggttc atttgcgcaa tagcattcac atcaacgctt    900

tgccccgggc aatcttgagt tcctaccaga aaaagatctt ctttcagcaa agcctgactg    960

gatacaccag ccacagggga atgctcataa atcaccgcca tatcgagttg gtgatttatc   1020

aatttttcgt taagcactgc accactattt tcatgaagat agataacgat ctccggaaat   1080

tcagcgcgaa ccgcctgtaa taagggcatg gtgatggatg acgcagcggt tcctggtgca   1140

aagccaatcg agacttgccc cgataatgcc tgaccaacgt tatgcaccgc cagttgggcc   1200

tgttcacact gacgtaaaat ggcccgcgca tgggtataga gaatttttcc ggcgtctgtt   1260

ggtgtaacgc cccgctttgt acggatcaaa agttgttgat ttaactcacc ttccagtgtg   1320

gcaacctgct ggctgagcgc tggttgtgcg atatgcaata cttcagcagc ctgggtcagg   1380

ctaccaatat ctacaatttt tacgaagtat ttcaggcgtc tgaagttcat gttgcctccg   1440

gtttttaaga atcggcccaa gtgccgccat tacttacaac cagattgcaa gatgcttgcc   1500

agttttattt tggtgttgat gtacaagcta accaactgtc aaataagaga ttatgataga   1560

ttcgtcattt gctcctttaa tcagctgtcg cgttcccctg ccctataaaa ggagggtatg   1620

caccacgatg gttcattacc caataagatt gaaagctcac cactttgttg aaattgacag   1680

caaacaaaca aaaaaatgca tttcaccctt tgacatcacc atgcactgcc attaatatgc   1740

gccccgttca cacgattcct ctgtagttca gtcggtagaa cggcggactg ttaatccgta   1800

tgtcactggt tcgagtccag tcagaggagc caaattcaaa aaagcctgct ttctagcagg   1860

ctttttgctt tctaattacc aacgctctta aaacatctgt cttgaaccag aactaatttg   1920

cacaggcatt cccgatcgac gttgcaacgc agcatttg                           1958
```

<210> SEQ ID NO 118
<211> LENGTH: 1058
<212> TYPE: DNA
<213> ORGANISM: artificial sequence
<220> FEATURE:
<223> OTHER INFORMATION: edited nac locus

<400> SEQUENCE: 118

```
caatgtcgca atttcctgtg gcgtcccctg gattagctcg agccgaacct ccgggaaaag     60

ttcgcgaaaa gctttaatga cctctggcaa gctataacgt gcctgagtat gcgtcgttgc    120

aatagtgaga acgccagacg tatcgttggt aaacaggtct gcaagccgac gaacattact    180

ggcttcattc agaatacgtt ctgcaatgac cagtaatgct ttgcccggtt cagtcatgcc    240
```

cagcagtcgc ttacctcgtc gaacaaatat ttcgatgcca agttcatcct ccagttcccg 300
aatatgacgg ctgacgcctg actgtgaggt aaaaagcata ttcgcaacct ctgtcaggtt 360
gtaatcctga cgtgcagcct cgcggattat ctttagttgt tggaaattca cggtaaactc 420
cgggcagttc agatttcccg ttattgttaa agtctaatgc ccggcataac aaataataaa 480
aacccgcatc ttattccatc ccgatataac acttagctca cgaagttcat gttgcctccg 540
gtttttaaga atcggcccaa gtgccgccat tacttacaac cagattgcaa gatgcttgcc 600
agttttattt tggtgttgat gtacaagcta accaactgtc aaataagaga ttatgataga 660
ttcgtcattt gctcctttaa tcagctgtcg cgttcccctg ccctataaaa ggagggtatg 720
caccacgatg gttcattacc caataagatt gaaagctcac cactttgttg aaattgacag 780
caaacaaaca aaaaaatgca tttcaccctt tgacatcacc atgcactgcc attaatatgc 840
gccccgttca cacgattcct ctgtagttca gtcggtagaa cggcggactg ttaatccgta 900
tgtcactggt tcgagtccag tcagaggagc caaattcaaa aaagcctgct ttctagcagg 960
ctttttgctt tctaattacc aacgctctta aaacatctgt cttgaaccag aactaatttg 1020
cacaggcatt cccgatcgac gttgcaacgc agcatttg 1058

<210> SEQ ID NO 119
<211> LENGTH: 20
<212> TYPE: DNA
<213> ORGANISM: Artificial sequence
<220> FEATURE:
<223> OTHER INFORMATION: primer

<400> SEQUENCE: 119
caatgtcgca atttcctgtg 20

<210> SEQ ID NO 120
<211> LENGTH: 19
<212> TYPE: DNA
<213> ORGANISM: Artificial sequence
<220> FEATURE:
<223> OTHER INFORMATION: primer

<400> SEQUENCE: 120
caaatgctgc gttgcaacg 19

<210> SEQ ID NO 121
<211> LENGTH: 4104
<212> TYPE: DNA
<213> ORGANISM: Streptococcus pyogenes

<400> SEQUENCE: 121
atggataaaa aatacagcat tggtctggat atcggaacca acagcgttgg gtgggcagta 60
ataacagatg aatacaaagt gccgtcaaaa aaatttaagg ttctggggaa tacagatcgc 120
cacagcataa aaaagaatct gattggggca ttgctgtttg attcgggtga gacagctgag 180
gccacgcgtc tgaaacgtac agcaagaaga cgttacacac gtcgtaaaaa tcgtatttgc 240
tacttacagg aaattttttc taacgaaatg gccaaggtag atgatagttt cttccatcgt 300
ctcgaagaat cttttctggt tgaggaagat aaaaaacacg aacgtcaccc tatctttggc 360
aatatcgtgg atgaagtggc ctatcatgaa aaataccta cgatttatca tcttcgcaag 420
aagttggttg atagtacgga caaagcggat ctgcgtttaa tctatcttgc gttagcgcac 480
atgatcaaat ttcgtggtca tttcttaatt gaaggtgatc tgaatcctga taactctgat 540

-continued

```
gtggacaaat tgtttataca attagtgcaa acctataatc agctgttcga ggaaaacccc    600
attaatgcct ctggagttga tgccaaagcg attttaagcg cgagactttc taagtcccgg    660
cgtctggaga atctgatcgc ccagttacca ggggaaaaga aaaatggtct gtttggtaat    720
ctgattgccc tcagtctggg gcttaccccg aacttcaaat ccaattttga cctggctgag    780
gacgcaaagc tgcagctgag caaagatact tatgatgatg acctcgacaa tctgctcgcc    840
cagattggtg accaatatgc ggatctgttt ctggcagcga agaatctttc ggatgctatc    900
ttgctgtcgg atattctgcg tgttaatacc gaaatcacca aagcgcctct gtctgcaagt    960
atgatcaaga gatacgacga gcaccaccag gacctgactc ttcttaaggc actggtacgc   1020
caacagcttc cggagaaata caaagaaata ttcttcgacc agtccaagaa tggttacgcg   1080
ggctacatcg atggtggtgc atcacaggaa gagttctata aatttattaa accaatcctt   1140
gagaaaatgg atggcacgga agagttactt gttaaactta accgcgaaga cttgcttaga   1200
aagcaacgta cattcgacaa cggctccatc ccacaccaga ttcatttagg tgaacttcac   1260
gccatcttgc gcagacaaga agatttctat cccttcttaa aagacaatcg ggagaaaatc   1320
gagaagatcc tgacgttccg cattccctat tatgtcggtc ccctggcacg tggtaattct   1380
cggtttgcct ggatgacgcg caaaagtgag gaaaccatca ccccttggaa ctttgaagaa   1440
gtcgtggata aaggtgctag cgcgcagtct tttatagaaa gaatgacgaa cttcgataaa   1500
aacttgccca acgaaaaagt cctgcccaag cactctcttt tatatgagta ctttactgtg   1560
tacaacgaac tgactaaagt gaaatacgtt acggaaggta tgcgcaaacc tgcctttctt   1620
agtggcgagc agaaaaaagc aattgtcgat cttctcttta aaacgaatcg caaggtaact   1680
gtaaaacagc tgaaggaaga ttatttcaaa aagatcgaat gctttgattc tgtcgagatc   1740
tcgggtgtcg aagatcgttt caacgcttcc ttagggacct atcatgattt gctgaagata   1800
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
attgtccctc agagcttcct caaggatgat tctatagata ataaagtact tacgagatcg   2580
gacaaaaatc gcggtaaatc ggataacgtc ccatcggagg aagtcgttaa aaagatgaaa   2640
aactattggc gtcaactgct gaacgccaag ctgatcacac agcgtaagtt tgataatctg   2700
actaaagccg aacgcggtgg tcttagtgaa ctcgataaag caggatttat aaaacggcag   2760
ttagtagaaa cgcgccaaat tacgaaacac gtggctcaga tcctcgattc tagaatgaat   2820
acaaagtacg atgaaaacga taaactgatc cgtgaagtaa aagtcattac cttaaaatct   2880
aaacttgtgt ccgatttccg caaagatttt cagttttaca aggtccggga aatcaataac   2940
```

tatcaccatg cacatgatgc atatttaaat gcggttgtag gcacggccct tattaagaaa 3000
taccctaaac tcgaaagtga gtttgtttat ggggattata aagtgtatga cgttcgcaaa 3060
atgatcgcga aatcagaaca ggaaatcggt aaggctaccg ctaaatactt tttttattcc 3120
aacattatga attttttaa gaccgaaata actctcgcga atggtgaaat ccgtaaacgg 3180
cctcttatag aaaccaatgg tgaaacggga gaaatcgttt gggataaagg tcgtgacttt 3240
gccaccgttc gtaaagtcct ctcaatgccg caagttaaca ttgtcaagaa gacggaagtt 3300
caaacagggg gattctccaa agaatctatc ctgccgaagc gtaacagtga taaacttatt 3360
gccagaaaaa aagattggga tccaaaaaaa tacggaggct ttgattcccc taccgtcgcg 3420
tatagtgtgc tggtggttgc taaagtcgag aaagggaaaa gcaagaaatt gaaatcagtt 3480
aaagaactgc tgggtattac aattatggaa agatcgtcct ttgagaaaaa tccgatcgac 3540
tttttagagg ccaaggggta taaggaagtg aaaaaagatc tcatcatcaa attaccgaag 3600
tatagtcttt ttgagctgga aaacggcaga aaaagaatgc tggcctccgc gggcgagtta 3660
cagaagggaa atgagctggc gctgccttcc aaatatgtta attttctgta ccttgccagt 3720
cattatgaga aactgaaggg cagccccgaa gataacgaac agaaacaatt attcgtggaa 3780
cagcataagc actatttaga tgaaattata gagcaaatta gtgaattttc taagcgcgtt 3840
atcctcgcgg atgctaattt agacaaagta ctgtcagctt ataataaaca tcgggataag 3900
ccgattagag aacaggccga aaatatcatt catttgttta ccttaaccaa ccttggagca 3960
ccagctgcct tcaaatattt cgataccaca attgatcgta aacggtatac aagtacaaaa 4020
gaagtcttgg acgcaaccct cattcatcaa tctattactg gattatatga gacacgcatt 4080
gatctttcac agctgggcgg agac 4104

<210> SEQ ID NO 122
<211> LENGTH: 4104
<212> TYPE: DNA
<213> ORGANISM: Artificial sequence
<220> FEATURE:
<223> OTHER INFORMATION: synthesized Cas9 Y155H DNA

<400> SEQUENCE: 122
atggataaaa aatacagcat tggtctggat atcggaacca acagcgttgg gtgggcagta 60
ataacagatg aatacaaagt gccgtcaaaa aaatttaagg ttctggggaa tacagatcgc 120
cacagcataa aaaagaatct gattggggca ttgctgtttg attcgggtga gacagctgag 180
gccacgcgtc tgaaacgtac agcaagaaga cgttacacac gtcgtaaaaa tcgtatttgc 240
tacttacagg aaattttttc taacgaaatg gccaaggtag atgatagttt cttccatcgt 300
ctcgaagaat cttttctggt tgaggaagat aaaaaacacg aacgtcaccc tatctttggc 360
aatatcgtgg atgaagtggc ctatcatgaa aaataccta cgatttatca tcttcgcaag 420
aagttggttg atagtacgga caaagcggat ctgcgtttaa tccatcttgc gttagcgcac 480
atgatcaaat ttcgtggtca tttcttaatt gaaggtgatc tgaatcctga taactctgat 540
gtggacaaat tgtttataca attagtgcaa acctataatc agctgttcga ggaaaacccc 600
attaatgcct ctggagttga tgccaaagcg attttaagcg cgagactttc taagtcccgg 660
cgtctggaga atctgatcgc ccagttacca ggggaaaaga aaaatggtct gtttggtaat 720
ctgattgccc tcagtctggg gcttaccccg aacttcaaat ccaattttga cctggctgag 780
gacgcaaagc tgcagctgag caaagatact tatgatgatg acctcgacaa tctgctcgcc 840

-continued

```
cagattggtg accaatatgc ggatctgttt ctggcagcga agaatctttc ggatgctatc    900
ttgctgtcgg atattctgcg tgttaatacc gaaatcacca aagcgcctct gtctgcaagt    960
atgatcaaga gatacgacga gcaccaccag gacctgactc ttcttaaggc actggtacgc   1020
caacagcttc cggagaaata caaagaaata ttcttcgacc agtccaagaa tggttacgcg   1080
ggctacatcg atggtggtgc atcacaggaa gagttctata aatttattaa accaatcctt   1140
gagaaaatgg atggcacgga agagttactt gttaaactta accgcgaaga cttgcttaga   1200
aagcaacgta cattcgacaa cggctccatc ccacaccaga ttcatttagg tgaacttcac   1260
gccatcttgc gcagacaaga agatttctat cccttcttaa aagacaatcg ggagaaaatc   1320
gagaagatcc tgacgttccg cattccctat tatgtcggtc ccctggcacg tggtaattct   1380
cggtttgcct ggatgacgcg caaaagtgag gaaaccatca ccccttggaa ctttgaagaa   1440
gtcgtggata aaggtgctag cgcgcagtct tttatagaaa gaatgacgaa cttcgataaa   1500
aacttgccca acgaaaaagt cctgcccaag cactctcttt tatatgagta ctttactgtg   1560
tacaacgaac tgactaaagt gaaatacgtt acggaaggta tgcgcaaacc tgcctttctt   1620
agtggcgagc agaaaaaagc aattgtcgat cttctcttta aaacgaatcg caaggtaact   1680
gtaaaacagc tgaaggaaga ttatttcaaa aagatcgaat gctttgattc tgtcgagatc   1740
tcgggtgtcg aagatcgttt caacgcttcc ttagggacct atcatgattt gctgaagata   1800
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
attgtccctc agagcttcct caaggatgat tctatagata ataaagtact tacgagatcg   2580
gacaaaaatc gcggtaaatc ggataacgtc ccatcggagg aagtcgttaa aaagatgaaa   2640
aactattggc gtcaactgct gaacgccaag ctgatcacac agcgtaagtt tgataatctg   2700
actaaagccg aacgcggtgg tcttagtgaa ctcgataaag caggatttat aaaacggcag   2760
ttagtagaaa cgcgccaaat tacgaaacac gtggctcaga tcctcgattc tagaatgaat   2820
acaaagtacg atgaaaacga taaactgatc cgtgaagtaa aagtcattac cttaaaatct   2880
aaacttgtgt ccgatttccg caaagatttt cagttttaca aggtccggga aatcaataac   2940
tatcaccatg cacatgatgc atatttaaat gcggttgtag gcacggccct tattaagaaa   3000
taccctaaac tcgaaagtga gtttgtttat ggggattata aagtgtatga cgttcgcaaa   3060
atgatcgcga aatcagaaca ggaaatcggt aaggctaccg ctaaatactt tttttattcc   3120
aacattatga attttttaa gaccgaaata actctcgcga atggtgaaat ccgtaaacgg   3180
cctcttatag aaaccaatgg tgaaacggga gaaatcgttt gggataaagg tcgtgacttt   3240
```

gccaccgttc gtaaagtcct ctcaatgccg caagttaaca ttgtcaagaa gacggaagtt 3300
caaacagggg gattctccaa agaatctatc ctgccgaagc gtaacagtga taaacttatt 3360
gccagaaaaa aagattggga tccaaaaaaa tacggaggct ttgattcccc taccgtcgcg 3420
tatagtgtgc tggtggttgc taaagtcgag aaagggaaaa gcaagaaatt gaaatcagtt 3480
aaagaactgc tgggtattac aattatggaa agatcgtcct ttgagaaaaa tccgatcgac 3540
tttttagagg ccaaggggta taaggaagtg aaaaaagatc tcatcatcaa attaccgaag 3600
tatagtcttt ttgagctgga aaacggcaga aaaagaatgc tggcctccgc gggcgagtta 3660
cagaagggaa atgagctggc gctgccttcc aaatatgtta attttctgta ccttgccagt 3720
cattatgaga aactgaaggg cagccccgaa gataacgaac agaaacaatt attcgtggaa 3780
cagcataagc actatttaga tgaaattata gagcaaatta gtgaattttc taagcgcgtt 3840
atcctcgcgg atgctaattt agacaaagta ctgtcagctt ataataaaca tcgggataag 3900
ccgattagag aacaggccga aaatatcatt catttgttta ccttaaccaa ccttggagca 3960
ccagctgcct tcaaatattt cgataccaca attgatcgta aacggtatac aagtacaaaa 4020
gaagtcttgg acgcaaccct cattcatcaa tctattactg gattatatga gacacgcatt 4080
gatctttcac agctgggcgg agac 4104

<210> SEQ ID NO 123
<211> LENGTH: 1368
<212> TYPE: PRT
<213> ORGANISM: Artificial sequence
<220> FEATURE:
<223> OTHER INFORMATION: synthesized Cas9 Y155N variant

<400> SEQUENCE: 123

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Asn Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

-continued

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
```

```
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365
```

<210> SEQ ID NO 124
<211> LENGTH: 4104
<212> TYPE: DNA
<213> ORGANISM: Artificial sequence
<220> FEATURE:
<223> OTHER INFORMATION: synthesized Cas9 Y155N

<400> SEQUENCE: 124

```
atggataaaa aatacagcat tggtctggat atcggaacca acagcgttgg gtgggcagta      60

ataacagatg aatacaaagt gccgtcaaaa aaatttaagg ttctggggaa tacagatcgc     120
```

```
cacagcataa aaaagaatct gattggggca ttgctgtttg attcgggtga gacagctgag    180
gccacgcgtc tgaaacgtac agcaagaaga cgttacacac gtcgtaaaaa tcgtatttgc    240
tacttacagg aaatttttc taacgaaatg gccaaggtag atgatagttt cttccatcgt    300
ctcgaagaat cttttctggt tgaggaagat aaaaaacacg aacgtcaccc tatctttggc    360
aatatcgtgg atgaagtggc ctatcatgaa aaataccta cgatttatca tcttcgcaag     420
aagttggttg atagtacgga caaagcggat ctgcgtttaa tcaatcttgc gttagcgcac    480
atgatcaaat ttcgtggtca tttcttaatt gaaggtgatc tgaatcctga taactctgat    540
gtggacaaat tgtttataca attagtgcaa acctataatc agctgttcga ggaaaacccc    600
attaatgcct ctggagttga tgccaaagcg attttaagcg cgagactttc taagtcccgg    660
cgtctggaga atctgatcgc ccagttacca ggggaaaaga aaaatggtct gtttggtaat    720
ctgattgccc tcagtctggg gcttaccccg aacttcaaat ccaattttga cctggctgag    780
gacgcaaagc tgcagctgag caaagatact tatgatgatg acctcgacaa tctgctcgcc    840
cagattggtg accaatatgc ggatctgttt ctggcagcga agaatctttc ggatgctatc    900
ttgctgtcgg atattctgcg tgttaatacc gaaatcacca aagcgcctct gtctgcaagt    960
atgatcaaga gatacgacga gcaccaccag gacctgactc ttcttaaggc actggtacgc   1020
caacagcttc cggagaaata caaagaaata ttcttcgacc agtccaagaa tggttacgcg   1080
ggctacatcg atggtggtgc atcacaggaa gagttctata aatttattaa accaatcctt   1140
gagaaaatgg atggcacgga agagttactt gttaaactta accgcgaaga cttgcttaga   1200
aagcaacgta cattcgacaa cggctccatc ccacaccaga ttcatttagg tgaacttcac   1260
gccatcttgc gcagacaaga agatttctat cccttcttaa aagacaatcg ggagaaaatc   1320
gagaagatcc tgacgttccg cattccctat tatgtcggtc ccctggcacg tggtaattct   1380
cggtttgcct ggatgacgcg caaaagtgag gaaaccatca ccccttggaa ctttgaagaa   1440
gtcgtggata aaggtgctag cgcgcagtct tttatagaaa gaatgacgaa cttcgataaa   1500
aacttgccca acgaaaaagt cctgcccaag cactctcttt tatatgagta ctttactgtg   1560
tacaacgaac tgactaaagt gaaatacgtt acggaaggta tgcgcaaacc tgcctttctt   1620
agtggcgagc agaaaaaagc aattgtcgat cttctcttta aaacgaatcg caaggtaact   1680
gtaaaacagc tgaaggaaga ttatttcaaa aagatcgaat gctttgattc tgtcgagatc   1740
tcgggtgtcg aagatcgttt caacgcttcc ttagggacct atcatgattt gctgaagata   1800
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
```

-continued

```
attgtccctc agagcttcct caaggatgat tctatagata ataaagtact tacgagatcg   2580

gacaaaaatc gcggtaaatc ggataacgtc ccatcggagg aagtcgttaa aaagatgaaa   2640

aactattggc gtcaactgct gaacgccaag ctgatcacac agcgtaagtt tgataatctg   2700

actaaagccg aacgcggtgg tcttagtgaa ctcgataaag caggatttat aaaacggcag   2760

ttagtagaaa cgcgccaaat tacgaaacac gtggctcaga tcctcgattc tagaatgaat   2820

acaaagtacg atgaaaacga taaactgatc cgtgaagtaa aagtcattac cttaaaatct   2880

aaacttgtgt ccgatttccg caaagatttt cagttttaca aggtccggga aatcaataac   2940

tatcaccatg cacatgatgc atatttaaat gcggttgtag gcacggccct tattaagaaa   3000

taccctaaac tcgaaagtga gtttgtttat ggggattata aagtgtatga cgttcgcaaa   3060

atgatcgcga aatcagaaca ggaaatcggt aaggctaccg ctaaatactt tttttattcc   3120

aacattatga attttttaa gaccgaaata actctcgcga atggtgaaat ccgtaaacgg   3180

cctcttatag aaaccaatgg tgaaacggga gaaatcgttt gggataaagg tcgtgacttt   3240

gccaccgttc gtaaagtcct ctcaatgccg caagttaaca ttgtcaagaa gacggaagtt   3300

caaacagggg gattctccaa agaatctatc ctgccgaagc gtaacagtga taaacttatt   3360

gccagaaaaa aagattggga tccaaaaaaa tacggaggct ttgattcccc taccgtcgcg   3420

tatagtgtgc tggtggttgc taaagtcgag aaagggaaaa gcaagaaatt gaaatcagtt   3480

aaagaactgc tgggtattac aattatggaa agatcgtcct ttgagaaaaa tccgatcgac   3540

tttttagagg ccaaggggta taaggaagtg aaaaaagatc tcatcatcaa attaccgaag   3600

tatagtcttt ttgagctgga aaacggcaga aaaagaatgc tggcctccgc gggcgagtta   3660

cagaagggaa atgagctggc gctgccttcc aaatatgtta attttctgta ccttgccagt   3720

cattatgaga aactgaaggg cagccccgaa gataacgaac agaaacaatt attcgtggaa   3780

cagcataagc actatttaga tgaaattata gagcaaatta gtgaattttc taagcgcgtt   3840

atcctcgcgg atgctaattt agacaaagta ctgtcagctt ataataaaca tcgggataag   3900

ccgattagag aacaggccga aaatatcatt catttgttta ccttaaccaa ccttggagca   3960

ccagctgcct tcaaatattt cgataccaca attgatcgta aacggtatac aagtacaaaa   4020

gaagtcttgg acgcaaccct cattcatcaa tctattactg gattatatga gacacgcatt   4080

gatctttcac agctgggcgg agac                                          4104
```

```
<210> SEQ ID NO 125
<211> LENGTH: 1368
<212> TYPE: PRT
<213> ORGANISM: Artificial sequence
<220> FEATURE:
<223> OTHER INFORMATION: synthesized Cas9 Y155E

<400> SEQUENCE: 125

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

-continued

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Glu Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
```

```
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320
```

```
Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 126
<211> LENGTH: 4104
<212> TYPE: DNA
<213> ORGANISM: Artificial sequence
<220> FEATURE:
<223> OTHER INFORMATION: synthesized Cas9 Y155E

<400> SEQUENCE: 126

atggataaaa aatacagcat tggtctggat atcggaacca acagcgttgg gtgggcagta     60

ataacagatg aatacaaagt gccgtcaaaa aaatttaagg ttctggggaa tacagatcgc    120

cacagcataa aaaagaatct gattggggca ttgctgtttg attcgggtga gacagctgag    180

gccacgcgtc tgaaacgtac agcaagaaga cgttacacac gtcgtaaaaa tcgtatttgc    240

tacttacagg aaatttttc taacgaaatg gccaaggtag atgatagttt cttccatcgt    300

ctcgaagaat cttttctggt tgaggaagat aaaaaacacg aacgtcaccc tatctttggc    360

aatatcgtgg atgaagtggc ctatcatgaa aaataccta cgatttatca tcttcgcaag    420

aagttggttg atagtacgga caaagcggat ctgcgtttaa tcgagcttgc gttagcgcac    480

atgatcaaat ttcgtggtca tttcttaatt gaaggtgatc tgaatcctga taactctgat    540

gtggacaaat tgtttataca attagtgcaa acctataatc agctgttcga ggaaaacccc    600

attaatgcct ctggagttga tgccaaagcg attttaagcg cgagactttc taagtcccgg    660

cgtctggaga atctgatcgc ccagttacca ggggaaaaga aaaatggtct gtttggtaat    720

ctgattgccc tcagtctggg gcttaccccg aacttcaaat ccaattttga cctggctgag    780

gacgcaaagc tgcagctgag caaagatact tatgatgatg acctcgacaa tctgctcgcc    840

cagattggtg accaatatgc ggatctgttt ctggcagcga agaatctttc ggatgctatc    900

ttgctgtcgg atattctgcg tgttaatacc gaaatcacca aagcgcctct gtctgcaagt    960

atgatcaaga gatacgacga gcaccaccag gacctgactc ttcttaaggc actggtacgc   1020

caacagcttc cggagaaata caaagaaata ttcttcgacc agtccaagaa tggttacgcg   1080

ggctacatcg atggtggtgc atcacaggaa gagttctata aatttattaa accaatcctt   1140

gagaaaatgg atggcacgga agagttactt gttaaactta accgcgaaga cttgcttaga   1200

aagcaacgta cattcgacaa cggctccatc ccacaccaga ttcatttagg tgaacttcac   1260

gccatcttgc gcagacaaga agatttctat cccttcttaa aagacaatcg ggagaaaatc   1320

gagaagatcc tgacgttccg cattccctat tatgtcggtc ccctggcacg tggtaattct   1380

cggtttgcct ggatgacgcg caaaagtgag gaaaccatca ccccttggaa ctttgaagaa   1440

gtcgtggata aaggtgctag cgcgcagtct tttatagaaa gaatgacgaa cttcgataaa   1500

aacttgccca acgaaaaagt cctgcccaag cactctcttt tatatgagta ctttactgtg   1560

tacaacgaac tgactaaagt gaaatacgtt acggaaggta tgcgcaaacc tgcctttctt   1620

agtggcgagc agaaaaaagc aattgtcgat cttctcttta aaacgaatcg caaggtaact   1680

gtaaaacagc tgaaggaaga ttatttcaaa aagatcgaat gctttgattc tgtcgagatc   1740

tcgggtgtcg aagatcgttt caacgcttcc ttagggacct atcatgattt gctgaagata   1800
```

```
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
attgtccctc agagcttcct caaggatgat tctatagata ataaagtact tacgagatcg   2580
gacaaaaatc gcggtaaatc ggataacgtc ccatcggagg aagtcgttaa aaagatgaaa   2640
aactattggc gtcaactgct gaacgccaag ctgatcacac agcgtaagtt tgataatctg   2700
actaaagccg aacgcggtgg tcttagtgaa ctcgataaag caggatttat aaaacggcag   2760
ttagtagaaa cgcgccaaat tacgaaacac gtggctcaga tcctcgattc tagaatgaat   2820
acaaagtacg atgaaaacga taaactgatc cgtgaagtaa aagtcattac cttaaaatct   2880
aaacttgtgt ccgatttccg caaagatttt cagttttaca aggtccggga aatcaataac   2940
tatcaccatg cacatgatgc atatttaaat gcggttgtag gcacggccct tattaagaaa   3000
taccctaaac tcgaaagtga gtttgtttat ggggattata aagtgtatga cgttcgcaaa   3060
atgatcgcga aatcagaaca ggaaatcggt aaggctaccg ctaaatactt tttttattcc   3120
aacattatga attttttaa gaccgaaata actctcgcga atggtgaaat ccgtaaacgg   3180
cctcttatag aaaccaatgg tgaaacggga gaaatcgttt gggataaagg tcgtgacttt   3240
gccaccgttc gtaaagtcct ctcaatgccg caagttaaca ttgtcaagaa gacggaagtt   3300
caaacagggg gattctccaa agaatctatc ctgccgaagc gtaacagtga taaacttatt   3360
gccagaaaaa aagattggga tccaaaaaaa tacggaggct ttgattcccc taccgtcgcg   3420
tatagtgtgc tggtggttgc taaagtcgag aaagggaaaa gcaagaaatt gaaatcagtt   3480
aaagaactgc tgggtattac aattatggaa agatcgtcct ttgagaaaaa tccgatcgac   3540
tttttagagg ccaaggggta taaggaagtg aaaaaagatc tcatcatcaa attaccgaag   3600
tatagtcttt ttgagctgga aaacggcaga aaaagaatgc tggcctccgc gggcgagtta   3660
cagaagggaa atgagctggc gctgccttcc aaatatgtta attttctgta ccttgccagt   3720
cattatgaga aactgaaggg cagccccgaa gataacgaac agaaacaatt attcgtggaa   3780
cagcataagc actatttaga tgaaattata gagcaaatta gtgaattttc taagcgcgtt   3840
atcctcgcgg atgctaattt agacaaagta ctgtcagctt ataataaaca tcgggataag   3900
ccgattagag aacaggccga aaatatcatt catttgttta ccttaaccaa ccttggagca   3960
ccagctgcct tcaaatattt cgataccaca attgatcgta aacggtatac aagtacaaaa   4020
gaagtcttgg acgcaaccct cattcatcaa tctattactg gattatatga gacacgcatt   4080
gatctttcac agctgggcgg agac                                           4104
```

<210> SEQ ID NO 127
<211> LENGTH: 1368
<212> TYPE: PRT
<213> ORGANISM: Artificial sequence
<220> FEATURE:
<223> OTHER INFORMATION: synthesized Cas9 Y155F

<400> SEQUENCE: 127

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Phe Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

-continued

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

-continued

```
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200
```

-continued

```
Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 128
<211> LENGTH: 4104
<212> TYPE: DNA
<213> ORGANISM: Artificial sequence
<220> FEATURE:
<223> OTHER INFORMATION: synthesized Cas9 Y155F

<400> SEQUENCE: 128

```
atggataaaa aatacagcat tggtctggat atcggaacca acagcgttgg gtgggcagta     60

ataacagatg aatacaaagt gccgtcaaaa aaatttaagg ttctggggaa tacagatcgc    120

cacagcataa aaaagaatct gattggggca ttgctgtttg attcgggtga gacagctgag    180

gccacgcgtc tgaaacgtac agcaagaaga cgttacacac gtcgtaaaaa tcgtatttgc    240

tacttacagg aaatttttc taacgaaatg gccaaggtag atgatagttt cttccatcgt    300

ctcgaagaat cttttctggt tgaggaagat aaaaaacacg aacgtcaccc tatctttggc    360

aatatcgtgg atgaagtggc ctatcatgaa aaatacccta cgatttatca tcttcgcaag    420

aagttggttg atagtacgga caaagcggat ctgcgtttaa tctttcttgc gttagcgcac    480

atgatcaaat ttcgtggtca tttcttaatt gaaggtgatc tgaatcctga taactctgat    540

gtggacaaat tgtttataca attagtgcaa acctataatc agctgttcga ggaaaacccc    600

attaatgcct ctggagttga tgccaaagcg attttaagcg cgagactttc taagtcccgg    660

cgtctggaga atctgatcgc ccagttacca ggggaaaaga aaaatggtct gtttggtaat    720

ctgattgccc tcagtctggg gcttaccccg aacttcaaat ccaattttga cctggctgag    780

gacgcaaagc tgcagctgag caaagatact tatgatgatg acctcgacaa tctgctcgcc    840

cagattggtg accaatatgc ggatctgttt ctggcagcga agaatctttc ggatgctatc    900

ttgctgtcgg atattctgcg tgttaatacc gaaatcacca aagcgcctct gtctgcaagt    960

atgatcaaga gatacgacga gcaccaccag gacctgactc ttcttaaggc actggtacgc   1020

caacagcttc cggagaaata caaagaaata ttcttcgacc agtccaagaa tggttacgcg   1080
```

```
ggctacatcg atggtggtgc atcacaggaa gagttctata aatttattaa accaatcctt   1140
gagaaaatgg atggcacgga agagttactt gttaaactta accgcgaaga cttgcttaga   1200
aagcaacgta cattcgacaa cggctccatc ccacaccaga ttcatttagg tgaacttcac   1260
gccatcttgc gcagacaaga agatttctat ccccttctaa aagacaatcg ggagaaaatc   1320
gagaagatcc tgacgttccg cattccctat tatgtcggtc ccctggcacg tggtaattct   1380
cggtttgcct ggatgacgcg caaaagtgag gaaaccatca ccccttggaa ctttgaagaa   1440
gtcgtggata aaggtgctag cgcgcagtct tttatagaaa gaatgacgaa cttcgataaa   1500
aacttgccca acgaaaaagt cctgcccaag cactctcttt tatatgagta ctttactgtg   1560
tacaacgaac tgactaaagt gaaatacgtt acggaaggta tgcgcaaacc tgcctttctt   1620
agtggcgagc agaaaaaagc aattgtcgat cttctcttta aaacgaatcg caaggtaact   1680
gtaaaacagc tgaaggaaga ttatttcaaa aagatcgaat gctttgattc tgtcgagatc   1740
tcgggtgtcg aagatcgttt caacgcttcc ttagggacct atcatgattt gctgaagata   1800
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
attgtccctc agagcttcct caaggatgat tctatagata ataaagtact tacgagatcg   2580
gacaaaaatc gcggtaaatc ggataacgtc ccatcggagg aagtcgttaa aaagatgaaa   2640
aactattggc gtcaactgct gaacgccaag ctgatcacac agcgtaagtt tgataatctg   2700
actaaagccg aacgcggtgg tcttagtgaa ctcgataaag caggatttat aaaacggcag   2760
ttagtagaaa cgcgccaaat tacgaaacac gtggctcaga tcctcgattc tagaatgaat   2820
acaaagtacg atgaaaacga taaactgatc cgtgaagtaa aagtcattac cttaaaatct   2880
aaacttgtgt ccgatttccg caaagatttt cagttttaca aggtccggga aatcaataac   2940
tatcaccatg cacatgatgc atatttaaat gcggttgtag gcacggccct tattaagaaa   3000
taccctaaac tcgaaagtga gtttgtttat ggggattata aagtgtatga cgttcgcaaa   3060
atgatcgcga aatcagaaca ggaaatcggt aaggctaccg ctaaatactt tttttattcc   3120
aacattatga atttttttaa gaccgaaata actctcgcga atggtgaaat ccgtaaacgg   3180
cctcttatag aaaccaatgg tgaaacggga gaaatcgttt gggataaagg tcgtgacttt   3240
gccaccgttc gtaaagtcct ctcaatgccg caagttaaca ttgtcaagaa gacggaagtt   3300
caaacagggg gattctccaa agaatctatc ctgccgaagc gtaacagtga taaacttatt   3360
gccagaaaaa aagattggga tccaaaaaaa tacggaggct ttgattcccc taccgtcgcg   3420
```

```
tatagtgtgc tggtggttgc taaagtcgag aaagggaaaa gcaagaaatt gaaatcagtt   3480

aaagaactgc tgggtattac aattatggaa agatcgtcct ttgagaaaaa tccgatcgac   3540

tttttagagg ccaaggggta taaggaagtg aaaaaagatc tcatcatcaa attaccgaag   3600

tatagtcttt ttgagctgga aacggcagaa aaaagaatgc tggcctccgc gggcgagtta   3660

cagaagggaa atgagctggc gctgccttcc aaatatgtta attttctgta ccttgccagt   3720

cattatgaga aactgaaggg cagccccgaa gataacgaac agaaacaatt attcgtggaa   3780

cagcataagc actatttaga tgaaattata gagcaaatta gtgaattttc taagcgcgtt   3840

atcctcgcgg atgctaattt agacaaagta ctgtcagctt ataataaaca tcgggataag   3900

ccgattagag aacaggccga aaatatcatt catttgttta ccttaaccaa ccttggagca   3960

ccagctgcct tcaaatattt cgataccaca attgatcgta aacggtatac aagtacaaaa   4020

gaagtcttgg acgcaaccct cattcatcaa tctattactg gattatatga gacacgcatt   4080

gatctttcac agctgggcgg agac                                          4104
```

```
<210> SEQ ID NO 129
<211> LENGTH: 1368
<212> TYPE: PRT
<213> ORGANISM: Artificial sequence
<220> FEATURE:
<223> OTHER INFORMATION: synthesized Cas9 F86A F98A variant

<400> SEQUENCE: 129

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Ala Ser Asn Glu Met Ala Lys Val Asp Asp Ser
                85                  90                  95

Ala Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile His Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

-continued

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
```

```
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080
```

```
Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 130
<211> LENGTH: 498
<212> TYPE: DNA
<213> ORGANISM: Artificial sequence
<220> FEATURE:
<223> OTHER INFORMATION: synthesized F86A F98A synthetic fragment

<400> SEQUENCE: 130

```
cacgtcgtaa aaatcgtatt tgctacttac aggaaattgc gtctaacgaa atggccaagg     60

tagatgatag tgcgttccat cgtctcgaag aatcttttct ggttgaggaa gataaaaaac    120

acgaacgtca ccctatcttt ggcaatatcg tggatgaagt ggcctatcat gaaaaatacc    180

ctacgattta tcatcttcgc aagaagttgg ttgatagtac ggacaaagcg gatctgcgtt    240

taatccatct tgcgttagcg cacatgatca aatttcgtgg tcatttctta attgaaggtg    300

atctgaatcc tgataactct gatgtggaca aattgtttat acaattagtg caaacctata    360
```

atcagctgtt cgaggaaaac cccattaatg cctctggagt tgatgccaaa gcgattttaa 420
gcgcgagact ttctaagtcc cggcgtctgg agaatctgat cgcccagtta ccaggggaaa 480
agaaaaatgg tctgtttg 498

<210> SEQ ID NO 131
<211> LENGTH: 9266
<212> TYPE: DNA
<213> ORGANISM: Artificial sequence
<220> FEATURE:
<223> OTHER INFORMATION: plasmid pRF801 backbone for F86A-F98A

<400> SEQUENCE: 131
aaagaaaaat ggtctgtttg gtaatctgat tgccctcagt ctggggctta ccccgaactt 60
caaatccaat tttgacctgg ctgaggacgc aaagctgcag ctgagcaaag atacttatga 120
tgatgacctc gacaatctgc tcgcccagat tggtgaccaa tatgcggatc tgtttctggc 180
agcgaagaat ctttcggatg ctatcttgct gtcggatatt ctgcgtgtta ataccgaaat 240
caccaaagcg cctctgtctg caagtatgat caagagatac gacgagcacc accaggacct 300
gactcttctt aaggcactgg tacgccaaca gcttccggag aaatacaaag aaatattctt 360
cgaccagtcc aagaatggtt acgcgggcta catcgatggt ggtgcatcac aggaagagtt 420
ctataaattt attaaaccaa tccttgagaa aatggatggc acggaagagt tacttgttaa 480
acttaaccgc gaagacttgc ttagaaagca acgtacattc gacaacggct ccatcccaca 540
ccagattcat ttaggtgaac ttcacgccat cttgcgcaga caagaagatt tctatccctt 600
cttaaaagac aatcgggaga aaatcgagaa gatcctgacg ttccgcattc cctattatgt 660
cggtcccctg gcacgtggta attctcggtt tgcctggatg acgcgcaaaa gtgaggaaac 720
catcacccct tggaactttg aagaagtcgt ggataaaggt gctagcgcgc agtcttttat 780
agaaagaatg acgaacttcg ataaaaactt gcccaacgaa aaagtcctgc ccaagcactc 840
tcttttatat gagtacttta ctgtgtacaa cgaactgact aaagtgaaat acgttacgga 900
aggtatgcgc aaacctgcct ttcttagtgg cgagcagaaa aaagcaattg tcgatcttct 960
ctttaaaacg aatcgcaagg taactgtaaa acagctgaag gaagattatt tcaaaaagat 1020
cgaatgcttt gattctgtcg agatctcggg tgtcgaagat cgtttcaacg cttccttagg 1080
gacctatcat gatttgctga agataataaa agacaaagac tttctcgaca atgaagaaaa 1140
tgaagatatt ctggaggata ttgttttgac cttgacctta ttcgaagata gagagatgat 1200
cgaggagcgc ttaaaaacct atgcccacct gtttgatgac aaagtcatga agcaattaaa 1260
gcgccgcaga tatacggggt ggggccgctt gagccgcaag ttgattaacg gtattagaga 1320
caagcagagc ggaaaaacta tcctggattt cctcaaatct gacggatttg cgaaccgcaa 1380
ttttatgcag cttatacatg atgattcgct tacattcaaa gaggatattc agaaggctca 1440
ggtgtctggg caaggtgatt cactccacga acatatagca aatttggccg gctctcctgc 1500
gattaagaag gggatcctgc aaacagttaa agttgtggat gaacttgtaa aagtaatggg 1560
ccgccacaag ccggagaata tcgtgataga aatggcgcgc gagaatcaaa cgacacaaaa 1620
aggtcaaaag aactcaagag agagaatgaa gcgcattgag gaggggataa aggaacttgg 1680
atctcaaatt ctgaaagaac atccagttga aaacactcag ctgcaaaatg aaaaattgta 1740
cctgtactac ctgcagaatg gaagagacat gtacgtggat caggaattgg atatcaatag 1800
actctcggac tatgacgtag atcacattgt ccctcagagc ttcctcaagg atgattctat 1860

```
agataataaa gtacttacga gatcggacaa aaatcgcggt aaatcggata acgtcccatc   1920
ggaggaagtc gttaaaaaga tgaaaaacta ttggcgtcaa ctgctgaacg ccaagctgat   1980
cacacagcgt aagtttgata atctgactaa agccgaacgc ggtggtctta gtgaactcga   2040
taaagcagga tttataaaac ggcagttagt agaaacgcgc caaattacga aacacgtggc   2100
tcagatcctc gattctagaa tgaatacaaa gtacgatgaa aacgataaac tgatccgtga   2160
agtaaaagtc attaccttaa aatctaaact tgtgtccgat ttccgcaaag attttcagtt   2220
ttacaaggtc cgggaaatca ataactatca ccatgcacat gatgcatatt taaatgcggt   2280
tgtaggcacg gcccttatta agaaataccc taaactcgaa agtgagtttg tttatgggga   2340
ttataaagtg tatgacgttc gcaaaatgat cgcgaaatca gaacaggaaa tcggtaaggc   2400
taccgctaaa tacttttttt attccaacat tatgaatttt tttaagaccg aaataactct   2460
cgcgaatggt gaaatccgta aacggcctct tatagaaacc aatggtgaaa cgggagaaat   2520
cgtttgggat aaaggtcgtg actttgccac cgttcgtaaa gtcctctcaa tgccgcaagt   2580
taacattgtc aagaagacgg aagttcaaac aggggggattc tccaaagaat ctatcctgcc   2640
gaagcgtaac agtgataaac ttattgccag aaaaaaagat tgggatccaa aaaaatacgg   2700
aggctttgat tcccctaccg tcgcgtatag tgtgctggtg gttgctaaag tcgagaaagg   2760
gaaaagcaag aaattgaaat cagttaaaga actgctgggt attacaatta tggaaagatc   2820
gtcctttgag aaaaatccga tcgacttttt agaggccaag gggtataagg aagtgaaaaa   2880
agatctcatc atcaaattac cgaagtatag tctttttgag ctggaaaacg gcagaaaaag   2940
aatgctggcc tccgcgggcg agttacagaa gggaaatgag ctggcgctgc cttccaaata   3000
tgttaatttt ctgtaccttg ccagtcatta tgagaaactg aagggcagcc ccgaagataa   3060
cgaacagaaa caattattcg tggaacagca taagcactat ttagatgaaa ttatagagca   3120
aattagtgaa ttttctaagc gcgttatcct cgcggatgct aatttagaca aagtactgtc   3180
agcttataat aaacatcggg ataagccgat tagagaacag gccgaaaata tcattcattt   3240
gtttacctta accaaccttg gagcaccagc tgccttcaaa tatttcgata ccacaattga   3300
tcgtaaacgg tatacaagta caaaagaagt cttggacgca accctcattc atcaatctat   3360
tactggatta tatgagacac gcattgatct ttcacagctg ggcggagaca agaagaaaaa   3420
actgaaactg caccatcatc accatcatca tcaccatcat tgataactcg agaaagctta   3480
cataaaaaac cggccttggc cccgccggtt ttttattatt tttcttcctc cgcatgttca   3540
atccgctcca taatcgacgg atggctccct ctgaaaattt taacgagaaa cggcgggttg   3600
acccggctca gtcccgtaac ggccaagtcc tgaaacgtct caatcgccgc ttcccggttt   3660
ccggtcagct caatgccgta acggtcggcg gcgttttcct gataccggga gacggcattc   3720
gtaatcgggt gaagtggtca agacctcact aggcacctta aaaatagcgc accctgaaga   3780
agatttattt gaggtagccc ttgcctacct agcttccaag aaagatatcc taacagcaca   3840
agagcggaaa gatgttttgt tctacatcca gaacaacctc tgctaaaatt cctgaaaaat   3900
tttgcaaaaa gttgttgact ttatctacaa ggtgtggcat aatgtgtgga ctcgacttcg   3960
aatacatcca gttttagagc tagaaatagc aagttaaaat aaggctagtc cgttatcaac   4020
ttgaaaaagt ggcaccgagt cggtgcgact cctgttgata gatccagtaa tgacctcaga   4080
actccatctg gatttgttca gaacgctcgg ttgccgccgg gcgttttttta ttggtgagaa   4140
tgtcgacctc gagagttacg ctagggataa cagggtaata taggagctcc agtcggctta   4200
aaccagtttt cgctggtgcg aaaaaagagt gtcttgtgac acctaaattc aaaatctatc   4260
```

```
ggtcagattt ataccgattt gattttatat attcttgaat aacatacgcc gagttatcac   4320
ataaaagcgg gaaccaatca taaaatttaa acttcattgc ataatccatt aaactcttaa   4380
attctacgat tccttgttca tcaataaact caatcatttc tttaattaat ttatatctat   4440
ctgttgttgt tttctttaat aattcattaa catctacacc gccataaact atcatatctt   4500
ctttttgata tttaaattta ttaggatcgt ccatgtgaag catatatctc acaagacctt   4560
tcacacttcc tgcaatctgc ggaatagtcg cattcaattc ttctgttaat tatttttatc   4620
tgttcataag atttattacc ctcatacatc actagaatat gataatgctc tttttcatc    4680
ctaccttctg tatcagtatc cctatcatgt aatggagaca ctacaaattg aatgtgtaac   4740
tcttttaaat actctaacca ctcggctttt gctgattctg gatataaaac aaatgtccaa   4800
ttacgtcctc ttgaattttt cttgttttca gtttctttta ttacattttc gctcatgata   4860
taataacggt gctaatacac ttaacaaaat ttagtcatag ataggcagca tgccagtgct   4920
gtctatcttt ttttgtttaa aatgcaccgt attcctcctt tgcatatttt tttattagaa   4980
taccggttgc atctgatttg ctaatattat atttttcttt gattctattt aatatctcat   5040
tttcttctgt tgtaagtctt aaagtaacag caactttttt ctcttctttt ctatctacaa   5100
ctatcactgt acctcccaac atctgttttt ttcactttaa cataaaaaac aacctttttaa  5160
cattaaaaac ccaatattta tttatttgtt tggacaatgg acactggaca cctaggggggg  5220
aggtcgtagt acccccctat gttttctccc ctaaataacc ccaaaaatct aagaaaaaaa   5280
gacctcaaaa aggtctttaa ttaacatctc aaatttcgca tttattccaa tttccttttt   5340
gcgtgtgatg cgagctcatc ggctccgtcg atactatgtt atacgccaac tttcaaaaca   5400
actttgaaaa agctgtttc tggtatttaa ggttttagaa tgcaaggaac agtgaattgg    5460
agttcgtctt gttataatta gcttcttggg gtatctttaa atactgtaga aaagaggaag   5520
gaaataataa atggctaaaa tgagaatatc accggaattg aaaaaactga tcgaaaaata   5580
ccgctgcgta aaagatacgg aaggaatgtc tcctgctaag gtatataagc tggtgggaga   5640
aaatgaaaac ctatatttaa aaatgacgga cagccggtat aaagggacca cctatgatgt   5700
ggaacgggaa aaggacatga tgctatggct ggaaggaaag ctgcctgttc caaaggtcct   5760
gcactttgaa cggcatgatg gctggagcaa tctgctcatg agtgaggccg atggcgtcct   5820
ttgctcggaa gagtatgaag atgaacaaag ccctgaaaag attatcgagc tgtatgcgga   5880
gtgcatcagg ctctttcact ccatcgacat atcggattgt ccctatacga atagcttaga   5940
cagccgctta gccgaattgg attacttact gaataacgat ctggccgatg tggattgcga   6000
aaactgggaa gaagacactc catttaaaga tccgcgcgag ctgtatgatt ttttaaagac   6060
ggaaaagccc gaagaggaac ttgtcttttc ccacggcgac ctgggagaca gcaacatctt   6120
tgtgaaagat ggcaaagtaa gtggctttat tgatcttggg agaagcggca gggcggacaa   6180
gtggtatgac attgccttct gcgtccggtc gatcagggag gatatcgggg aagaacagta   6240
tgtcgagcta ttttttgact tactggggat caagcctgat tgggagaaaa taaaatatta   6300
tattttactg gatgaattgt tttagtgact gcagtgagat ctggtaatga ctctctagct   6360
tgaggcatca aataaaacga aaggctcagt cgaaagactg ggcctttcgt tttatctgtt   6420
gtttgtcggt gaacgctctc ctgagtagga caaatccgcc gctctagcta agcagaaggc   6480
catcctgacg gatggccttt ttgcgtttct acaaactctt gttaactcta gagctgcctg   6540
ccgcgtttcg gtgatgaaga tcttcccgat gattaattaa ttcagaacgc tcggttgccg   6600
```

```
ccgggcgttt tttatgaagc ttcgttgctg gcgtttttcc ataggctccg ccccccctgac   6660
gagcatcaca aaaatcgacg ctcaagtcag aggtggcgaa acccgacagg actataaaga   6720
taccaggcgt ttcccccctgg aagctccctc gtgcgctctc ctgttccgac cctgccgctt   6780
accggatacc tgtccgcctt tctcccttcg ggaagcgtgg cgctttctca tagctcacgc   6840
tgtaggtatc tcagttcggt gtaggtcgtt cgctccaagc tgggctgtgt gcacgaaccc   6900
cccgttcagc ccgaccgctg cgccttatcc ggtaactatc gtcttgagtc caacccggta   6960
agacacgact tatcgccact ggcagcagcc actggtaaca ggattagcag agcgaggtat   7020
gtaggcggtg ctacagagtt cttgaagtgg tggcctaact acggctacac tagaaggaca   7080
gtatttggta tctgcgctct gctgaagcca gttaccttcg gaaaaagagt tggtagctct   7140
tgatccggca aacaaaccac cgctggtagc ggtggttttt ttgtttgcaa gcagcagatt   7200
acgcgcagaa aaaaaggatc tcaagaagat cctttgatct tttctacggg gtctgacgct   7260
cagtggaacg aaaactcacg ttaagggatt ttggtcatga gattatcaaa aaggatcttc   7320
acctagatcc ttttaaatta aaaatgaagt tttaaatcaa tctaaagtat atatgagtaa   7380
acttggtctg acaaatggtt ctttcccctg tcctaaacaa aaaacccgct ttattgaaaa   7440
agcggggctg ttttacagac aggtcaaata aacgtttgaa aatgttcatt tcaaaacgcg   7500
cggaacctcc atcttctccc atccagacta tactgtcggc ttcggaatcg caccgaatcc   7560
tgcccataaa aaggctcgcg ggcttagagc gcttgctcat caccgccggt agggaatttc   7620
accctgcccc gaagattgat cttatttatt tttaatactg atattattat aaattaattg   7680
tgaaaaaatg tacaggtgca aagcttattg cgctgttttg ggacatcctg cacgatattt   7740
cggtaaactc actttttccg catactaaaa accgcacatt cacagttatt tcatttttaa   7800
ttttcgtctt tccgcgtgaa actcattgac actctttatg gaatatggta aattatcaga   7860
tatttatgac gcttatttag gaggaaatct tacacagaag ctgcggaacc tgaaaagaat   7920
tcctttcagg ttccgttttt tttaggaatt ctccctgatc tcaagcatct ggcggggata   7980
aatccgctct cctttcaaat cgttccattc tttgaggcgc tgtacagtta cgcccatttt   8040
ttcggcgata tgatgaagcg tatcccctttt ccgcactaca tatgtaccgg tcttcgattc   8100
atcgtcatga aggcggagtg tttggccggc cttgagattt gaatgtttca acccgtttat   8160
tctcatgatc tcctcgatgg atataccgct atccttgctg attctccaga gcgtgtcccc   8220
tttttgaacg gtcaccgcac cgctcattgt cccggcgttt tgataaacgt ggatagaatt   8280
ttgccggaac gcctcctcac gaagcaccgt cagcggattg attgcatatc ttttatcttc   8340
agtccatgaa ccgtgatgca tttcaaaatg caggtgggtt ccggtcgata ttcgaattcc   8400
tccattttct tctgctatca aaataacaga ctcgtgattt tccaaacgag ctttcaaaaa   8460
agcctctgcc ccttgcaaat cggatgcctg tctataaaat tcccgatatt ggttaaacag   8520
cggcgcaatg gcggccgcat ctgatgtctt tgcttggcga atgttcatct tatttcttcc   8580
tccctctcaa taatttttttc attctatccc ttttctgtaa agtttatttt tcagaatact   8640
tttatcatca tgctttgaaa aaatatcacg ataatatcca ttgttctcac ggaagcacac   8700
gcaggtcatt tgaacgaatt ttttcgacag gaatttgccg ggactcagga gcatttaacc   8760
taaaaaagca tgacatttca gcataatgaa catttactca tgtctatttt cgttcttttc   8820
tgtatgaaaa tagttatttc gagtctctac ggaaatagcg agagatgata tacctaaata   8880
gagataaaat catctcaaaa aaatgggtct actaaaatat tattccatct attacaataa   8940
attcacagaa tagtctttta agtaagtcta ctctgaattt ttttaaaagg agagggtaac   9000
```

tagtggcccc aaaaaagaaa cgcaaggtta tggataaaaa atacagcatt ggtctggata 9060
tcggaaccaa cagcgttggg tgggcagtaa taacagatga atacaaagtg ccgtcaaaaa 9120
aatttaaggt tctggggaat acagatcgcc acagcataaa aaagaatctg attggggcat 9180
tgctgtttga ttcgggtgag acagctgagg ccacgcgtct gaaacgtaca gcaagaagac 9240
gttacacacg tcgtaaaaat cgtatt 9266

<210> SEQ ID NO 132
<211> LENGTH: 20
<212> TYPE: DNA
<213> ORGANISM: Artificial sequence
<220> FEATURE:
<223> OTHER INFORMATION: primer pRF801 backbone forward

<400> SEQUENCE: 132
aaagaaaaat ggtctgtttg 20

<210> SEQ ID NO 133
<211> LENGTH: 20
<212> TYPE: DNA
<213> ORGANISM: Artificial sequence
<220> FEATURE:
<223> OTHER INFORMATION: primer pRF801 backbone reverse

<400> SEQUENCE: 133
aatacgattt ttacgacgtg 20

<210> SEQ ID NO 134
<211> LENGTH: 20
<212> TYPE: DNA
<213> ORGANISM: Artificial sequence
<220> FEATURE:
<223> OTHER INFORMATION: primer F86A F98A synthetic forward

<400> SEQUENCE: 134
cacgtcgtaa aaatcgtatt 20

<210> SEQ ID NO 135
<211> LENGTH: 20
<212> TYPE: DNA
<213> ORGANISM: Artificial sequence
<220> FEATURE:
<223> OTHER INFORMATION: primer F86A F98A synthetic reverse

<400> SEQUENCE: 135
caaacagacc atttttcttt 20

<210> SEQ ID NO 136
<211> LENGTH: 9724
<212> TYPE: DNA
<213> ORGANISM: Artificial sequence
<220> FEATURE:
<223> OTHER INFORMATION: plasmid pRF866

<400> SEQUENCE: 136
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggactcgac ttcgaataca 240
tccagtttta gagctagaaa tagcaagtta aaataaggct agtccgttat caacttgaaa 300

```
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgtttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgtt ttcagtttct tttattacat tttcgctcat gatataataa   1140
cggtgctaat acacttaaca aaatttagtc atagataggc agcatgccag tgctgtctat   1200
ctttttttgt ttaaaatgca ccgtattcct cctttgcata ttttttatt agaataccgg    1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgtttc tcccctaaat aaccccaaaa atctaagaaa aaaagacctc    1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt ttctggtat ttaaggtttt agaatgcaag gaacagtgaa ttggagttcg    1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gattttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
```

```
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacaaat ggttctttcc cctgtcctaa acaaaaaacc cgctttattg aaaaagcggg   3720
gctgttttac agacaggtca aataaacgtt tgaaaatgtt catttcaaaa cgcgcggaac   3780
ctccatcttc tcccatccag actatactgt cggcttcgga atcgcaccga atcctgccca   3840
taaaaaggct cgcgggctta gagcgcttgc tcatcaccgc cggtagggaa tttcaccctg   3900
ccccgaagat tgatcttatt tatttttaat actgatatta ttataaatta attgtgaaaa   3960
aatgtacagg tgcaaagctt attgcgctgt tttgggacat cctgcacgat atttcggtaa   4020
actcactttt tccgcatact aaaaaccgca cattcacagt tatttcattt ttaattttcg   4080
tctttccgcg tgaaactcat tgacactctt tatggaatat ggtaaattat cagatattta   4140
tgacgcttat ttaggaggaa atcttacaca gaagctgcgg aacctgaaaa gaattccttt   4200
caggttccgt tttttttagg aattctccct gatctcaagc atctggcggg gataaatccg   4260
ctctcctttc aaatcgttcc attctttgag gcgctgtaca gttacgccca ttttttcggc   4320
gatatgatga agcgtatccc ctttccgcac tacatatgta ccggtcttcg attcatcgtc   4380
atgaaggcgg agtgtttggc cggccttgag atttgaatgt ttcaacccgt ttattctcat   4440
gatctcctcg atggatatac cgctatcctt gctgattctc cagagcgtgt ccccttttttg   4500
aacggtcacc gcaccgctca ttgtcccggc gttttgataa acgtggatag aatttgccg   4560
gaacgcctcc tcacgaagca ccgtcagcgg attgattgca tatcttttat cttcagtcca   4620
tgaaccgtga tgcatttcaa aatgcaggtg ggttccggtc gatattcgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tcccttttct gtaaagttta tttttcagaa tacttttatc   4920
atcatgcttt gaaaaaatat cacgataata tccattgttc tcacggaagc acacgcaggt   4980
catttgaacg aatttttttcg acaggaattt gccgggactc aggagcattt aacctaaaaa   5040
```

-continued

```
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga atttttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaattgc gtctaacgaa atggccaagg   5580
tagatgatag tgcgttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatccatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcacccyttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
```

```
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
taggcacggc ccttattaag aaatacccta aactcgaaag tgagtttgtt tatggggatt   8340
ataaagtgta tgacgttcgc aaaatgatcg cgaaatcaga acaggaaatc ggtaaggcta   8400
ccgctaaata ctttttttat tccaacatta tgaatttttt taagaccgaa ataactctcg   8460
cgaatggtga aatccgtaaa cggcctctta tagaaaccaa tggtgaaacg ggagaaatcg   8520
tttgggataa aggtcgtgac tttgccaccg ttcgtaaagt cctctcaatg ccgcaagtta   8580
acattgtcaa gaagacggaa gttcaaacag gggattctc caaagaatct atcctgccga   8640
agcgtaacag tgataaactt attgccagaa aaaaagattg ggatccaaaa aaatacggag   8700
gctttgattc ccctaccgtc gcgtatagtg tgctggtggt tgctaaagtc gagaaaggga   8760
aaagcaagaa attgaaatca gttaaagaac tgctgggtat tacaattatg gaaagatcgt   8820
cctttgagaa aaatccgatc gactttttag aggccaaggg gtataaggaa gtgaaaaaag   8880
atctcatcat caaattaccg aagtatagtc tttttgagct ggaaaacggc agaaaaagaa   8940
tgctggcctc cgcgggcgag ttacagaagg gaaatgagct ggcgctgcct tccaaatatg   9000
ttaattttct gtaccttgcc agtcattatg agaaactgaa gggcagcccc gaagataacg   9060
aacagaaaca attattcgtg gaacagcata agcactattt agatgaaatt atagagcaaa   9120
ttagtgaatt ttctaagcgc gttatcctcg cggatgctaa tttagacaaa gtactgtcag   9180
cttataataa acatcgggat aagccgatta gagaacaggc cgaaaatatc attcatttgt   9240
ttaccttaac caaccttgga gcaccagctg ccttcaaata tttcgatacc acaattgatc   9300
gtaaacggta tacaagtaca aaagaagtct tggacgcaac cctcattcat caatctatta   9360
ctggattata tgagacacgc attgatcttt cacagctggg cggagacaag aagaaaaaac   9420
tgaaactgca ccatcatcac catcatcatc accatcattg ataactcgag aaagcttaca   9480
taaaaaaccg gccttggccc cgccggtttt ttattatttt tcttcctccg catgttcaat   9540
ccgctccata atcgacggat ggctccctct gaaaatttta acgagaaacg gcgggttgac   9600
ccggctcagt cccgtaacgg ccaagtcctg aaacgtctca atcgccgctt cccggtttcc   9660
ggtcagctca atgccgtaac ggtcggcggc gttttcctga taccgggaga cggcattcgt   9720
aatc                                                                9724
```

<210> SEQ ID NO 137
<211> LENGTH: 5042
<212> TYPE: DNA
<213> ORGANISM: Artificial sequence
<220> FEATURE:
<223> OTHER INFORMATION: Bacillus F86A-F98A expression cassette

<400> SEQUENCE: 137

```
attcctccat tttcttctgc tatcaaaata acagactcgt gattttccaa acgagctttc     60
aaaaaagcct ctgccccttg caaatcggat gcctgtctat aaaattcccg atattggtta    120
aacagcggcg caatggcggc cgcatctgat gtctttgctt ggcgaatgtt catcttattt    180
cttcctccct ctcaataatt ttttcattct atccctttc tgtaaagttt atttttcaga     240
atacttttat catcatgctt tgaaaaaata tcacgataat atccattgtt ctcacggaag    300
cacacgcagg tcatttgaac gaatttttc gacaggaatt tgccgggact caggagcatt     360
taacctaaaa aagcatgaca tttcagcata atgaacattt actcatgtct attttcgttc    420
ttttctgtat gaaaatagtt atttcgagtc tctacggaaa tagcgagaga tgatatacct    480
aaatagagat aaaatcatct caaaaaaatg ggtctactaa aatattattc catctattac    540
aataaattca cagaatagtc ttttaagtaa gtctactctg aatttttta aaaggagagg     600
gtaactagtg gccccaaaaa agaaacgcaa ggttatggat aaaaaataca gcattggtct    660
ggatatcgga accaacagcg ttgggtgggc agtaataaca gatgaataca aagtgccgtc    720
aaaaaaattt aaggttctgg ggaatacaga tcgccacagc ataaaaaaga atctgattgg    780
ggcattgctg tttgattcgg gtgagacagc tgaggccacg cgtctgaaac gtacagcaag    840
aagacgttac acacgtcgta aaaatcgtat ttgctactta caggaaattg cgtctaacga    900
aatggccaag gtagatgata gtgcgttcca tcgtctcgaa gaatcttttc tggttgagga    960
agataaaaaa cacgaacgtc accctatctt tggcaatatc gtggatgaag tggcctatca   1020
tgaaaaatac cctacgattt atcatcttcg caagaagttg gttgatagta cggacaaagc   1080
ggatctgcgt ttaatccatc ttgcgttagc gcacatgatc aaatttcgtg gtcatttctt   1140
aattgaaggt gatctgaatc ctgataactc tgatgtggac aaattgttta tacaattagt   1200
gcaaacctat aatcagctgt tcgaggaaaa ccccattaat gcctctggag ttgatgccaa   1260
agcgatttta agcgcgagac tttctaagtc ccggcgtctg gagaatctga tcgcccagtt   1320
accaggggaa aagaaaaatg gtctgtttgg taatctgatt gccctcagtc tggggcttac   1380
cccgaacttc aaatccaatt ttgacctggc tgaggacgca aagctgcagc tgagcaaaga   1440
tacttatgat gatgacctcg acaatctgct cgcccagatt ggtgaccaat atgcggatct   1500
gtttctggca gcgaagaatc tttcggatgc tatcttgctg tcggatattc tgcgtgttaa   1560
taccgaaatc accaaagcgc ctctgtctgc aagtatgatc aagagatacg acgagcacca   1620
ccaggacctg actcttctta aggcactggt acgccaacag cttccggaga aatacaaaga   1680
aatattcttc gaccagtcca agaatggtta cgcgggctac atcgatggtg gtgcatcaca   1740
ggaagagttc tataaattta ttaaaccaat ccttgagaaa atggatggca cggaagagtt   1800
acttgttaaa cttaaccgcg aagacttgct tagaaagcaa cgtacattcg acaacggctc   1860
catcccacac cagattcatt taggtgaact tcacgccatc ttgcgcagac aagaagattt   1920
ctatcccttc ttaaaagaca atcgggagaa aatcgagaag atcctgacgt tccgcattcc   1980
ctattatgtc ggtcccctgg cacgtggtaa ttctcggttt gcctggatga cgcgcaaaag   2040
tgaggaaacc atcacccctt ggaactttga agaagtcgtg gataaaggtg ctagcgcgca   2100
```

-continued

```
gtcttttata gaaagaatga cgaacttcga taaaaacttg cccaacgaaa aagtcctgcc   2160
caagcactct cttttatatg agtactttac tgtgtacaac gaactgacta aagtgaaata   2220
cgttacggaa ggtatgcgca aacctgcctt tcttagtggc gagcagaaaa aagcaattgt   2280
cgatcttctc tttaaaacga atcgcaaggt aactgtaaaa cagctgaagg aagattattt   2340
caaaaagatc gaatgctttg attctgtcga gatctcgggt gtcgaagatc gtttcaacgc   2400
ttccttaggg acctatcatg atttgctgaa gataataaaa gacaaagact ttctcgacaa   2460
tgaagaaaat gaagatattc tggaggatat tgttttgacc ttgaccttat tcgaagatag   2520
agagatgatc gaggagcgct taaaaaccta tgcccacctg tttgatgaca aagtcatgaa   2580
gcaattaaag cgccgcagat atacggggtg gggccgcttg agccgcaagt tgattaacgg   2640
tattagagac aagcagagcg gaaaaactat cctggatttc ctcaaatctg acggatttgc   2700
gaaccgcaat tttatgcagc ttatacatga tgattcgctt acattcaaag aggatattca   2760
gaaggctcag gtgtctgggc aaggtgattc actccacgaa catatagcaa atttggccgg   2820
ctctcctgcg attaagaagg ggatcctgca aacagttaaa gttgtggatg aacttgtaaa   2880
agtaatgggc cgccacaagc cggagaatat cgtgatagaa atggcgcgcg agaatcaaac   2940
gacacaaaaa ggtcaaaaga actcaagaga gagaatgaag cgcattgagg aggggataaa   3000
ggaacttgga tctcaaattc tgaaagaaca tccagttgaa aacactcagc tgcaaaatga   3060
aaaattgtac ctgtactacc tgcagaatgg aagagacatg tacgtggatc aggaattgga   3120
tatcaataga ctctcggact atgacgtaga tcacattgtc cctcagagct tcctcaagga   3180
tgattctata gataataaag tacttacgag atcggacaaa aatcgcggta aatcggataa   3240
cgtcccatcg gaggaagtcg ttaaaaagat gaaaaactat tggcgtcaac tgctgaacgc   3300
caagctgatc acacagcgta agtttgataa tctgactaaa gccgaacgcg gtggtcttag   3360
tgaactcgat aaagcaggat ttataaaacg gcagttagta gaaacgcgcc aaattacgaa   3420
acacgtggct cagatcctcg attctagaat gaatacaaag tacgatgaaa acgataaact   3480
gatccgtgaa gtaaaagtca ttaccttaaa atctaaactt gtgtccgatt tccgcaaaga   3540
ttttcagttt tacaaggtcc gggaaatcaa taactatcac catgcacatg atgcatattt   3600
aaatgcggtt gtaggcacgg cccttattaa gaaataccct aaactcgaaa gtgagtttgt   3660
ttatggggat tataaagtgt atgacgttcg caaaatgatc gcgaaatcag aacaggaaat   3720
cggtaaggct accgctaaat acttttttta ttccaacatt atgaattttt ttaagaccga   3780
aataactctc gcgaatggtg aaatccgtaa acggcctctt atagaaacca atggtgaaac   3840
gggagaaatc gtttgggata aaggtcgtga ctttgccacc gttcgtaaag tcctctcaat   3900
gccgcaagtt aacattgtca agaagacgga agttcaaaca gggggattct ccaaagaatc   3960
tatcctgccg aagcgtaaca gtgataaact tattgccaga aaaaaagatt gggatccaaa   4020
aaaatacgga ggctttgatt cccctaccgt cgcgtatagt gtgctggtgg ttgctaaagt   4080
cgagaaaggg aaaagcaaga aattgaaatc agttaaagaa ctgctgggta ttacaattat   4140
ggaaagatcg tcctttgaga aaaatccgat cgacttttta gaggccaagg ggtataagga   4200
agtgaaaaaa gatctcatca tcaaattacc gaagtatagt ctttttgagc tggaaaacgg   4260
cagaaaaaga atgctggcct ccgcgggcga gttacagaag ggaaatgagc tggcgctgcc   4320
ttccaaatat gttaattttc tgtaccttgc cagtcattat gagaaactga agggcagccc   4380
cgaagataac gaacagaaac aattattcgt ggaacagcat aagcactatt tagatgaaat   4440
```

tatagagcaa attagtgaat tttctaagcg cgttatcctc gcggatgcta atttagacaa 4500
agtactgtca gcttataata aacatcggga taagccgatt agagaacagg ccgaaaatat 4560
cattcatttg tttaccttaa ccaaccttgg agcaccagct gccttcaaat atttcgatac 4620
cacaattgat cgtaaacggt atacaagtac aaaagaagtc ttggacgcaa ccctcattca 4680
tcaatctatt actggattat atgagacacg cattgatctt tcacagctgg gcggagacaa 4740
gaagaaaaaa ctgaaactgc accatcatca ccatcatcat caccatcatt gataaacata 4800
aaaaaccggc cttggccccg ccggtttttt attatttttc ttcctccgca tgttcaatcc 4860
gctccataat cgacggatgg ctccctctga aaattttaac gagaaacggc gggttgaccc 4920
ggctcagtcc cgtaacggcc aagtcctgaa acgtctcaat cgccgcttcc cggtttccgg 4980
tcagctcaat gccgtaacgg tcggcggcgt tttcctgata ccgggagacg gcattcgtaa 5040
tc 5042

<210> SEQ ID NO 138
<211> LENGTH: 54
<212> TYPE: DNA
<213> ORGANISM: Artificial Sequence
<220> FEATURE:
<223> OTHER INFORMATION: primer

<400> SEQUENCE: 138
aaagaaatat atagagagat actcttatca atgatggtga tgatgatggt gatg 54

<210> SEQ ID NO 139
<211> LENGTH: 58
<212> TYPE: DNA
<213> ORGANISM: Artificial Sequence
<220> FEATURE:
<223> OTHER INFORMATION: primer

<400> SEQUENCE: 139
acacgtattt atttgtccaa ttaccatggc cccaaaaaag aaacgcaagg ttatggat 58

<210> SEQ ID NO 140
<211> LENGTH: 767
<212> TYPE: DNA
<213> ORGANISM: Artificial Sequence
<220> FEATURE:
<223> OTHER INFORMATION: synthesized RNR2p promoter

<400> SEQUENCE: 140
gccaatctaa agcgttgtct tcctcgttcc tcgcgcacgc gattttgcgt tctgcatagg 60
aagccgaagt cgaacaagaa gcaggcaaag tttagagcac tgcccctccg cactcaaaaa 120
agaaaaaact aggaggaaaa taaaattctc aaccacacaa acacataaac acatacaaat 180
acaaatacaa gcttatttac ttgacatcgc gcgatcttcc actattcagc gccgtccgcc 240
ctctctcgtg tttttttgttt acgcgacaac tatgcgaaat ccggagcaac gggcaaccgt 300
ttggggaaag accacaccca cgcgcgatcg ccatggcaac gaggtcgcac acgccccaca 360
cccagacctc cctgcgagcg ggcatgggta caatgtcccc gttgccacag agaccacttc 420
gtagcacagc gcagagcgta gcgtgttgtt gctgctgaca aaagaaaatt tttcttagca 480
aagcaaagga ggggaagcac gggcagatag caccgtacca taccccttgga aactcgaaat 540 gaacgaagca ggaaatgaga gaatgagagt tttgtaggta tatatagcgg tagtgtttgc 600
gcgttaccat catcttctgg atctatctat tgttcttttc ctcatcactt tccccttttt 660
cgctcttctt cttgtctttt atttctttct ttttttaat tgttccctcg attggctatc 720
taccaaagaa tccaaactta atacacgtat ttatttgtcc aattacc 767

<210> SEQ ID NO 141
<211> LENGTH: 1346
<212> TYPE: DNA
<213> ORGANISM: Artificial Sequence
<220> FEATURE:
<223> OTHER INFORMATION: synthesized 2-micron replication origin 1

<400> SEQUENCE: 141
aacgaagcat ctgtgcttca ttttgtagaa caaaaatgca acgcgagagc gctaattttt 60
caaacaaaga atctgagctg catttttaca gaacagaaat gcaacgcgaa agcgctattt 120
taccaacgaa gaatctgtgc ttcatttttg taaaacaaaa atgcaacgcg agagcgctaa 180
tttttcaaac aaagaatctg agctgcattt ttacagaaca gaaatgcaac gcgagagcgc 240
tattttacca acaaagaatc tatacttctt ttttgttcta caaaaatgca tcccgagagc 300
gctatttttc taacaaagca tcttagatta cttttttttct cctttgtgcg ctctataatg 360
cagtctcttg ataacttttt gcactgtagg tccgttaagg ttagaagaag gctactttgg 420
tgtctatttt ctcttccata aaaaaagcct gactccactt cccgcgttta ctgattacta 480
gcgaagctgc gggtgcattt tttcaagata aaggcatccc cgattatatt ctataccgat 540
gtggattgcg catactttgt gaacagaaag tgatagcgtt gatgattctt cattggtcag 600
aaaattatga acggtttctt ctattttgtc tctatatact acgtatagga aatgtttaca 660
ttttcgtatt gttttcgatt cactctatga atagttctta ctacaatttt tttgtctaaa 720
gagtaatact agagataaac ataaaaaatg tagaggtcga gtttagatgc aagttcaagg 780
agcgaaaggt ggatgggtag gttatatagg gatatagcac agagatatat agcaaagaga 840
tacttttgag caatgtttgt ggaagcggta ttcgcaatat tttagtagct cgttacagtc 900
cggtgcgttt ttggtttttt gaaagtgcgt cttcagagcg cttttggttt tcaaaagcgc 960
tctgaagttc ctatactttc tagagaatag gaacttcgga ataggaactt caaagcgttt 1020
ccgaaaacga gcgcttccga aaatgcaacg cgagctgcgc acatacagct cactgttcac 1080
gtcgcaccta tatctgcgtg ttgcctgtat atatatatac atgagaagaa cggcatagtg 1140
cgtgtttatg cttaaatgcg tacttatatg cgtctattta tgtaggatga aaggtagtct 1200
agtacctcct gtgatattat cccattccat gcggggtatc gtatgcttcc ttcagcacta 1260
ccctttagct gttctatatg ctgccactcc tcaattggat tagtctcatc cttcaatgct 1320
atcatttcct ttgatattgg atcata 1346

<210> SEQ ID NO 142
<211> LENGTH: 1705
<212> TYPE: DNA
<213> ORGANISM: Artificial Sequence
<220> FEATURE:
<223> OTHER INFORMATION: KanMX expression cassette

<400> SEQUENCE: 142
ctagggattc ataaccattt tctcaatcga attacacaga acacaccgta caaacctctc 60
tatcataact acttaatagt cacacacgta ctcgtctaaa tacacatcat cgtcctacaa 120
gttcatcaaa gtgttggaca gacaactata ccagcatgga tctcttgtat cggttctttt 180
ctcccgctct ctcgcaataa caatgaacac tgggtcaatc atagcctaca caggtgaaca 240
gagtagcgtt tatacagggt ttatacggtg attcctacgg caaaaatttt tcatttctaa 300
aaaaaaaaag aaaaattttt ctttccaacg ctagaaggaa aagaaaaatc taattaaatt 360
gatttggtga ttttctgaga gttccctttt tcatatatcg aattttgaat ataaaaggag 420
atcgaaaaaa tttttctatt caatctgttt tctggtttta tttgatagtt tttttgtgta 480
ttattattat ggattagtac tggtttatat gggtttttct gtataacttc tttttatttt 540
agtttgttta atcttatttt gagttacatt atagttccct aactgcaaga gaagtaacat 600
taaaactcga gatgggtaag gaaaagactc acgtttcgag gccgcgatta aattccaaca 660
tggatgctga tttatatggg tataaatggg ctcgcgataa tgtcgggcaa tcaggtgcga 720
caatctatcg attgtatggg aagcccgatg cgccagagtt gtttctgaaa catggcaaag 780
gtagcgttgc caatgatgtt acagatgaga tggtcagact aaactggctg acggaattta 840
tgcctcttcc gaccatcaag cattttatcc gtactcctga tgatgcatgg ttactcacca 900
ctgcgatccc cggcaaaaca gcattccagg tattagaaga atatcctgat tcaggtgaaa 960
atattgttga tgcgctggca gtgttcctgc gccggttgca ttcgattcct gtttgtaatt 1020
gtccttttaa cagcgatcgc gtatttcgtc tggctcaggc gcaatcacga atgaataacg 1080
gtttggttga tgcgagtgat tttgatgacg agcgtaatgg ctggcctgtt gaacaagtct 1140
ggaaagaaat gcataagctt ttgccattct caccggattc agtcgtcact catggtgatt 1200
tctcacttga taaccttatt tttgacgagg ggaaattaat aggttgtatt gatgttggac 1260
gagtcggaat cgcagaccga taccaggatc ttgccatcct atggaactgc ctcggtgagt 1320
tttctccttc attacagaaa cggctttttc aaaaatatgg tattgataat cctgatatga 1380
ataaattgca gtttcatttg atgctcgatg agtttttcta agtttaactt gatactacta 1440
gatttttctc ttcatttata aaatttttgg ttataattga agctttagaa gtatgaaaaa 1500
atcctttttt ttcattcttt gcaaccaaaa taagaagctt cttttattca ttgaaatgat 1560
gaatataaac ctaacaaaag aaaaagactc gaatatcaaa cattaaaaaa aaataaaaga 1620
ggttatctgt tttcccattt agttggagtt tgcattttct aatagataga actctcaatt 1680
aatgtggatt tagtttctct gttcg 1705

<210> SEQ ID NO 143
<211> LENGTH: 299
<212> TYPE: DNA
<213> ORGANISM: Artificial Sequence
<220> FEATURE:
<223> OTHER INFORMATION: synthesized SNR52p promoter

<400> SEQUENCE: 143
ccctcactaa agggaacaaa agctggagct tctttgaaaa gataatgtat gattatgctt 60
tcactcatat ttatacagaa acttgatgtt ttctttcgag tatatacaag gtgattacat 120
gtacgtttga agtacaactc tagattttgt agtgccctct tgggctagcg ggaaaggtgc 180
gcattttttc acaccctaca atgttctgtt caaaagattt tggtcaaacg ctgtagaagt 240
gaaagttggt gcgcatgttt cggcgttcga aacttctccg cagtgaaaga taaatgatc 299

<210> SEQ ID NO 144
<211> LENGTH: 11555
<212> TYPE: DNA
<213> ORGANISM: Artificial Sequence
<220> FEATURE:
<223> OTHER INFORMATION: pSE087 plasmid

<400> SEQUENCE: 144
gatcctctag tttctcggta ctatgcatat gatccaatat caaaggaaat gatagcattg 60

-continued

```
aaggatgaga ctaatccaat tgaggagtgg cagcatatag aacagctaaa gggtagtgct   120
gaaggaagca tacgataccc cgcatggaat gggataatat cacaggaggt actagactac   180
ctttcatcct acataaatag acgcatataa gtacgcattt aagcataaac acgcactatg   240
ccgttcttct catgtatata tatatacagg caacacgcag atataggtgc gacgtgaaca   300
gtgagctgta tgtgcgcagc tcgcgttgca ttttcggaag cgctcgtttt cggaaacgct   360
ttgaagttcc tattccgaag ttcctattct ctagaaagta taggaacttc agagcgcttt   420
tgaaaaccaa aagcgctctg aagacgcact ttcaaaaaac caaaaacgca ccggactgta   480
acgagctact aaaatattgc gaataccgct tccacaaaca ttgctcaaaa gtatctcttt   540
gctatatatc tctgtgctat atccctatat aacctaccca tccacctttc gctccttgaa   600
cttgcatcta aactcgacct ctacattttt tatgtttatc tctagtatta ctctttagac   660
aaaaaaattg tagtaagaac tattcataga gtgaatcgaa aacaatacga aaatgtaaac   720
atttcctata cgtagtatat agagacaaaa tagaagaaac cgttcataat tttctgacca   780
atgaagaatc atcaacgcta tcactttctg ttcacaaagt atgcgcaatc cacatcggta   840
tagaatataa tcggggatgc ctttatcttg aaaaaatgca cccgcagctt cgctagtaat   900
cagtaaacgc gggaagtgga gtcaggcttt ttttatggaa gagaaaatag acaccaaagt   960
agccttcttc taaccttaac ggacctacag tgcaaaaagt tatcaagaga ctgcattata  1020
gagcgcacaa aggagaaaaa aagtaatcta agatgctttg ttagaaaaat agcgctctcg  1080
ggatgcattt ttgtagaaca aaaaagaagt atagattctt tgttggtaaa atagcgctct  1140
cgcgttgcat ttctgttctg taaaaatgca gctcagattc tttgtttgaa aaattagcgc  1200
tctcgcgttg catttttgtt ttacaaaaat gaagcacaga ttcttcgttg gtaaaatagc  1260
gctttcgcgt tgcatttctg ttctgtaaaa atgcagctca gattctttgt ttgaaaaatt  1320
agcgctctcg cgttgcattt ttgttctaca aaatgaagca cagatgcttc gttaacaaag  1380
atatgctatt gaagtgcaag atggaaacgc agaaaatgaa ccggggatgc gacgtgcaag  1440
attacctatg caatagatgc aatagtttcg gcatgccgaa cagagaaact aaatccacat  1500
taattgagag ttctatctat tagaaaatgc aaactccaac taaatgggaa aacagataac  1560
ctcttttatt ttttttaat gtttgatatt cgagtctttt tcttttgtta ggtttatatt  1620
catcatttca atgaataaaa gaagcttctt attttggttg caaagaatga aaaaaaagga  1680
ttttttcata cttctaaagc ttcaattata accaaaaatt ttataaatga agagaaaaat  1740
ctagtagtat caagttaaac ttagaaaaac tcatcgagca tcaaatgaaa ctgcaattta  1800
ttcatatcag gattatcaat accatatttt tgaaaaagcc gtttctgtaa tgaaggagaa  1860
aactcaccga ggcagttcca taggatggca agatcctggt atcggtctgc gattccgact  1920
cgtccaacat caatacaacc tattaatttc ccctcgtcaa aaataaggtt atcaagtgag  1980
aaatcaccat gagtgacgac tgaatccggt gagaatggca aaagcttatg catttctttc  2040
cagacttgtt caacaggcca gccattacgc tcgtcatcaa aatcactcgc atcaaccaaa  2100
ccgttattca ttcgtgattg cgcctgagcc agacgaaata cgcgatcgct gttaaaagga  2160
caattacaaa caggaatcga atgcaaccgg cgcaggaaca ctgccagcgc atcaacaata  2220
ttttcacctg aatcaggata ttcttctaat acctggaatg ctgttttgcc ggggatcgca  2280
gtggtgagta accatgcatc atcaggagta cggataaaat gcttgatggt cggaagaggc  2340
ataaattccg tcagccagtt tagtctgacc atctcatctg taacatcatt ggcaacgcta  2400
```

```
cctttgccat gtttcagaaa caactctggc gcatcgggct tcccatacaa tcgatagatt   2460
gtcgcacctg attgcccgac attatcgcga gcccatttat acccatataa atcagcatcc   2520
atgttggaat ttaatcgcgg cctcgaaacg tgagtctttt ccttacccat ctcgagtttt   2580
aatgttactt ctcttgcagt tagggaacta taatgtaact caaaataaga ttaaacaaac   2640
taaaataaaa agaagttata cagaaaaacc catataaacc agtactaatc cataataata   2700
atacacaaaa aaactatcaa ataaaaccag aaaacagatt gaatagaaaa attttttcga   2760
tctcctttta tattcaaaat tcgatatatg aaaaagggaa ctctcagaaa atcaccaaat   2820
caatttaatt agatttttct tttccttcta gcgttggaaa gaaaaatttt tcttttttt    2880
tttagaaatg aaaaattttt gccgtaggaa tcaccgtata aaccctgtat aaacgctact   2940
ctgttcacct gtgtaggcta tgattgaccc agtgttcatt gttattgcga gagagcggga   3000
gaaaagaacc gatacaagag atccatgctg gtatagttgt ctgtccaaca ctttgatgaa   3060
cttgtaggac gatgatgtgt atttagacga gtacgtgtgt gactattaag tagttatgat   3120
agagaggttt gtacggtgtg ttctgtgtaa ttcgattgag aaaatggtta tgaatcccta   3180
gacccgggaa tctctaagta aatgcatgta tactaaactc acaaattaga gcttcaattt   3240
aattatatca gttattaccc gggttacgcc aagcgcgcaa ttaaccctca ctaaagggaa   3300
caaaagctgg agctcccctc actaaaggga acaaaagctg gagcttcttt gaaaagataa   3360
tgtatgatta tgctttcact catatttata cagaaacttg atgttttctt tcgagtatat   3420
acaaggtgat tacatgtacg tttgaagtac aactctagat tttgtagtgc cctcttgggc   3480
tagcgggaaa ggtgcgcatt ttttcacacc ctacaatgtt ctgttcaaaa gattttggtc   3540
aaacgctgta gaagtgaaag ttggtgcgca tgtttcggcg ttcgaaactt ctccgcagtg   3600
aaagataaat gatcggagac ggatacgttc tctatggagg agttttagag ctagaaatag   3660
caagttaaaa taaggctagt ccgttatcaa cttgaaaaag tggcaccgag tcggtggtgc   3720
tttttttctg gccgtctcta agggcccggt acccaattcg ccctatagtg agtcgtatta   3780
cgccagctgc attaatgaat cggccaacgc gcggggagag gcggtttgcg tattgggcgc   3840
tcttccgctt cctcgctcac tgactcgctg cgctcggtcg ttcggctgcg gcgagcggta   3900
tcagctcact caaaggcggt aatacggtta tccacagaat caggggataa cgcaggaaag   3960
aacatgtgag caaaaggcca gcaaaaggcc aggaaccgta aaaaggccgc gttgctggcg   4020
tttttccata ggctccgccc ccctgacgag catcacaaaa atcgacgctc aagtcagagg   4080
tggcgaaacc cgacaggact ataaagatac caggcgtttc cccctggaag ctccctcgtg   4140
cgctctcctg ttccgaccct gccgcttacc ggatacctgt ccgcctttct cccttcggga   4200
agcgtggcgc tttctcatag ctcacgctgt aggtatctca gttcggtgta ggtcgttcgc   4260
tccaagctgg gctgtgtgca cgaacccccc gttcagcccg accgctgcgc cttatccggt   4320
aactatcgtc ttgagtccaa cccggtaaga cacgacttat cgccactggc agcagccact   4380
ggtaacagga ttagcagagc gaggtatgta ggcggtgcta cagagttctt gaagtggtgg   4440
cctaactacg gctacactag aagaacagta tttggtatct gcgctctgct gaagccagtt   4500
accttcggaa aaagagttgg tagctcttga tccggcaaac aaaccaccgc tggtagcggt   4560
ggtttttttg tttgcaagca gcagattacg cgcagaaaaa aaggatctca agaagatcct   4620
ttgatctttt ctacggggtc tgacgctcag tggaacgaaa actcacgtta agggattttg   4680
gtcatgagat tatcaaaaag gatcttcacc tagatccttt taaattaaaa atgaagtttt   4740
aaatcaatct aaagtatata tgagtaaact tggtctgaca gttaccaatg cttaatcagt   4800
```

gaggcaccta tctcagcgat ctgtctattt cgttcatcca tagttgcctg actccccgtc 4860
gtgtagataa ctacgatacg ggagggctta ccatctggcc ccagtgctgc aatgataccg 4920
cgagacccac gctcaccggc tccagattta tcagcaataa accagccagc cggaagggcc 4980
gagcgcagaa gtggtcctgc aactttatcc gcctccatcc agtctattaa ttgttgccgg 5040
gaagctagag taagtagttc gccagttaat agtttgcgca acgttgttgc cattgctaca 5100
ggcatcgtgg tgtcacgctc gtcgtttggt atggcttcat tcagctccgg ttcccaacga 5160
tcaaggcgag ttacatgatc ccccatgttg tgcaaaaaag cggttagctc cttcggtcct 5220
ccgatcgttg tcagaagtaa gttggccgca gtgttatcac tcatggttat ggcagcactg 5280
cataattctc ttactgtcat gccatccgta agatgctttt ctgtgactgg tgagtactca 5340
accaagtcat tctgagaata gtgtatgcgg cgaccgagtt gctcttgccc ggcgtcaata 5400
cgggataata ccgcgccaca tagcagaact ttaaaagtgc tcatcattgg aaaacgttct 5460
tcggggcgaa aactctcaag gatcttaccg ctgttgagat ccagttcgat gtaacccact 5520
cgtgcaccca actgatcttc agcatctttt actttcacca gcgtttctgg gtgagcaaaa 5580
acaggaaggc aaaatgccgc aaaaaaggga ataagggcga cacggaaatg ttgaatactc 5640
atactcttcc tttttcaata ttattgaagc atttatcagg gttattgtct catgagcgga 5700
tacatatttg aatgtattta gaaaaataaa caaatagggg ttccgcgcac atttccccga 5760
aaagtgccac ctgacgtcgg cgcgccattt aaatagatcc ggtccgctcg agctgtaccg 5820
cagatgggac ctcttatgaa agtagacatc cttaagtgat gtaggggtat gtccgagtag 5880
ttcgttcaac tatttttaaa gacacatcgt tccaggttta tattcatata catatgtatg 5940
tattgtatag gttttttttat tttttatttt ttattttttt tttttttttt ttcaattttt 6000
ttaagctttt cttacttttc cgatgccctt tccactttaa tcaatatacg tatgaaattc 6060
agccgaagtt tccgtttgat aatatattag attcaatata aaaaaaagtt tatatgattc 6120
agtgtatata tatatatata aataagaggt gcgaaagccc acataaagag attgaagaga 6180
ctgcgtaaaa agaaatatat agagagatac tcttaactag acctttcttt tcttctttgg 6240
gtcggctctg gagtcgccac ccaattgaga taagtcaatt ctagtttcgt acaaaccagt 6300
aatagattga tggatcaagg tggcgtccaa gacttccttg gtagaggtgt aacgcttacg 6360
gtcaatagtg gtgtcgaagt acttgaaggc agcaggagca cccaaattgg tcaaagtgaa 6420
caagtgaatg atgttttcag cttgttctct gattggcttg tctctgtgct tgttgtaggc 6480
ggacaaaacc ttgtccaagt tagcgtcagc caaaatgact ctcttggaga actcggagat 6540
ttgttcaatg atttcgtcca agtagtgctt gtgttgttcg acgaatagtt gcttttgttc 6600
gttgtcttct ggactaccct tcaacttttc gtagtgagaa gccaagtata ggaagttaac 6660
gtacttgctt ggcaaggcca attcgttacc cttttgcaat tcaccagcgg aagccaacat 6720
tctctttcta ccgttttcca attcgaacaa tgagtacttt ggcaacttta tgatcaagtc 6780
tttcttgact tccttgtaac ccttagcttc taggaagtcg attgggttct tttcgaaaga 6840
acttctttcc atgatggtaa tacctaacaa ttccttgacg ctcttcaatt tcttagactt 6900
acccttttca accttagcga caaccaaaac gctgtaggca acggtaggag agtcgaagcc 6960
accgtatttc tttgggtccc aatctttctt tctagcgatc aacttatcag agtttctctt 7020
tggtaagata gattccttag agaagccacc agtttggact tcggttttct tgacgatgtt 7080
gacttgtggc atagacaaaa cctttctaac ggtagcgaaa tcacgaccct tgtcccaaac 7140

-continued

```
aatttcacct gtttcaccgt ttgtttcgat caatggtctc tttctgattt caccgttagc   7200
caaggtgatt tcggtcttaa agaagttcat aatgttagag taaaagaagt acttagcagt   7260
ggccttaccg atttcttgtt cagacttagc gatcatcttt ctgacatcgt agaccttgta   7320
atcaccgtag acaaattcag attctagctt tgggtatttc ttgattagag cggtacccac   7380
gacagcgttc aagtaagcat cgtgagcatg gtggtaattg ttgatttctc taaccttgta   7440
gaattggaag tcctttctga agtcagaaac caacttggac ttcaaagtga tgaccttgac   7500
ttctctaatc aacttatcat tttcgtcgta cttggtgttc atacgggaat ctaggatttg   7560
ggcaacgtgc ttggtgattt gtctggtttc gaccaattgt ctcttgatga agccagcctt   7620
atccaattcg gacaatccac ctctttcagc cttagttagg ttatcgaact ttctttgagt   7680
gattagctta gcgtttagca attgtctcca gtagttcttc atctttttca cgacctcttc   7740
ggatggaacg ttgtcagact tacctctgtt cttgtcggat ctggtcaaaa ccttgttgtc   7800
aatagaatcg tccttcaaga aagattgtgg gacgatgtgg tcaacgtcgt agtcggataa   7860
tctgttgata tctaattctt ggtcaacgta catatctcta ccgttttgca agtagtacaa   7920
gtataacttt tcgttttgta gttgggtgtt ttcaacgggg tgttccttca agatttgaga   7980
acccaattcc ttgataccct cttcgattct cttcattctt tctctagagt tcttttgacc   8040
cttttgtgta gtttgatttt ctctagccat ttctatgacg atgttttctg gcttgtgtct   8100
acccataacc ttaactagtt cgtctacaac cttgacagtt tgtagaatac ctttctttat   8160
ggctggggaa ccagccaagt tagcgatgtg ttcgtgcaag gaatcacctt gaccagaaac   8220
ttgagccttt tggatatctt ccttgaaggt caaagaatcg tcgtggatca attgcatgaa   8280
gtttctgttg gcgaaaccat cggacttcaa gaaatccaag atggtcttac cagattgctt   8340
gtctctgata ccgttaatca actttcttga caatctaccc caaccagtgt acctacgtct   8400
tttcaattgc ttcataacct tgtcatcaaa caagtgggcg taggtcttca atctctcttc   8460
gatcatttct ctgtcttcga acaaggttaa agttaggaca atgtcttcca aaatgtcttc   8520
gttctcttcg ttatccaaga agtccttgtc cttaatgatc tttagtaagt cgtggtaggt   8580
acccaaagaa gcgttgaatc tatcttcaac accagagatt tcaacagaat cgaaacattc   8640
gattttcttg aagtagtctt cctttagttg cttaacagtg acctttctgt ttgtcttgaa   8700
taacaagtca acgatagctt tcttttgttc gccagacaag aaggctggct ttctcatacc   8760
ttcagtaacg tacttgacct tggtcaattc gttgtaaaca gtgaagtatt cgtataacaa   8820
ggaatgcttt ggcaagacct tttcgtttgg caagtttttg tcgaagttgg tcattctttc   8880
gatgaaagat tgagcggaag cacccttatc tacgacctct tcgaaattcc aaggggtgat   8940
ggtctcttcg gactttctgg tcatccaagc gaatctggag ttacctctag ctagaggacc   9000
gacgtagtat gggattctaa aagttaggat cttttcaatc ttttctctgt tgtccttcaa   9060
gaatgggtag aagtcttctt gccttctcaa gatagcgtgt agttcaccta agtggatttg   9120
gtgtggaatg gaaccgttgt cgaaggttct ttgctttctt aacaagtctt ctctattcaa   9180
cttaactagc aactcttcgg taccgtccat cttttccaag attggcttga tgaacttgta   9240
gaactcttct tgactagctc caccgtcgat gtaaccagcg taaccgttct tagattgatc   9300
aaagaagatt tccttgtact tttcgggcaa ttgttgtcta accaaagcct tcaatagagt   9360
caagtcttga tggtgttcgt cgtatctctt aatcatggaa gcagacaatg gagccttagt   9420
gatttcagtg ttaactctca aaatgtcaga tagcaaaatg gcatcagaca agttcttggc   9480
agccaagaac aagtcagcgt attggtcacc aatttgggct aacaagttat ctaaatcgtc   9540
```

```
atcgtaagtg tccttggaca attgcaactt agcatcttca gccaaatcga agttagactt   9600

gaagtttgga gtcaaaccca aagacaaagc aatcaagtta ccgaacaaac cgtttttctt   9660

ttcacctggt aattgggcaa tcaagttttc caaacgtctg gacttggata atctagcgga   9720

caaaatggcc ttagcgtcaa caccagaggc gttgatagga ttctcttcga acaattggtt   9780

gtaagtttga accaattgga tgaacaactt atcgacgtca gagttgtctg ggttcaagtc   9840

accttcgatt aggaagtgac cacggaactt gatcatgtgg gccaaagcca agtagatcaa   9900

tctcaagtca gccttgtcgg tggagtcaac caatttcttt ctcaagtggt agatagttgg   9960

gtacttttcg tggtaagcga cttcgtcaac gatgttaccg aagattgggt gtctttcgtg  10020

ctttttgtcc tcttcgacca agaaagactc ttccaatctg tgaaagaaag aatcgtcaac  10080

cttagccatt tcattagaga agatttcttg caagtaacag attctgttct tacgtctagt  10140

gtaacgtcta cgggctgttc tcttcaatct agtagcttcg gcagtttcac cagagtcgaa  10200

taacaaagca ccgattaggt ttttcttgat ggagtgtcta tcggtgttac ccaagacctt  10260

gaatttctta gatgggacct tgtattcgtc agtaatgaca gcccaaccaa cagagttggt  10320

accgatgtcc aaaccgatag agtatttctt gtccatggta attggacaaa taaatacgtg  10380

tattaagttt ggattctttg gtagatagcc aatcgaggga acaattaaaa aaaagaaaga  10440

aataaaagac aagaagaaga gcgaaaaagg ggaaagtgat gaggaaaaga acaatagata  10500

gatccagaag atgatggtaa cgcgcaaaca ctaccgctat atatacctac aaaactctca  10560

ttctctcatt tcctgcttcg ttcatttcga gtttccaagg gtatggtacg gtgctatctg  10620

cccgtgcttc ccctcctttg ctttgctaag aaaaattttc ttttgtcagc agcaacaaca  10680

cgctacgctc tgcgctgtgc tacgaagtgg tctctgtggc aacggggaca ttgtacccat  10740

gcccgctcgc agggaggtct gggtgtgggg cgtgtgcgac ctcgttgcca tggcgatcgc  10800

gcgtgggtgt ggtctttccc caaacggttg cccgttgctc cggatttcgc atagttgtcg  10860

cgtaaacaaa aaacacgaga gagggcggac ggcgctgaat agtggaagat cgcgcgatgt  10920

caagtaaata agcttgtatt tgtatttgta tgtgtttatg tgtttgtgtg gttgagaatt  10980

ttattttcct cctagttttt tctttttga gtgcggaggg gcagtgctct aaactttgcc  11040

tgcttcttgt tcgacttcgg cttcctatgc agaacgcaaa atcgcgtgcg cgaggaacga  11100

ggaagacaac gctttagatt ggcgcggccg cccgcaaatt aaagccttcg agcgtcccaa  11160

aaccttctca agcaaggttt tcagtataat gttacatgcg tacacgcgtc tgtacagaaa  11220

aaaaagaaaa atttgaaata taaataacgt tcttaatact aacataacta taaaaaaata  11280

aatagggacc tagacttcag gttgtctaac tccttccttt tcggttagag cggatgtggg  11340

gggagggcgt gaatgtaagc gtgacataac taattacatg attaatctag taacaaggct  11400

aagatatcag cctgaaataa agggtggtga agtaataatt aaatcatccg tataaaccta  11460

tacacatata tgaggaaaaa taatacaaaa gtgttttaaa tacagataca tacatgaaca  11520

tatgcacgta tagcgcccaa atgtcggtaa tggga                            11555
```

<210> SEQ ID NO 145
<211> LENGTH: 57
<212> TYPE: DNA
<213> ORGANISM: Artificial Sequence
<220> FEATURE:
<223> OTHER INFORMATION: primer

<400> SEQUENCE: 145
ctccgcagtg aaagataaat gatcgcccaa aatttgttta ctaaaaacac atgtgga 57

<210> SEQ ID NO 146
<211> LENGTH: 58
<212> TYPE: DNA
<213> ORGANISM: Artificial Sequence
<220> FEATURE:
<223> OTHER INFORMATION: primer

<400> SEQUENCE: 146
gaattgggta ccgggccctt agagtaaaaa attgtacttg gcggataatg cctttagc 58

<210> SEQ ID NO 147
<211> LENGTH: 106
<212> TYPE: DNA
<213> ORGANISM: Artificial Sequence
<220> FEATURE:
<223> OTHER INFORMATION: synthesized targeting sgRNA + T(6) terminator

<400> SEQUENCE: 147
gatacgttct ctatggagga gttttagagc tagaaatagc aagttaaaat aaggctagtc 60
cgttatcaac ttgaaaaagt ggcaccgagt cggtggtgct tttttt 106

<210> SEQ ID NO 148
<211> LENGTH: 50
<212> TYPE: DNA
<213> ORGANISM: Artificial Sequence
<220> FEATURE:
<223> OTHER INFORMATION: synthesized 50 bp upstream homology arm

<400> SEQUENCE: 148
cccaaaattt gtttactaaa aacacatgtg gatatcttga ctgatttttc 50

<210> SEQ ID NO 149
<211> LENGTH: 106
<212> TYPE: DNA
<213> ORGANISM: Artificial Sequence
<220> FEATURE:
<223> OTHER INFORMATION: synthesized URA3 targeting sgRNA + T(6)
terminator

<400> SEQUENCE: 149
tatcttgact gatttttcca gttttagagc tagaaatagc aagttaaaat aaggctagtc 60
cgttatcaac ttgaaaaagt ggcaccgagt cggtggtgct tttttt 106

<210> SEQ ID NO 150
<211> LENGTH: 50
<212> TYPE: DNA
<213> ORGANISM: Artificial Sequence
<220> FEATURE:
<223> OTHER INFORMATION: synthesized 50 bp downstream homology arm

<400> SEQUENCE: 150
gcacagttaa gccgctaaag gcattatccg ccaagtacaa tttttactc 50

<210> SEQ ID NO 151
<211> LENGTH: 57
<212> TYPE: DNA
<213> ORGANISM: Artificial Sequence
<220> FEATURE:
<223> OTHER INFORMATION: primer

<400> SEQUENCE: 151
ccgccaagta caatttttta ctctaagggc ccggtaccca attcgcccta tagtgag 57

<210> SEQ ID NO 152
<211> LENGTH: 57
<212> TYPE: DNA
<213> ORGANISM: Artificial Sequence
<220> FEATURE:
<223> OTHER INFORMATION: primer

<400> SEQUENCE: 152
catcatcacc atcattgata agagtatctc tctatatatt tctttttacg cagtctc 57

<210> SEQ ID NO 153
<211> LENGTH: 566
<212> TYPE: DNA
<213> ORGANISM: Artificial Sequence
<220> FEATURE:
<223> OTHER INFORMATION: synthesized 2-micron replication origin 2

<400> SEQUENCE: 153
gtaatctgct gcttgcaaac aaaaaaacca ccgctaccag cggtggtttg tttgccggat 60
caagagctac caactctttt tccgaaggta actggcttca gcagagcgca gataccaaat 120
actgttcttc tagtgtagcc gtagttaggc caccacttca agaactctgt agcaccgcct 180
acatacctcg ctctgctaat cctgttacca gtggctgctg ccagtggcga taagtcgtgt 240
cttaccgggt tggactcaag acgatagtta ccggataagg cgcagcggtc gggctgaacg 300 ggggggttcgt gcacacagcc cagcttggag cgaacgacct acaccgaact gagataccta 360
cagcgtgagc tatgagaaag cgccacgctt cccgaaggga gaaaggcgga caggtatccg 420
gtaagcggca gggtcggaac aggagagcgc acgagggagc ttccaggggg aaacgcctgg 480
tatctttata gtcctgtcgg gtttcgccac ctctgacttg agcgtcgatt tttgtgatgc 540
tcgtcagggg ggcggagcct atggaa 566

<210> SEQ ID NO 154
<211> LENGTH: 859
<212> TYPE: DNA
<213> ORGANISM: Artificial Sequence
<220> FEATURE:
<223> OTHER INFORMATION: synthesized ampicillin resistant gene

<400> SEQUENCE: 154
atgagtattc aacatttccg tgtcgccctt attccctttt ttgcggcatt ttgccttcct 60
gtttttgctc acccagaaac gctggtgaaa gtaaaagatg ctgaagatca gttgggtgca 120
cgagtgggtt acatcgaact ggatctcaac agcggtaaga tccttgagag ttttcgcccc 180
gaagaacgtt ttccaatgat gagcactttt aaagttctgc tatgtggcgc ggtattatcc 240
cgtattgacg ccgggcaaga gcaactcggt cgccgcatac actattctca gaatgacttg 300
gttgagtact caccagtcac agaaaagcat cttacggatg gcatgacagt aagagaatta 360
tgcagtgctg ccataaccat gagtgataac actgcggcca acttacttct gacaacgatc 420
ggaggaccga aggagctaac cgcttttttg cacaacatgg gggatcatgt aactcgcctt 480
gatcgttggg aaccggagct gaatgaagcc ataccaaacg acgagcgtga caccacgatg 540
cctgtagcaa tggcaacaac gttgcgcaaa ctattaactg gcgaactact tactctagct 600
tcccggcaac aattaataga ctggatggag gcggataaag ttgcaggacc acttctgcgc 660
tcggcccttc cggctggctg gtttattgct gataaatctg gagccggtga gcgtgggtct 720
cgcggtatca ttgcagcact ggggccagat ggtaagccct cccgtatcgt agttatctac 780
acgacgggga gtcaggcaac tatggatgaa cgaaatagac agatcgctga gataggtgcc 840

-continued

```
tcactgatta agcattggt                                              859


<210> SEQ ID NO 155
<211> LENGTH: 400
<212> TYPE: DNA
<213> ORGANISM: Artificial Sequence
<220> FEATURE:
<223> OTHER INFORMATION: synthesized RNR2 terminator

<400> SEQUENCE: 155

gagtatctct ctatatattt ctttttacgc agtctcttca atctctttat gtgggctttc     60

gcacctctta tttatatata tatatataca ctgaatcata taaacttttt tttatattga    120

atctaatata ttatcaaacg gaaacttcgg ctgaatttca tacgtatatt gattaaagtg    180

gaaagggcat cggaaaagta agaaaagctt aaaaaaattg aaaaaaaaaa aaaaaaaaat    240

aaaaaataaa aaataaaaaa acctatacaa tacatacata tgtatatgaa tataaacctg    300

gaacgatgtg tctttaaaaa tagttgaacg aactactcgg acatacccct acatcactta    360

aggatgtcta ctttcataag aggtcccatc tgcggtacag                          400


<210> SEQ ID NO 156
<211> LENGTH: 56
<212> TYPE: DNA
<213> ORGANISM: Artificial Sequence
<220> FEATURE:
<223> OTHER INFORMATION: primer

<400> SEQUENCE: 156

ccttgcgttt ctttttgggg gccatggtaa ttggacaaat aaatacgtgt attaag         56


<210> SEQ ID NO 157
<211> LENGTH: 56
<212> TYPE: DNA
<213> ORGANISM: Artificial Sequence
<220> FEATURE:
<223> OTHER INFORMATION: primer

<400> SEQUENCE: 157

tgtttttagt aaacaaattt tgggcgatca tttatctttc actgcggaga agtttc         56
```